United States Patent
Naidu et al.

(10) Patent No.: US 9,663,536 B2
(45) Date of Patent: May 30, 2017

(54) INHIBITORS OF HUMAN IMMUNODEFICIENCY VIRUS REPLICATION

(71) Applicant: VIIV HEALTHCARE UK (NO.5) LIMITED, Brentford, Middlesex (GB)

(72) Inventors: B. Narasimhulu Naidu, Durham, CT (US); Manoj Patel, Berlin, CT (US); Kevin Peese, Haddam, CT (US); Zhongyu Wang, Tolland, CT (US)

(73) Assignee: ViiV HEALTHCARE UK (NO.5) LIMITED, Brentford, Middlesex (GB)

( * ) Notice: Subject to any disclaimer, the term of this patent is extended or adjusted under 35 U.S.C. 154(b) by 0 days.

(21) Appl. No.: 14/769,646

(22) PCT Filed: Mar. 10, 2014

(86) PCT No.: PCT/US2014/022405
§ 371 (c)(1),
(2) Date: Aug. 21, 2015

(87) PCT Pub. No.: WO2014/164428
PCT Pub. Date: Oct. 9, 2014

(65) Prior Publication Data
US 2016/0002263 A1    Jan. 7, 2016

Related U.S. Application Data

(60) Provisional application No. 61/779,589, filed on Mar. 13, 2013.

(51) Int. Cl.
| | | |
|---|---|---|
| *C07D 498/22* | (2006.01) |
| *A61K 31/529* | (2006.01) |
| *C07D 487/04* | (2006.01) |
| *C07D 498/18* | (2006.01) |
| *C07D 513/22* | (2006.01) |
| *C07D 515/22* | (2006.01) |
| *A61K 45/06* | (2006.01) |

(52) U.S. Cl.
CPC .......... *C07D 498/22* (2013.01); *A61K 31/529* (2013.01); *A61K 45/06* (2013.01); *C07D 487/04* (2013.01); *C07D 498/18* (2013.01); *C07D 513/22* (2013.01); *C07D 515/22* (2013.01)

(58) Field of Classification Search
None
See application file for complete search history.

(56) References Cited

FOREIGN PATENT DOCUMENTS

| WO | WO 2012/033735 A1 | 3/2012 |
| WO | WO 2013/025584 A1 | 2/2013 |
| WO | WO 2013/134113 A1 | 9/2013 |
| WO | WO 2013/134142 A1 | 9/2013 |
| WO | WO 2014/028384 A1 | 2/2014 |

*Primary Examiner* — Noble Jarrell
(74) *Attorney, Agent, or Firm* — Robert H. Brink; R. Steve Thomas; Edward R. Gimmi

(57) ABSTRACT

The disclosure generally relates to compounds of formula I, including compositions and methods for treating human immunodeficiency virus (HIV) infection. The disclosure provides novel inhibitors of HIV, pharmaceutical compositions containing such compounds, and methods for using these compounds in the treatment of HIV infection. Formule (I).

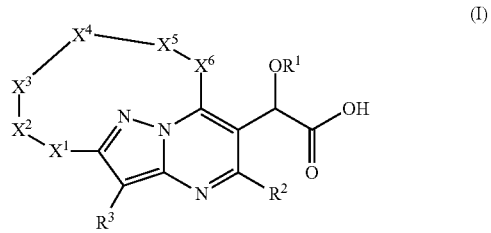

13 Claims, No Drawings

INHIBITORS OF HUMAN IMMUNODEFICIENCY VIRUS REPLICATION

CROSS-REFERENCE TO RELATED APPLICATIONS

This application claims priority to U.S. Provisional Patent Application Ser. No. 61/779,589, filed Mar. 13, 2013, which is incorporated by reference in its entirety.

BACKGROUND OF THE INVENTION

The disclosure generally relates to compounds, compositions, and methods for the treatment of human immunodeficiency virus (HIV) infection. The disclosure provides novel inhibitors of HIV, pharmaceutical compositions containing such compounds, and methods for using these compounds in the treatment of HIV infection.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that as many as 33.3 million people worldwide are infected with the virus (UNAIDS Report on the Global AIDS Epidemic 2010). In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into classes based on the viral protein they target or their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleos(t)ide reverse transcriptase inhibitors that behave as substrate mimics to halt viral cDNA synthesis. The non-nucleoside reverse transcriptase inhibitors nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. An HIV integrase inhibitor, raltegravir (MK-0518, Isentress®), has also been approved for use in treatment experienced patients, and it is clear that this class of inhibitors is very effective as part of a combination regimen containing HIV inhibitors of different classes.

Used alone, these drugs are effective in reducing viral replication: However, the effect is only temporary as the virus readily develops resistance to all known agents used as monotherapy. On the other hand, combination therapy has proven very effective at both reducing virus and suppressing the emergence of resistance in a number of patients. In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See WO2007131350, WO2009062285, WO2009062288, WO2009062289, WO2009062308, WO2010130034, WO2010130842, WO2011015641, WO2011076765, WO2012003497, WO2012003498, WO2012033735, WO2012065963 and WO2012066442

The invention provides technical advantages, for example, the compounds are novel and are useful in the treatment of HIV. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention is a compound of Formula I

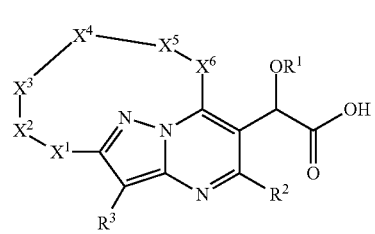

where:
$R^1$ is hydrogen or alkyl;
$R^2$ is hydrogen or alkyl;
$R^3$ is hydrogen, alkyl or halo;
$X^1$ is pyrrolyl, furanyl, thienyl, pyrazolyl, isoxazolyl, isothiazolyl, imidazolyl, oxazolyl, or thiazolyl;
$X^2$ is benzyl wherein the benzyl can be substituted with 0-3 substituents selected from halo, alkyl, haloalkyl, alkoxy, and haloalkoxy;
$X^3$ is O or absent;
$X^4$ is alkylene or alkenylene;
$X^5$ is O or absent; and
$X^6$ is azetidinyl, pyrrolidinyl, piperidinyl, piperazinyl, morpholinyl, homopiperidinyl, homopiperazinyl, or homomorpholinyl, and is substituted with 0-3 halo or alkyl substituents;
or a pharmaceutically acceptable salt thereof.

Another aspect of the invention is a compound of Formula I where $R^1$ is alkyl; $R^2$ is alkyl; $R^3$ is hydrogen; $X^1$ is pyrazolyl, oxazolyl, or thiazolyl; $X^2$ is absent or benzyl wherein the benzyl can be substituted with 0-3 substituents selected from halo, alkyl, haloalkyl, alkoxy, and haloalkoxy;

$X^3$ is O or absent; $X^4$ is alkylene or alkenylene; $X^5$ is O or absent; and $X^6$ is azetidinyl, pyrrolidinyl, piperidinyl, piperazinyl, morpholinyl, homopiperidinyl, homopiperazinyl, or homomorpholinyl, and is substituted with 0-3 halo or alkyl substituents; or a pharmaceutically acceptable salt thereof.

Another aspect of the invention is a compound of Formula I where $R^1$ is alkyl, $R^2$ is alkyl, and $R^3$ is hydrogen.

Another aspect of the invention is a compound of Formula I where $X^1$ is pyrazolyl.

Another aspect of the invention is a compound of Formula I where $X^1$ is oxazolyl.

Another aspect of the invention is a compound of Formula I where $X^1$ is thiazolyl.

Another aspect of the invention is a compound of Formula I where $X^4$ is propylene, propenylene, butylene, butenylene, pentylene, pentenylene, hexylene, or hexenylene.

Another aspect of the invention is a compound of Formula I where $X^4$ is propylene, propenylene, butylene, butenylene, pentylene, or pentenylene.

Another aspect of the invention is a compound of Formula I where $X^6$ is piperidinyl substituted with 0-1 alkyl substituents.

Any scope of any variable, including $R^1$, $R^2$, $R^3$, $X^1$, $X^2$, $X^3$, $X^4$, $X^5$, and $X^6$ can be used independently with the scope of any other instance of a variable.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkylene" means a straight or branched divalent alkyl group composed of 1 to 6 carbons. "Alkenylene" means a straight or branched divalent alkene group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" includes fluoro, chloro, bromo, and iodo. "Halo" includes all halogenated isomers from monohalo substituted to perhalo substituted in substituents defined with halo, for example, "Haloalkyl" and "haloalkoxy", "halophenyl", and "halophenoxy." "Aryl" includes carbocyclic and heterocyclic aromatic substituents. Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereromers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Inhibition of HIV Replication.

A recombinant NL-Rluc virus was constructed in which a section of the nef gene from NL4-3 was replaced with the Renilla Luciferase gene. The NL-RLuc virus was prepared by co-transfection of two plasmids, pNLRLuc and pVSVenv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to pVSVenv in 293T cells using the LipofectAMINE PLUS kit from Invitrogen (Carlsbad, Calif.) according to the manufacturer, and the pseudotype virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. This provides a simple and easy method for quantitating the extent of virus growth and consequently, the antiviral activity of test compounds. Luciferase was quantitated using the Dual Luciferase kit from Promega (Madison, Wis.).

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. In *Techniques in HIV Research*. ed. Aldovini A, Walker B D. 71-76. New York: Stockton Press. 1990). The anti-viral activity of compounds was evaluated under three serum conditions, 10% FBS, 15 mg/ml human serum albumin/10% FBS or 40% human serum/5% FBS, and the results from at least 2 experiments were used to calculate the $EC_{50}$ values. Results are shown in Table 1.

TABLE 1

| Example | EC$_{50}$ µM |
|---|---|
| 1 | 0.002 |
| 2 | 0.002 |
| 3 | 0.003 |
| 4 | 0.022 |
| 5 | 0.006 |
| 6 | 0.004 |
| 7 | 0.006 |
| 8 | 0.008 |
| 9 | 0.002 |
| 10 | 0.002 |
| 11 | 0.003 |
| 12 | 0.008 |
| 13 | 0.012 |
| 14 | 0.041 |
| 15 | 0.013 |
| 16 | 0.012 |
| 17 | 0.018 |
| 18 | 0.011 |
| 19 | 0.017 |
| 20 | 0.032 |
| 21 | 0.013 |
| 22 | 0.035 |
| 23 | 0.007 |
| 24 | 0.011 |
| 25 | 0.005 |
| 26 | 0.002 |
| 27 | 0.048 |
| 28 | 0.011 |
| 29 | 0.002 |
| 30 | 0.002 |
| 31 | 0.002 |
| 32 | 0.006 |
| 33 | 0.002 |
| 34 | 0.008 |
| 35 | 0.020 |
| 36 | 0.014 |
| 37 | 0.003 |
| 38 | 0.022 |
| 39 | 0.006 |
| 40 | 0.004 |
| 41 | 0.003 |

Pharmaceutical Composition and Methods of Use

The compounds of this invention inhibit HIV replication. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent" and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-

Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; and "DIEA" for diisopropylethylamine.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "A" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds can be synthesized from an appropriately substituted heterocycle I-1 according to Scheme I, Compound I-1 and I-2 are commercially available or synthesized by reactions known in the art. Intermediates I-3 can be prepared by procedure known in the art or as set forth in the examples below using compound I-1 and compound I-2. Intermediates I-3 can be transformed to intermediates I-4 using conditions known to those skilled in the art. Intermediates I-4 can be oxidized to intermediates I-5 by reactions known in the art, including Davis oxidation. Intermediates I-5 can be oxidized to intermediates I-6 by known conditions, including Dess-Martin oxidation. Intermediates I-6 can be reduced to chiral intermediates I-7 using known conditions in the presence of catalytic chiral ligands. Intermediates I-7 can be converted to the intermediates I-8 by known conditions, including tertiary-butyl acetate and perchloric acid. Coupling of amine to Intermediates I-8 using conditions known in the art can provide intermediates I-9. Intermediates I-9 can be converted to intermediates I-10 by conditions known in the art, including hydrolysis. Intermediates I-10 can be converted to intermediates I-11 by the methods well known to those skilled in art. Intermediates I-11 can be transformed to macrocycles I-12 by the methods well known in the art, including, including ring closing metathesis. Saponification of intermediates I-12 provide desired compounds I-13. Alternatively, intermediates I-11 can be converted to final compounds I-13 via intermediates I-14 by the methods well known to those skilled in the art.

Scheme I.

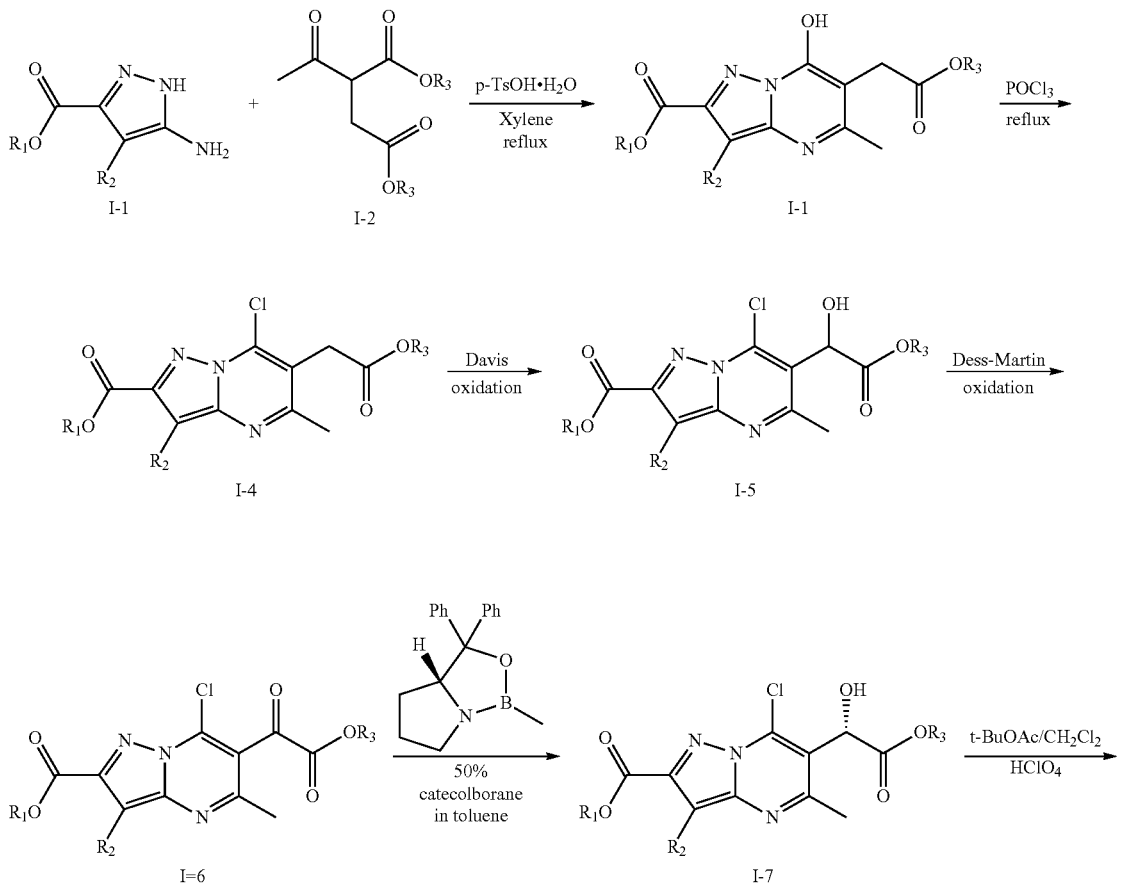

-continued
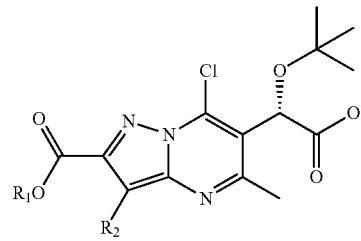 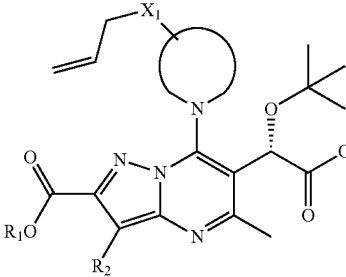
I-8 → I-9
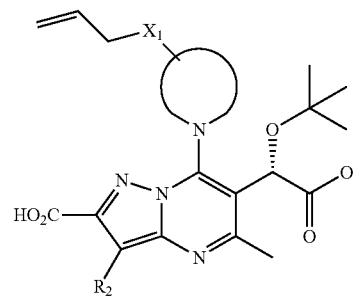 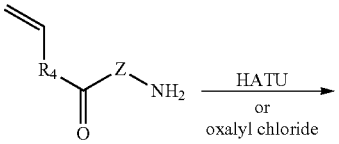
I-10
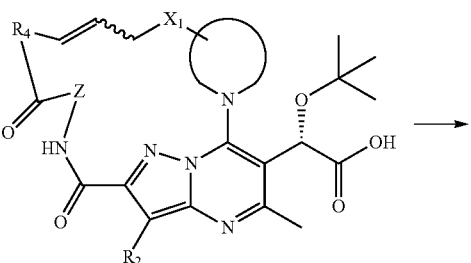
I-11 → I-12
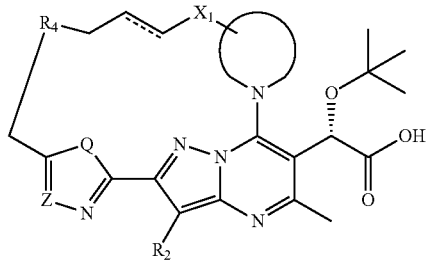
I-13
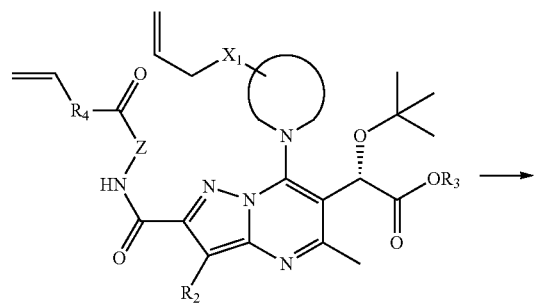
I-11 → I-14

Some compounds of this invention can also be prepared by the methods outlined in Scheme II.
Scheme II
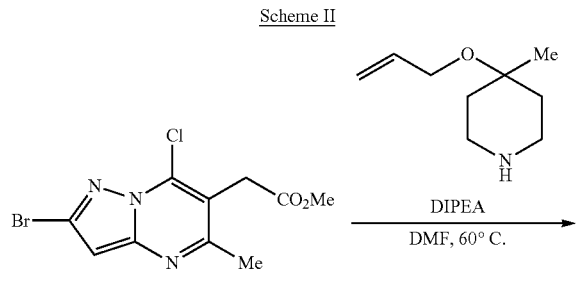
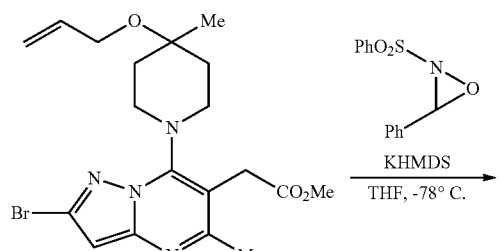
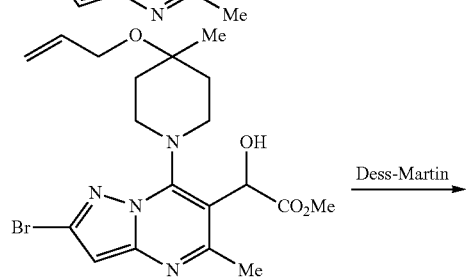
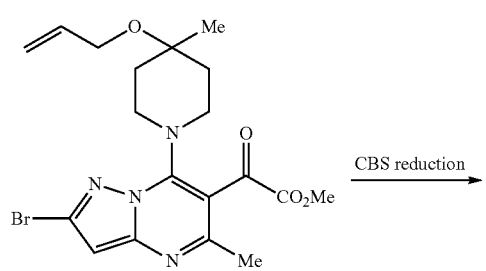
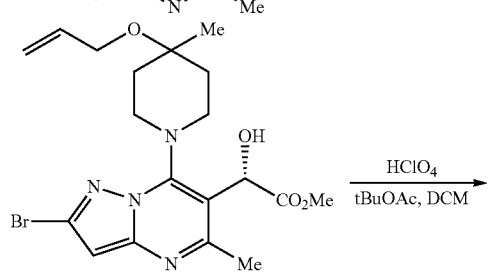
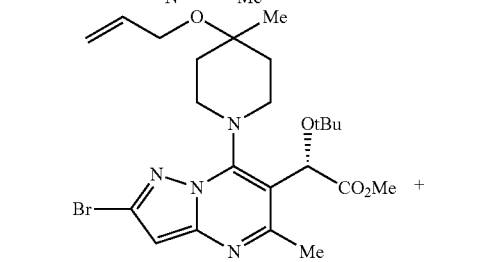
-continued
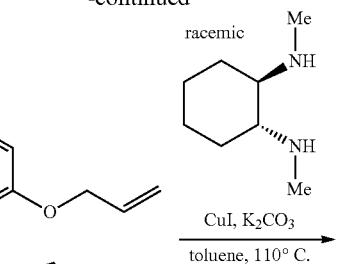
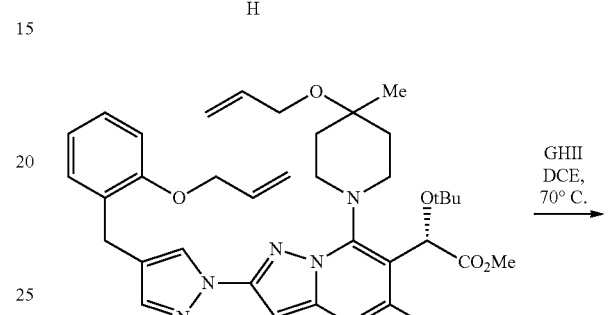
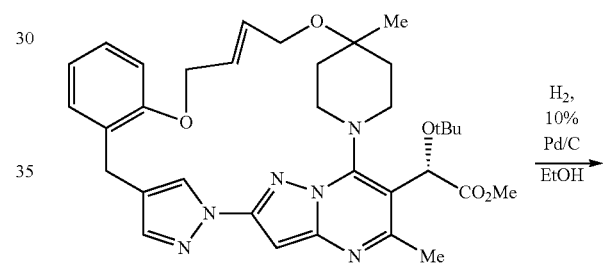
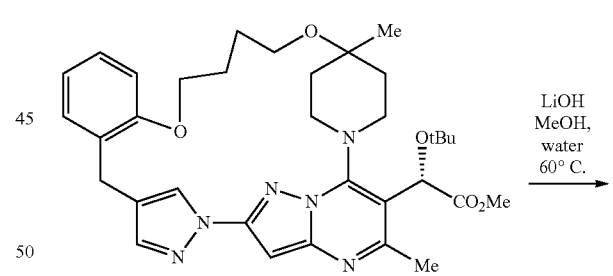
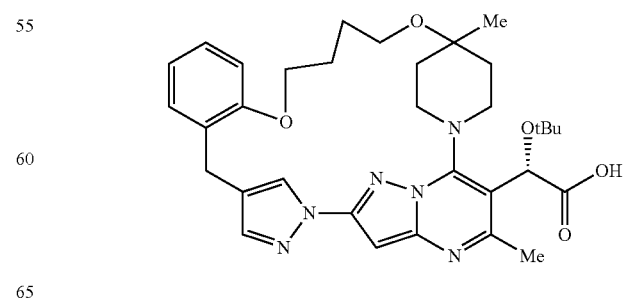
Some compounds of this invention can also be prepared by the outlined in Scheme III.

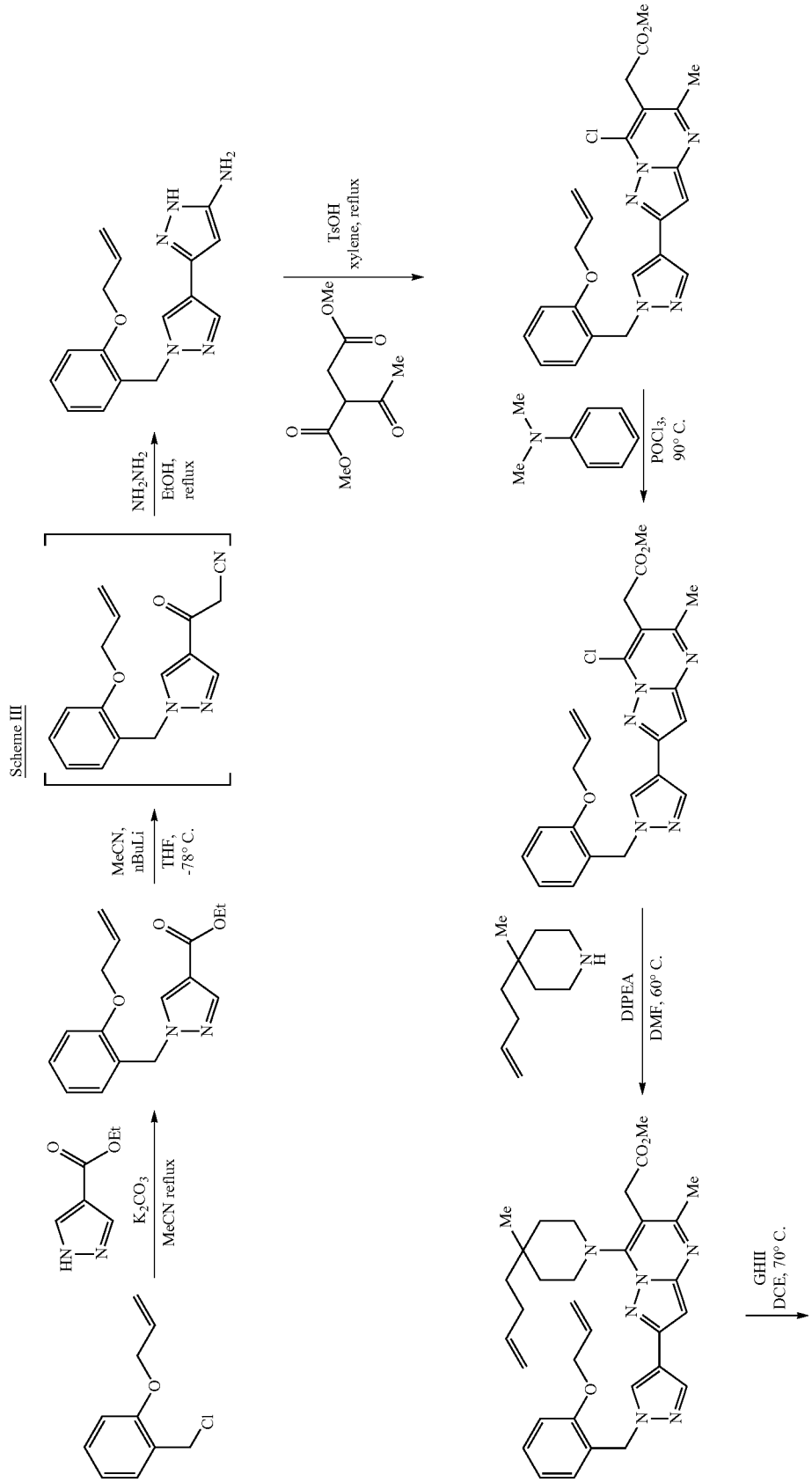

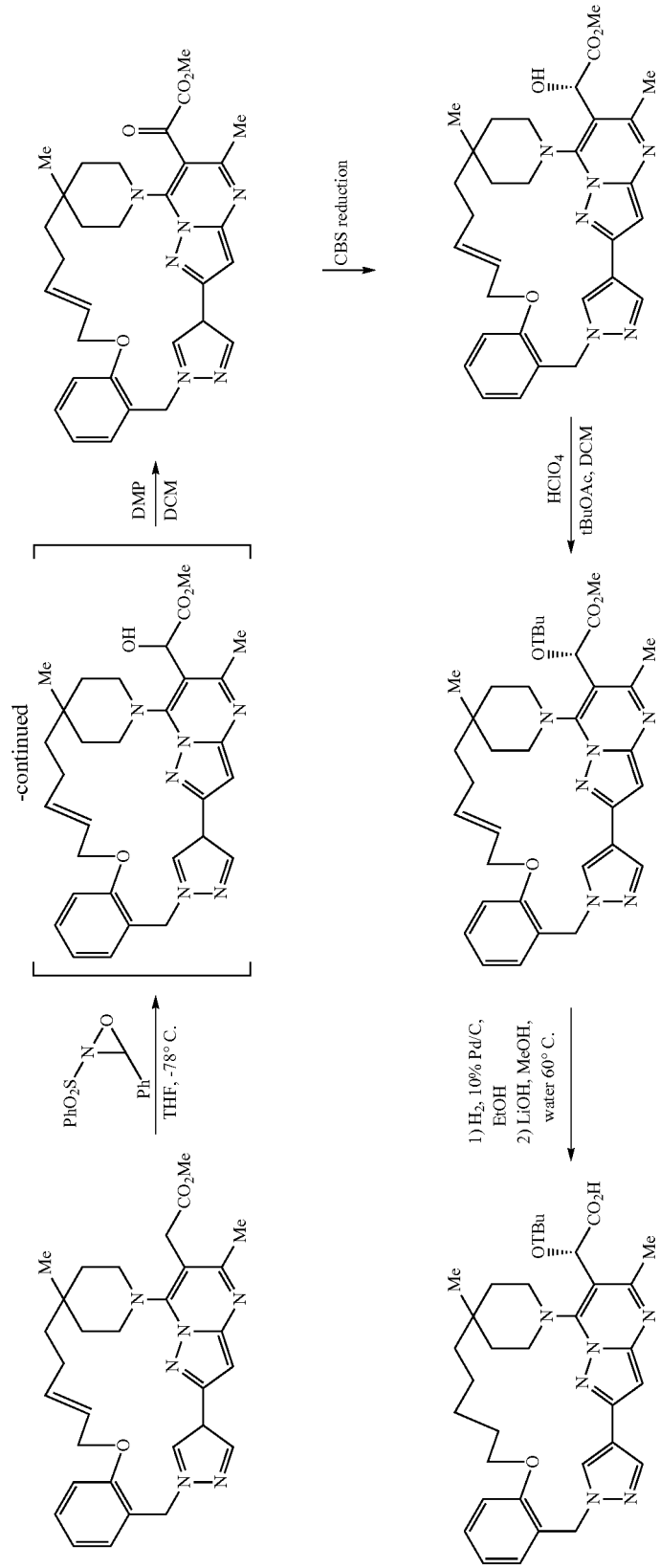

The compounds described herein were purified by the methods known to those skilled in art by normal phase column chromatography on silica gel column using appropriate solvent systems. Preparative HPLC purifications mentioned in this experimentation section were carried out by gradient elution on C18 prep-columns (5 μm) using either mobile phase A: 9:1 H₂O/acetonitrile with 10 mM NH₄OAc and mobile phase B: A: 9:1 acetonitrile/H₂O with: 10 mM NH₄OAc or mobile phase A: 95:5 H₂O/MeOH with 20 mM NH₄OAc and mobile phase B: 95:5 MeOH/H₂O with 20 mM NH₄OAc.

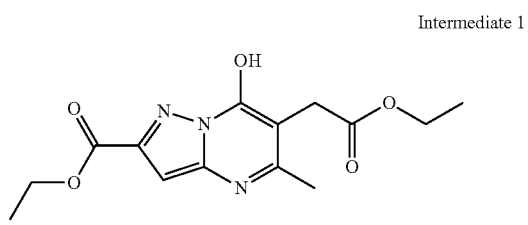 [SMILES: CCOC(=O)Cc1c(C)nc2cc(C(=O)OCC)nn2c1O]

Intermediate 1

Ethyl 6-(2-ethoxy-2-oxoethyl)-7-hydroxy-5-methyl-pyrazolo[1,5-a]pyrimidine-2-carboxylate A suspension of ethyl 5-amino-1H-pyrazole-3-carboxylate (35.5 g, 229 mmol, prepared according to WO 2008015271), diethyl 2-acetylsuccinate (51.2 mL, 275 mmol) and TsOH.H₂O (0.218 g, 1.144 mmol) in o-xylene (500 mL) was refluxed using a Dean-Stork condenser for 5 h. (Note: The suspension turned into a clear homogeneous solution and then in about 15 min a yellow solid started precipitated out of solution). Then, the reaction mixture was cooled, diluted with hexanes (250 mL), filtered, washed with hexanes and dried to afford ethyl 6-(2-ethoxy-2-oxoethyl)-7-hydroxy-5-methylpyrazolo[1,5-a]pyrimidine-2-carboxylate (53 g, 75% yield) as light yellow solid. ¹H NMR (500 MHz, DMSO-d₆) δ 12.61 (br. s., 1H), 6.49 (s, 1H), 4.34 (q, J=7.1 Hz, 2H), 4.09 (q, J=7.1 Hz, 2H), 3.57 (s, 2H), 2.34 (s, 3H), 1.33 (t, J=7.2 Hz, 3H), 1.19 (t, J=7.0 Hz, 3H). LCMS (M+1)=308.04.

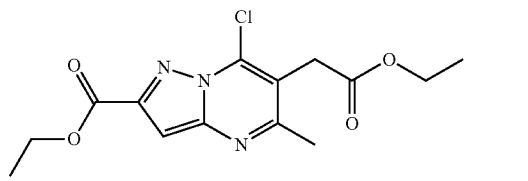

Intermediate 2

Ethyl 7-chloro-6-(2-ethoxy-2-oxoethyl)-5-methyl-pyrazolo[1,5-a]pyrimidine-2-carboxylate A mixture of ethyl 6-(2-ethoxy-2-oxoethyl)-7-hydroxy-5-methylpyrazolo[1,5-a]pyrimidine-2-carboxylate (25 g, 81 mmol), and N,N-dimethylaniline (20.6 mL, 163 mmol) in POCl₃ (100 mL) was heated at 120° C. for 3 h. Then the reaction was cooled to rt and concentrated in vacuo to half the volume. It was poured into a large quantity of ice water and stirred for 20 min. Precipitates formed and were collected by filtration. This solid was dissolved in ethyl acetate (1 L) and washed with water. The aqueous phase was back-extracted with ethyl acetate and the combined organic layers were washed with brine (200 mL), dried (Na₂SO₄), filtered and concentrated in vacuo. The crude was then triturated with EtOAc/hexane to afford ethyl 7-chloro-6-(2-ethoxy-2-oxoethyl)-5-methylpyrazolo[1,5-a]pyrimidine-2-carboxylate (22 g, 67.5 mmol, 83% yield) as light yellow solid. ¹H NMR (500 MHz, CDCl₃) δ 7.21 (s, 1H), 4.52 (q, J=7.2 Hz, 2H), 4.24 (q, J=7.2 Hz, 2H), 3.94 (s, 2H), 2.66 (s, 3H), 1.48 (t, J=7.0 Hz, 3H), 1.30 (t, J=7.2 Hz, 3H). LCMS (M+1)=326.2.

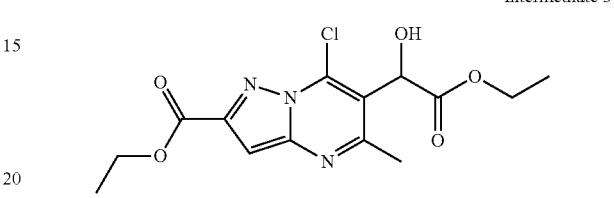

Intermediate 3

Ethyl 7-chloro-6-(2-ethoxy-1-hydroxy-2-oxoethyl)-5-methylpyrazolo[1,5-a]pyrimidine-2-carboxylate To a stirred solution of 0.9M KHMDS (40.9 mL, 36.8 mmol) in THF (100 mL) at −78° C. was added a THF (50 mL) solution of ethyl 7-chloro-6-(2-ethoxy-2-oxoethyl)-5-methylpyrazolo[1,5-a]pyrimidine-2-carboxylate (10 g, 30.7 mmol) was added over the course of 20 min. After 30 min, a THF (15 mL) solution of 3-phenyl-2-(phenylsulfonyl)-1,2-oxaziridine (10.43 g, 39.9 mmol) was added to the red reaction mixture and stirring was continued for an additional 30 min at −78° C. Then, the resulting orange reaction mixture was quenched with sat. aq. NH₄Cl (50 mL), diluted with EtOAc (200 mL), washed with water (100 mL), brine (100 mL), dried (Na₂SO₄), filtered and concentrated in vacuo to give a solid. This solid was triturated with small amount of ethyl acetate and solids were filtered, washed with hexanes and dried under high vacuum to afford ethyl 7-chloro-6-(2-ethoxy-1-hydroxy-2-oxoethyl)-5-methylpyrazolo[1,5-a]pyrimidine-2-carboxylate (5 g, 16.85 mmol, 43% yield, 90% pure) as light yellow solid. ¹H NMR (400 MHz, CDCl₃) δ 7.21 (s, 1H), 5.76 (s, 1H), 4.58-4.49 (m, 2H), 4.33 (dtt, J=10.7, 7.1, 3.7 Hz, 2H), 2.71-2.64 (s, 3H), 1.48 (t, J=7.2 Hz, 3H), 1.29-1.24 (m, 3H). LCMS (M+1)=342.16.

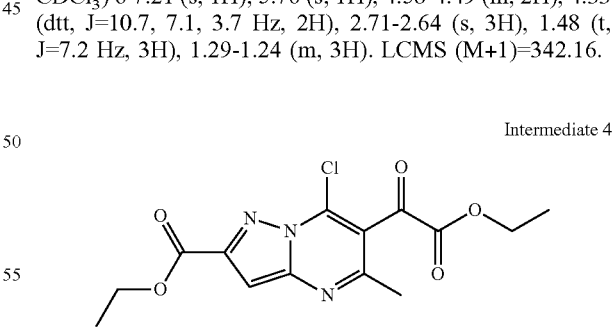

Intermediate 4

Ethyl 6-(2-ethoxy-2-oxoacetyl)-7-chloro-5-methyl-pyrazolo[1,5-a]pyrimidine-2-carboxylate To a mixture of 7-chloro-6-(2-ethoxy-1-hydroxy-2-oxoethyl)-5-methylpyrazolo[1,5-a]pyrimidine-2-carboxylate (5.9 g 13.81 mmol) in CH₂Cl₂ (100 mL) was added Dess-Martin (5.86 g, 13.81 mmol) and the resulting mixture was stirred at rt for 1 h. The reaction mixture was diluted with ethyl acetate (100 mL) and washed with sat. aq. NaHCO₃ solution (30 mL), dried (Na₂SO₄), filtered, and concentrated in vacuo. The residue was purified by silica gel chromatography (5-70% EtOAc/hexane) to afford the desired ethyl 7-chloro-6-(2-ethoxy-2-oxoacetyl)-5-methylpyrazolo[1,5-a]pyrimidine-2-carboxylate (3.5 g, 9.27 mmol, 67.1% yield) as an off-white solid. ¹H NMR (400 MHz, CDCl₃) δ 7.24 (s, 1H), 4.56-4.43 (m, 4H), 2.63 (s, 3H), 1.50-1.41 (m, 6H). LCMS (M+1)=340.13.

Intermediate 5

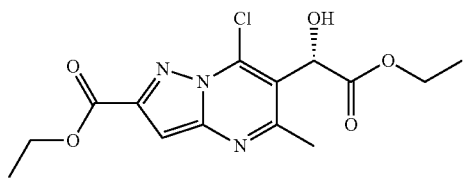

(S)-Ethyl 7-chloro-6-(2-ethoxy-1-hydroxy-2-oxo-ethyl)-5-methylpyrazolo[1,5-a]pyrimidine-2-carboxylate To a stirred yellow solution of ethyl 6-(2-ethoxy-2-oxoacetyl)-7-chloro-5-methylpyrazolo[1,5-a]pyrimidine-2-carboxylate (264 mg, 0.777 mmol) in anhydrous toluene (5 mL) was added 1.0M (R)-1-methyl-3,3-diphenylhexahydro-pyrrolo[1,2-c][1,3,2]oxazaborole/toluene (0.311 mL, 0.311 mmol). The mixture was cooled to −35° C. and a solution of 50% catechoborane/toluene (0.272 mL, 1.088 mmol) was added over the course of 10 min. After 30 min, the reaction mixture was slowly warmed to −15° C. and stirred for additional 2 h, then diluted with EtOAc (30 mL) and sat.aq. Na₂CO₃ (5 mL). The mixture was stirred vigorously for 30 min, and the organic phase was washed with sat. aq. Na₂CO₃ (2×5 mL), dried (Na₂SO₄), filtered, concentrated. The residue was purified by silica gel chromatography (5-100% EtOAc/hexane) to afford the desired (S)-ethyl 7-chloro-6-(2-ethoxy-1-hydroxy-2-oxoethyl)-5-methylpyrazolo[1,5-a]pyrimidine-2-carboxylate (200 mg, 0.585 mmol, 75% yield) as an off-white solid. ¹H NMR (400 MHz, CDCl₃) δ 7.21 (s, 1H), 5.77 (d, J=2.7 Hz, 1H), 4.53 (d, J=7.1 Hz, 2H), 4.33 (dd, J=7.1, 5.5 Hz, 2H), 3.61 (br. s., 1H), 2.68 (s, 3H), 1.50-1.46 (t, J=7.09 Hz, 3H), 1.28 (t, J=7.09 Hz, 3H). LCMS (M+1)=342.13.

Intermediate 6

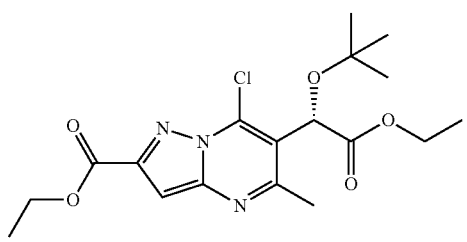

(S)-Ethyl 6-(1-(tert-butoxy)-2-ethoxy-2-oxoethyl)-7-chloro-5-methylpyrazolo[1,5-a]pyrimidine-2-carboxylate To a stirred solution of (S)-ethyl 7-chloro-6-(2-ethoxy-1-hydroxy-2-oxoethyl)-5-methylpyrazolo[1,5-a]pyrimidine-2-carboxylate (200 mg, 0.585 mmol) in CH₂Cl₂ (6 mL) and t-butyl acetate (4 mL) at rt was added perchloric acid (0.151 mL, 1.756 mmol). The reaction flask was sealed. After stirring for 3 h, the reaction mixture was diluted with CH₂Cl₂ (50 mL), carefully quenched with sat. aq. NaHCO₃ (5 mL). The organic layer was separated and washed with brine (5 mL), dried (Na₂SO₄), filtered and concentrated in vacuo to give a yellow liquid. This crude product was purified by flash column chromatography on a silica gel column using (10-50% EtOAc/Hex as eluant) to afford the desired (S)-ethyl 6-(1-(tert-butoxy)-2-ethoxy-2-oxoethyl)-7-chloro-5-methylpyrazolo[1,5-a]pyrimidine-2-carboxylate (200 mg, 0.503 mmol, 86% yield) as viscous oil. ¹H NMR (400 MHz, CDCl₃) δ 7.19 (s, 1H), 5.66 (s, 1H), 4.52 (q, J=7.2 Hz, 2H), 4.25-4.19 (m, 2H), 2.72 (s, 3H), 1.51-1.45 (m, 3H), 1.28 (s, 9H), 1.26-1.21 (m, 3H). LCMS (M+1)= 398.25.

Intermediate 7

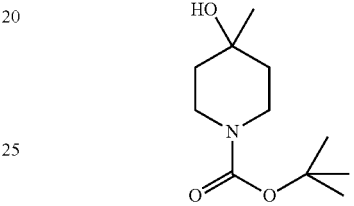

tert-Butyl 4-hydroxy-4-methylpiperidine-1-carboxylate

Under an N2 atmosphere, a 3N solution in ether of methylmagnesium bromide (1.67 mL, 5.02 mmol) was added dropwise to a cooled (−25° C.) solution of tert-butyl 4-hydroxy-4-methylpiperidine-1-carboxylate (4 g, 20.08 mmol) in ether (20 mL). The reaction mixture was allowed to warm to rt and was stirred for 2 h. It was then cooled to 0° C. and quenched by the addition of sat. aq. ammonium chloride. Another 20 mL of ether was added and the mixture was partitioned in a separatory funnel. The organic phase was set aside and the aqueous phase was extracted with another 20 mL of ether. The combined ether extracts were dried over MgSO₄, filtered and evaporated to obtain an oil, which was then purified by biotage, eluting with 0-50% EtOAc/hexane to obtain tert-butyl 4-hydroxy-4-methylpiperidine-1-carboxylate (4.30 g, 18.0 mmol, 90%) as a colorless oil. ¹H NMR (400 MHz, CDCl₃) δ 3.84-3.65 (m, 2H), 3.34-3.18 (m, 2H), 2.59-2.39 (m, 1H), 1.61-1.53 (m, 4H), 1.50-1.45 (m, 9H), 1.32-1.27 (m, 3H).

Intermediate 8

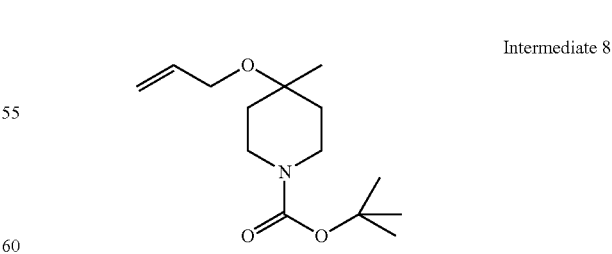

tert-Butyl 4-(allyloxy)-4-methylpiperidine-1-carboxylate

To a mixture of tert-butyl 4-hydroxy-4-methylpiperidine-1-carboxylate (4.30 g, 20.0 mmol) in DMF (50 mL) at 0° C.

was added NaH (60 wt %) (1.60 g, 39.9 mmol). The mixture was then stirred at rt for 2 h. At this time allyl bromide (8.64 mL, 100 mmol) was added slowly over the course of 5 min. The reaction mixture was stirred at rt for 3 h. It was then cooled to 0° C. and quenched with sat. aq. ammonium chloride. The reaction mixture was extracted with ether. The organic phase was dried over MgSO$_4$, filtered and concentrated to obtain a colorless oil, which was then purified by biotage, eluting with 0-25% EtOAc/hexane to isolate 3.1 g (61%) of tert-butyl 4-(allyloxy)-4-methylpiperidine-1-carboxylate as a colorless oil. $^1$H NMR (500 MHz, CDCl$_3$) δ 6.02-5.90 (m, 1H), 5.32 (dd, J=17.2, 1.7 Hz, 1H), 5.16 (dd, J=10.4, 1.4 Hz, 1H), 3.94-3.88 (m, 2H), 3.73 (br. s., 2H), 3.19 (br. s., 2H), 1.78 (d, J=13.1 Hz, 2H), 1.53-1.42 (m, 11H), 1.21 (s, 3H).

Intermediate 9

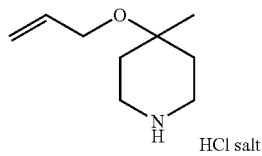

HCl salt 4-(Allyloxy)-4-methylpiperidine Hydrogen Chloride Salt

A mixture of tert-butyl 4-(allyloxy)-4-methylpiperidine-1-carboxylate (3.10 g, 12.1 mmol) and 4N HCl/dioxane (15 mL, 60.0 mmol) was stirred at rt for 3 h. It was then concentrated in vacuum to obtain 2.2 g (95%) of 4-(allyloxy)-4-methylpiperidine hydrochloride as a light brown solid. $^1$H NMR (500 MHz, CD$_3$OD) δ 6.02-5.92 (m, 1H), 5.33 (dd, J=17.2, 1.7 Hz, 1H), 5.15 (dd, J=10.6, 1.7 Hz, 1H), 3.96 (dt, J=5.1, 1.6 Hz, 2H), 3.23-3.18 (m, 4H), 2.06 (dd, J=15.3, 2.5 Hz, 2H), 1.77-1.69 (m, 2H), 1.31-1.28 (s, 3H).

Intermediate 10

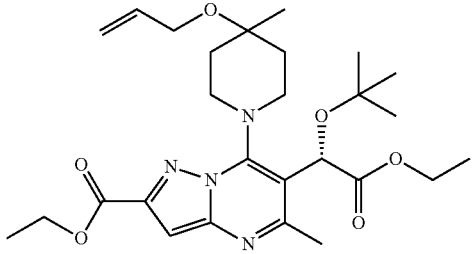

(S)-Ethyl 7-(4-(allyloxy)-4-methylpiperidin-1-yl)-6-(1-tert-butoxy-2-ethoxy-2-oxoethyl)-5-methylpyrazolo[1,5-a]pyrimidine-2-carboxylate A mixture of (S)-ethyl 6-(1-(tert-butoxy)-2-ethoxy-2-oxoethyl)-7-chloro-5-methylpyrazolo[1,5-a]pyrimidine-2-carboxylate (1 g, 2.51 mmol), 4-(allyloxy)-4-methylpiperidine hydrogen chloride salt (0.723 g, 3.77 mmol), Hunig's Base (1.317 mL, 7.54 mmol) in DMF (15 mL) was stirred at rt for 16 h. It was then concentrated and purified by biotage to isolate (S)-ethyl 7-(4-(allyloxy)-4-methylpiperidin-1-yl)-6-(1-tert-butoxy-2-ethoxy-2-oxoethyl)-5-methylpyrazolo[1,5-a]pyrimidine-2-carboxylate (1 g, 69%) as a white solid. $^1$H NMR (400 MHz, CDCl$_3$) 7.03 (s, 1H), 6.11-6.01 (m, 1H), 5.86 (br. s., 1H), 5.45 (d, J=17.8 Hz, 1H), 5.22 (dd, J=10.4, 1.6 Hz, 1H), 4.50-4.43 (m, 2H), 4.29-4.18 (m, 2H), 4.06-4.01 (m, 2H), 3.90-3.25 (br. s, 4H), 2.63 (s, 3H), 2.05-1.90 (m, 2H), 1.80-1.69 (m, 1H), 1.66-1.59 (m, 1H), 1.45 (t, J=7.1 Hz, 3H), 1.37 (s, 3H), 1.25-1.21 (m, 12H). LCMS (M+1)=517.43.

Intermediate 11

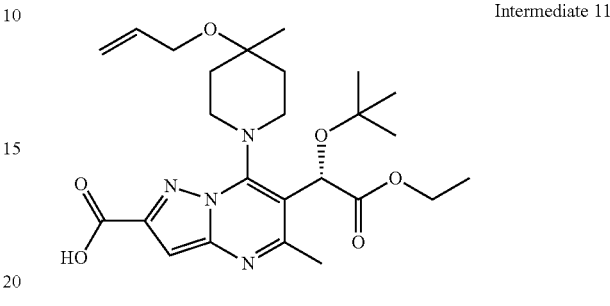

(S)-7-(4-(Allyloxy)-4-methylpiperidin-1-yl)-6-(1-tert-butoxy-2-ethoxy-2-oxoethyl)-5-methylpyrazolo[1,5-a]pyrimidine-2-carboxylic Acid A mixture of (S)-Ethyl 7-(4-(allyloxy)-4-methylpiperidin-1-yl)-6-(1-tert-butoxy-2-ethoxy-2-oxoethyl)-5-methylpyrazolo[1,5-a]pyrimidine-2-carboxylate (1 g, 1.936 mmol), NaOH (1.936 mL, 1.936 mmol) in EtOH (10 mL) was stirred at rt for 16 h. It was then concentrated and adjusted pH=4 by adding 1 N HCl. It was then extracted by EtOAc. The organic layer was dried over MgSO$_4$, filtered and concentrated to obtain (S)-7-(4-(allyloxy)-4-methylpiperidin-1-yl)-6-(1-tert-butoxy-2-ethoxy-2-oxoethyl)-5-methylpyrazolo[1,5-a]pyrimidine-2-carboxylic acid (700 mg, 68%) as a white solid. $^1$H NMR (400 MHz, CDCl$_3$) 7.20-7.13 (m, 1H), 6.17-6.00 (m, 1H), 5.99-5.82 (m, 1H), 5.76-5.58 (m, 1H), 5.46 (d, J=17.2 Hz, 2H), 5.31-5.19 (m, 2H), 4.50-3.50 (m, 2H), 4.34-4.12 (m, 2H), 4.08-3.99 (m, 2H), 2.66 (s, 3H), 2.07-1.93 (m, 3H), 1.80-1.65 (m, 1H), 1.37 (s, 2H), 1.31-1.18 (m, 12H) LCMS (M+1)=489.19.

Intermediate 12

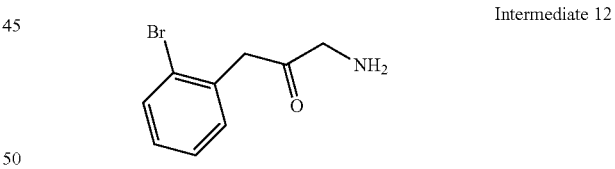

1-Amino-3-(2-bromophenyl)propan-2-one.HCl

To a −78° C. solution of 1M LiHMDS/THF (35.5 mL, 35.5 mmol) in THF (100 mL) was added dropwise THF (10 mL) solution of methyl 2-isocyanoacetate (3.18 g, 32.1 mmol) over 5 min. After 30 min, THF (20 mL) solution of 2-(2-bromophenyl)acetyl chloride (5 g, 21.41 mmol) was added over 5 min. After 1 h, the cold bath was removed and the mixture was stirred at room temp for 16 h. Water (50 mL) was then added and the mixture was extracted with ethyl acetate (100 mL), washed with brine (50 mL), dried (Na$_2$SO$_4$), filtered and concentrated. The residue was then refluxed with conc. HCl (60 mL) for 3 h. Mixture was then cooled to room temperature and the solids were collected by filtration, washed with ethyl acetate and dried under high vacuo to afford 1-amino-3-(2-bromophenyl)propan-2-one-.HCl (2.7 g, 10.21 mmol, 47.7% yield) as tan solid. $^1$H NMR (500 MHz, DMSO-$d_6$) δ 7.64 (dd, J=8.0, 0.9 Hz, 1H), 7.44-7.33 (m, 2H), 7.26 (ddd, J=8.0, 6.9, 2.2 Hz, 1H), 4.08 (s, 2H), 4.07 (s., 2H). LCMS (M+2+H)=230.1.

Intermediate 13

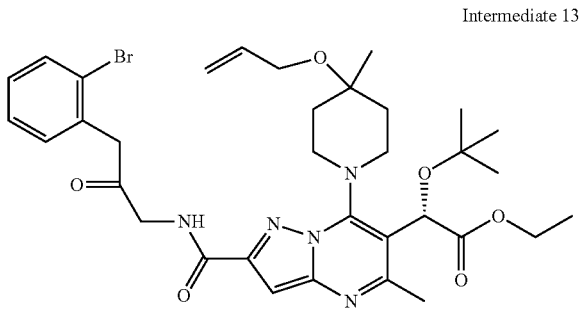 [SMILES: C=CCOC1(C)CCN(c2c([C@H](OC(C)(C)C)C(=O)OCC)c(C)nc3cc(C(=O)NCC(=O)Cc4ccccc4Br)nn23)CC1]

(S)-Ethyl 2-(7-(4-(allyloxy)-4-methylpiperidin-1-yl)-2-((3-(2-bromophenyl)-2-oxopropyl)carbamoyl)-5-methylpyrazolo[1,5-a]pyrimidin-6-yl)-2-(tert-butoxy)acetate To a solution of (S)-7-(4-(allyloxy)-4-methylpiperidin-1-yl)-6-(1-(tert-butoxy)-2-ethoxy-2-oxoethyl)-5-methylpyrazolo[1,5-a]pyrimidine-2-carboxylic acid (500 mg, 1.023 mmol) in CH$_2$Cl$_2$ (10 mL, contains cat DMF) was added oxalyl chloride (0.099 mL, 1.126 mmol) and the mixture was stirred at room temp for 1 h. The crude acid chloride was then added to a pre-stirred solution of 1-amino-3-(2-bromophenyl)propan-2-one.HCl (406 mg, 1.535 mmol) and DIEA (1.072 mL, 6.14 mmol) in CH$_2$Cl$_2$ (10.0 mL) and the resulting solution was stirred at room temperature for 4 h. Water was then added and the mixture was extracted with dichloromethane, dried (Na$_2$SO$_4$), filtered and concentrated. The crude was then purified by flash column chromatography on silica gel column using (5-70% EtOAc/Hex as eluant) to afford (S)-ethyl 2-(7-(4-(allyloxy)-4-methylpiperidin-1-yl)-2-((3-(2-bromophenyl)-2-oxopropyl)carbamoyl)-5-methylpyrazolo[1,5-a]pyrimidin-6-yl)-2-(tert-butoxy)acetate (520 mg, 0.744 mmol, 72.7% yield) as light yellow solid. $^1$H NMR (500 MHz, CDCl$_3$) δ 7.79 (br. s., 1H), 7.62 (dd, J=8.0, 1.0 Hz, 1H), 7.38-7.30 (m, 2H), 7.23-7.18 (m, 1H), 7.06 (s, 1H), 6.02 (ddt, J=17.2, 10.4, 5.2 Hz, 1H), 5.90 (br. s., 1H), 5.40-5.35 (m, 1H), 5.12 (br. s., 1H), 4.45 (dd, J=8.1, 5.0 Hz, 2H), 4.32-4.12 (m, 3H), 4.04-4.02 (m, 1H), 4.01 (s, 2H), 2.64 (s, 3H), 2.05-1.95 (m, 2H), 1.72-1.70 (m, 1H), 1.37 (s., 3H), 1.26-1.22 (m, 12H). LCMS (M+2+H)=700.5.

Intermediate 14

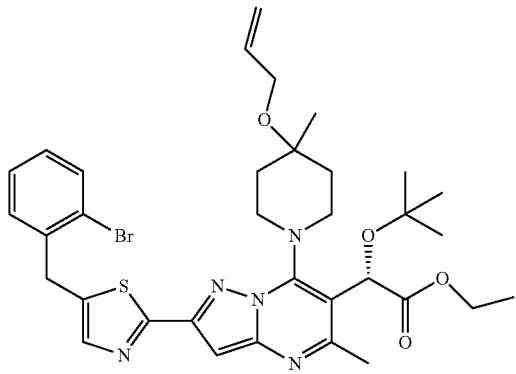

(S)-Ethyl 2-(7-(4-(allyloxy)-4-methylpiperidin-1-yl)-2-(5-(2-bromobenzyl)thiazol-2-yl)-5-methylpyrazolo[1,5-a]pyrimidin-6-yl)-2-(tert-butoxy)acetate To a solution of (S)-ethyl 2-(7-(4-(allyloxy)-4-methylpiperidin-1-yl)-2-((3-(2-bromophenyl)-2-oxopropyl)carbamoyl)-5-methylpyrazolo[1,5-a]pyrimidin-6-yl)-2-(tert-butoxy)acetate (520 mg, 0.744 mmol) in toluene was added Lawesson's Reagent (331 mg, 0.819 mmol) and stirred for 15 min at rt, and at 60° C. for 5 h. Mixture was then cooled, concentrated and the residue was purified by Biotage (0-30% EtOAc/hexane; 40 g column) to afford (S)-ethyl 2-(7-(4-(allyloxy)-4-methylpiperidin-1-yl)-2-(5-(2-bromobenzyl)thiazol-2-yl)-5-methylpyrazolo[1,5-a]pyrimidin-6-yl)-2-(tert-butoxy)acetate (320 mg, 0.459 mmol, 61.7% yield) as thick paste. $^1$H NMR (500 MHz, CDCl$_3$) δ 7.68 (s, 1H), 7.61 (d, J=7.9 Hz, 1H), 7.33-7.30 (m, 2H), 7.19-7.13 (m, 1H), 7.05 (s, 1H), 6.09-6.00 (m, 1H), 5.92 (br. s., 1H), 5.43 (d, J=17.2 Hz, 1H), 5.15 (d, J=9.5 Hz, 1H), 4.36 (s, 2H), 4.29-4.27 (m, 2H), 4.06-3.98 (m, 2H), 2.63 (s, 3H), 2.05-1.92 (m, 3H), 1.72 (br. s., 1H), 1.37 (br. s., 3H), 1.30-1.21 (m, 12H). LCMS (M+2+H)=698.5.

Intermediate 15

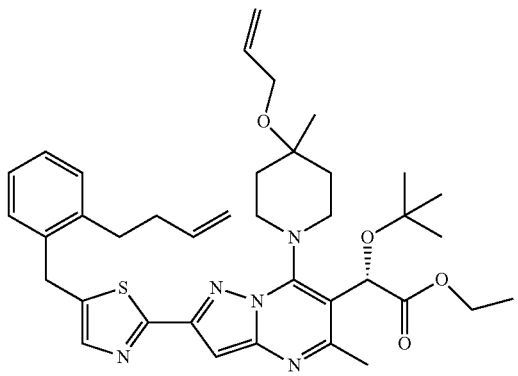

(S)-Ethyl 2-(7-(4-(allyloxy)-4-methylpiperidin-1-yl)-2-(5-(2-(but-3-en-1-yl)benzyl)thiazol-2-yl)-5-methylpyrazolo[1,5-a]pyrimidin-6-yl)-2-(tert-butoxy)acetate In a 5 mL by 1 was placed (S)-ethyl 2-(7-(4-(allyloxy)-4-methylpiperidin-1-yl)-2-(5-(2-bromobenzyl)thiazol-2-yl)-5-methylpyrazolo[1,5-a]pyrimidin-6-yl)-2-(tert-butoxy)acetate (100 mg, 0.144 mmol), but-3-en-1-ylboronic acid (43.0 mg, 0.431 mmol), Ag$_2$O (83 mg, 0.359 mmol), K$_2$CO$_3$ (79 mg, 0.574 mmol) and THF (1 mL) and the resulting mixture was degassed for 15 min. PdCl$_2$(dppf).CH$_2$Cl$_2$ adduct (11.72 mg, 0.014 mmol) was then added and the degassing was continued for another 5 min. The by 1 was then sealed and the mixture was heated at 80° C. (oil bath temp) for 72 h. The reaction mixture was then cooled, diluted with ethyl acetate, washed with water, sat. NaHCO$_3$, brine, dried (Na$_2$SO$_4$), filtered and concentrated. The residue was then purified by Biotage (0-30% EtOAc/hexane; 25 g column) to afford(S)-ethyl 2-(7-(4-(allyloxy)-4-methylpiperidin-1-yl)-2-(5-(2-(but-3-en-1-yl)benzyl)thiazol-2-yl)-5-methylpyrazolo[1,5-a]pyrimidin-6-yl)-2-(tert-butoxy)acetate (37 mg, 0.055 mmol, 38.4% yield) as colorless oil. $^1$H NMR (500 MHz, CDCl$_3$) δ 7.59-7.54 (m, 1H), 7.27-7.17 (m, 4H), 7.04 (s, 1H), 6.07-5.83 (m, 3H), 5.41 (dd, J=17.1, 1.5 Hz, 1H), 5.16-4.97 (m, 3H), 4.30-4.14 (m, 5H), 4.01 (d, J=4.7 Hz, 2H), 3.52 (d, J=5.4 Hz, 1H), 2.83-2.76 (m, 1H), 2.63 (s, 3H), 2.38-2.31 (m, 1H), 2.27-2.17 (m, 1H), 2.07-1.98 (m, 1H), 2.03-1.94 (m, 3H), 1.78-1.65 (m, 2H), 1.36 (br. s., 3H), 1.27-1.19 (m, 12H). LCMS (M+H)=672.6.

Intermediates 16 and 17

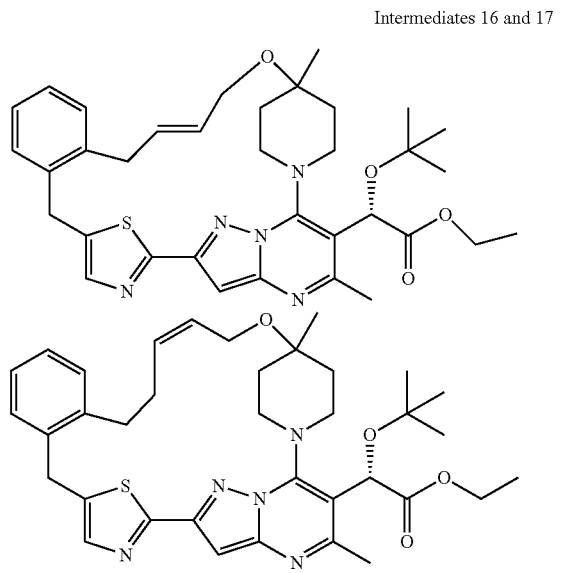

Ethyl (2S)-2-(tert-butoxy)-2-[(22E)-4,26-dimethyl-25-oxa-31-thia-1,5,7,8,11-pentaazahexacyclo[24.2.2.1$^{6,9}$.1$^{10,13}$.0$^{2,7}$.0$^{15,20}$]dotriaconta and ethyl (2S)-2-(tert-butoxy)-2-[(22Z)-4,26-dimethyl-25-oxa-31-thia-1,5,7,8,11-pentaazahexacyclo[24.2.2.1$^{6,9}$.1$^{10,13}$.0$^{2,7}$.0$^{15,20}$]dotriaconta To a solution of (S)-ethyl 2-(7-(4-(allyloxy)-4-methylpiperidin-1-yl)-2-(5-(2-(but-3-en-1-yl)benzyl)thiazol-2-yl)-5-methylpyrazolo[1,5-a]pyrimidin-6-yl)-2-(tert-butoxy)acetate (37 mg, 0.055 mmol) in DCE (15 mL) at 70° C. was added Hoveyda-Grubbs catalyst 2$^{nd}$ generation (2.415 mg, 3.85 μmol) and the mixture was heated at 70° C. for 2 h. Mixture was then cooled, concentrated and purified by prep HPLC to afford two products. first eluting, smaller ring Intermedia 16: First eluting, small ring compound; ethyl (2S)-2-(tert-butoxy)-2-[(22E)-4,26-dimethyl-25-oxa-31-thia-1,5,7,8,11-pentaazahexacyclo[24.2.2.1$^{6,9}$.1$^{10,13}$.0$^{2,7}$.0$^{15,20}$]dotriaconta-(3 mg, 4.76 μmol, 8.65% yield): $^{1}$H NMR (500 MHz, CDCl$_{3}$) δ 7.74 (s, 1H), 7.36-7.32 (m, 1H), 7.27-7.22 (m, 2H), 7.20-7.14 (m, 1H), 6.98 (s, 1H), 6.21 (s, 1H), 6.15 (dt, J=15.6, 5.9 Hz, 1H), 5.96 (dt, J=15.6, 5.7 Hz, 1H), 4.63-4.54 (m, 1H), 4.28-4.08 (m, 6H), 4.07-3.99 (m, 2H), 3.71 (d, J=4.3 Hz, 2H), 2.83 (d, J=10.9 Hz, 1H), 2.66 (s, 3H), 2.57 (d, J=10.9 Hz, 1H), 2.04-1.92 (m, 2H), 1.78-1.68 (m, 2H), 1.66-1.61 (m, 2H), 1.34 (s, 3H), 1.27 (s, 9H), 1.19 (t, J=7.2 Hz, 3H). LCMS (M+H)=630.45. Intermediate 17: Second eluting, larger ring compound; ring, ethyl (2S)-2-(tert-butoxy)-2-[(22E)-4,26-dimethyl-25-oxa-31-thia-1,5,7,8,11-pentaazahexacyclo[24.2.2.1$^{6,9}$.1$^{10,13}$.0$^{2,7}$.0$^{15,20}$]dotriaconta (7 mg, 10.87 μmol, 19.74% yield): $^{1}$H NMR (500 MHz, CDCl3) δ 7.74 (s, 1H), 7.34-7.29 (m, 1H), 7.26-7.22 (m, 2H), 7.22-7.17 (m, 1H), 7.04-7.02 (m, 1H), 6.17 (s, 1H), 5.99-5.89 (m, 2H), 4.64 (t, J=11.0 Hz, 1H), 4.28-4.09 (m, 5H), 4.08-4.00 (m, 1H), 3.95 (d, J=4.4 Hz, 2H), 3.14-3.00 (m, 2H), 2.96-2.89 (m, 1H), 2.66 (s, 3H), 2.62-2.46 (m, 2H), 2.07-2.00 (m, 2H), 0.77-1.60 (m, 2H), 1.32 (s, 3H), 1.27 (s, 9H), 1.22-1.18 (m, 3H). LCMS (M+H)=644.5

Examples 1 and 2

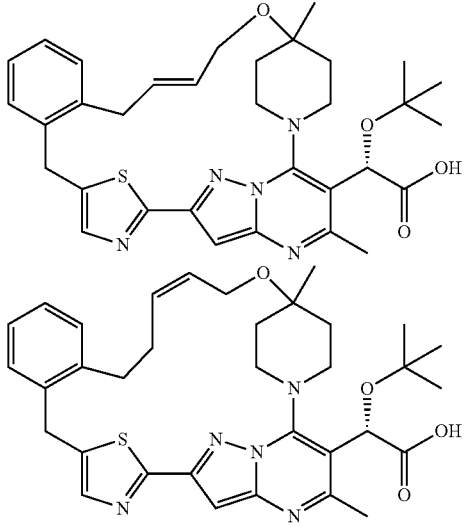

(2S)-2-(tert-Butoxy)-2-[(22E)-4,26-dimethyl-25-oxa-31-thia-1,5,7,8,11-pentaazahexacyclo[24.2.2.1$^{6,9}$.1$^{10,13}$.0$^{2,7}$.0$^{15,20}$]dotriaconta-2,4,6(32),8,10,12,15(20),16,18,22-decaen-3-yl]acetic acid and (2S)-2-(tert-Butoxy)-2-[(23Z)-4,27-dimethyl-26-oxa-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,23-decaen-3-yl]acetic acid Mixture of esters from step above were treated with 1N NaOH (0.033 mL, 0.033 mmol) in MeOH (0.7 mL) at 70° C. for 3 h. Mixture was then cooled and purified by prep HPLC to afford two compounds.

Example 1

First eluting; (2S)-2-(tert-Butoxy)-2-[(22E)-4,26-dimethyl-25-oxa-31-thia-1,5,7,8,11-pentaazahexacyclo[24.2.2.1$^{6,9}$.1$^{10,13}$.0$^{2,7}$.0$^{15,20}$]dotriaconta-2,4,6(32),8,10,12,15(20),16,18,22-decaen-3-yl]acetic acid (1.1 mg, 1.737 μmol, 36.5 yield). $^{1}$H NMR (400 MHz, CDCl3) δ 7.75 (s, 1H), 7.35-7.32 (m, 1H), 7.28-7.22 (m, 2H), 7.20-7.14 (m, 1H), 7.00 (s, 1H), 6.18-6.09 (m, 1H), 5.98-5.91 (m, 2H), 4.61 (t, J=11.0 Hz, 1H), 4.22 (d, J=3.8 Hz, 2H), 4.20-4.10 (m, 1H), 4.02 (d, J=5.5 Hz, 2H), 3.70 (d, J=5.3 Hz, 2H), 2.98 (d, J=10.3 Hz, 1H), 2.68 (s, 3H), 2.56 (d, J=10.8 Hz, 1H), 2.03-1.95 (m, 2H), 1.74-1.59 (m, 2H), 1.32 (s, 12H). LCMS (M+H)=602.5.

Example 2

Second eluting; (2S)-2-(tert-Butoxy)-2-[(23Z)-4,27-dimethyl-26-oxa-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,23-decaen-3-yl]acetic acid (2.5 mg, 3.86 μmol, 81% yield): $^{1}$H NMR (400 MHz, CDCl$_{3}$) 7.75 (s, 1H), 7.33-7.29 (m, 1H), 7.26-7.14 (m, 4H), 7.04 (s, 1H), 6.00 (br. s., 1H), 5.95-5.90 (m, 2H), 4.66 (t, J=11.3 Hz, 1H), 4.26-

4.19 (m, 2H), 4.15-3.99 (m, 1H), 3.95 (d, J=4.3 Hz, 2H), 3.13-2.99 (m, 3H), 2.67 (s, 3H), 2.62-2.41 (m, 2H), 2.06-1.92 (m, 2H), 1.76-1.61 (m, 2H), 1.32 (s, 9H), 1.28 (s, 3H). LCMS (M+H)=616.5

Intermediate 18

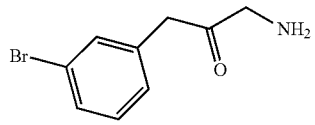

1-Amino-3-(3-bromophenyl)propan-2-one.HCl

To a −78° C. solution of 1M LiHMDS/THF (35.5 mL, 35.5 mmol) in THF (100 mL) was added dropwise THF (10 mL) solution of methyl 2-isocyanoacetate (3.18 g, 32.1 mmol) over 5 min. After 30 min, a THF (20 mL) solution of 2-(3-bromophenyl)acetyl chloride (5 g, 21.41 mmol) was added over 5 min. After 1 h, the cold bath was removed and the mixture was stirred at rom temp for 16 h. Water (25 mL) was then added and the mixture was extracted with ethyl acetate (100 mL), washed with brine (50 mL), dried ($Na_2SO_4$), filtered and concentrated. The residue was then refluxed with conc. HCl (60 mL) for 3 h. Mixture was then cooled to room temperature and the solids were collected by filtration, washed with ethyl acetate and dried under high vac to afford 1-amino-3-(3-bromophenyl)propan-2-one.HCl (3.7 g, 13.99 mmol, 65.3% yield) as tan solid. $^1$H NMR (500 MHz, DMSO-$d_6$) δ 7.51-7.44 (m, 2H), 7.32 (t, J=7.8 Hz, 1H), 7.24 (d, J=7.7 Hz, 1H), 4.03 (s, 2H), 3.94 (s, 2H). LCMS (M+2+H)=230.1.

Intermediate 19

(S)-Ethyl 2-(7-(4-(allyloxy)-4-methylpiperidin-1-yl)-2-((3-(3-bromophenyl)-2-oxopropyl)carbamoyl)-5-methylpyrazolo[1,5-c]pyrimidin-6-yl)-2-(tert-butoxy)acetate To a solution of (S)-7-(4-(allyloxy)-4-methylpiperidin-1-yl)-6-(1-(tert-butoxy)-2-ethoxy-2-oxoethyl)-5-methylpyrazolo[1,5-a]pyrimidine-2-carboxylic acid (520 mg, 1.064 mmol) in $CH_2Cl_2$ (10 mL, contains cat. DMF) was added oxalyl chloride (0.585 mL, 1.171 mmol) and the mixture was stirred at room temp for 1 h. The crude acid chloride was then added to a pre-stirred solution of 1-amino-3-(3-bromophenyl)propan-2-one.HCl (422 mg, 1.596 mmol) and DIEA (1.115 mL, 6.39 mmol) in $CH_2Cl_2$ (10.00 mL) and the resulting solution was stirred at room temperature for 4 h. Water was then added and the mixture was extracted with dichloromethane, dried ($Na_2SO_4$), filtered and concentrated. The crude was then purified by flash column chromatography on silica gel column using (5-70% EtOAc/Hex as eluant) to afford (S)-ethyl 2-(7-(4-(allyloxy)-4-methylpiperidin-1-yl)-2-((3-(3-bromophenyl)-2-oxopropyl)carbamoyl)-5-methylpyrazolo[1,5-a]pyrimidin-6-yl)-2-(tert-butoxy)acetate (600 mg, 0.859 mmol, 81% yield) as light yellow solid. $^1$H NMR (500 MHz, $CDCl_3$) δ 7.75 (br. s., 1H), 7.48-7.43 (m, 2H), 7.28-7.19 (m, 2H), 7.06 (s, 1H), 6.03 (ddt, J=17.1, 10.4, 5.2 Hz, 1H), 5.90 (br. s., 1H), 5.38 (dq, J=17.2, 1.7 Hz, 1H), 5.11 (br. s., 1H), 4.45-4.39 (m, 2H), 4.30-4.15 (m, 3H), 4.06-4.00 (m, 2H), 3.82 (s, 2H), 2.64 (s, 3H), 2.05-1.99 (m, 2H), 1.73 (br. s., 1H), 1.39 (br. s., 3H), 1.27-1.19 (m, 12H). LCMS (M+2+H)=700.5.

Intermediate 20

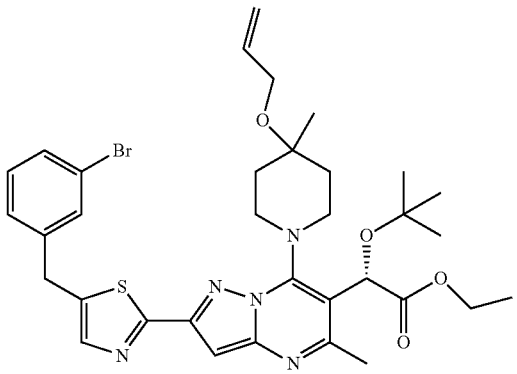

(S)-Ethyl 2-(7-(4-(allyloxy)-4-methylpiperidin-1-yl)-2-(5-(3-bromobenzyl)thiazol-2-yl)-5-methylpyrazolo[1,5-a]pyrimidin-6-yl)-2-(tert-butoxy)acetate To a solution of (S)-ethyl 2-(7-(4-(allyloxy)-4-methylpiperidin-1-yl)-2-((3-(3-bromophenyl)-2-oxopropyl)carbamoyl)-5-methylpyrazolo[1,5-a]pyrimidin-6-yl)-2-(tert-butoxy)acetate (400 mg, 0.573 mmol) in toluene was added Lawesson's Reagent (255 mg, 0.630 mmol) and stir for 15 min at rt, and 60° C. for 5 h. Mixture was then cooled, concentrated and the residue was purified by Biotage (0-30% EtOAc/hexane; 40 g column) to afford (S)-ethyl 2-(7-(4-(allyloxy)-4-methylpiperidin-1-yl)-2-(5-(3-bromobenzyl)thiazol-2-yl)-5-methylpyrazolo[1,5-a]pyrimidin-6-yl)-2-(tert-butoxy)acetate (250 mg, 0.359 mmol, 62.7% yield) as thick paste. $^1$H NMR (400 MHz, $CDCl_3$) δ 7.68 (s, 1H), 7.46-7.44 (m, 1H), 7.43-7.38 (m, 1H), 7.24-7.21 (m, 2H), 7.06 (s, 1H), 6.03 (ddt, J=17.1, 10.4, 5.2 Hz, 1H), 5.91 (br. s., 1H), 5.41 (dd, J=17.1, 1.5 Hz, 1H), 5.12 (d, J=8.8 Hz, 1H), 4.31-4.11 (m, 5H), 4.02 (d, J=5.0 Hz, 2H), 2.63 (s, 3H), 2.07-1.89 (m, 3H), 1.79-1.65 (m, 1H), 1.37 (br. s., 3H), 1.27-1.18 (m, 12H). LCMS (M+2+H)=698.5.

Intermediate 21

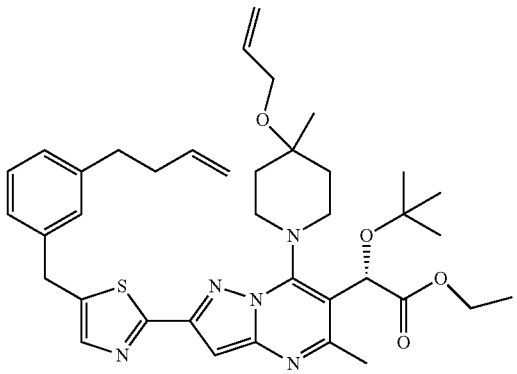

(S)-Ethyl 2-(7-(4-(allyloxy)-4-methylpiperidin-1-yl)-2-(5-(3-(but-3-en-1-yl)benzyl)thiazol-2-yl)-5-methylpyrazolo[1,5-a]pyrimidin-6-yl)-2-(tert-butoxy)acetate A 5 mL microwave by 1 was changed with (S)-ethyl 24744-(allyloxy)-4-methylpiperidin-1-yl)-2-(5-(3-bromobenzyl)thiazol-2-yl)-5-methylpyrazolo[1,5-a]pyrimidin-6-yl)-2-(tert-butoxy)acetate (150 mg, 0.215 mmol), but-3-en-1-ylboronic acid (64.5 mg, 0.646 mmol), $Ag_2O$ (125 mg, 0.538 mmol), $K_2CO_3$ (119 mg, 0.861 mmol) and THF (3 mL) and the resulting mixture was degassed for 15 min. $PdCl_2(dppf)\cdot CH_2Cl_2$ adduct (17.58 mg, 0.022 mmol) was then added and the degassing was continued for another 5 min. The by 1 was then sealed and the mixture was heated at 80° C. (oil bath temp) for 18 h. The reaction mixture was then cooled, diluted with ethyl acetate, washed with water, sat. $NaHCO_3$, brine, dried ($Na_2SO_4$), filtered and concentrated. The residue was then purified by Biotage (0-30% EtOAc/hexane; 25 g column) to afford(S)-ethyl 2-(7-(4-(allyloxy)-4-methylpiperidin-1-yl)-2-(5-(3-(but-3-en-1-yl)benzyl)thiazol-2-yl)-5-methylpyrazolo[1,5-a]pyrimidin-6-yl)-2-(tert-butoxy)acetate (20 mg, 0.030 mmol, 13.83% yield) as thick paste. $^1H$ NMR (500 MHz, $CDCl_3$) δ 7.68-7.64 (m, 1H), 7.28-7.25 (m, 1H), 7.16-7.09 (m, 3H), 7.05 (s, 1H), 6.07-5.84 (m, 4H), 5.41 (dd, J=17.2, 1.6 Hz, 1H), 5.16-4.97 (m, 4H), 4.29-4.14 (m, 6H), 4.01 (d, J=5.0 Hz, 2H), 2.74-2.69 (m, 2H), 2.63 (s, 3H), 2.43-2.34 (m, 2H), 2.08-1.90 (m, 3H), 1.71 (br. s., 1H), 1.37 (d, J=2.8 Hz, 3H), 1.27-1.20 (m, 12H). LCMS (M+H)=672.5.

Intermediate 22

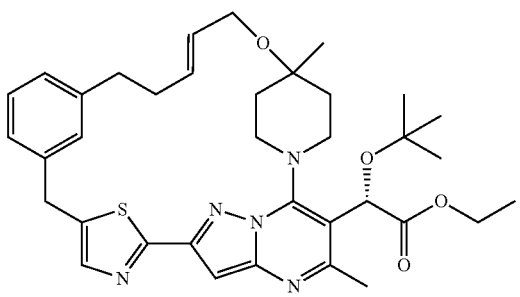

Ethyl (2S)-2-(tert-butoxy)-2-[(22E)-4,26-dimethyl-25-oxa-32-thia-1,5,7,8,11-pentaazahexacyclo[24.2.2.1$^{6,9}$.1$^{10,13}$.1$^{15,19}$.0$^{2,7}$]tritriaconta-2,4,6(33),8,10,12,15(31),16,18,22-decaen-3-yl]acetate To a solution of (S)-ethyl 2-(7-(4-(allyloxy)-4-methylpiperidin-1-yl)-2-(5-(3-(but-3-en-1-yl)benzyl)thiazol-2-yl)-5-methylpyrazolo[1,5-a]pyrimidin-6-yl)-2-(tert-butoxy)acetate (15 mg, 0.022 mmol) in DCE (5 mL) at 70° C. was added Hoveyda-Grubbs catalyst $2^{nd}$ generation (0.979 mg, 1.563 μmol) and the mixture was heated at 70° C. for 2 h. Mixture was then cooled, concentrated and purified by prep HPLC to afford desired product (3 mg, 4.66 μmol, 20.87% yield) as thick paste contaminated with some impurities. Used as is in the next step without further purification. $^1H$ NMR (500 MHz, $CDCl_3$) δ 7.76-7.75 (m, 1H), 7.27-7.23 (m, 1H), 7.14-7.05 (m, 3H), 7.04 (s, 1H), 6.03 (s, 1H), 5.72-5.55 (m, 3H), 4.45-4.38 (m, 1H), 4.28-4.18 (m, 4H), 4.17-4.09 (m, 2H), 3.89 (td, J=11.9, 2.4 Hz, 1H), 3.83 (d, J=6.3 Hz, 2H), 3.04 (d, J=11.3 Hz, 1H), 2.94 (ddd, J=13.9, 7.1, 3.5 Hz, 1H), 2.74-2.66 (m, 2H), 2.64 (s, 3H), 2.61-2.53 (m, 1H), 2.04 (dd, J=14.0, 2.4 Hz, 1H), 1.86 (dd, J=13.6, 2.5 Hz, 1H), 1.74 (td, J=12.8, 4.4 Hz, 1H), 1.27 (s, 3H), 1.25 (s, 9H), 1.20 (t, J=7.2 Hz, 3H). LCMS (M+H)=644.5.

Example 3

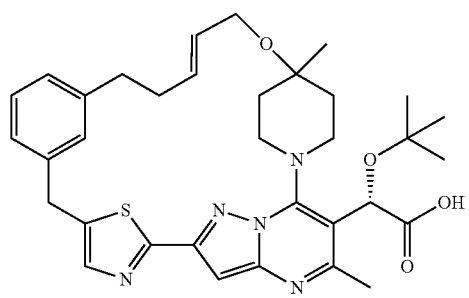 [SMILES: Cc1nc2cc3nn2c(c1[C@H](OC(C)(C)C)C(=O)O)N1CCC(C)(CC1)OC/C=C/CCc1cccc(c1)Cc1cnc-3s1]

(2S)-2-(tert-Butoxy)-2-[(22E)-4,26-dimethyl-25-oxa-32-thia-1,5,7,8,11-pentaazahexacyclo[24.2.2.1$^{6,9}$.1$^{10,13}$.1$^{15,19}$.0$^{2,7}$]tritriaconta-2,4,6(33),8,10,12,15(31),16,18,22-decaen-3-yl]acetic acid To a solution of ethyl (2S)-tert-butoxy((22E)-4,26-dimethyl-25-oxa-32-thia-1,5,7,8,11-pentaazahexacyclo[24.2.2.1~6,9~.1~10,13~.1~15,19~.0~2,7]tritriaconta-2,4,6(33),8,10,12,15(31),16,18,22-decaen-3-yl)acetate (3 mg, 4.66 μmol) in MeOH (1 mL) was added 1N NaOH (0.023 mL, 0.023 mmol) and the mixture was heated at 70° C. for 3 h. Mixture was then colled and purified by prep HPLC to afford (2S)-2-(tert-butoxy)-2-[(22E)-4,26-dimethyl-25-oxa-32-thia-1,5,7,8,11-pentaazahexacyclo[24.2.2.1$^{6,9}$.1$^{10,13}$1$^{15,19}$.0$^{2,7}$]tritriaconta-2,4,6(33),8,10,12,15(31),16,18,22-decaen-3-yl]acetic acid (1.5 mg, 2.314 μmol, 49.7% yield) as white solid. $^1H$ NMR (500 MHz, $CDCl_3$) δ 7.75 (s, 1H), 7.28 (s, 1H), 7.25 (t, J=7.5 Hz, 1H), 7.12-7.01 (m, 3H), 5.90 (br. s., 1H), 5.71-5.61 (m, 1H), 5.61-5.53 (m, 1H), 4.43 (t, J=11.8 Hz, 1H), 4.20 (s, 2H), 3.94-3.82 (m, 3H), 3.26 (br. s., 1H), 3.02-2.88 (m, 1H), 2.73-2.56 (m, 7H), 2.12-2.02 (m, 2H), 1.82-1.65 (m, 3H), 1.28 (s, 3H), 1.25 (s, 9H). LCMS (M+H)=616.4.

Example 4

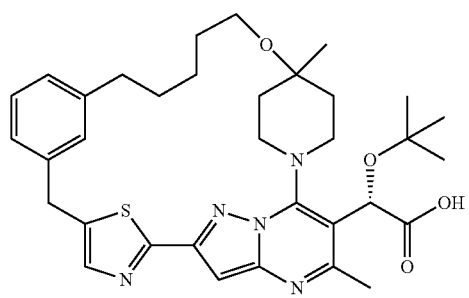 [SMILES: Cc1nc2cc3nn2c(c1[C@H](OC(C)(C)C)C(=O)O)N1CCC(C)(CC1)OCCCCCc1cccc(c1)Cc1cnc-3s1]

(2S)-2-(tert-Butoxy)-2-{4,26-dimethyl-25-oxa-32-thia-1,5,7,8,11-pentaazahexacyclo[24.2.2.1$^{6,9}$.1$^{10,13}$.1$^{15,19}$.0$^{2,7}$]tritriaconta-2,4,6(33),8,10,12,15(31),16,18-nonaen-3-yl}acetic acid To a mixture of (2S)-tert-butoxy((22E)-4,26-dimethyl-25-oxa-32-thia-1,5,7,8,11-pentaazahexacyclo

[24.2.2.1⁶,⁹.1¹⁰,¹³.1¹⁵,¹⁹.0²,⁷]tritriaconta-2,4,6(33),8,10,12, 15(31),16,18,22-decaen-3-yl)acetic acid (20 mg, 0.032 mmol) in MeOH (2 mL) was added 10% Pd/C (3.46 mg, 3.25 µmol) and the mixture was stirred under balloon hydrogen atmosphere for 5 h. Mixture was then filtered and purified by prep HPLC to afford (2S)-2-(tert-butoxy)-2-{4, 26-dimethyl-25-oxa-32-thia-1,5,7,8,11-pentaazahexacyclo [24.2.2.1⁶,⁹.1¹⁰,¹³.1¹⁵,¹⁹.0²,⁷]tritriaconta-2,4,6(33),8,10,12, 15(31),16,18-nonaen-3-yl}acetic acid (9 mg, 0.014 mmol, 42.6% yield) as off-white solid. ¹H NMR (400 MHz, CDCl₃) 7.88 (s, 1H), 7.29-7.24 (m, 2H), 7.12 (d, J=7.3 Hz, 3H), 5.88 (br. s., 1H), 4.36-4.15 (m, 4H), 3.88-3.77 (m, 1H), 3.44-3.23 (m, 4H), 2.87-2.76 (m, 2H), 2.73-2.62 (m, 3H), 2.06 (d, J=13.1 Hz, 4H), 1.94-1.78 (m, 3H), 1.71-1.48 (m, 4H), 1.40 (td, J=11.5, 5.9 Hz, 1H), 1.32-1.26 (m, 14H), 1.25 (s, 3H). LCMS (M+H)=618.4.

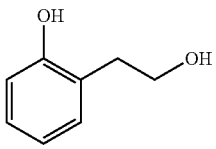

Intermediate 23

2-(2-Hydroxyethyl)phenol

To a cold (0° C.) solution of 2-(2-hydroxyphenyl)acetic acid (10 g, 65.7 mmol) in THF (150 mL) was added Et₃N (10.08 mL, 72.3 mmol) followed by ethyl chloroformate (6.31 mL, 65.7 mmol) dropwise. The mixture was stirred at 0° C. for 1 h and then solids were filtered and the filterate was added to a cooled (0° C.) solution of NaBH₄ (3.73 g, 99 mmol) in 50% aqueous THF. The mixture was stirred at 0° C. for 1 h and then at room temp for 2 h. The solvent was removed in vacuo and the residue was digested in water (200 mL) and ether (500 mL). The ether layer was separated, washed with 2M Na₂CO₃, water, 1M citric acid and water, dried (Na₂SO₄), filtered and concentrated to afford 2-(2-hydroxyethyl)phenol (7 g, 50.7 mmol, 77% yield) as colorless oil, which was used in the next step without purification. ¹H NMR (500 MHz, CDCl₃) δ 7.17 (td, J=7.7, 1.7 Hz, 1H), 7.09 (dd, J=7.5, 1.5 Hz, 1H), 6.92 (dd, J=8.0, 1.0 Hz, 1H), 6.88 (td, J=7.4, 1.3 Hz, 1H), 3.98 (dd, J=5.8, 5.0 Hz, 2H), 2.94-2.88 (m, 2H).

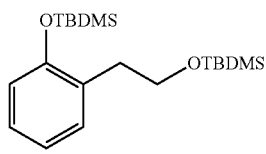

Intermediate 24

Tert-Butyl(2-(2-((tert-butyldimethylsilyl)oxy)ethyl) phenoxy)dimethylsilane

To a solution of 2-(2-hydroxyethyl)phenol (6 g, 43.4 mmol) in DMF (150 mL) at 0° C. was added imidazole (8.87 g, 130 mmol) followed by TBDMS-Cl (19.64 g, 130 mmol) and the resulting mixture was stirred at room temp for 72 h. Water (50 mL) was then added and the mixture was extracted with ether (2×200 mL). Ether layer was then washed with brine (50 mL), dried (Na₂SO₄), filtered and concentrated. The residue was purified by Biotage (0-10% EtOAc/hexane; 300 g column) to afford tert-butyl(2-(2-((tert-butyldimethylsilyl)oxy)ethyl)phenoxy)dimethylsilane (10.4 g, 28.4 mmol, 65.3% yield) as colorless oil. ¹H NMR (500 MHz, CDCl₃) δ 7.19 (d, J=1.7 Hz, 1H), 6.89 (d, J=1.3 Hz, 1H), 6.80 (dd, J=8.0, 1.1 Hz, 1H), 3.81 (t, J=7.3 Hz, 2H), 2.87 (t, J=7.3 Hz, 2H), 1.06 (s, 9H), 0.90 (s, 9H), 0.28 (s, 6H), 0.02 (s, 6H).

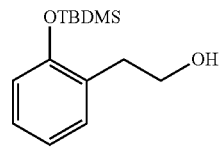

Intermediate 25

2-(2-((tert-Butyldimethylsilyl)oxy)phenyl)ethanol

To a solution of tert-butyl(2-(2-((tert-butyldimethylsilyl) oxy)ethyl)phenoxy)dimethylsilane (8.87 g, 24.19 mmol) in ethanol (100 mL) was added PPTS (0.608 g, 2.419 mmol) and the mixture was heated at 50° C. for 1 h. The solvents were then removed and the residue was purified by flash chromatography (5-30% EtOAc/hexane) to afford 2-(2-((tert-butyldimethylsilyl)oxy)phenyl)ethanol (4.4 g, 17.43 mmol, 72.1% yield) as colorless oil. ¹H NMR (500 MHz, CDCl₃) 7.20 (dd, J=7.4, 1.6 Hz, 1H), 7.14 (td, J=7.7, 1.7 Hz, 1H), 6.97-6.90 (m, 1H), 6.84 (dd, J=8.1, 1.0 Hz, 1H), 3.86 (q, J=6.5 Hz, 2H), 2.91 (t, J=6.5 Hz, 2H), 1.62 (t, J=5.8 Hz, 1H), 1.05 (s, 9H), 0.28 (s, 6H).

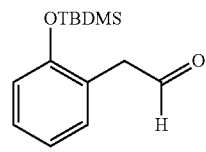

Intermediate 26

2-(2-((tert-Butyldimethylsilyl)oxy)phenyl)acetaldehyde

To a solution of 2-(2-((tert-butyldimethylsilyl)oxy)phenyl)ethanol (4.3 g, 17.03 mmol) in CH₂Cl₂ (120 mL) at 0° C. was added Dess-Martin periodinane (10.84 g, 25.6 mmol) and the mixture was stirred at 0° C. for 1 h, and then mixture was warmed to room temp and stir for additional 1 h. Mixture was then diluted with CH₂Cl₂ (100 mL) and washed with sat. NaHCO₃ (50 mL) solution, dried (Na₂SO₄), filtered and concentrated. The residue was then purified by flash chromatography (5-30% EtOAc/hexane) to afford 2-(2-((tert-butyldimethylsilyl)oxy)phenyl)acetaldehyde (3.4 g, 13.58 mmol, 80% yield) as colorless oil. ¹H NMR (500 MHz, CDCl₃) δ 9.72 (t, J=2.2 Hz, 1H), 7.22 (td, J=7.8, 1.8 Hz, 1H), 7.17 (dd, J=7.5, 1.5 Hz, 1H), 7.01-6.94 (m, 1H), 6.90 (dd, J=8.1, 0.9 Hz, 1H), 3.66 (d, J=2.2 Hz, 2H), 1.04 (s, 9H), 0.29 (s, 6H).

Intermediate 27

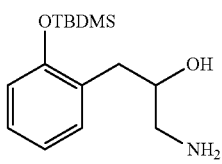

1-Amino-3-(2-((tert-butyldimethylsilypoxy)phenyl)propan-2-ol

TMS-CN (2.002 mL, 14.94 mmol) was added dropwise to a mixture of 2-(2-((tert-butyldimethylsilyl)oxy)phenyl)acetaldehyde (3.4 g, 13.58 mmol) and ZnI$_2$ (0.217 g, 0.679 mmol) in a dry roundbottom flask and the mixture was stirred at room temp for 1 h. The crude cyanohydrin ether was then dissolved in ether (5 mL) and added dropwise to a solution of 2M LAH 2M/THF (7.47 mL, 14.94 mmol) in ether (20 mL) and stirred at room temp for 1 h. Water (1 mL) was then added dropwise, followed by 15% NaOH (1 mL) and then water (2 mL). Mixture was the stirred for 15 min (granular yellow precipitate were formed). Filtration, drying (Na$_2$SO$_4$) and concentration gave a 1-amino-3-(2-((tert-butyldimethylsilyl)oxy)phenyl)propan-2-ol (2.2 g, 7.82 mmol, 57.6% yield) as yellow oil, which was used in the next step without further purification. $^1$H NMR (500 MHz, CDCl$_3$) δ 7.19 (dd, J=7.4, 1.7 Hz, 1H), 7.13 (td, J=7.7, 1.7 Hz, 1H), 6.95-6.91 (m, 1H), 6.84 (dd, J=8.1, 1.0 Hz, 1H), 3.85-3.78 (m, 1H), 2.86-2.73 (m, 3H), 2.62 (dd, J=12.9, 7.7 Hz, 1H), 1.06 (s, 9H), 0.29 (s, 6H).

Intermediates 28 and 29

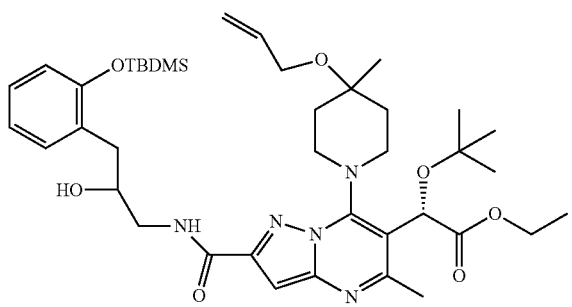

(2S)-Ethyl 2-(7-(4-(allyloxy)-4-methylpiperidin-1-yl)-2-((3-(2-((tert-butyldimethylsilypoxy)phenyl)-2-hydroxypropyl)carbamoyl)-5-methylpyrazolo[1,5-a]pyrimidin-6-yl)-2-(tert-butoxy)acetate and (2S)-ethyl 2-(7-(4-(allyloxy)-4-methylpiperidin-1-yl)-2-((2-hydroxy-3-(2-hydroxyphenyl)propyl)carbamoyl)-5-methylpyrazolo[1,5-a]pyrimidin-6-yl)-2-(tert-butoxy)acetate To a solution of (S)-7-(4-(allyloxy)-4-methylpiperidin-1-yl)-6-(1-(tert-butoxy)-2-ethoxy-2-oxoethyl)-5-methylpyrazolo[1,5-a]pyrimidine-2-carboxylic acid (2.2 g, 4.50 mmol) in CH$_2$Cl$_2$ (30 mL, contains cat. DMF) was added oxalyl chloride (2.477 mL, 4.95 mmol) and the mixture was stirred at room temp for 1 h. The crude acid chloride was then added to a pre-stirred solution of 1-amino-3-(2-((tert-butyldimethylsilyl)oxy)phenyl)propan-2-ol.HCl (1.861 g, 5.85 mmol) and DIEA (3.93 mL, 22.51 mmol) in CH$_2$Cl$_2$ (30.0 mL) and the resulting solution was stirred at room temperature for 4 h. Water was then added and the mixture was extracted with dichloromethane, dried (Na$_2$SO$_4$), filtered and concentrated. The crude was then purified by flash column chromatography on silica gel column using (5-70% EtOAc/Hex as eluant) to afford (2S)-ethyl 2-(7-(4-(allyloxy)-4-methylpiperidin-1-yl)-2-((3-(2-((tert-butyldimethylsilyl)oxy)phenyl)-2-hydroxypropyl)carbamoyl)-5-methylpyrazolo[1,5-a]pyrimidin-6-yl)-2-(tert-butoxy)acetate (1.7 g, 2.261 mmol, 50.2% yield) as white solid. $^1$H NMR (500 MHz, CDCl$_3$) δ 7.53-7.47 (m, 1H), 7.21 (dt, J=7.4, 1.6 Hz, 1H), 7.18-7.12 (m, 1H), 7.08 (d, J=1.3 Hz, 1H), 6.95 (tt, J=7.4, 1.1 Hz, 1H), 6.87-6.83 (m, 1H), 5.95 (td, J=11.1, 5.2 Hz, 2H), 5.35 (dd, J=17.2, 1.9 Hz, 1H), 5.03 (br. s., 1H), 4.29-4.16 (m, 2H), 4.13-4.07 (m, 1H), 4.03-3.94 (m, 2H), 3.72 (br. s., 2H), 3.53-3.38 (m, 1H), 3.15 (br. s., 1H), 3.09 (br. s., 1H), 2.98-2.82 (m, 3H), 2.64 (s, 3H), 2.06-1.91 (m, 2H), 1.88 (br. s., 1H), 1.69 (d, J=11.5 Hz, 1H), 1.33 (s, 3H), 1.26-1.23 (m, 12H), 1.04 (s, 9H), 0.27 (s, 6H). LCMS (M+H)=753.7, and deprotected phenol (2S)-ethyl 2-(7-(4-(allyloxy)-4-methylpiperidin-1-yl)-2-((2-hydroxy-3-(2-hydroxyphenyl)propyl)carbamoyl)-5-methylpyrazolo[1,5-a]pyrimidin-6-yl)-2-(tert-butoxy)acetate (0.8 g, 1.254 mmol, 27.9% yield) as white solid. $^1$H NMR (500 MHz, CDCl3) δ 8.37 (br. s., 1H), 7.20-7.07 (m, 3H), 6.87 (qd, J=7.4, 6.3 Hz, 2H), 6.12-5.94 (m, 2H), 5.45-5.35 (m, 1H), 5.14 (d, J=10.4 Hz, 1H), 4.62 (br. s., 1H), 4.28-4.04 (m, 6H), 3.85-3.73 (m, 1H), 3.62 (ddd, J=14.3, 6.9, 3.4 Hz, 1H), 3.43 (d, J=6.9 Hz, 1H), 3.29 (br. s., 1H), 3.11-2.96 (m, 2H), 2.89 (dd, J=14.1, 6.1 Hz, 1H), 2.85-2.76 (m, 1H), 2.67 (s, 3H), 2.12-1.99 (m, 2H), 1.86 (br. s., 1H), 1.83-1.70 (m, 1H), 1.42 (s, 3H), 1.33-1.18 (m, 12H). LCMS (M+H)=638.7.

Intermediate 30

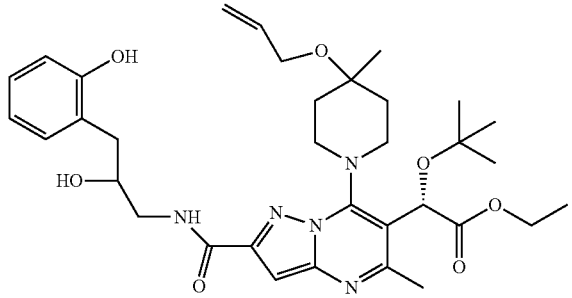

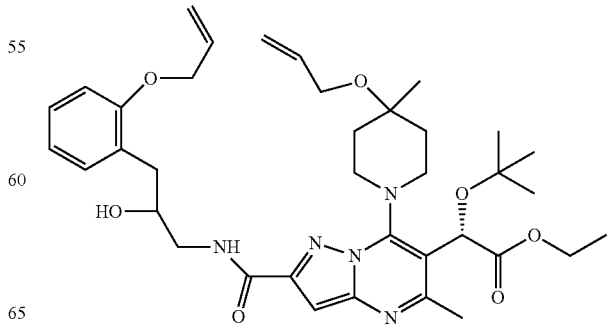

(2S)-Ethyl 2-(7-(4-(allyloxy)-4-methylpiperidin-1-yl)-2-((3-(2-(allyloxy)phenyl)-2-hydroxypropyl)carbamoyl)-5-methylpyrazolo[1,5-a]pyrimidin-6-yl)-2-(tert-butoxy)acetate To a solution of (2S)-ethyl 2-(7-(4-(allyloxy)-4-methylpiperidin-1-yl)-2-((2-hydroxy-3-(2-hydroxyphenyl)propyl)carbamoyl)-5-methylpyrazolo[1,5-a]pyrimidin-6-yl)-2-(tert-butoxy)acetate (400 mg, 0.627 mmol) in DMF (6 mL) was added $K_2CO_3$ (87 mg, 0.627 mmol) and the mixture was heated at 70° C. for 10 min. Mixture was then cooled to room temp and added 3-bromoprop-1-ene (0.064 mL, 0.753 mmol) and the resulting mixture was stirred at room temp for 16 h. Water was then added and the mixture was extracted with ether (2×25 mL), washed with brine (10 mL), dried ($Na_2SO_4$), filtered and concentrated. The residue was purified by Biotage (0-40% EtOAc/hexane; 40 g column) to afford (2S)-ethyl 2-(7-(4-(allyloxy)-4-methylpiperidin-1-yl)-2-((3-(2-(allyloxy)phenyl)-2-hydroxypropyl)carbamoyl)-5-methylpyrazolo[1,5-a]pyrimidin-6-yl)-2-(tert-butoxy)acetate (310 mg, 0.457 mmol, 72.9% yield) as white solid. $^1$H NMR (500 MHz, $CDCl_3$) δ 7.55-7.50 (m, 1H), 7.26-7.19 (m, 2H), 7.08 (d, J=1.3 Hz, 1H), 6.95 (t, J=7.4 Hz, 1H), 6.90 (d, J=8.0 Hz, 1H), 6.12-6.03 (m, 1H), 6.01-5.79 (m, 2H), 5.47-5.40 (m, 1H), 5.39-5.33 (m, 1H), 5.28 (dd, J=10.6, 1.1 Hz, 1H), 5.04 (br. s., 1H), 4.59 (dt, J=5.1, 1.5 Hz, 2H), 4.31-4.10 (m, 4H), 3.98 (d, J=4.6 Hz, 2H), 3.76 (br. s., 2H), 3.45-3.39 (m, 1H), 3.01-2.83 (m, 2H), 2.64 (s, 3H), 2.04-1.91 (m, 2H), 1.71 (br. s., 1H), 1.34 (s, 3H), 1.26-1.20 (m, 12H), 4 missing protons from piperidine. LCMS (M+H)= 678.7.

Intermediate 31

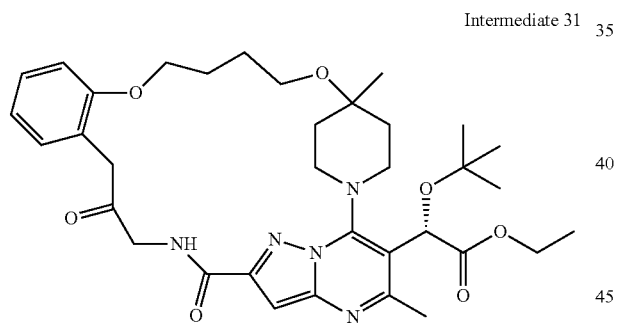

Ethyl (2S)-2-(tert-butoxy)-2-{4,27-dimethyl-10,13-dioxo-21,26-dioxa-1,5,7,8,11-pentaazapentacyclo[25.2.2.1$^{6,9}$.0$^{2,7}$.0$^{15,20}$]dotriaconta-2,4,6(32),8,15(20),16,18-heptaen-3-yl}acetate To a solution of (2S)-ethyl 2-(7-(4-(allyloxy)-4-methylpiperidin-1-yl)-2-((3-(2-(allyloxy)phenyl)-2-hydroxypropyl)carbamoyl)-5-methylpyrazolo[1,5-a]pyrimidin-6-yl)-2-(tert-butoxy)acetate (150 mg, 0.221 mmol) in DCE (30 mL) at 70° C. was added Hoveyda-Grubbs catalyst 2$^{nd}$ generation (11.09 mg, 0.018 mmol) and the mixture was heated at 70° C. for 2 h. At this point LCMS indicated consumption of starting material and presence of desired product as major (cyclized, approx 1:1 mixture of diastereomers). Mixture was then cooled and concentrated under reduced pressure. The residue was then diluted with MeOH (5 mL) and added 10% Pd/C (23.55 mg, 0.022 mmol). The mixture was then stirred under balloon hydrogen atmosphere for 1 h. At this point LCMS indicates reduction of double bond. Mixture was then filtered through a pad of celite and the pad was washed with methanol. Filterate was then concentrated, dried under high vac. The residue was then diluted with $CH_2Cl_2$ (5 mL) and added powdered 4 A° sieves (300 m g) and NMO (38.9 mg, 0.332 mmol). After stirring the mixture for 10 min, TPAP (7.78 mg, 0.022 mmol) was added and the mixture was stirred at room temp for 1 h. Mixture was then filtered through a pad of silica gel and filterate was concentrated and purified by Biotage (0-30% EtOAc/hexane; 25 g column) to afford desired product (62 mg, 0.095 mmol, 43.1% yield) as white solid. $^1$H NMR (500 MHz, $CDCl_3$) δ 7.84 (t, J=5.0 Hz, 1H), 7.32-7.27 (m, 1H), 7.25 (d, J=7.4 Hz, 1H), 7.05 (s, 1H), 6.98 (t, J=7.1 Hz, 1H), 6.87 (d, J=8.0 Hz, 1H), 6.14 (s, 1H), 4.61-4.53 (m, 1H), 4.32 (dd, J=5.0, 3.9 Hz, 2H), 4.26-4.21 (m, 1H), 4.19-4.10 (m, 2H), 4.08-3.94 (m, 2H), 3.73 (d, J=5.0 Hz, 2H), 3.52-3.40 (m, 2H), 2.98 (d, J=11.0 Hz, 1H), 2.74 (d, J=11.2 Hz, 1H), 2.67 (s, 3H), 2.07-2.02 (m, 1H), 1.93 (dd, J=13.6, 2.2 Hz, 1H), 1.88-1.73 (m, 5H), 1.68-1.63 (m, 1H), 1.31 (s, 3H), 1.28 (s, 9H), 1.22 (t, J=7.1 Hz, 3H). LCMS (M+H)=650.6.

Example 5

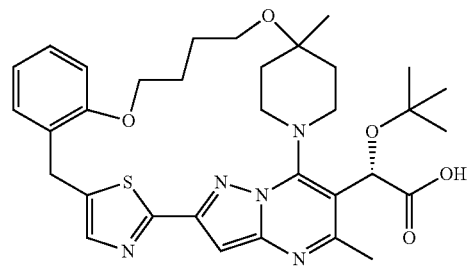

(2S)-2-(tert-Butoxy)-2-{4,27-dimethyl-21,26-dioxa-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18-nonaen-3-yl}Acetic Acid To a solution of ethyl ethyl (2S)-2-(tert-butoxy)-2-{4,27-dimethyl-10,13-dioxo-21,26-dioxa-1,5,7,8,11-pentaazapentacyclo[25.2.2.1$^{6,9}$.0$^{2,7}$.0$^{15,20}$]dotriaconta-2,4,6(32),8,15(20),16,18-heptaen-3-yl}acetate (20 mg, 0.031 mmol) in toluene (1 mL) was added Lawesson's Reagent (24.90 mg, 0.062 mmol) and the resulting mixture was heated at 60° C. for 3 h. Mixture was then cooled, concentrated and treated with 1N NaOH (0.363 mL, 0.363 mmol) in MeOH (2 mL) at 70° C. for 3 h. Mixture was then cooled and purified by prep HPLC to afford (2S)-2-(tert-butoxy)-2-{4,27-dimethyl-21,26-dioxa-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18-nonaen-3-yl}acetic acid (26 mg, 0.040 mmol, 54.9% yield) as white solid. $^1$H NMR (500 MHz, $CDCl_3$) δ 7.71 (s, 1H), 7.27 (br. s., 1H), 7.22 (t, J=7.6 Hz, 1H), 7.03 (s, 1H), 6.95-6.81 (m, 2H), 5.99 (br. s., 1H), 4.59 (t, J=11.9 Hz, 1H), 4.28-4.18 (m, 2H), 4.16 (br. s., 2H), 4.06-3.93 (m, 1H), 3.52 (d, J=5.0 Hz, 2H), 3.18 (br. s., 1H), 2.65 (br. s., 4H), 2.29 (br. s., 1H), 2.22-2.07 (m, 3H), 1.98-1.81 (m, 2H), 1.81-1.70 (m, 1H), 1.69-1.53 (m, 1H), 1.31 (br. s., 12H). LCMS (M+H)=620.5.

Intermediate 32

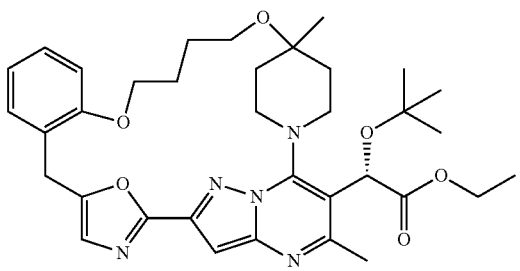

Ethyl (2S)-2-(tert-butoxy)-2-{4,27-dimethyl-21,26, 32-trioxa-1,5,7,8,11-pentaazahexacyclo [25.2.2.1$^{6,9}$.1$^{10,13}$.0$^{2,7}$.0$^{15,20}$]tritriaconta-2,4,6(33),8, 10,12,15(20),16,18-nonaen-3-yl}acetate To a stirred solution of ethyl (2S)-2-(tert-butoxy)-2-{4, 27-dimethyl-10,13-dioxo-21,26-dioxa-1,5,7,8,11-pentaazapentacyclo[25.2.2.1$^{6,9}$.0$^{2,7}$.0$^{15,20}$]dotriaconta-2,4,6(32),8,15 (20),16,18-heptaen-3-yl}acetate (60 mg, 0.092 mmol), Ph3P (72.7 mg, 0.277 mmol) and TEA (0.064 mL, 0.462 mmol) in acetonitrile (2 mL) was added CCl$_4$ (0.027 mL, 0.277 mmol) and the mixture was stirred at room temp for 5 h. and then 40° C. for 16 h. Mixture was then cooled, concentrated and purified by prep HPLC to afford desired product (8 mg, 0.013 mmol, 13.71% yield) as thick paste. $^1$H NMR (500 MHz, CDCl$_3$) δ 7.26 (dd, J=8.0, 1.7 Hz, 1H), 7.21 (td, J=7.8, 1.7 Hz, 1H), 7.06 (s, 1H), 7.05 (s, 1H), 6.94-6.87 (m, 2H), 6.09 (s, 1H), 4.66-4.56 (m, 1H), 4.28-4.07 (m, 6H), 4.00-3.91 (m, 1H), 3.57-3.45 (m, 2H), 3.12-3.03 (m, 1H), 2.75 (d, J=11.7 Hz, 1H), 2.65 (s, 3H), 2.23-2.11 (m, 1H), 2.10-2.01 (m, 2H), 1.99-1.87 (m, 3H), 1.77 (td, J=13.0, 4.7 Hz, 1H), 1.68-1.62 (m, 1H), 1.32 (s, 3H), 1.27 (s, 9H), 1.22 (t, J=7.2 Hz, 3H). LCMS (M+H)=632.6.

Example 6

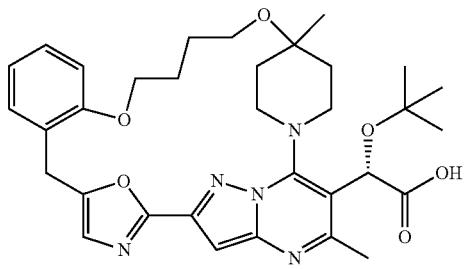 [SMILES: Cc1nc2cc3nn2c(c1[C@H](OC(C)(C)C)C(=O)O)N1CCC(C)(CC1)OCCCCOc1ccccc1Cc1cnc-3s1]

(2S)-2-(tert-Butoxy)-2-{4,27-dimethyl-21,26,32-trioxa-1,5,7,8,11-pentaazahexacyclo [25.2.2.1$^{6,9}$.1$^{10,13}$.0$^{2,7}$.0$^{15,20}$]tritriaconta-2,4,6(33),8, 10,12,15(20),16,18-nonaen-3-yl}acetic acid To a solution of ethyl (2S)-2-(tert-butoxy)-2-{4,27-dimethyl-21,26,32-trioxa-1,5,7,8,11-pentaazahexacyclo [25.2.2.1$^{6,9}$.1$^{10,13}$.0$^{2,7}$.0$^{15,20}$]tritriaconta-2,4,6(33),8,10,12, 15(20),16,18-nonaen-3-yl}acetate (8 mg, 0.013 mmol) in MeOH (0.5 mL) was added 1N NaOH (0.063 mL, 0.063 mmol) and the mixture was heated at 70° C. for 3 h. Mixture was then cooled and purified by prep HPLC to afford desired product (5.9 mg, 9.77 μmol, 77% yield) as white solid. $^1$H NMR (500 MHz, DMSO-d$_6$) δ 7.26 (d, J=7.3 Hz, 1H), 7.23 (s, 1H), 7.18 (t, J=7.6 Hz, 1H), 6.99 (d, J=8.2 Hz, 1H), 6.90-6.83 (m, 2H), 5.63 (s, 1H), 4.36 (t, J=11.9 Hz, 1H), 4.07 (s, 4H), 3.47-3.31 (m, 2H), 2.64 (d, J=11.6 Hz, 1H), 2.01-1.95 (m, 2H), 1.89 (s, 3H), 1.82-1.65 (m, 4H), 1.56-1.42 (m, 1H), 1.21 (s, 3H), 1.13 (s, 9H). LCMS (M+H)=604.6.

Intermediate 33

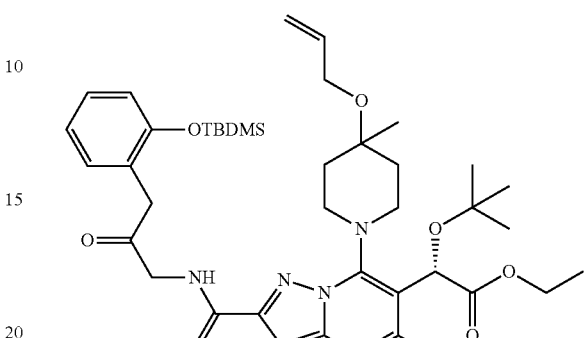

(S)-Ethyl 2-(7-(4-(allyloxy)-4-methylpiperidin-1-yl)-2-((3-(2-((tert-butyldimethylsilyl)oxy)phenyl)-2-oxopropyl)carbamoyl)-5-methylpyrazolo[1,5-a]pyrimidin-6-yl)-2-(tert-butoxy)acetate To a solution of (2S)-ethyl 2-(7-(4-(allyloxy)-4-methylpiperidin-1-yl)-2-((3-(2-((tert-butyldimethylsilyl)oxy)phenyl)-2-hydroxypropyl)carbamoyl)-5-methylpyrazolo[1,5-a]pyrimidin-6-yl)-2-(tert-butoxy)acetate (1.5 g, 1.995 mmol) in CH$_2$Cl$_2$ (20 mL) was added powdered 4 Å sieves (2 g) and NMO (0.350 g, 2.99 mmol). After stirring the mixture for 10 min, TPAP (0.070 g, 0.199 mmol) was added and the mixture was stirred at room temp for 1 h. Mixture was then filtered through a pad of silica gel. Filtrate was then concentrated and purified by Biotage (0-30% EtOAc/hexane; 80 g column) to afford (S)-ethyl 2-(7-(4-(allyloxy)-4-methylpiperidin-1-yl)-2-((3-(2-((tert-butyldimethylsilyl) oxy)phenyl)-2-oxopropyl)carbamoyl)-5-methylpyrazolo[1, 5-a]pyrimidin-6-yl)-2-(tert-butoxy)acetate (850 mg, 1.133 mmol, 56.8% yield) as white solid. 330 mg of starting material was also recovered. $^1$H NMR (500 MHz, CDCl$_3$) δ 7.81 (br. s., 1H), 7.25-7.16 (m, 2H), 7.04 (s, 1H), 6.97 (td, J=7.4, 1.1 Hz, 1H), 6.91-6.84 (m, 1H), 6.03 (ddt, J=17.2, 10.4, 5.2 Hz, 1H), 5.85 (br. s., 1H), 5.38 (dd, J=17.2, 1.7 Hz, 1H), 5.13 (br. s., 1H), 4.35 (t, J=5.0 Hz, 2H), 4.29-4.16 (m, 2H), 4.08-3.98 (m, 3H), 3.81 (s, 2H), 2.63 (s, 3H), 2.07-1.95 (m, 2H), 1.75 (br. s., 1H), 1.45 (s, 3H), 1.27-1.20 (m, 12H), 1.01 (s, 9H), 0.29 (s, 6H). 4 missing piperidine hydrogens. LCMS (M+H)=750.7.

Intermediate 34

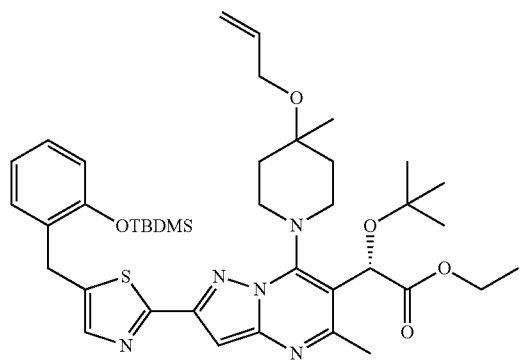

(S)-Ethyl 2-(7-(4-(allyloxy)-4-methylpiperidin-1-yl)-2-(5-(2-((tert-butyldimethylsilypoxy)benzyl)thiazol-2-yl)-5-methylpyrazolo[1,5-a]pyrimidin-6-yl)-2-(tert-butoxy)acetate To a solution of (S)-ethyl 2-(7-(4-(allyloxy)-4-methylpiperidin-1-yl)-2-((3-(2-((tert-butyldimethylsilypoxy)phenyl)-2-oxopropyl)carbamoyl)-5-methylpyrazolo[1,5-a]pyrimidin-6-yl)-2-(tert-butoxy)acetate (200 mg, 0.267 mmol) in toluene (5 mL) was added Lawesson's Reagent (162 mg, 0.400 mmol) and stir for 15 min at rt, and 60° C. for 5 h. Mixture was then cooled, concentrated and the residue was purified by Biotage (0-40% EtOAc/hexane; 40 g column) to afford (S)-ethyl 2-(7-(4-(allyloxy)-4-methylpiperidin-1-yl)-2-(5-(2-((tert-butyldimethylsilypoxy)benzyl)thiazol-2-yl)-5-methylpyrazolo[1,5-a]pyrimidin-6-yl)-2-(tert-butoxy)acetate (110 mg, 0.147 mmol, 55.1% yield) as white solid. $^1$H NMR (500 MHz, CDCl$_3$) δ 7.62 (s, 1H), 7.22-7.13 (m, 2H), 7.04 (s, 1H), 6.93 (td, J=7.5, 1.1 Hz, 1H), 6.87 (dd, J=8.0, 0.9 Hz, 1H), 6.03-5.99 (m, 1H), 5.88 (br. s., 1H), 5.41 (dd, J=17.2, 1.6 Hz, 1H), 5.14 (d, J=7.6 Hz, 1H), 4.30-4.11 (m, 5H), 4.02 (d, J=5.0 Hz, 2H), 2.63 (s, 3H), 2.04-1.90 (m, 2H), 1.73 (br. s., 1H), 1.37 (s, 3H), 1.27-1.19 (m, 12H), 1.03 (s, 9H), 0.29 (s, 6H). 4 piperidine hydrogens are missing. LCMS (M+H)=749.5.

Intermediate 35

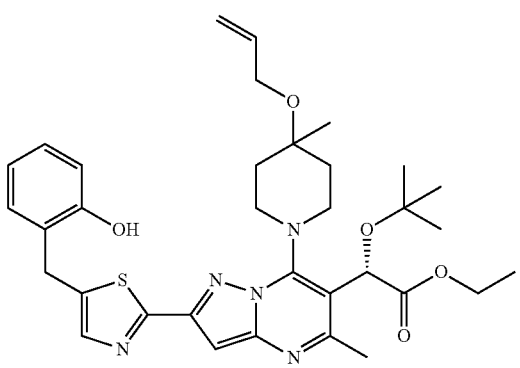

(S)-Ethyl 2-(7-(4-(allyloxy)-4-methylpiperidin-1-yl)-2-(5-(2-hydroxybenzyl)thiazol-2-yl)-5-methylpyrazolo[1,5-a]pyrimidin-6-yl)-2-(tert-butoxy)acetate To a solution of (S)-ethyl 2-(7-(4-(allyloxy)-4-methylpiperidin-1-yl)-2-(5-(2-((tert-butyldimethylsilyl)oxy)benzyl)thiazol-2-yl)-5-methylpyrazolo[1,5-a]pyrimidin-6-yl)-2-(tert-butoxy)acetate (106 mg, 0.142 mmol) in THF (3 mL) was added dropwise 1M solution of TBAF (0.156 mL, 0.156 mmol) and the resulting mixture was stirred at room temp for 1 h. At this point LCMS indicates completion of reaction. Mixture was then concentrated and the residue was purified by Biotage (5-70%, EtOAc/hexane; 25 g column) to afford (S)-ethyl 2-(7-(4-(allyloxy)-4-methylpiperidin-1-yl)-2-(5-(2-hydroxybenzyl)thiazol-2-yl)-5-methylpyrazolo[1,5-a]pyrimidin-6-yl)-2-(tert-butoxy)acetate (74 mg, 0.117 mmol, 82% yield) as white solid. $^1$H NMR (400 MHz, CDCl$_3$) o 7.69 (s, 1H), 7.22 (dd, J=7.5, 1.5 Hz, 1H), 7.16 (td, J=7.7, 1.6 Hz, 1H), 7.04 (s, 1H), 6.93 (td, J=7.5, 1.1 Hz, 1H), 6.81 (dd, J=7.9, 0.9 Hz, 1H), 6.14-6.00 (m, 1H), 5.92 (br. s., 1H), 5.44 (d, J=16.8 Hz, 1H), 5.36 (s, 1H), 5.17 (d, J=10.3 Hz, 1H), 4.30-4.12 (m, 5H), 4.02 (d, J=5.0 Hz, 2H), 2.63 (s, 3H), 2.06-1.88 (m, 3H), 1.74-1.70 (m, 1H), 1.37 (s, 3H), 1.27-1.19 (m, 12H). LCMS (M+H)=634.4.

Intermediate 36

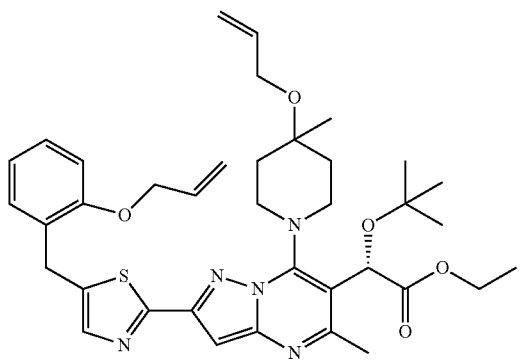

(S)-Ethyl 2-(7-(4-(allyloxy)-4-methylpiperidin-1-yl)-2-(5-(2-(allyloxy)benzyl)thiazol-2-yl)-5-methylpyrazolo[1,5-a]pyrimidin-6-yl)-2-(tert-butoxy)acetate To a solution of (S)-ethyl 2-(7-(4-(allyloxy)-4-methylpiperidin-1-yl)-2-(5-(2-hydroxybenzyl)thiazol-2-yl)-5-methylpyrazolo[1,5-a]pyrimidin-6-yl)-2-(tert-butoxy)acetate (68 mg, 0.107 mmol) in DMF (2 mL) was added K$_2$CO$_3$ (29.7 mg, 0.215 mmol) and the mixture was heated at 70° C. for 10 min. Mixture was then cooled to room temp and added 3-bromoprop-1-ene (0.018 mL, 0.215 mmol) and the resulting mixture was stirred at room temp for 16 h. Water was then added and the mixture was extracted with ether (2×25 mL), washed with brine (10 mL), dried (Na$_2$SO$_4$), filtered and concentrated. The residue was purified by Biotage (0-40% EtOAc/hexane; 25 g column) to afford (S)-ethyl 2-(7-(4-(allyloxy)-4-methylpiperidin-1-yl)-2-(5-(2-(allyloxy)benzyl)thiazol-2-yl)-5-methylpyrazolo[1,5-a]pyrimidin-6-yl)-2-(tert-butoxy)acetate (60 mg, 0.089 mmol, 83% yield) as white solid. $^1$H NMR (500 MHz, CDCl$_3$) δ 7.68-7.66 (m, 1H), 7.26-7.21 (m, 2H), 7.03 (s, 1H), 6.94 (td, J=7.4, 1.0 Hz, 1H), 6.90 (d, J=8.7 Hz, 1H), 6.15-6.00 (m, 2H), 5.89 (br. s., 1H), 5.48-5.39 (m, 2H), 5.32-5.28 (m, 1H), 5.16 (d, J=10.9 Hz, 1H), 4.61 (dt, J=5.1, 1.5 Hz, 2H), 4.30-4.12 (m, 5H), 4.03 (d, J=5.0 Hz, 2H), 2.63 (s, 3H), 2.05-1.91 (m, 2H), 1.78-1.73 (m, 1H), 1.38 (s., 3H), 1.26-1.22 (m, 12H). 4 missing four piperidine hydrogens. LCMS (M+H)=674.6.

Intermediate 37

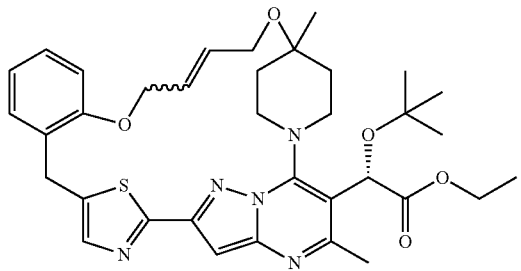

Ethyl (2S)-2-(tert-butoxy)-2-[4,27-dimethyl-21,26-dioxa-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,23-decaen-3-yl]acetate To a solution of (S)-ethyl 2-(7-(4-(allyloxy)-4-methylpiperidin-1-yl)-2-(5-(2-(allyloxy)benzyl)thiazol-2-yl)-5-methylpyrazolo[1,5-a]pyrimidin-6-yl)-2-(tert-butoxy)acetate (55 mg, 0.082 mmol) in DCE (50 mL) at 70° C. was added Hoveryda-Grubbs catalys 2$^{nd}$ generation (5.11 mg, 8.16 μmol) and the mixture was heated for 2 h. Mixture was then cooled, concentrated and purified by Biotage (0-40% EtOAc/hexane) to afford desired product (40 mg, 0.062 mmol, 76% yield) as off-white solid (Geometry and position of the double bond unknown). $^1$H NMR (500 MHz, CDCl$_3$) 7.71 (s, 1H), 7.28-7.26 (m, 1H), 7.22 (td, J=7.8, 1.7 Hz, 1H), 7.03-7.01 (m, 1H), 6.93-6.88 (m, 2H), 6.28 (dt, J=15.6, 5.0 Hz, 1H), 6.35-6.21 (m, 1H), 6.16 (s, 1H), 4.88-4.75 (m, 2H), 4.64-4.56 (m, 1H), 4.26-4.21 (m, 1H), 4.19 (s, 2H), 4.16-4.10 (m, 1H), 4.07-4.03 (m, 3H), 3.00-2.92 (m, 1H), 2.66 (s, 3H), 2.65-2.60 (m, 1H), 2.11-2.05 (m, 1H), 1.95 (dd, J=13.6, 2.4 Hz, 1H), 1.79 (td, J=13.0, 4.6 Hz, 1H), 1.69-1.62 (m, 1H), 1.36 (s, 3H), 1.29-1.27 (s, 9H), 1.21-1.19 (t, J=7.2 Hz, 3H). LCMS (M+H)=646.6.

Example 7

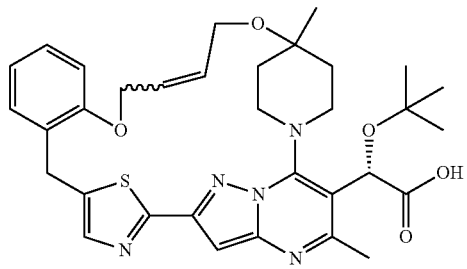 [SMILES: Cc1nc2cc3nn2c(c1[C@H](OC(C)(C)C)C(=O)O)N1CCC(C)(CC1)OCC=CCOc1ccccc1Cc1cnc-3s1]

(2S)-2-(tert-Butoxy)-2-[4,27-dimethyl-21,26-dioxa-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,23-decaen-3-yl]acetic acid To a solution of ethyl (2S)-2-(tert-butoxy)-2-[(23E)-4,27-dimethyl-21,26-dioxa-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,23-decaen-3-yl]acetate (40 mg, 0.062 mmol) in MeOH (2 mL) was added 1N NaOH (0.310 mL, 0.310 mmol) and the resulting mixture was heated at 70° C. for 3 h. Mixture was then cooled and purified by prep HPLC to desired product (24 mg, 0.039 mmol, 62.7% yield) as white solid. $^1$H NMR (500 MHz, CDCl$_3$) δ 7.72 (s, 1H), 7.27 (dd, J=7.4, 1.6 Hz, 1H), 7.22 (td, J=7.9, 1.7 Hz, 1H), 7.04 (s, 1H), 6.94-6.88 (m, 2H), 6.33-6.21 (m, 2H), 6.01 (br. s., 1H), 4.86-4.74 (m, 2H), 4.62 (t, J=11.2 Hz, 1H), 4.19 (s, 2H), 4.09-4.02 (m, 3H), 3.11 (d, J=10.6 Hz, 1H), 2.66 (s, 3H), 2.63 (d, J=11.7 Hz, 1H), 2.09-2.04 (m, 1H), 1.96 (dd, J=13.8, 2.1 Hz, 1H), 1.75 (td, J=13.2, 4.6 Hz, 1H), 1.65 (td, J=13.3, 4.3 Hz, 1H), 1.34 (s, 3H), 1.31 (s, 9H). LCMS (M+H)=618.5.

Intermediate 38

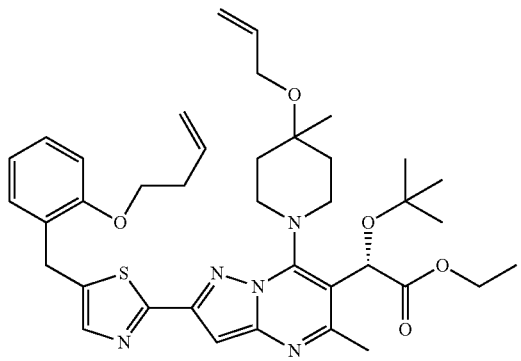

(S)-Ethyl 2-(7-(4-(allyloxy)-4-methylpiperidin-1-yl)-2-(5-(2-(but-3-en-1-yloxy)benzyl)thiazol-2-yl)-5-methylpyrazolo[1,5-a]pyrimidin-6-yl)-2-(tert-butoxy)acetate To a mixture of (S)-ethyl 2-(7-(4-(allyloxy)-4-methylpiperidin-1-yl)-2-(5-(2-hydroxybenzyl)thiazol-2-yl)-5-methylpyrazolo[1,5-a]pyrimidin-6-yl)-2-(tert-butoxy)acetate (100 mg, 0.158 mmol), but-3-en-1-ol (0.036 mL, 0.473 mmol), Ph$_3$P (124 mg, 0.473 mmol) in THF (3 mL) was added DIAD (0.092 mL, 0.473 mmol) and the mixture was stirred at rt for 16 h. Water was then added and the mixture was extracted with ether (2×25 mL), dried (Na$_2$SO$_4$), filtered and concentrated. The residue was then purified by Biotage (0-40% EtOAc/hexane) to afford (S)-ethyl 2-(7-(4-(allyloxy)-4-methylpiperidin-1-yl)-2-(5-(2-(but-3-en-1-yloxy)benzyl)thiazol-2-yl)-5-methylpyrazolo[1,5-a]pyrimidin-6-yl)-2-(tert-butoxy)acetate (90 mg, 0.131 mmol, 83% yield) as thick paste. $^1$H NMR (500 MHz, CDCl$_3$) δ 7.66 (s, 1H), 7.27-7.19 (m, 2H), 7.03 (s, 1H), 6.93 (td, J=7.4, 1.0 Hz, 1H), 6.89 (d, J=8.2 Hz, 1H), 6.34 (br. s., 1H), 6.08-6.00 (m, 1H), 5.97-5.88 (m, 2H), 5.43 (d, J=17.0 Hz, 1H), 5.24-5.10 (m, 3H), 5.05-4.94 (m, 2H), 4.28-4.22 (m, 1H), 4.21 (s, 2H), 4.19-4.11 (m, 2H), 4.08 (t, J=6.5 Hz, 2H), 4.03 (d, J=4.9 Hz, 2H), 2.66-2.62 (m, 3H), 2.62-2.57 (m, 2H), 2.05-1.89 (m, 3H), 1.73 (br. s., 1H), 1.38 (br. s., 3H), 1.26-1.20 (m, 12H). LCMS (M+H)=688.7.

Intermediate 39

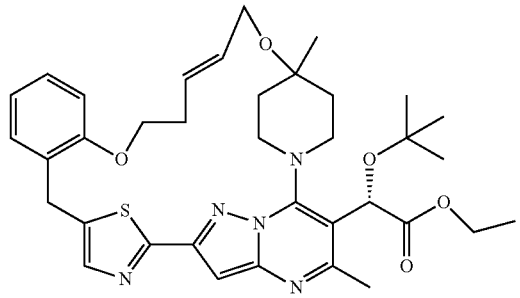

Ethyl (2S)-2-(tert-butoxy)-21(24E)-4,28-dimethyl-21,27-dioxa-33-thia-1,5,7,8,11-pentaazahexacyclo[26.2.2.1$^{6,9}$.1$^{10,13}$.0$^{2,7}$.0$^{15,20}$]tetratriaconta-2,4,6(34),8,10,12,15(20),16,18,24-decaen-3-yl 1 acetate To a solution of (S)-ethyl 2-(7-(4-(allyloxy)-4-methylpiperidin-1-yl)-2-(5-(2-(but-3-en-1-yloxy)benzyl)thiazol-2- yl)-5-methylpyrazolo[1,5-a]pyrimidin-6-yl)-2-(tert-butoxy) acetate (90 mg, 0.131 mmol) in DCE (90 mL) at 70° C. was added Hoveyda-Grubbs catalyst 2$^{nd}$ generation (8.20 mg, 0.013 mmol) and the mixture was heated for 2 h. Mixture was then cooled, concentrated and purified by Biotage (0-40% EtOAc/hexane) to afforddesired product (70 mg, 0.106 mmol, 81% yield) (position of the double bond not confirmed, contaminated with small amount of other isomer). $^1$H NMR (500 MHz, CDCl$_3$) δ 7.76 (s, 1H), 7.29-7.25 (m, 1H), 7.22-7.17 (m, 1H), 7.05 (s, 1H), 6.93-6.88 (m, 2H), 6.38-6.29 (m, 2H), 6.13 (s, 1H), 5.95-5.87 (m, 1H), 5.01 (dt, J=12.5, 6.3 Hz, 1H), 4.56 (t, J=11.2 Hz, 1H), 4.30-4.09 (m, 7H), 4.06-3.99 (m, 2H), 3.01 (d, J=10.9 Hz, 1H), 2.73-2.68 (m, 2H), 2.66 (s, 3H), 1.95 (d, J=12.1 Hz, 1H), 1.77 (td, J=13.0, 4.5 Hz, 1H), 1.70-1.63 (m, 1H), 1.32 (s, 3H), 1.34-1.27 (m, 12H). LCMS (M+H)=660.6.

Example 8

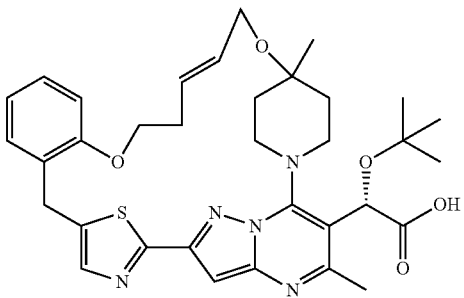 [SMILES: Cc1nc2cc3nn2c(c1[C@H](OC(C)(C)C)C(=O)O)N1CCC(C)(CC1)OC/C=C/CCOc1ccccc1Cc1cnc-3s1]

(2S)-2-(tert-Butoxy)-2-[(24E)-4,28-dimethyl-21,27-dioxa-33-thia-1,5,7,8,11-pentaazahexacyclo [26.2.2.1$^{6,9}$.1$^{10,13}$.0$^{2,7}$.0$^{15,20}$]tetratriaconta-2,4,6(34), 8,10,12,15(20),16,18,24-decaen-3-yl]acetic Acid To a solution of ethyl (2S)-2-(tert-butoxy)-2-[(24E)-4,28-dimethyl-21,27-dioxa-33-thia-1,5,7,8,11-pentaazahexacyclo[26.2.2.1$^{6,9}$.1$^{10,13}$.0$^{2,7}$.0$^{15,20}$]tetratriaconta-2,4,6(34),8, 10,12,15(20),16,18,24-decaen-3-yl]acetate (70 mg, 0.106 mmol) in MeOH (2 mL) was added 1N NaOH (0.530 mL, 0.530 mmol) and the resulting mixture was heated at 70° C. for 3 h. Mixture was then cooled and purified by prep HPLC to afford desired product (50 mg, 0.075 mmol, 70.9% yield) as white solid. $^1$H NMR (500 MHz, CDCl$_3$) δ 7.77 (s, 1H), 7.30-7.27 (m, 1H), 7.23-7.18 (m, 1H), 7.08-7.05 (m, 1H), 6.95-6.88 (m, 2H), 6.33 (dt, J=15.4, 6.2 Hz, 1H), 5.97 (br. s., 1H), 5.91 (dt, J=15.4, 6.2 Hz, 1H), 4.59 (t, J=11.1 Hz, 1H), 4.30-4.25 (m, 1H), 4.25-4.18 (m, 2H), 4.18-4.12 (m, 1H), 4.09-3.97 (m, 3H), 3.16 (d, J=10.7 Hz, 1H), 2.73-2.67 (m, 3H), 2.66 (s, 3H), 2.09-2.04 (m, 1H), 1.97 (dd, J=13.8, 2.3 Hz, 1H), 1.77-1.62 (m, 2H), 1.35-1.30 (m, 12H). LCMS (M+H)=632.6.

Example 9

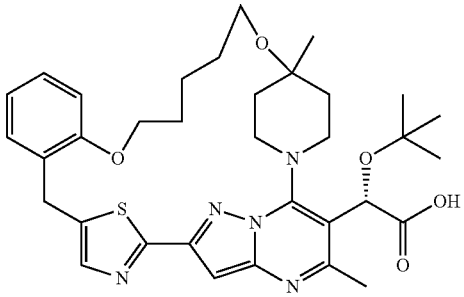 [SMILES: Cc1nc2cc3nn2c(c1[C@H](OC(C)(C)C)C(=O)O)N1CCC(C)(CC1)OCCCCCOc1ccccc1Cc1cnc-3s1]

(2S)-2-(tert-Butoxy)-2-{4,28-dimethyl-21,27-dioxa-33-thia-1,5,7,8,11-pentaazahexacyclo [26.2.2.1$^{6,9}$.1$^{10,13}$.0$^{2,7}$.0$^{15,20}$]tetratriaconta-2,4,6(34), 8,10,12,15(20),16,18-nonaen-3-yl}acetic acid To a solution of example 8 (15 mg, 0.024 mmol) in MeOH (2 mL) was added 10% Pd/C (2.53 mg, 2.374 μmol) and the mixture was stirred under balloon hydrogen atmosphere for 16 h. Mixture was then filtered and purified by prep HPLC to afford desired product (7 mg, 0.011 mmol, 46.5% yield) as white solid. $^1$H NMR (500 MHz, DMSO-d$_6$) δ 7.60 (s, 1H), 7.11 (d, J=7.0 Hz, 1H), 6.95 (t, J=7.6 Hz, 1H), 6.76 (d, J=8.2 Hz, 1H), 6.63 (t, J=7.3 Hz, 1H), 6.60 (s, 1H), 5.46 (s, 1H), 4.03 (t, J=11.3 Hz, 1H), 3.98-3.84 (m, 3H), 3.84-3.70 (m, 1H), 3.47 (t, J=10.5 Hz, 1H), 2.97 (d, J=9.2 Hz, 1H), 2.65 (s, 1H), 2.49 (s, 1H), 2.40 (d, J=11.3 Hz, 1H), 2.28 (s, 3H), 2.32-2.27 (m, 2H), 1.81-1.68 (m, 2H), 1.63-1.49 (m, 1H), 1.47-1.35 (m, 1H), 0.96 (s, 3H), 0.91 (s, 9H). 4 missing hydrogens from piperidine. LCMS (M+H)=634.6.

Intermediate 40

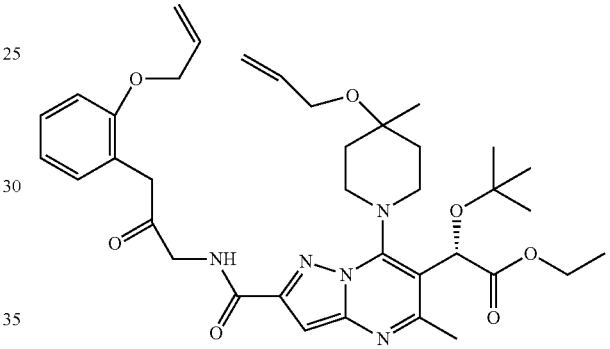

(S)-Ethyl 2-(7-(4-(allyloxy)-4-methylpiperidin-1-yl)-2-((3-(2-(allyloxy)phenyl)-2-oxopropyl)carbamoyl)-5-methylpyrazolo[1,5-a]pyrimidin-6-yl)-2-(tert-butoxy)acetate To a solution of (2S)-ethyl 2-(7-(4-(allyloxy)-4-methylpiperidin-1-yl)-2-((3-(2-(allyloxy)phenyl)-2-hydroxypropyl)carbamoyl)-5-methylpyrazolo[1,5-a]pyrimidin-6-yl)-2-(tert-butoxy)acetate (220 mg, 0.325 mmol) in CH$_2$Cl$_2$ (6 mL) was added powdered 4 A° sieves (1 g) and NMO (57.0 mg, 0.487 mmol). After stirring the mixture for 10 min, TPAP (11.41 mg, 0.032 mmol) was added and the mixture was stirred at room temp for 1 h. At this point LCMS indicaters completion of reaction. Mixture was then filtered through a pad of silica gel. Filterate was then concentrated and purified by Biotage (0-50% EtOAc/hexane; 25 g column) to afford (S)-ethyl 2-(7-(4-(allyloxy)-4-methylpiperidin-1-yl)-2-((3-(2-(allyloxy)phenyl)-2-oxopropyl)carbamoyl)-5-methylpyrazolo[1,5-a]pyrimidin-6-yl)-2-(tert-butoxy)acetate (130 mg, 0.192 mmol, 59.3% yield) as white solid. $^1$H NMR (400 MHz, CDCl$_3$) δ 7.81 (br. s., 1H), 7.32-7.26 (m, 1H), 7.23 (dd, J=7.4, 1.6 Hz, 1H), 7.07-7.02 (m, 1H), 7.00-6.94 (m, 1H), 6.91 (d, J=8.3 Hz, 1H), 6.10-5.96 (m, 2H), 5.87 (br. s., 1H), 5.44-5.34 (m, 2H), 5.31-5.24 (m, 1H), 5.10 (br. s., 1H), 4.59 (dt, J=5.2, 1.4 Hz, 2H), 4.41 (t, J=4.6 Hz, 2H), 4.30-4.11 (m, 3H), 4.07-3.96 (m, 2H), 3.83 (s, 2H), 2.63 (s, 3H), 2.06-1.95 (m, 2H), 1.78-1.73 (m, 1H), 1.39 (br. s., 3H), 1.28-1.21 (m, 12H). 4 piperidine hydrogens are missing. LCMS (M+H)=676.7.

Intermediate 41

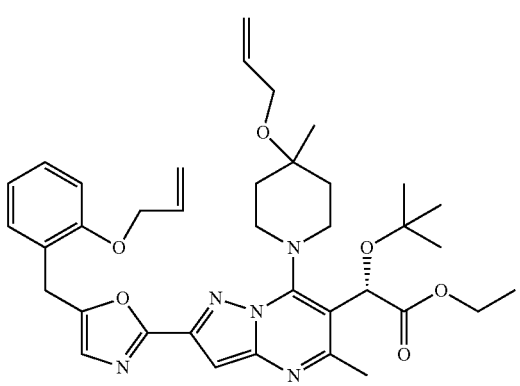

(S)-Ethyl 2-(7-(4-(allyloxy)-4-methylpiperidin-1-yl)-2-(5-(2-(allyloxy)benzyoxazol-2-yl)-5-methylpyrazolo[1,5-a]pyrimidin-6-yl)-2-(tert-butoxy)acetate To a stirred solution of (S)-ethyl 2-(7-(4-(allyloxy)-4-methylpiperidin-1-yl)-2-((3-(2-(allyloxy)phenyl)-2-oxopropyl)carbamoyl)-5-methylpyrazolo[1,5-a]pyrimidin-6-yl)-2-(tert-butoxy)acetate (120 mg, 0.178 mmol), Ph₃P (140 mg, 0.533 mmol) and TEA (0.124 mL, 0.888 mmol) in CH₂Cl₂ (3 mL) was added hexachloroethane (126 mg, 0.533 mmol) and the mixture was stirred at room temp for 16 h. Mixture was then loaded directly on a silica gel cartridge and purified by Biotage (0-30% EtOAc/hexane) to afford (S)-ethyl 2-(7-(4-(allyloxy)-4-methylpiperidin-1-yl)-2-(5-(2-(allyloxy)benzyl)oxazol-2-yl)-5-methylpyrazolo[1,5-a]pyrimidin-6-yl)-2-(tert-butoxy)acetate (80 mg, 0.122 mmol, 68.5% yield) as white solid. ¹H NMR (500 MHz, CDCl₃) δ 7.28-7.23 (m, 2H), 7.01 (s, 1H), 6.98-6.93 (m, 1H), 6.91 (d, J=8.0 Hz, 1H), 6.89 (s, 1H), 6.05 (dt, J=10.4, 5.1 Hz, 1H), 6.09 (dt, J=10.5, 5.2 Hz, 1H), 5.88 (br. s., 1H), 5.50-5.40 (m, 2H), 5.29 (dq, J=10.6, 1.4 Hz, 1H), 5.21 (dd, J=10.4, 1.6 Hz, 1H), 4.60 (dt, J=5.1, 1.5 Hz, 2H), 4.31-4.18 (m, 2H), 4.17 (s, 2H), 4.08-3.97 (m, 2H), 2.64 (s, 3H), 2.02-1.97 (m, 3H), 1.78-1.72 (m, 1H), 1.39 (s, 3H), 1.27-1.21 (m, 12H). 4 piperidine hydrogens missing. LCMS (M+H)=658.7.

Intermediate 42

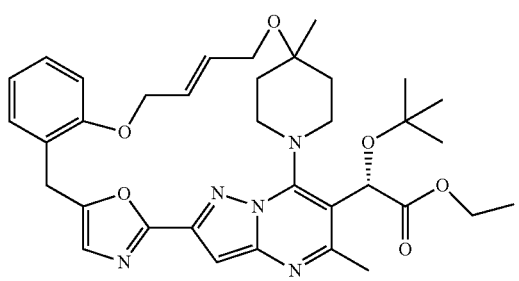

Ethyl (2S)-2-(tert-butoxy)-2-[(23E)-4,27-dimethyl-21,26,32-trioxa-1,5,7,8,11-pentaazahexacyclo [25.2.2.1⁶,⁹.1¹⁰,¹³.0²,⁷.0¹⁵,²⁰]tritriaconta-2,4,6(33),8,10,12,15(20),16,18,23-decaen-3-yl]acetate To a solution of (S)-ethyl 2-(7-(4-(allyloxy)-4-methylpiperidin-1-yl)-2-(5-(2-(allyloxy)benzyl)oxazol-2-yl)-5-methylpyrazolo[1,5-a]pyrimidin-6-yl)-2-(tert-butoxy)acetate (75 mg, 0.114 mmol) in DCE (75 mL) at 70° C. was added Hoveyda-Grubbs catalyst 2ⁿᵈ generation (7.14 mg, 0.011 mmol) and the mixture was heated for 2 h. Mixture was then cooled, concentrated and purified by Biotage (0-40% EtOAc/hexane) to afford desired product (35 mg, 0.056 mmol, 48.7% yield) as off-white solid (Geometry and position of the double bond unknown, contaminated with other isomer). ¹H NMR (500 MHz, CDCl₃) δ 7.27 (dd, J=7.5, 1.7 Hz, 1H), 7.23-7.17 (m, 1H), 7.09-7.04 (m, 2H), 6.95-6.91 (m, 1H), 6.88 (d, J=8.2 Hz, 1H), 6.33-6.25 (m, 1H), 6.20-6.11 (m, 1H), 6.10 (s, 1H), 4.75-4.60 (m, 3H), 4.34 (d, J=15.0 Hz, 1H), 4.17-4.12 (m, 2H), 4.10-3.93 (m, 4H), 3.06 (dt, J=11.3, 1.9 Hz, 1H), 2.76-2.70 (m, 1H), 2.66 (s, 3H), 2.09 (dd, J=13.7, 2.2 Hz, 1H), 1.97 (dd, J=13.7, 2.2 Hz, 1H), 1.77 (td, J=13.2, 4.6 Hz, 1H), 1.71-1.64 (m, 1H), 1.35 (s, 3H), 1.27 (s, 9H), 1.21 (t, J=7.2 Hz, 3H). LCMS (M+H)=630.6.

Example 10

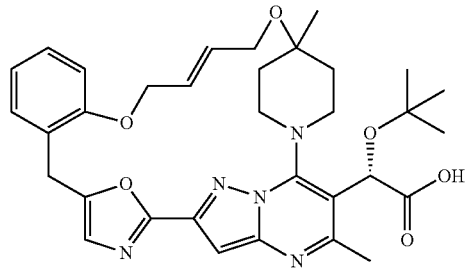 [SMILES: Cc1nc2cc3nn2c(c1[C@H](OC(C)(C)C)C(=O)O)N1CCC(C)(CC1)OC/C=C/COc1ccccc1Cc1cnc-3o1]

(2S)-2-(tert-Butoxy)-2-[(23E)-4,27-dimethyl-21,26,32-trioxa-1,5,7,8,11-pentaazahexacyclo [25.2.2.1⁶,⁹.1¹⁰,¹³.0²,⁷.0¹⁵,²⁰]tritriaconta-2,4,6(33),8,10,12,15 (20),16,18,23-decaen-3-yl]acetic acid A solution of ethyl (2S)-2-(tert-butoxy)-2-[(23E)-4,27-dimethyl-21,26,32-trioxa-1,5,7,8,11-pentaazahexacyclo [25.2.2.1⁶,⁹.1¹⁰,¹³.0²,⁷.0¹⁵,²⁰]tritriaconta-2,4,6(33),8,10,12,15(20),16,18,23-decaen-3-yl]acetate (35 mg, 0.056 mmol) in MeOH (1.5 mL) was treated with 1N NaOH (0.278 mL, 0.278 mmol) at 70° C. for 3 h. Mixture was then cooled to room temp and purified by prep HPLC to afford desired product (22 mg, 0.035 mmol, 62.5% yield) as white solid. ¹H NMR (500 MHz, CDCl₃) δ 7.27 (dd, J=7.5, 1.7 Hz, 1H), 7.24-7.19 (m, 1H), 7.10-7.08 (m, 1H), 7.08-7.06 (m, 1H), 6.93 (td, J=7.5, 0.9 Hz, 1H), 6.88 (d, J=8.4 Hz, 1H), 6.35-6.27 (m, 1H), 6.14 (dt, J=15.6, 4.7 Hz, 1H), 6.03 (br. s., 1H), 4.81-4.67 (m, 2H), 4.65-4.59 (m, 1H), 4.35 (d, J=15.0 Hz, 1H), 4.15-3.91 (m, 4H), 3.25 (d, J=10.7 Hz, 1H), 2.73 (d, J=11.7 Hz, 1H), 2.65 (s, 3H), 2.11-2.07 (m, 1H), 2.00 (d, J=13.7 Hz, 1H), 1.79-1.62 (m, 2H), 1.34 (s, 3H), 1.32 (s, 9H). LCMS (M+H)=602.6.

Intermediate 43

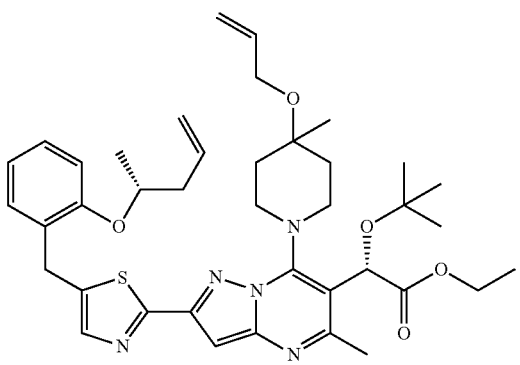

(S)-Ethyl 2-(7-(4-(allyloxy)-4-methylpiperidin-1-yl)-5-methyl-2-(5-(2-((R)-pent-4-en-2-yloxy)benzyl)thiazol-2-yl)pyrazolo[1,5-c]pyrimidin-6-yl)-2-(tert-butoxy)acetate To a mixture of (S)-ethyl 2-(7-(4-(allyloxy)-4-methylpiperidin-1-yl)-2-(5-(2-hydroxybenzyl)thiazol-2-yl)-5-methylpyrazolo[1,5-a]pyrimidin-6-yl)-2-(tert-butoxy)acetate (100 mg, 0.158 mmol), (R)-pent-4-en-2-ol (40.8 mg, 0.473 mmol), Ph$_3$P (124 mg, 0.473 mmol) in THF (3 mL) was added DEAD (0.075 mL, 0.473 mmol) and the mixture was stirred at rt for 16 h. Water was then added and the mixture was extracted with ether (2×25 mL), dried (Na$_2$SO$_4$), filtered and concentrated. The residue was then purified by Biotage (0-40% EtOAc/hexane) to afford (S)-ethyl 2-(7-(4-(allyloxy)-4-methylpiperidin-1-yl)-5-methyl-2-(5-(24(R)-pent-4-en-2-yloxy)benzyl)thiazol-2-yl)pyrazolo[1,5-a]pyrimidin-6-yl)-2-(tert-butoxy)acetate (30 mg, 0.043 mmol, 27.1% yield) as thick paste. $^1$H NMR (500 MHz, CDCl$_3$) δ 7.66 (s, 1H), 7.26-7.18 (m, 2H), 7.03 (s, 1H), 6.93-6.86 (m, 2H), 6.10-5.96 (m, 1H), 5.86 (ddt, J=17.1, 10.0, 7.1 Hz, 2H), 5.42 (d, J=17.0 Hz, 1H), 5.21-5.07 (m, 3H), 4.58-4.45 (m, 1H), 4.30-4.13 (m, 6H), 4.02 (d, J=4.9 Hz, 2H), 2.62 (s, 3H), 2.58-2.49 (m, 1H), 2.40 (dt, J=13.8, 6.7 Hz, 1H), 2.05-1.86 (m, 2H), 1.73 (br. s., 1H), 1.37 (br. s., 3H), 1.32-1.27 (m, 2H), 1.26-1.21 (m, 12H). 4 missing protons from piperidine LCMS (M+H)=702.7.

Intermediate 44

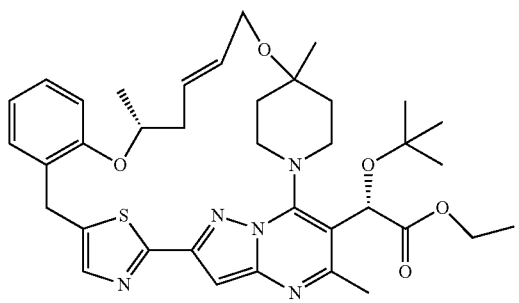

Ethyl (2S)-2-(tert-butoxy)-2-[(22R,24E)-4,22,28-trimethyl-21,27-dioxa-33-thia-1,5,7,8,11-pentaazahexacyclo[26.2.2.1$^{6,9}$.1$^{10,13}$.0$^{2,7}$.0$^{15,20}$]tetratriaconta-2,4,6(34),8,10,12,15(20),16,18,24-decaen-3-yl]acetate To a solution of (S)-ethyl 2-(7-(4-(allyloxy)-4-methylpiperidin-1-yl)-5-methyl-2-(5-(2-((R)-pent-4-en-2-yloxy)benzyl)thiazol-2-yl)pyrazolo[1,5-a]pyrimidin-6-yl)-2-(tert-butoxy)acetate (30 mg, 0.043 mmol) in DCE (30 mL) at 70° C. was added Hoveyda-Grubbs catalyst 2$^{nd}$ generation (2.68 mg, 4.27 μmol) and the mixture was heated for 2 h. Mixture was then cooled, concentrated and purified by Biotage (0-40% EtOAc/hexane) to afford desired product (16 mg, 0.024 mmol, 55.6% yield) (position of the double bond not confirmed, contaminated with small amount of other isomer). used as is in the next step without further purification. LCMS (M+H)=674.5.

Example 11

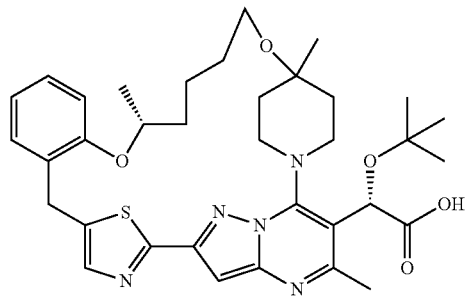 [SMILES: Cc1nc2cc3nn2c(c1[C@H](OC(C)(C)C)C(=O)O)N1CCC(C)(CC1)OCCCC[C@@H](C)Oc1ccccc1Cc1cnc-3s1]

((2S)-2-(tert-Butoxy)-2-[(22R)-4,22,28-trimethyl-21,27-dioxa-33-thia-1,5,7,8,11-pentaazahexacyclo[26.2.2.1$^{6,9}$.1$^{10,13}$.0$^{2,7}$.0$^{15,20}$]tetratriaconta-2,4,6(34),8,10,12,15(20),16,18-nonaen-3-yl]acetic acid To a solution of ethyl (2S)-2-(tert-butoxy)-2-[(22R,24E)-4,22,28-trimethyl-21,27-dioxa-33-thia-1,5,7,8,11-pentaazahexacyclo[26.2.2.1$^{6,9}$.1$^{10,13}$.0$^{2,7}$.0$^{15,20}$]tetratriaconta-2,4,6(34),8,10,12,15(20),16,18,24-decaen-3-yl]acetate (16 mg, 0.024 mmol) in MeOH (2 mL) was added 10% Pd/C (2.53 mg, 2.374 μmol) and the resulting mixture was stirred under balloon hydrogen atmosphere for 16 h. At this point LCMS indicates reduction of double bond. Mixture was then filtered through a pad of celite and concentrated. The resulting residue was treated with 1N NaOH (0.071 mL, 0.071 mmol) in MeOH (2 mL) at 70° C. for 3 h. Mixture was then cooled purified by prep HPLC to afford desired product (9 mg, 0.014 mmol, 58.5% yield). $^1$H NMR (500 MHz, DMSO-d$_6$) δ 7.83 (s, 1H), 7.30 (d, J=7.3 Hz, 1H), 7.23-7.18 (m, 1H), 7.10 (d, J=8.2 Hz, 1H), 6.89-6.82 (m, 2H), 5.74 (s, 1H), 4.71 (br. s., 1H), 4.26 (t, J=11.4 Hz, 1H), 4.20 (d, J=14.0 Hz, 1H), 4.03 (d, J=13.7 Hz, 1H), 3.72-3.63 (m, 2H), 3.20 (d, J=11.0 Hz, 1H), 2.60 (d, J=10.7 Hz, 1H), 2.55 (s, 3H), 2.52 (br. s., 3H), 1.96 (t, J=13.0 Hz, 2H), 1.87-1.65 (m, 4H), 1.59-1.45 (m, 2H), 1.20 (s, 6H), 1.15 (s, 9H). LCMS (M+H)=648.5.

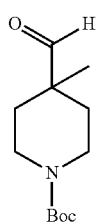

Intermediate 45 tert-Butyl 4-formyl-4-methylpiperidine-1-carboxylate

Prepared according to the procedure reported in WO2008/118718. To a solution of tert-butyl 4-formylpiperidine-1-carboxylate (4.5 g, 21.10 mmol) in $CH_2Cl_2$ (50 mL) at 0° C. was added KOtBu (3.08 g, 27.4 mmol) followed by MeI (3.96 mL, 63.3 mmol) and the resulting mixture was stirred at 0° C. for 30 min, and then warmed to room temp and stirr for 1.5 h. The reaction mixture was then poured into brine and the mixture was extracted with dichloromethane, dried ($Na_2SO_4$), filtered and concentrated. The residue was then purified by Biotage (0-20% EtOAc/hexane) to afford tert-butyl 4-formyl-4-methylpiperidine-1-carboxylate (1.8 g, 7.92 mmol, 37.5% yield) as colorless oil. $^1$H NMR (500 MHz, $CDCl_3$) δ 9.48 (s, 1H), 3.71-3.66 (m, 2H), 3.19-3.05 (m, 2H), 1.93 (dt, J=13.7, 4.1 Hz, 2H), 1.47 (s, 9H), 1.46-1.37 (m, 2H), 1.10 (s, 3H). LCMS (M+H)=228.1.

Intermediate 46

(E)-tert-Butyl 4-(buta-1,3-dien-1-yl)-4-methylpiperidine-1-carboxylate

To a solution of diethyl allylphosphonate (2.82 g, 15.84 mmol) in THF (50 mL) at −78° C. was added 1.6 M MeLi (9.90 mL, 15.84 mmol) and the resulting mixture was stirred for 30 min. HMPT (9.68 mL, 52.8 mmol) followed by (E)-tert-butyl 4-(buta-1,3-dien-1-yl)-4-methylpiperidine-1-carboxylate (1.8 g, 7.16 mmol, 54.3% yield) in THF (10 mL) was then added and the mixture was stirred at −78° C. for 1 h and then allowed to warm to room temp. After 16 h, the mixture was quenched with sat.$NH_4Cl$ solution and extracted with ether (2×100 mL). The combined organic extractes were dried ($Na_2SO_4$), filtered and concentrated. The residue was then purified by Biotage (0-20% EtOAc/hexane; 80 g column) to afford ((E)-tert-butyl 4-(buta-1,3-dien-1-yl)-4-methylpiperidine-1-carboxylate (1.8 g, 7.16 mmol, 54.3% yield) as colorless oil. $^1$H NMR (500 MHz, $CDCl_3$) δ 6.42-6.27 (m, 1H), 6.05 (dd, J=15.8, 10.2 Hz, 1H), 5.68 (d, J=15.8 Hz, 1H), 5.21-5.09 (m, 1H), 5.08-4.91 (m, 1H), 3.61-3.44 (m, 2H), 3.37-3.15 (m, 2H), 1.61 (dd, J=9.5, 2.8 Hz, 2H), 1.47 (s, 9H), 1.45-1.37 (m, 2H), 1.07 (s, 3H).

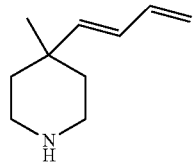

Intermediate 47

(E)-4-(Buta-1,3-dien-1-yl)-4-methylpiperidine.HCl

A mixture of (E)-tert-butyl 4-(buta-1,3-dien-1-yl)-4-methylpiperidine-1-carboxylate (1.8 g, 7.16 mmol) and 4M HCl/dioxane (8.95 ml, 35.8 mmol) was stirred at room temp for 3 h. Mixture was then concentrated and the solids were triturated with ether/hexane, filtered and dried under high vaccuo to afford (E)-4-(buta-1,3-dien-1-yl)-4-methylpiperidine.HCl (1.2 g, 6.39 mmol, 89% yield) as off-white solid. $^1$H NMR (500 MHz, DMSO-$d_6$) δ 6.35 (dt, J=16.9, 10.2 Hz, 1H), 6.12 (dd, J=15.7, 10.3 Hz, 1H), 5.78-5.73 (m, 1H), 5.21 (d, J=17.0 Hz, 1H), 5.06 (d, J=10.1 Hz, 1H), 3.14-3.00 (m, 2H), 2.97-2.79 (m, 2H), 1.83-1.69 (m, 2H), 1.64-1.53 (m, 2H), 1.06 (s, 3H). LCMS (M+H)=152.1.

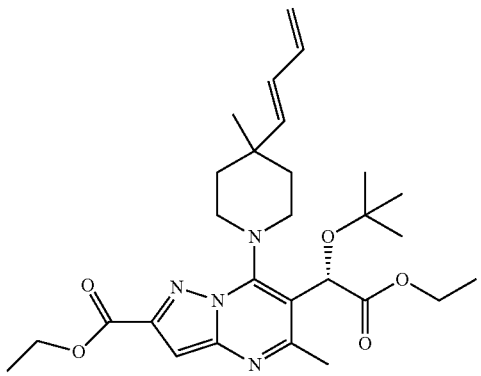

Intermediate 48

(S,E)-Ethyl 7-(4-(buta-1,3-dien-1-yl)-4-methylpiperidin-1-yl)-6-(1-(tert-butoxy)-2-ethoxy-2-oxoethyl)-5-methylpyrazolo[1,5-a]pyrimidine-2-carboxylate To a solution of (S)-ethyl 6-(1-(tert-butoxy)-2-ethoxy-2-oxoethyl)-7-iodo-5-methylpyrazolo[1,5-a]pyrimidine-2-carboxylate (2.5 g, 5.11 mmol) and (E)-4-(buta-1,3-dien-1-yl)-4-methylpiperidine.HCl (1.247 g, 6.64 mmol) in NMP (20 mL) was added DIEA (2.68 mL, 15.33 mmol) and the mixture was heated at 60° C. for 72 h. At this point LCMS indicates completion of reaction. Mixture was then cooled to room temp, diluted with water and extracted with ethyl acetate (2×50 mL), dried ($Na_2SO_4$), filtered and concentrated. The residue was then purified by flash chromatography (5-40% EtOAc/hexane) to afford (S,E)-ethyl 7-(4-(buta-1,3-dien-1-yl)-4-methylpiperidin-1-yl)-6-(1-(tert-butoxy)-2-ethoxy-2-oxoethyl)-5-methylpyrazolo[1,5-a]pyrimidine-2-carboxylate (1.2 g, 2.341 mmol, 45.8% yield) as thick paste. $^1$H NMR (500 MHz, $CDCl_3$) 7.16 (br. s., 1H), 6.42 (dt, J=16.9, 10.1 Hz, 1H), 6.15 (dd, J=15.8, 10.2 Hz, 1H), 5.89-5.82 (m, 1H), 5.78 (br. s., 1H), 5.27-5.18 (m, 1H), 5.09 (d, J=10.1 Hz, 1H), 4.48-4.43 (m, 2H), 4.32-4.16 (m, 2H), 2.73 (s, 3H), 1.84 (br. s., 2H), 1.66 (br. s., 2H), 1.47-1.43 (m, 3H), 1.28-1.25 (m, 6H), 1.24 (s, 9H). 4 missing piperidine hydrogens. LCMS (M+H)=513.6.

Intermediate 49

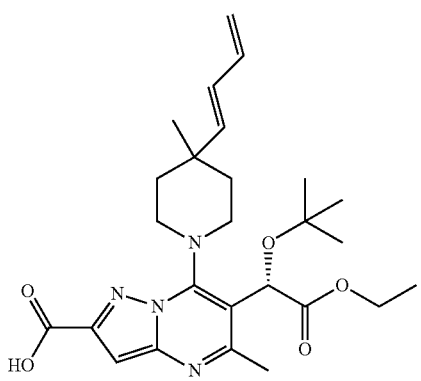

(S,E)-7-(4-(Buta-1,3-dien-1-yl)-4-methylpiperidin-1-yl)-6-(1-(tert-butoxy)-2-ethoxy-2-oxoethyl)-5-methylpyrazolo[1,5-a]pyrimidine-2-carboxylic acid To a solution of (S,E)-ethyl 7-(4-(buta-1,3-dien-1-yl)-4-methylpiperidin-1-yl)-6-(1-(tert-butoxy)-2-ethoxy-2-oxoethyl)-5-methylpyrazolo[1,5-a]pyrimidine-2-carboxylate (1.1 g, 2.146 mmol) in Ethanol (15 mL) was added 1N NaOH (2.146 mL, 2.146 mmol) and teh mixture was stirred at room temp for 16 h. At this point LCMS indiactes desired product as major along with bis-acid (approx 10%) and starting material (approx 30%). So another 0.5 mL equiv of NaOH was added and the mixture was stirred for another 5 h. Mixture was then concentrated and the residue was dissolved in water and acidified with 1N HCl. Mixture was then extracetd with wther (2×50 mL), washed with brine (25 mL), dried filtered ans concentrated to afford (S,E)-7-(4-(buta-1,3-dien-1-yl)-4-methylpiperidin-1-yl)-6-(1-(tert-butoxy)-2-ethoxy-2-oxoethyl)-5-methylpyrazolo[1,5-a]pyrimidine-2-carboxylic acid (700 mg, 1.445 mmol, 67.3% yield) as white solid contaminated with bis-acid. Used as is in the next step without further purification. $^1$H NMR (500 MHz, CDCl$_3$) 7.29 (s, 1H), 6.42 (dt, J=16.9, 10.1 Hz, 1H), 6.16 (dd, J=15.8, 10.2 Hz, 1H), 5.88-5.79 (m, 1H), 5.73 (br. s., 1H), 5.23 (d, J=16.9 Hz, 1H), 5.11 (d, J=9.6 Hz, 1H), 4.35-4.19 (m, 2H), 3.87-3.60 (m, 4H), 2.77 (s, 3H), 1.97-1.76 (m, 3H), 1.70-1.64 (m, 1H), 1.31-1.25 (m, 15H). LCMS (M+H)=485.3.

Intermediate 50

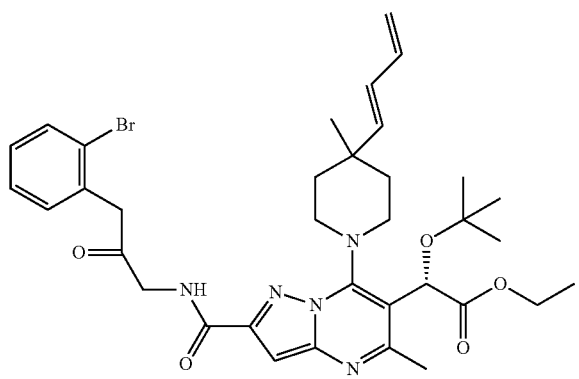

(S,E)-Ethyl 2-(24(3-(2-bromophenyl)-2-oxopropyl)carbamoyl)-7-(4-(buta-1,3-dien-1-yl)-4-methylpiperidin-1-yl)-5-methylpyrazolo[1,5-a]pyrimidin-6-yl)-2-(tert-butoxy)acetate To a solution of (S,E)-7-(4-(buta-1,3-dien-1-yl)-4-methylpiperidin-1-yl)-6-(1-(tert-butoxy)-2-ethoxy-2-oxoethyl)-5-methylpyrazolo[1,5-a]pyrimidine-2-carboxylic acid (370 mg, 0.764 mmol) in CH$_2$Cl$_2$ (7 mL, contains cat. DMF) was added oxalyl chloride (0.420 mL, 0.840 mmol) and the mixture was stirred at room temp for 1 h. The crude acid chloride was then added to a pre-stirred solution of 1-amino-3-(2-bromophenyl)propan-2-oneFlC1 (303 mg, 1.145 mmol) and DIEA (0.800 mL, 4.58 mmol) in CH$_2$Cl$_2$ (7.0 mL) and the resulting solution was stirred at room temperature for 4 h. Water was then added and the mixture was extracted with dichloromethane, dried (Na$_2$SO$_4$), filtered and concentrated. The crude was then purified by flash column chromatograpgy on silica gel column using (5-70% EtOAc/Hexane as eluant) to afford (S,E)-ethyl 2-(2-((3-(2-bromophenyl)-2-oxopropyl)carbamoyl)-7-(4-(buta-1,3-dien-1-yl)-4-methylpiperidin-1-yl)-5-methylpyrazolo[1,5-a]pyrimidin-6-yl)-2-(tert-butoxy)acetate (450 mg, 0.648 mmol, 85% yield) as light yellow solid. $^1$H NMR (500 MHz, CDCl$_3$) δ 7.73 (br. s., 1H), 7.63 (d, J=8.0 Hz, 1H), 7.42-7.32 (m, 3H), 7.23 (t, J=7.4 Hz, 1H), 6.40 (dt, J=17.1, 10.1 Hz, 1H), 6.20 (dd, J=15.7, 10.3 Hz, 1H), 5.79 (d, J=15.8 Hz, 1H), 5.43 (br. s., 1H), 5.20 (d, J=16.6 Hz, 1H), 5.07 (d, J=9.5 Hz, 1H), 4.53-4.42 (m, 3H), 4.35-4.24 (m, 2H), 4.01 (s, 1H), 3.92-3.70 (m, 4H), 2.90 (br. s., 3H), 2.08-1.70 (m, 4H), 1.27-1.23 (m, 6H), 1.21 (s, 9H). LCMS (M+2+H)=696.4.

Intermediate 51

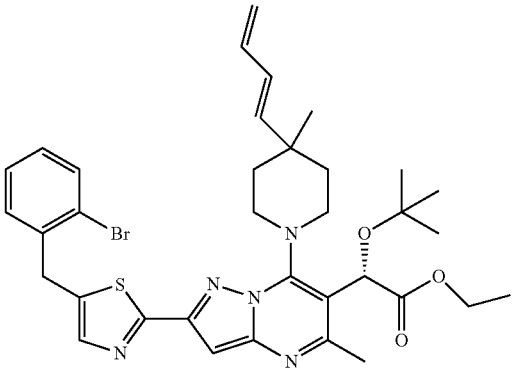

(S,E)-Ethyl 2-(2-(5-(2-bromobenzyl)thiazol-2-yl)-7-(4-(buta-1,3-dien-1-yl)-4-methylpiperidin-1-yl)-5-methylpyrazolo[1,5-a]pyrimidin-6-yl)-2-(tert-butoxy)acetate To a solution of (S,E)-ethyl 2-(2-((3-(2-bromophenyl)-2-oxopropyl)carbamoyl)-7-(4-(buta-1,3-dien-1-yl)-4-methylpiperidin-1-yl)-5-methylpyrazolo[1,5-a]pyrimidin-6-yl)-2-(tert-butoxy)acetate (450 mg, 0.648 mmol) in toluene was added Lawesson's Reagent (288 mg, 0.713 mmol) and stirr for 15 min at rt, and 60° C. for 5 h. At this point LCMS indicates desired product along with Lawessons aduct (LCMS (M+H)=896.3). Mixture was then heated at 100° C. for 3 h. At this point LCMS indicates completion of reaction. Mixture was then cooled, concentrated and the residue was purified by Biotage (0-30% EtOAc/hexane; 40 g column) to afford (S,E)-ethyl 2-(2-(5-(2-bromobenzyl)thiazol-2-yl)-7-(4-(buta-1,3-dien-1-yl)-4-methylpiperidin-1-yl)-5-methylpyrazolo[1,5-a]pyrimidin-6-yl)-2-(tert-butoxy)acetate (170 mg, 0.245 mmol, 37.9% yield) as thick paste. $^1$H NMR (500 MHz, CDCl$_3$) δ 7.72 (s, 1H), 7.63 (d, J=7.9 Hz, 2H), 7.36-7.30 (m, 2H), 7.22-7.16 (m, 1H), 6.42 (dt, J=17.2, 10.2 Hz, 1H), 6.21-6.12 (m, 1H), 5.87-5.77 (m, 1H), 5.39 (s, 1H), 5.24 (d, J=16.7 Hz, 1H), 5.12 (d, J=9.6 Hz, 1H), 4.42-4.34 (m, 4H), 4.33-4.13 (m, 4H), 2.90 (s, 3H), 1.86-1.71 (m, 4H), 1.26-1.24 (m, 6H), 1.21 (s, 9H). LCMS (M+H)=694.4.

Intermediate 52

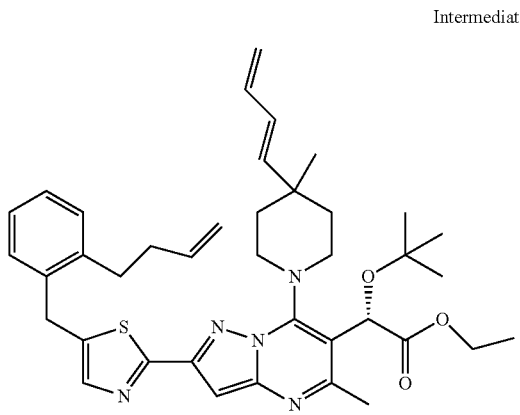

(S,E)-Ethyl 2-(2-(5-(2-(but-3-en-1-yl)benzyl)thiazol-2-yl)-7-(4-(buta-1,3-dien-1-yl)-4-methylpiperidin-1-yl)-5-methylpyrazolo[1,5-a]pyrimidin-6-yl)-2-(tert-butoxy)acetate A mixture of (S,E)-ethyl 2-(2-(5-(2-bromobenzyl)thiazol-2-yl)-7-(4-(buta-1,3-dien-1-yl)-4-methylpiperidin-1-yl)-5-methylpyrazolo[1,5-a]pyrimidin-6-yl)-2-(tert-butoxy)acetate (170 mg, 0.245 mmol), but-3-enyltrifluoroborate (119 mg, 0.736 mmol), Cs$_2$CO$_3$ (240 mg, 0.736 mmol) in toluene (4 mL) and water (0.4 mL) was degassed for 5 min. Pd(OAc)$_2$ (11.02 mg, 0.049 mmol) followed by dicyclohexyl(2',6'-diisopropoxy-[1,1'-biphenyl]-2-yl)phosphine (45.8 mg, 0.098 mmol) was then added and the mixture was heated at 80° C. for 16 h. The reaction mixture was then cooled, diluted with ethyl acetate, washed with water, brine, dried (Na$_2$SO$_4$), filtered and concentrated. The residue was then purified by Biotage (0-30% EtOAc/hexane; 40 g column) to (S,E)-ethyl 2-(2-(5-(2-(but-3-en-1-yl)benzyl)thiazol-2-yl)-7-(4-(buta-1,3-dien-1-yl)-4-methylpiperidin-1-yl)-5-methylpyrazolo[1,5-a]pyrimidin-6-yl)-2-(tert-butoxy)acetate (90 mg, 0.135 mmol, 54.9% yield) as thick paste. $^1$H NMR (500 MHz, CDCl$_3$) δ 7.58 (s, 1H), 7.27-7.20 (m, 4H), 7.15 (br. s., 1H), 6.42 (dt, J=16.9, 10.1 Hz, 1H), 6.16 (dd, J=15.7, 10.2 Hz, 1H), 5.93-5.80 (m, 3H), 5.21 (d, J=17.0 Hz, 1H), 5.10-5.04 (m, 2H), 5.04-4.99 (m, 1H), 4.31-4.16 (m, 5H), 2.83-2.76 (m, 2H), 2.70 (s, 3H), 2.40-2.28 (m, 2H), 1.98-1.89 (m, 1H), 1.85-1.79 (m, 2H), 1.31-1.09 (m, 15H). 4 missing piperidine hydrogens. LCMS (M+H)=668.6.

Example 12

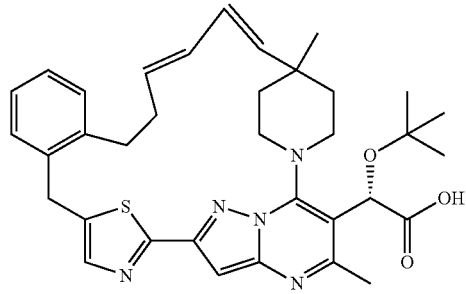 [SMILES: Cc1nc2cc3nn2c(c1[C@H](OC(C)(C)C)C(=O)O)N1CCC(C)(/C=C/C=C/CCc2ccccc2Cc2cnc-3s2)CC1]

(2S)-2-(tert-Butoxy)-2-[(23E,25E)-4,27-dimethyl-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,23,25-undecaen-3-yl]acetic acid To a solution of (S,E)-ethyl 2-(2-(5-(2-(but-3-en-1-yl)benzyl)thiazol-2-yl)-7-(4-(buta-1,3-dien-1-yl)-4-methylpiperidin-1-yl)-5-methylpyrazolo[1,5-a]pyrimidin-6-yl)-2-(tert-butoxy)acetate (90 mg, 0.135 mmol) and CuI (25.7 mg, 0.135 mmol) in DCE (100 mL) at 70° C. was added Grubbs II (11.44 mg, 0.013 mmol) and the mixture was heated at 70° C. for 4 h. Mixture was then cooled, filtered through a pad of silica gel and concentrated. The residue was then treated with 1N NaOH (0.539 mL, 0.539 mmol) in MeOH (3 mL) at 70° C. for 3 h. Mixture was then cooled and purified by prep HPLC to afford desired product (46 mg, 0.071 mmol, 53.0% yield) as off-white solid. $^1$H NMR (500 MHz, CDCl$_3$) δ 7.79 (s, 1H), 7.41 (d, J=7.7 Hz, 1H), 7.28-7.25 (m, 1H), 7.23-7.15 (m, 2H), 7.10 (s, 1H), 6.28 (dd, J=15.2, 10.3 Hz, 1H), 6.12 (dd, J=15.8, 10.1 Hz, 1H), 6.02 (br. s., 1H), 5.83-5.76 (m, 1H), 5.69-5.64 (m, 1H), 4.53 (t, J=11.8 Hz, 1H), 4.31-4.16 (m, 2H), 3.85-3.75 (m, 1H), 3.13-3.07 (m, 2H), 2.93-2.82 (m, 1H), 2.74-2.69 (m, 1H), 2.66 (s, 3H), 2.59 (d, J=11.3 Hz, 1H), 1.90 (d, J=13.2 Hz, 1H), 1.78-1.63 (m, 4H), 1.32 (s, 9H), 1.13 (s, 3H). LCMS (M+H)=612.5.

Example 13 and 14

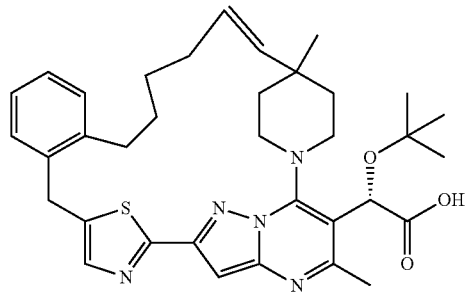

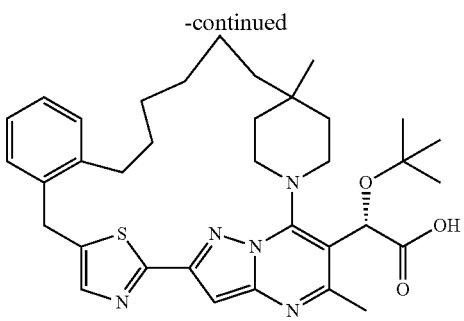

(2S)-2-(tert-Butoxy)-2-[(25E)-4,27-dimethyl-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,25-decaen-3-yl]acetic acid and (2S)-2-(tert-Butoxy)-2-{4,27-dimethyl-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18-nonaen-3-yl}acetic acid To a solution of (S,E)-ethyl 2-(2-(5-(2-(but-3-en-1-yl)benzyl)thiazol-2-yl)-7-(4-(buta-1,3-dien-1-yl)-4-methylpiperidin-1-yl)-5-methylpyrazolo[1,5-a]pyrimidin-6-yl)-2-(tert-butoxy)acetate (50 mg, 0.075 mmol) and CuI (14.26 mg, 0.075 mmol) in DCE (50 mL) at 70° C. was added Grubbs II (6.36 mg, 7.49 μmol) and the mixture was heated at 70° C. for 2 h. Mixture was then cooled, filtered through a pad of silica gel and concentrated. The residue was diluted with methanol (20 mL) and 10% Pd/C (120 mg, 0.112 mmol) was added. The mixture was then subjected to Par hydrogenation at 60 PSI for 16 h and then filtered and concentrated. The residue was then tretated with 1N NaOH (0.374 mL, 0.374 mmol) in MeOH (2 mL) at 70° C. for 3 h. Mixture was then cooled and purified by prep HPLC to afford two products.

Example 13

(2S)-2-(tert-Butoxy)-2-[(25E)-4,27-dimethyl-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,25-decaen-3-yl]acetic acid (3.1 mg, 5.05 μmol, 6.75% yield). $^1$H NMR (500 MHz, DMSO-d$_6$) δ 7.89 (br. s., 1H), 7.34 (d, J=7.0 Hz, 1H), 7.24-7.19 (m, 2H), 7.11 (d, J=7.0 Hz, 1H), 6.86 (s, 1H), 5.69 (s, 1H), 5.58-5.42 (m, 2H), 4.22 (s, 2H), 4.14 (d, J=11.9 Hz, 1H), 2.94-2.80 (m, 4H), 2.74 (s, 1H), 2.19-2.01 (m, 2H), 1.91 (s., 3H), 1.64-1.48 (m, 4H), 1.15 (s, 9H), 1.03 (br. s., 3H). 4 missing piperidine hydrogens. LCMS (M+H)=614.

Example 14

(2S)-2-(tert-Butoxy)-2-{4,27-dimethyl-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18-nonaen-3-yl}acetic acid (15.8 mg, 0.026 mmol, 34.3% yield). $^1$H NMR (500 MHz, DMSO-d$_6$) δ 7.90 (br. s., 1H), 7.31-7.26 (m, 1H), 7.22-7.15 (m, 2H), 7.13-7.08 (m, 1H), 6.89 (d, J=2.1 Hz, 1H), 5.80 (br. s., 1H), 4.21 (s, 2H), 4.18-4.12 (m, 2H), 3.08-3.04 (m, 1H), 2.95-2.89 (m, 1H), 2.85-2.79 (m, 1H), 2.65-2.56 (m, 1H), 1.91 (d, J=1.8 Hz, 3H), 1.80-1.66 (m, 2H), 1.47-1.23 (m, 8H), 1.16 (s, 9H), 0.93 (s, 3H). 4 missing piperidine hydrogens. LCMS (M+H)=616.7.

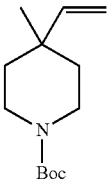

Intermediate 53 tert-Butyl 4-methyl-4-vinylpiperidine-1-carboxylate

To a solution of Ph$_3$PMeBr (4.84 g, 13.55 mmol) in THF (100 mL) at 0° C. was added 2.5 M n-BuLi (9.82 mL, 16.01 mmol) and the mixture was stirred for 30 min. at same temp. tert-Butyl 4-formyl-4-methylpiperidine-1-carboxylate (2.8 g, 12.32 mmol) in THF (10 mL) was then added dropwise and the mixture was stirred for 1 h at 0° C. The reaction mixture was then diluted with ethyl acetate and washed with sat. NH$_4$Cl and brine, dried (Na$_2$SO$_4$), filtered and concentrated. The rsidue was then purified by Biotage (0-30% EtOAc/hexane) to afford tert-butyl 4-methyl-4-vinylpiperidine-1-carboxylate (1.1 g, 4.88 mmol, 39.6% yield) as colorless liquid. $^1$H NMR (500 MHz, CDCl$_3$) δ 5.79 (dd, J=17.7, 10.9 Hz, 1H), 5.09-4.92 (m, 2H), 3.49 (ddd, J=13.4, 7.1, 3.9 Hz, 2H), 3.38-3.22 (m, 2H), 1.59 (ddd, J=13.0, 7.1, 3.5 Hz, 2H), 1.48 (s, 9H), 1.40 (ddd, J=13.2, 8.9, 3.9 Hz, 2H), 1.05 (s, 3H).

Intermediate 54

1-Amino-3-(2-bromo-4-fluorophenyl)propan-2-one.HCl

To a −78° C. solution of 1M LiHMDS/THF (28.9 mL, 28.9 mmol) in THF (70 mL) was added dropwise THF (10 mL) solution of methyl 2-isocyanoacetate (2.59 g, 26.1 mmol) over 5 min. After 30 min, a THF (20 mL) solution of 2-(4-fluoro-2-methylphenyl)acetyl chloride (3.25 g, 17.42 mmol) was added over 5 min. After 1 h, the cold bath was removed and the mixture was stirred at rom temp for 16 h. Water (25 mL) was then added and the mixture was extracted with ethyl acetate (100 mL), washed with brine (50 mL), dried (Na$_2$SO$_4$), filtered and concentrated. The residue was then refluxed with conc. HCl (40 mL) for 3 h. Mixture was then cooled to room temperature and concentraetd. The residue was then triturated with ethyl acetate and dried under high vac to afford 1-amino-3-(2-bromo-4-fluorophenyl)propan-2-one.HCl (2.5 g, 8.85 mmol, 50.8% yield) as tan solid. $^1$H NMR (500 MHz, DMSO-d$_6$) δ 7.62 (dd, J=8.6, 2.6 Hz, 1H), 7.41 (dd, J=8.6, 6.2 Hz, 1H), 7.29 (td, J=8.5, 2.7 Hz, 1H), 4.08 (s, 4H). LCMS (M+2+H)=247.08.

Intermediate 55

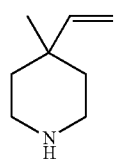

4-Methyl-4-vinylpiperidine.HCl

A mixture of tert-butyl 4-methyl-4-vinylpiperidine-1-carboxylate (1.1 g, 4.88 mmol) and 4M HCl in 1,4-dioxane (6.10 ml, 24.41 mmol) was stirred at room temp for 3 h. Mixture was then concentrated and dried under high vac to afford 4-methyl-4-vinylpiperidine.HCl (760 mg, 4.70 mmol, 96% yield) as off-white solid. $^1$H NMR (500 MHz, CDCl$_3$) δ 5.73 (dd, J=17.7, 11.0 Hz, 1H), 5.19 (d, J=10.9 Hz, 1H), 5.05 (d, J=17.7 Hz, 1H), 3.25 (br. s., 2H), 3.10 (br. s., 2H), 1.98-1.80 (m, 4H), 1.12 (s, 3H).

Intermediate 56

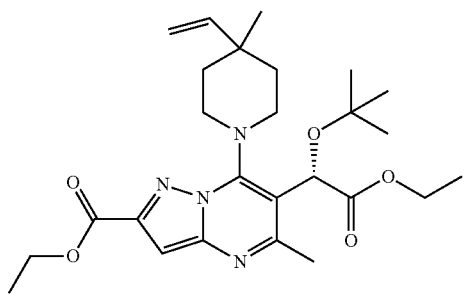

(S)-Ethyl 6-(1-(tert-butoxy)-2-ethoxy-2-oxoethyl)-5-methyl-7-(4-methyl-4-vinylpiperidin-1-yl)pyrazolo[1,5-a]pyrimidine-2-carboxylate To a solution of (S)-ethyl 6-(1-(tert-butoxy)-2-ethoxy-2-oxoethyl)-7-iodo-5-methylpyrazolo[1,5-a]pyrimidine-2-carboxylate (2, 4.09 mmol) and 4-methyl-4-vinylpiperidine-.HCl (0.727 g, 4.50 mmol) in NMP (20 mL) was added DIEA (2.142 mL, 12.26 mmol) and the mixture was heated at 60° C. for 16 h. At this point LCMS indicates completion of reaction. Mixture was then cooled to room temp, diluted with water and extracted with ethyl acetate (2×50 mL), dried (Na$_2$SO$_4$), filtered and concentrated. The residue was then purified by flash chromatography (5-40% EtOAc/hexane) to afford (S)-ethyl 6-(1-(tert-butoxy)-2-ethoxy-2-oxoethyl)-5-methyl-7-(4-methyl-4-vinylpiperidin-1-yl)pyrazolo[1,5-a]pyrimidine-2-carboxylate (1 g, 2.055 mmol, 50.3% yield) as thick paste. $^1$H NMR (500 MHz, CDCl$_3$) δ 7.03 (s, 1H), 6.07-5.91 (m, 2H), 5.11 (d, J=17.7 Hz, 2H), 4.50-4.41 (m, 2H), 4.31-4.12 (m, 2H), 2.70-2.65 (s, 3H), 1.93-1.88 (m, 1H), 1.81-1.71 (m, 2H), 1.65-1.59 (m, 2H), 1.46 (t, J=7.2 Hz, 3H), 1.27-1.22 (m, 15H). LCMS (M+H)=487.8.

Intermediate 57

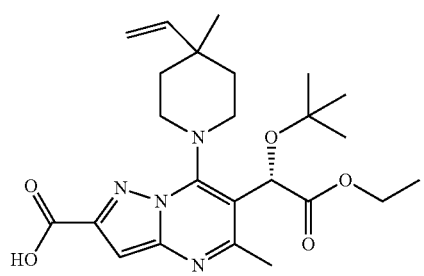

(S)-6-(1-(tert-Butoxy)-2-ethoxy-2-oxoethyl)-5-methyl-7-(4-methyl-4-vinylpiperidin-1-yl)pyrazolo[1,5-a]pyrimidine-2-carboxylic acid To a solution of (S)-ethyl 6-(1-(tert-butoxy)-2-ethoxy-2-oxoethyl)-5-methyl-7-(4-methyl-4-vinylpiperidin-1-yl)pyrazolo[1,5-a]pyrimidine-2-carboxylate (1 g, 2.055 mmol) in EtOH (10 mL) was added 1N NaOH (2.055 mL, 2.055 mmol) and the mixture was stirred at room temp for 16 h. Mixture was then concentrated and the residue was dissolved in water and acidified with 1N HCl. Mixture was then extracetd with ether (2×50 mL), washed with brine (25 mL), dried (Na$_2$SO$_4$), filtered and concentrated to afford(S)-6-(1-(tert-butoxy)-2-ethoxy-2-oxoethyl)-5-methyl-7-(4-methyl-4-vinylpiperidin-1-yl)pyrazolo[1,5-a]pyrimidine-2-carboxylic acid (830 mg, 1.810 mmol, 88% yield) as white solid contaminated with bis-acid. Used as is in the next step without further purification. $^1$H NMR (500 MHz, CDCl$_3$) δ 7.15 (s, 1H), 6.01-5.90 (m, 2H), 5.22-5.03 (m, 2H), 4.31-4.18 (m, 2H), 2.67 (s, 3H), 1.92-1.62 (m, 4H), 1.28-1.24 (m, 12H), 1.24 (s, 3H). LCMS (M+H)=459.3.

Intermediate 58

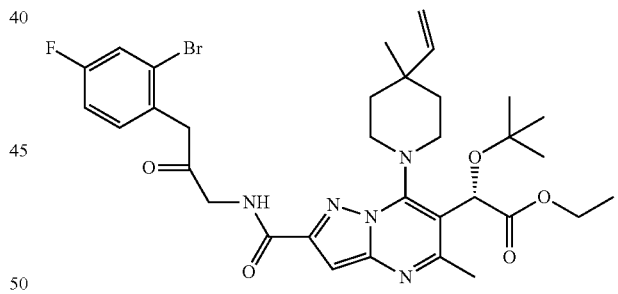

(S)-Ethyl 2-(2-((3-(2-bromo-4-fluorophenyl)-2-oxopropyl)carbamoyl)-5-methyl-7-(4-methyl-4-vinylpiperidin-1-yl)pyrazolo[1,5-a]pyrimidin-6-yl)-2-(tert-butoxy)acetate To a solution of (S)-6-(1-(tert-butoxy)-2-ethoxy-2-oxoethyl)-5-methyl-7-(4-methyl-4-vinylpiperidin-1-yl)pyrazolo[1,5-a]pyrimidine-2-carboxylic acid (400 mg, 0.872 mmol) in CH$_2$Cl$_2$ (7 mL, contains cat. DMF) was added oxalyl chloride (0.480 mL, 0.960 mmol) and the mixture was stirred at room temp for 1 h. The crude acid chloride was then added to a pre-stirred solution of 1-amino-3-(2-bromo-4-fluorophenyl)propan-2-one.HCl (370 mg, 1.308 mmol) and DIEA (0.914 mL, 5.23 mmol) in CH$_2$Cl$_2$ (7.00 mL) and the resulting solution was stirred at room temperature for 4 h. Water was then added and the mixture was extracted with dichloromethane, dried (Na₂SO₄), filtered and concentrated. The crude was then purified by flash column chromatograpgy on silica gel column using (5-70% EtOAc/Hexane as eluant) to afford (S)-ethyl 2-(2-((3-(2-bromo-4-fluorophenyl)-2-oxopropyl)carbamoyl)-5-methyl-7-(4-methyl-4-vinylpiperidin-1-yl)pyrazolo[1,5-a]pyrimidin-6-yl)-2-(tert-butoxy)acetate (440 mg, 0.641 mmol, 73.5% yield) as light yellow solid. ¹H NMR (500 MHz, CDCl₃) δ 7.83 (t, J=4.7 Hz, 1H), 7.38 (dd, J=8.2, 2.7 Hz, 1H), 7.32-7.29 (m, 1H), 7.11-7.05 (m, 2H), 6.05-5.90 (m, 2H), 5.21-5.13 (m, 2H), 4.48 (dd, J=4.7, 2.2 Hz, 2H), 4.29-4.10 (m, 2H), 3.99 (s, 2H), 2.65 (s, 3H), 1.98-1.87 (m, 1H), 1.85-1.72 (m, 2H), 1.69-1.61 (m, 1H), 1.27-1.20 (m, 15H). LCMS (M+2H)=688.3.

Potassium hex-5-enyltrifluoroborate

To a solution of hex-5-en-1-ylboronic acid (750 mg, 5.86 mmol) in acetonitrile (20 mL) and water (5 mL) was added KHF₂ (1831 mg, 23.44 mmol) and the mixture was stirred at room temp for 2 h. Miixture was then concentrated in vaccuo and the dried solids were triturated with hot acetone and filtered to remove inorganics salts. The resulting filtrate was concentrated and washed with ether to give potassium hex-5-enyltrifluoroborate (650 mg, 3.42 mmol, 58.4% yield) as white solid. ¹H NMR (500 MHz, DMSO-d₆) δ 5.84-5.77 (m, 1H), 5.02-4.90 (m, 2H), 2.05-1.96 (m, 2H), 1.37-1.27 (m, 4H), 0.58 (t, J=7.4 Hz, 2H).

Intermediate 59

Intermediate 61

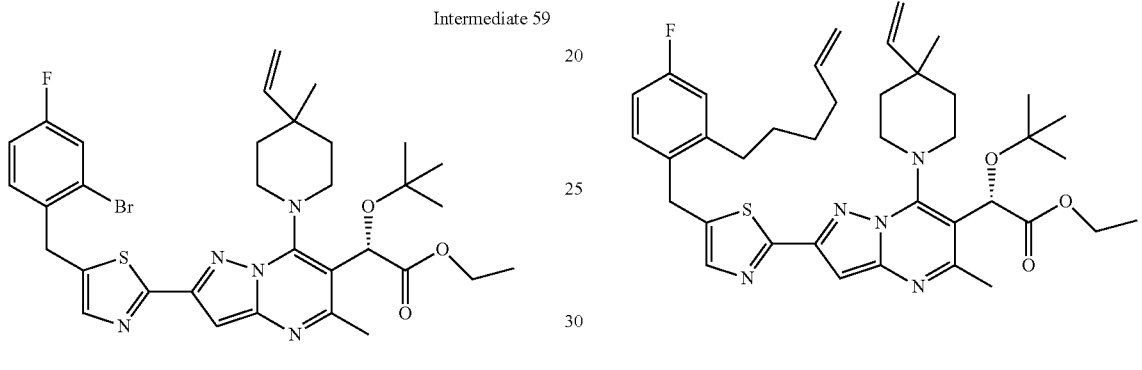

(S)-Ethyl 2-(2-(5-(2-bromo-4-fluorobenzyl)thiazol-2-yl)-5-methyl-7-(4-methyl-4-vinylpiperidin-1-yl)pyrazolo[1,5-a]pyrimidin-6-yl)-2-(tert-butoxy)acetate (S)-Ethyl 2-(tert-butoxy)-2-(2-(5-(4-fluoro-2-(hex-5-en-1-yl)benzyl)thiazol-2-yl)-5-methyl-7-(4-methyl-4-vinylpiperidin-1-yl)pyrazolo[1,5-a]pyrimidin-6-yl)acetate To a solution of (S)-ethyl 2-(2-((3-(2-bromo-4-fluorophenyl)-2-oxopropyl)carbamoyl)-5-methyl-7-(4-methyl-4-vinylpiperidin-1-yl)pyrazolo[1,5-a]pyrimidin-6-yl)-2-(tert-butoxy)acetate (440 mg, 0.641 mmol) in toluene was added Lawesson's Reagent (285 mg, 0.705 mmol) and stirr for 15 min at rt, and 60° C. for 5 h. At this point LCMS indicates completion of reaction. Mixture was then cooled, concentrated and the residue was purified by Biotage (0-30% EtOAc/hexane; 40 g column) to afford (S)-ethyl 2-(2-(5-(2-bromo-4-fluorobenzyl)thiazol-2-yl)-5-methyl-7-(4-methyl-4-vinylpiperidin-1-yl)pyrazolo[1,5-a]pyrimidin-6-yl)-2-(tert-butoxy)acetate (350 mg, 0.511 mmol, 80% yield) as light yellow solid. ¹H NMR (500 MHz, CDCl₃) δ 7.66 (s, 1H), 7.38 (dd, J=8.2, 2.7 Hz, 1H), 7.33-7.26 (m, 1H), 7.11-7.00 (m, 2H), 6.06-5.92 (m, 2H), 5.12 (d, J=17.8 Hz, 2H), 4.33 (s, 2H), 4.29-4.13 (m, 2H), 2.64 (s, 3H), 1.90 (br. s., 1H), 1.84-1.70 (m, 2H), 1.65-1.60 (m, 1H), 1.29-1.17 (m, 15H). LCMS (M+2H)=686.3.

A mixture of (S)-ethyl 2-(2-(5-(2-bromo-4-fluorobenzyl)thiazol-2-yl)-5-methyl-7-(4-methyl-4-vinylpiperidin-1-yl)pyrazolo[1,5-a]pyrimidin-6-yl)-2-(tert-butoxy)acetate (50 mg, 0.073 mmol), Potassium hex-5-enyltrifluoroborate (41.6 mg, 0.219 mmol), Cs₂CO₃ (71.4 mg, 0.219 mmol) in toluene (2 mL) and water (0.2 mL) was degassed for 5 min. Pd(OAc)₂ (3.28 mg, 0.015 mmol) followed by dicyclohexyl (2',6'-diisopropoxy-[1,1'-biphenyl]-2-yl)phosphine (13.63 mg, 0.029 mmol) were added and the mixture was heated at 80° C. for 16 h. The reaction mixture was then cooled, diluted with ethyl acetate, washed with water, brine, dried (Na₂SO₄), filtered and concentrated. The residue was then purified by Biotage (0-30% EtOAc/hexane; 25 g column) to (S)-ethyl 2-(tert-butoxy)-2-(2-(5-(4-fluoro-2-(hex-5-en-1-yl)benzyl)thiazol-2-yl)-5-methyl-7-(4-methyl-4-vinylpiperidin-1-yl)pyrazolo[1,5-a]pyrimidin-6-yl)acetate (30 mg, 0.044 mmol, 59.7% yield) as thick paste. ¹H NMR (500 MHz, CDCl₃) δ 7.56-7.51 (m, 1H), 7.20 (dd, J=8.3, 5.9 Hz, 1H), 7.04 (s, 1H), 6.97-6.86 (m, 2H), 6.03-5.93 (m, 2H), 5.81 (ddt, J=17.1, 10.3, 6.7 Hz, 1H), 5.57-5.38 (m, 1H), 5.17-5.07 (m, 2H), 5.05-4.92 (m, 1H), 4.30-4.11 (m, 4H), 2.69-2.65 (m, 1H), 2.64 (s, 3H), 2.14-2.05 (m, 2H), 1.89 (br. s., 1H), 1.82-1.70 (m, 2H), 1.69-1.60 (m, 6H), 1.26 (s, 9H), 1.24 (t, J=7.1 Hz, 6H). 4 missing piperidine hydrogens. LCMS (M+H)=688.2.

Intermediate 60

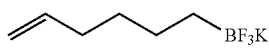

Examples 15 and 16

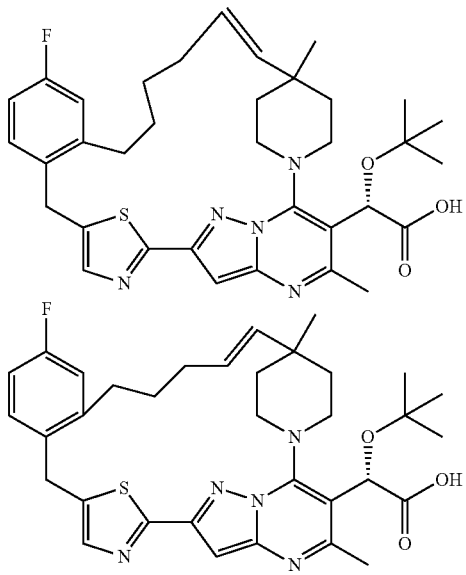

(2S)-2-(tert-Butoxy)-2-[(25E)-18-fluoro-4,27-dimethyl-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,25-decaen-3-yl]acetic acid and (2S)-2-(tert-Butoxy)-2-[(24E)-18-fluoro-4,26-dimethyl-31-thia-1,5,7,8,11-pentaazahexacyclo[24.2.2.1$^{6,9}$.1$^{10,13}$.0$^{2,7}$.0$^{15,20}$]dotriaconta-2,4,6(32),8,10,12,15(20),16,18,24-decaen-3-yl]acetic Acid To a solution of (S)-ethyl 2-(tert-butoxy)-2-(2-(5-(4-fluoro-2-(hex-5-en-1-yl)benzyl)thiazol-2-yl)-5-methyl-7-(4-methyl-4-vinylpiperidin-1-yl)pyrazolo[1,5-a]pyrimidin-6-yl)acetate (40 mg, 0.058 mmol) and CuI (11.07 mg, 0.058 mmol) in DCE (35 mL) at 70° C. was added Grubbs II (4.94 mg, 5.81 µmol) and the mixture was heated at 70° C. for 16 h. At this point LCMS indicates very small amount of desired product. Hoveyda-Grubbs catalyst 2$^{nd}$ generation (3.64 mg, 5.81 µmol) was then added and the mixture was heated at 85° C. for 5 h. At this point LCMS indicates completion of reaction and desired product as major along with smaller ring. Mixture was then cooled, filtered through a pad of silica gel and concentrated. The rsidue was then treated with 1N NaOH (0.233 mL, 0.233 mmol) in MeOH (2 mL) at 70° C. for 3 h. Mixture was then cooled and purified by prep HPLC to afford two compounds.

Example 15

Second eluting on HPLC, major compound; (2S)-2-(tert-butoxy)-2-[(25E)-18-fluoro-4,27-dimethyl-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,25-decaen-3-yl]acetic acid (12 mg, 0.019 mmol, 32% yield) $^1$H NMR (400 MHz, CDCl$_3$) δ 7.77 (s, 1H), 7.17 (dd, J=8.5, 6.0 Hz, 1H), 7.09-7.01 (m, 2H), 6.85 (td, J=8.3, 2.8 Hz, 1H), 6.00 (br. s., 1H), 5.63-5.49 (m, 2H), 4.40-4.32 (m, 1H), 4.27-4.09 (m, 2H), 3.79-3.64 (m, 1H), 3.24 (d, J=10.8 Hz, 1H), 3.06-2.86 (m, 2H), 2.74-2.66 (m, 1H), 2.63 (s, 3H), 2.29-1.89 (m, 4H), 1.73-1.58 (m, 2H), 1.31 (s, 9H), 1.11 (s, 3H). 4 missing piperidine hydrogens. LCMS (M+H)=632.3.

Example 16

First eluting on HPLC, minor compound; (2S)-2-(tert-butoxy)-2-[(24E)-18-fluoro-4,26-dimethyl-31-thia-1,5,7,8,11-pentaazahexacyclo[24.2.2.1$^{6,9}$.1$^{10,13}$.0$^{2,7}$.0$^{15,20}$]dotriaconta-2,4,6(32),8,10,12,15(20),16,18,24-decaen-3-yl]acetic acid (first eluting on HPLC minor) (5 mg, 0.009 mmol, 14% yield): $^1$H NMR (400 MHz, CDCl$_3$) 7.77 (s, 1H), 7.22 (dd, J=8.5, 6.0 Hz, 1H), 7.01 (s, 1H), 6.95 (dd, J=10.0, 2.8 Hz, 1H), 6.85 (td, J=8.3, 2.6 Hz, 1H), 5.99 (br. s., 1H), 5.89 (d, J=16.1 Hz, 1H), 5.68 (dt, J=16.0, 5.9 Hz, 1H), 4.49 (t, J=10.9 Hz, 1H), 4.26-4.12 (m, 2H), 4.04-3.94 (m, 1H), 3.08 (d, J=11.5 Hz, 1H), 2.96-2.79 (m, 2H), 2.66 (s, 3H), 2.58 (d, J=11.0 Hz, 1H), 2.42-2.28 (m, 2H), 2.15-2.01 (m, 2H), 1.82-1.61 (m, 4H), 1.31 (s, 9H), 1.16 (s, 3H). LCMS (M+H)=618.3.

Intermediate 62

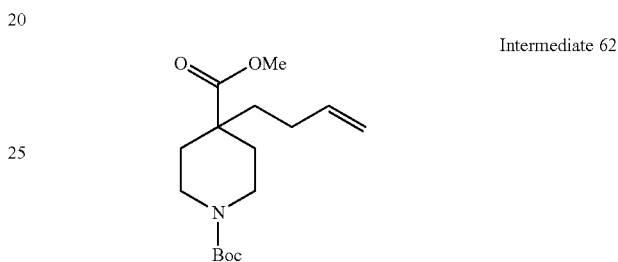

1-tert-Butyl 4-methyl 4-(but-3-en-1-yl)piperidine-1,4-dicarboxylate

A mixture of diisopropylamine (17.57 mL, 123 mmol) and THF (300 mL) was cooled to −78° C. and 1.6 M solution of n-BuLi (77 mL, 123 mmol) in hexane was added slowly. The mixture was stirred for 15 min, warmed to 0° C. for 20 min and cooled back to −78° C. 1-tert-Butyl 4-methyl piperidine-1,4-dicarboxylate (25 g, 103 mmol) in THF (25 mL) was added dropwise and the mixture was stirred for 40 min. Then, a mixture of HMPA (17.88 mL, 103 mmol) 4-bromobut-1-ene (27.7 g, 206 mmol) was added and the mixture was stirred for 1 h before it was warmed to room temp and stirr for 16 h. Sat. NH$_4$Cl was then added and the mixture was extracted with ether (2×500 mL), dried (Na$_2$SO$_4$), filtered and concentrated. The residue was purified by Biotage (0-20% EtOAc/hexane; 300 g column) to afford 1-tert-butyl 4-methyl 4-(but-3-en-1-yl)piperidine-1,4-dicarboxylate (22 g, 74.0 mmol, 72.0% yield) as light yellow oil. $^1$H NMR (500 MHz, CDCl$_3$) δ 5.76 (ddt, J=17.0, 10.3, 6.5 Hz, 1H), 5.06-4.92 (m, 2H), 3.94-3.85 (m, 2H), 3.73 (s, 3H), 2.95-2.80 (m, 2H), 2.13 (d, J=13.1 Hz, 2H), 2.02-1.93 (m, 2H), 1.64-1.58 (m, 2H), 1.47 (s, 9H), 1.42-1.32 (m, 2H). LCMS (M+H)=298.2.

Intermediate 63

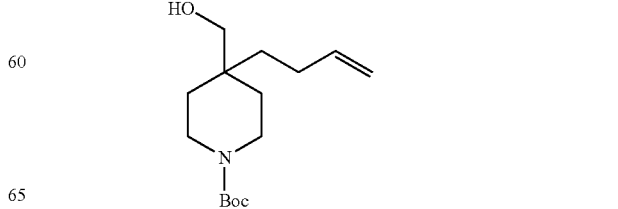

tert-Butyl 4-(but-3-en-1-yl)-4-(hydroxymethyl)piperidine-1-carboxylate

To a solution of 1-tert-butyl 4-methyl 4-(but-3-en-1-yl)piperidine-1,4-dicarboxylate (21.2 g, 71.3 mmol) in THF (300 mL) at 0° C. was added 2M LAH/THF (35.6 mL, 71.3 mmol) and the resulting mixture was stirred at 0° C. for 1 h and then stirred at room temp for 2 h. The mixture was then recooled to 0° C. and water (2.7 mL), 1N NaOH (2.7 mL) and water (8.2 mL) were added successively and the mixture was stirred for 5 min. The solids were filtered off and the cake was washed with ethyl acetate. The filterate was washed with water (2×50 mL), brine (100 mL), dried ($Na_2SO_4$), filtered and concentrated under reduced pressure to give tert-butyl 4-(but-3-en-1-yl)-4-(hydroxymethyl)piperidine-1-carboxylate (16.5 g, 61.3 mmol, 86% yield) as yellow oil. $^1$H NMR (500 MHz, $CDCl_3$) δ 5.90-5.78 (m, 1H), 5.13-5.01 (m, 1H), 5.01-4.86 (m, 1H), 3.57-3.42 (m, 4H), 3.39-3.28 (m, 2H), 2.46-2.33 (m, 1H), 2.06-1.99 (m, 2H), 1.54-1.38 (m, 14H).

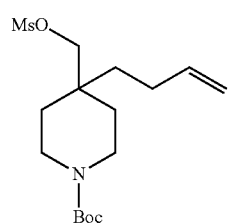

Intermediate 64 tert-Butyl 4-(but-3-en-1-yl)-4-(((methylsulfonyl)oxy)methyl)piperidine-1-carboxylate Ms-Cl (5.59 mL, 71.7 mmol) was added dropwise at 0° C. to a stirred solution of tert-butyl 4-(but-3-en-1-yl)-4-(hydroxymethyl)piperidine-1-carboxylate (16.1 g, 59.8 mmol) TEA (16.66 mL, 120 mmol) and DMAP (0.365 g, 2.99 mmol) in $CH_2Cl_2$ (300 mL) and the mixture was stirred at room temp for 2 h. Water was then added and the mixture was extracted with methylene chloride (100 mL), dried ($Na_2SO_4$), filtered and concentrated. The residue was purified by Biotage (0-40% Hex/EtOAc) to afford tert-butyl 4-(but-3-en-1-yl)-4-(((methylsulfonyl)oxy)methyl)piperidine-1-carboxylate (18 g, 51.8 mmol, 87% yield) as colorless oil. $^1$H NMR (500 MHz, $CDCl_3$) δ 5.88-5.75 (m, 1H), 5.11-4.90 (m, 2H), 4.09 (s, 2H), 3.58-3.44 (m, 2H), 3.40-3.32 (m, 2H), 3.05 (s, 3H), 2.07-2.02 (m, 2H), 1.59-1.54 (m, 2H), 1.53-1.49 (m, 4H), 1.48 (s, 9H).

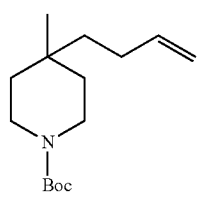

Intermediate 65 tert-Butyl 4-(but-3-en-1-yl)-4-methylpiperidine-1-carboxylate

To a solution of tert-butyl 4-(but-3-en-1-yl)-4-(((methylsulfonyl)oxy)methyl)piperidine-1-carboxylate (17 g, 48.9 mmol) in THF (250 mL) was added 1M solution of Superhydride (98 mL, 98 mmol) in THF and the resulting mixture was refluxed for 3 h. After cooling to room temp water was added and the mixture was extracted with ether (2×200 mL), washed with brine (100 mL), dried ($Na_2SO_4$), filtered and concentrated. The residue was purified by Biotage (0-20% EtOAc/hexane) to afford tert-butyl 4-(but-3-en-1-yl)-4-methylpiperidine-1-carboxylate (3.5 g, 13.81 mmol, 28.2% yield). $^1$H NMR (500 MHz, $CDCl_3$) δ 5.88-5.80 (m, 1H), 5.03 (dq, J=17.1, 1.7 Hz, 1H), 4.96 (ddt, J=10.2, 2.1, 1.1 Hz, 1H), 3.62-3.49 (m, 2H), 3.23 (ddd, J=13.4, 9.3, 3.8 Hz, 2H), 2.09-1.97 (m, 2H), 1.48 (s, 9H), 1.43-1.22 (m, 6H), 0.96 (s, 3H). LCMS (M+H)=254.2. 8 g of starting material was also recovered.

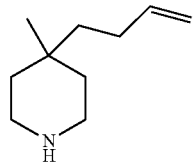

Intermediate 66

4-(But-3-en-1-yl)-4-methylpiperidine.HCl

A mixture of tert-butyl 4-(but-3-en-1-yl)-4-methylpiperidine-1-carboxylate (3.5 g, 13.81 mmol) and 4M HCl/dioxane (17.27 ml, 69.1 mmol) was stirred at room temp for 3 h. Mixture was then concentrated and dried under high vac to afford 4-(but-3-en-1-yl)-4-methylpiperidine.HCl (2.6 g, 13.70 mmol, 99% yield) as off-white solid. $^1$H NMR (500 MHz, DMSO-$d_6$) δ 5.83 (ddt, J=17.0, 10.3, 6.6 Hz, 1H), 5.05 (dq, J=17.1, 1.7 Hz, 1H), 5.00-4.80 (m, 1H), 3.11-2.90 (m, 5H), 2.05-1.90 (m, 2H), 1.56-1.42 (m, 5H), 1.38-1.26 (m, 2H), 0.95 (s, 3H). LCMS (M+H)=154.1.

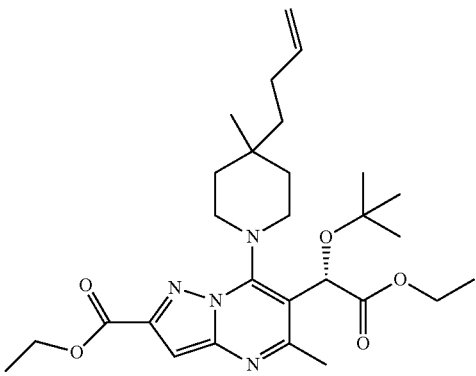

Intermediate 67

(S)-Ethyl 7-(4-(but-3-en-1-yl)-4-methylpiperidin-1-yl)-6-(1-(tert-butoxy)-2-ethoxy-2-oxoethyl)-5-methylpyrazolo[1,5-a]pyrimidine-2-carboxylate To a solution of (S)-ethyl 6-(1-(tert-butoxy)-2-ethoxy-2-oxoethyl)-7-iodo-5-methylpyrazolo[1,5-a]pyrimidine-2-carboxylate (3 g, 6.13 mmol) and 4-(but-3-en-1-yl)-4-methylpiperidine.HCl (1.512 g, 7.97 mmol) in NMP (20 mL) was added DIEA (3.21 mL, 18.39 mmol) and the mixture was heated at 60° C. for 72 h. At this point LCMS indicates completion of reaction. Mixture was then cooled to room temp, diluted with water and extracted with ethyl acetate (2×50 mL), dried (Na$_2$SO$_4$), filtered and concentrated. The residue was then purified by flash chromatography (5-40% EtOAc/hexane) to afford (S)-ethyl 7-(4-(but-3-en-1-yl)-4-methylpiperidin-1-yl)-6-(1-(tert-butoxy)-2-ethoxy-2-oxoethyl)-5-methylpyrazolo[1,5-a]pyrimidine-2-carboxylate (2.6 g, 5.05 mmol, 82% yield) as thick paste. $^1$H NMR (500 MHz, CDCl$_3$) δ 7.03 (s, 1H), 5.99 (s, 1H), 5.94-5.84 (m, 1H), 5.09 (dd, J=17.2, 1.7 Hz, 1H), 5.00 (dd, J=10.1, 1.9 Hz, 1H), 4.52-4.39 (m, 2H), 4.28-4.13 (m, 2H), 2.65 (s, 3H), 2.17-2.10 (m, 2H), 1.79-1.71 (m, 1H), 1.66-1.49 (m, 5H), 1.46 (t, J=7.1 Hz, 3H), 1.27-1.21 (m, 12H), 1.18-1.10 (m, 3H). LCMS (M+H)=515.6.

Intermediate 68

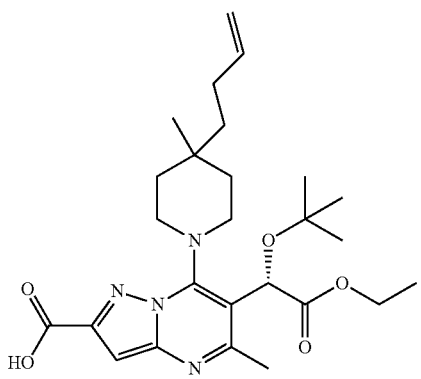

(S)-7-(4-(But-3-en-1-yl)-4-methylpiperidin-1-yl)-6-(1-(tert-butoxy)-2-ethoxy-2-oxoethyl)-5-methylpyrazolo[1,5-a]pyrimidine-2-carboxylic acid To a solution of (S)-ethyl 7-(4-(but-3-en-1-yl)-4-methylpiperidin-1-yl)-6-(1-(tert-butoxy)-2-ethoxy-2-oxoethyl)-5-methylpyrazolo[1,5-a]pyrimidine-2-carboxylate (2.6 g, 5.05 mmol) in ethanol (30 mL) was added 1N NaOH (5.05 mL, 5.05 mmol) and the resulting mixture was stirred at room temp for 16 h. Mixture was then concentrated and the residue was dissolved in water and acidified with 1N HCl. Mixture was then extracetd with ether (2×100 mL), washed with brine (50 mL), dried filtered ans concentrated to afford (S)-7-(4-(but-3-en-1-yl)-4-methylpiperidin-1-yl)-6-(1-(tert-butoxy)-2-ethoxy-2-oxoethyl)-5-methylpyrazolo[1,5-a]pyrimidine-2-carboxylic acid (2.3 g, 4.73 mmol, 94% yield) as light yellow solid. $^1$H NMR (500 MHz, CDCl$_3$) δ 7.15 (s, 1H), 6.00-5.85 (m, 2H), 5.10 (dd, J=17.0, 1.7 Hz, 1H), 5.01 (dd, J=10.1, 1.7 Hz, 1H), 4.29-4.18 (m, 2H), 2.67 (s, 3H), 2.17-2.10 (m, 2H), 1.79-1.72 (m, 1H), 1.63 (t, J=5.6 Hz, 2H), 1.59-1.50 (m, 3H), 1.28-1.23 (m, 12H), 1.15 (br. s., 3H). 4 missing piperidine hydrogens. LCMS (M+H)=487.3.

Intermediate 69

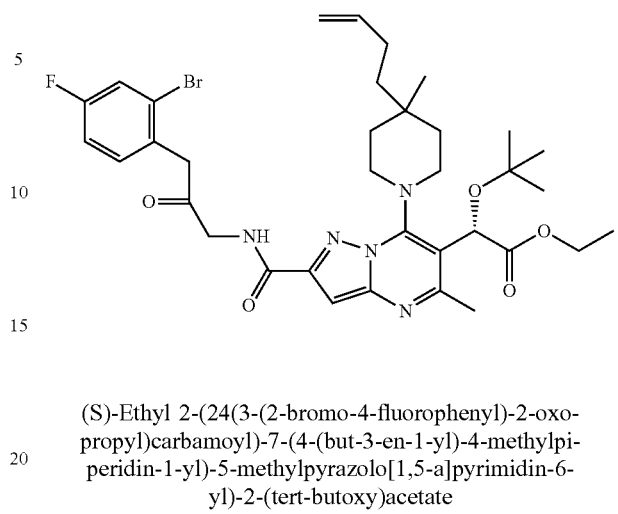

(S)-Ethyl 2-(24(3-(2-bromo-4-fluorophenyl)-2-oxopropyl)carbamoyl)-7-(4-(but-3-en-1-yl)-4-methylpiperidin-1-yl)-5-methylpyrazolo[1,5-a]pyrimidin-6-yl)-2-(tert-butoxy)acetate To a solution of (S)-7-(4-(but-3-en-1-yl)-4-methylpiperidin-1-yl)-6-(1-(tert-butoxy)-2-ethoxy-2-oxoethyl)-5-methylpyrazolo[1,5-a]pyrimidine-2-carboxylic acid (500 mg, 1.028 mmol) in CH$_2$Cl$_2$ (7 mL, contains cat. DMF) was added oxalyl chloride (0.565 mL, 1.130 mmol) and the mixture was stirred at room temp for 1 h. The crude acid chloride was then added to a pre-stirred solution of 1-amino-3-(2-bromo-4-fluorophenyl)propan-2-oneFlC1 (435 mg, 1.541 mmol) and DIEA (1.077 mL, 6.17 mmol) in CH$_2$Cl$_2$ (7.0 mL) and the resulting solution was stirred at room temperature for 4 h. Water was then added and the mixture was extracted with dichloromethane, dried (Na$_2$SO$_4$), filtered and concentrated. The crude was then purified by flash column chromatograpgy on silica gel column using (5-70% EtOAc/Hexane as eluant) to afford (S)-ethyl 2-(2-((3-(2-bromo-4-fluorophenyl)-2-oxopropyl)carbamoyl)-7-(4-(but-3-en-1-yl)-4-methylpiperidin-1-yl)-5-methylpyrazolo[1,5-a]pyrimidin-6-yl)-2-(tert-butoxy)acetate (475 mg, 0.665 mmol, 64.7% yield) as light yellow solid. $^1$H NMR (500 MHz, CDCl$_3$) δ 7.83 (t, J=4.7 Hz, 1H), 7.38 (dd, J=8.1, 2.6 Hz, 1H), 7.32-7.27 (m, 1H), 7.11-7.03 (m, 2H), 5.99 (br. s., 1H), 5.89 (ddt, J=17.0, 10.3, 6.5 Hz, 1H), 5.06 (d, J=16.4 Hz, 1H), 4.95 (br. s., 1H), 4.48 (dd, J=4.7, 1.7 Hz, 2H), 4.29-4.12 (m, 3H), 3.99 (s, 2H), 2.65 (s, 3H), 2.17-2.09 (m, 2H), 1.75 (br. s., 1H), 1.62 (t, J=5.5 Hz, 2H), 1.58-1.47 (m, 2H), 1.27-1.22 (m, 12H), 1.17 (s, 3H). 4 missing piperidine hydrogens. LCMS (M+2H)=716.2.

Intermediate 70

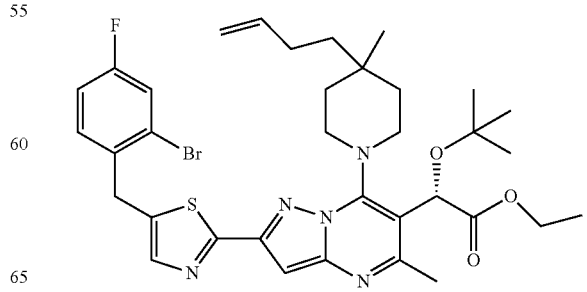

(S)-Ethyl 2-(2-(5-(2-bromo-4-fluorobenzyl)thiazol-2-yl)-7-(4-(but-3-en-1-yl)-4-methylpiperidin-1-yl)-5-methylpyrazolo[1,5-a]pyrimidin-6-yl)-2-(tert-butoxy)acetate To a solution of (S)-ethyl 2-(2-((3-(2-bromo-4-fluorophenyl)-2-oxopropyl)carbamoyl)-7-(4-(but-3-en-1-yl)-4-methylpiperidin-1-yl)-5-methylpyrazolo[1,5-a]pyrimidin-6-yl)-2-(tert-butoxy)acetate (465 mg, 0.651 mmol) in toluene was added Lawesson's Reagent (289 mg, 0.716 mmol) and stirr for 15 min at rt, and 60° C. for 5 h. At this point LCMS indicates completion of reaction. Mixture was then cooled, concentrated and the residue was purified by Biotage (0-30% EtOAc/hexane; 40 g column) to afford (S)-ethyl 2-(2-(5-(2-bromo-4-fluorobenzyl)thiazol-2-yl)-7-(4-(but-3-en-1-yl)-4-methylpiperidin-1-yl)-5-methylpyrazolo[1,5-a]pyrimidin-6-yl)-2-(tert-butoxy)acetate (300 mg, 0.421 mmol, 64.7% yield) as light yellow solid. $^1$H NMR (400 MHz, CDCl$_3$) δ 7.66 (s, 1H), 7.37 (dd, J=8.2, 2.6 Hz, 1H), 7.32-7.23 (m, 1H), 7.07-7.00 (m, 2H), 6.02 (s, 1H), 5.98-5.85 (m, 1H), 5.10 (dd, J=17.2, 1.9 Hz, 1H), 4.99 (d, J=10.0 Hz, 1H), 4.32 (s, 2H), 4.29-4.11 (m, 3H), 2.65 (s, 3H), 2.18-2.10 (m, 2H), 1.74 (br. s., 1H), 1.62 (t, J=5.5 Hz, 2H), 1.56-1.49 (m, 2H), 1.27 (s, 9H), 1.24 (t, J=7.2 Hz, 3H), 1.15 (br. s., 3H). LCMS (M+2H)=714.2.

Intermediate 71

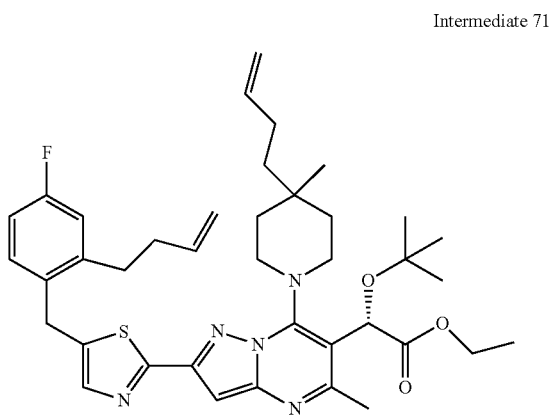 [SMILES: C=CCCc1cc(F)ccc1Cc1cnc(-c2cc3nc(C)c([C@H](OC(C)(C)C)C(=O)OCC)c(N4CCC(C)(CCC=C)CC4)n3n2)s1]

(S)-Ethyl 2-(2-(5-(2-(but-3-en-1-yl)-4-fluorobenzyl)thiazol-2-yl)-7-(4-(but-3-en-1-yl)-4-methylpiperidin-1-yl)-5-methylpyrazolo[1,5-a]pyrimidin-6-yl)-2-(tert-butoxy)acetate A mixture of (S)-ethyl 2-(2-(5-(2-bromo-4-fluorobenzyl)thiazol-2-yl)-7-(4-(but-3-en-1-yl)-4-methylpiperidin-1-yl)-5-methylpyrazolo[1,5-a]pyrimidin-6-yl)-2-(tert-butoxy)acetate (150 mg, 0.210 mmol), potassium but-3-enyltrifluoroborate (102 mg, 0.631 mmol), Cs$_2$CO$_3$ (206 mg, 0.631 mmol) in toluene (4 mL) and water (0.4 mL) was degassed for 5 min. Pd(OAc)$_2$ (9.45 mg, 0.042 mmol) followed by dicyclohexyl(2',6'-diisopropoxy-[1,1'-biphenyl]-2-yl)phosphine (39.3 mg, 0.084 mmol) was then added and the mixture was heated at 80° C. for 16 h. The reaction mixture was then cooled, diluted with ethyl acetate, washed with water, brine, dried (Na$_2$SO$_4$), filtered and concentrated. The residue was then purified by Biotage (0-30% EtOAc/hexane; 40 g column) to (S)-ethyl 2-(2-(5-(2-(but-3-en-1-yl)-4-fluorobenzyl)thiazol-2-yl)-7-(4-(but-3-en-1-yl)-4-methylpiperidin-1-yl)-5-methylpyrazolo[1,5-a]pyrimidin-6-yl)-2-(tert-butoxy)acetate (115 mg, 0.167 mmol, 79% yield) as thick paste. $^1$H NMR (500 MHz, CDCl$_3$) δ 7.55 (s, 1H), 7.21 (dd, J=8.5, 5.8 Hz, 1H), 7.04 (s, 1H), 6.97-6.87 (m, 2H), 6.02 (br. s., 1H), 5.96-5.80 (m, 2H), 5.13-4.94 (m, 4H), 4.29-4.13 (m, 5H), 2.80-2.74 (m, 2H), 2.64 (s, 3H), 2.38-2.31 (m, 2H), 2.18-2.08 (m, 2H), 1.80-1.69 (m, 1H), 1.64-1.57 (m, 2H), 1.56-1.49 (m, 2H), 1.26 (s, 9H), 1.24 (t, J=7.1 Hz, 3H), 1.14 (br. s., 3H). LCMS (M+H)=689.5.

Example 17 and 18

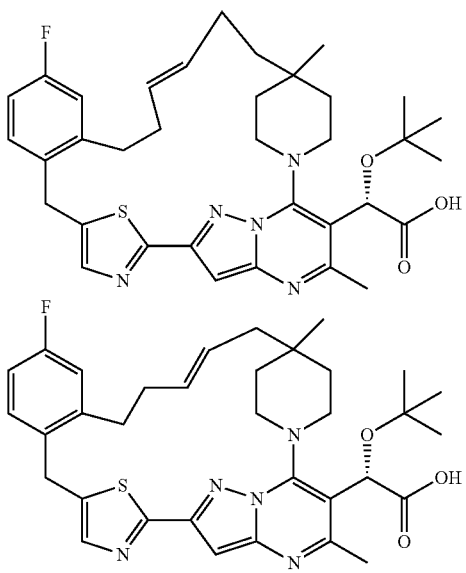

(2S)-2-(tert-Butoxy)-2-[(23E)-18-fluoro-4,27-dimethyl-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,23-decaen-3-yl]acetic acid and (2S)-2-(tert-Butoxy)-2-[(23E)-18-fluoro-4,26-dimethyl-31-thia-1,5,7,8,11-pentaazahexacyclo[24.2.2.1$^{6,9}$.1$^{10,13}$.0$^{2,7}$.0$^{15,20}$]dotriaconta-2,4,6(32),8,10,12,15(20),16,18,23-decaen-3-yl]acetic acid To a solution of (S)-ethyl 2-(2-(5-(2-(but-3-en-1-yl)-4-fluorobenzyl)thiazol-2-yl)-7-(4-(but-3-en-1-yl)-4-methylpiperidin-1-yl)-5-methylpyrazolo[1,5-a]pyrimidin-6-yl)-2-(tert-butoxy)acetate (110 mg, 0.160 mmol) and CuI (30.5 mg, 0.160 mmol) in DCE (100 mL) at 70° C. was added GrubbsII (13.58 mg, 0.016 mmol) and the mixture was heated at 70° C. for 4 h. Mixture was then cooled, filtered through a pad of selica gel and concentrated. The residue was then treated with 1N NaOH (0.640 mL, 0.640 mmol) in MeOH (3 mL) at 70° C. for 3 h. Mixture was then cooled and purified by prep HPLC to afford two products.

Example 17

(2S)-2-(tert-Butoxy)-2-[(23E)-18-fluoro-4,27-dimethyl-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,23-decaen-3-yl]acetic acid (68 mg, 0.108 mmol, 67.3% yield), second eluting on HPLC, off-white solid. $^1$H NMR (500 MHz, DMSO-d$_6$) δ 7.87 (s, 1H), 7.30-7.23 (m, 1H), 7.08 (d, J=11.3 Hz, 1H), 7.00-6.92 (m, 1H), 6.90 (s, 1H), 5.85 (s, 1H), 5.68-5.58 (m, 1H), 5.58-5.48

(m, 1H), 4.28 (t, J=10.8 Hz, 1H), 4.21 (br. s., 2H), 3.75-3.68 (m, 2H), 2.97 (s., 3H), 2.00-1.88 (m, 3H), 1.76 (br. s., 1H), 1.62 (d, J=12.8 Hz, 1H), 1.58-1.45 (m, 3H), 1.45-1.35 (m, 1H), 1.17 (s, 9H), 0.94 (s, 3H). 4 missinf piperidine hydrogens. LCMS (M+H)=632.3.

Example 18

(2S)-2-(tert-Butoxy)-2-[(23E)-18-fluoro-4,26-dimethyl-31-thia-1,5,7,8,11-pentaazahexacyclo [24.2.2.1$^{6,9}$.1$^{10,13}$.0$^{2,7}$.0$^{15,20}$]dotriaconta-2,4,6(32),8,10,12,15(20),16,18,23-decaen-3-yl]acetic acid (4 mg, 6.15 μmol, 3.85% yield) first eluting on HPLC, off-white solid. $^1$H NMR (400 MHz, CDCl$_3$) δ 7.77 (s, 1H), 7.21 (dd, J=8.5, 5.8 Hz, 1H), 7.02 (s, 1H), 6.99-6.95 (m, 1H), 6.92-6.83 (m, 1H), 5.92 (br. s., 1H), 5.85-5.68 (m, 2H), 4.53 (t, J=10.9 Hz, 1H), 4.18 (s, 2H), 4.14-4.00 (m, 1H), 3.58 (br. s., 2H), 3.02 (d, J=11.0 Hz, 1H), 2.68 (s, 3H), 2.58 (d, J=15.1 Hz, 1H), 2.05-1.95 (m, 1H), 1.78-1.48 (m, 5H), 1.32 (s, 9H), 1.31-1.27 (m, 2H), 1.03 (s, 3H). LCMS (M+H)=618.3.

Intermediate 72

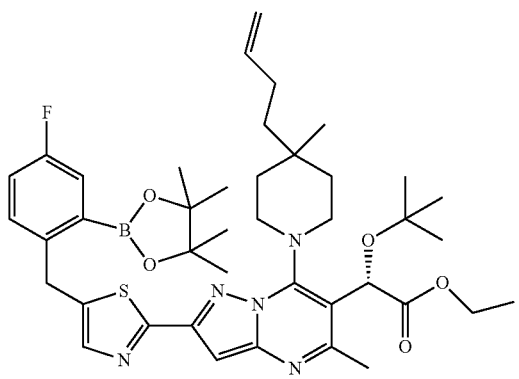

(S)-Ethyl 2-(7-(4-(but-3-en-1-yl)-4-methylpiperidin-1-yl)-2-(5-(4-fluoro-2-(4,4,5,5-tetramethyl-1,3,2-dioxaborolan-2-Abenzyl)thiazol-2-yl)-5-methylpyrazolo[1,5-a]pyrimidin-6-yl)-2-(tert-butoxy)acetate To a solution of (S)-ethyl 2-(2-(5-(2-bromo-4-fluorobenzyl)thiazol-2-yl)-7-(4-(but-3-en-1-yl)-4-methylpiperidin-1-yl)-5-methylpyrazolo[1,5-a]pyrimidin-6-yl)-2-(tert-butoxy)acetate (150 mg, 0.210 mmol) in anhydrous 1,4-dioxane (4 mL) was added bis(pinacolato)diborane (58.8 mg, 0.232 mmol) and potassium acetate (62.0 mg, 0.631 mmol), and the mixture was degassed for 15 min. To the degassed solution was added PdCl$_2$(dppf) (15.40 mg, 0.021 mmol) and degassing continued for a further 5 min, after which the reaction was heated at 90° C. for 16 h. At this oint LCMS indicates completion of reaction and appearance of desired product. After cooling to room temp, water (5 mL) was added and the mixture was extracted with ethyl ether (25 mL), washed with brine (10 mL), dried (Na$_2$SO$_4$), filtered and concentrated. Crude was then purified by Biotage using 0-30% EtOAc/hexane to afford (S)-ethyl 2-(7-(4-(but-3-en-1-yl)-4-methylpiperidin-1-yl)-2-(5-(4-fluoro-2-(4,4,5,5-tetramethyl-1,3,2-dioxaborolan-2-yl)benzyl)thiazol-2-yl)-5-methylpyrazolo[1,5-a]pyrimidin-6-yl)-2-(tert-butoxy) acetate (50 mg, 0.066 mmol, 31.3% yield) as thick paste. Used as is in the next step without further purification. LCMS (M+H)=760.4.

Intermediate 73

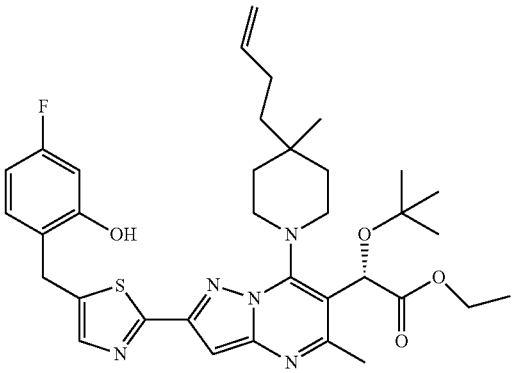

(S)-Ethyl 2-(7-(4-(but-3-en-1-yl)-4-methylpiperidin-1-yl)-2-(5-(4-fluoro-2-hydroxybenzyl)thiazol-2-yl)-5-methylpyrazolo[1,5-a]pyrimidin-6-yl)-2-(tert-butoxy)acetate To a solution of (S)-ethyl 2-(7-(4-(but-3-en-1-yl)-4-methylpiperidin-1-yl)-2-(5-(4-fluoro-2-(4,4,5,5-tetramethyl-1,3,2-dioxaborolan-2-yl)benzyl)thiazol-2-yl)-5-methylpyrazolo[1,5-a]pyrimidin-6-yl)-2-(tert-butoxy)acetate (40 mg, 0.053 mmol) in acetone (1 mL) was added solution of oxone (32.4 mg, 0.053 mmol) inWater (1 mL) and the resulting mixture was stirred at room temp for 1 h. Sat. sodium thiosulfate was then added and the mixture was extracted with ethyl acetate, dried (Na$_2$SO$_4$), filtered and concentrated. The residue was then purified by Biotage (0-50% EtOAc/hexane; 12 g column) to afford (S)-ethyl 2-(7-(4-(but-3-en-1-yl)-4-methylpiperidin-1-yl)-2-(5-(4-fluoro-2-hydroxybenzyl)thiazol-2-yl)-5-methylpyrazolo[1,5-a]pyrimidin-6-yl)-2-(tert-butoxy) acetate (24 mg, 0.037 mmol, 70.2% yield) as viscous oil. $^1$H NMR (500 MHz, CDCl$_3$) δ 7.66 (s, 1H), 7.16 (dd, J=8.4, 6.5 Hz, 1H), 7.07-6.98 (m, 1H), 6.66-6.50 (m, 2H), 6.06-5.99 (m, 1H), 5.92 (dd, J=16.9, 10.2 Hz, 1H), 5.11 (d, J=15.8 Hz, 1H), 5.01 (dd, J=10.2, 1.8 Hz, 1H), 4.28-4.11 (m, 6H), 2.65 (s, 3H), 2.17-2.10 (m, 2H), 1.52 (ddd, J=9.8, 6.3, 3.1 Hz, 2H), 1.31-1.22 (m, 15H), 1.14 (br. s., 3H). LCMS (M+H)=650.3.

Intermediate 74

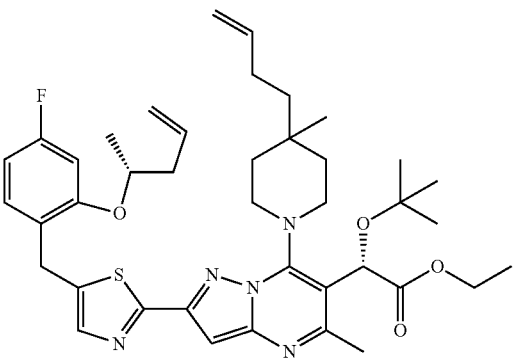

(S)-Ethyl 2-(7-(4-(but-3-en-1-yl)-4-methylpiperidin-1-yl)-2-(5-(4-fluoro-2-((R)-pent-4-en-2-yloxy)benzyl)thiazol-2-yl)-5-methylpyrazolo[1,5-a]pyrimidin-6-yl)-2-(tert-butoxy)acetate To a mixture of (S)-ethyl 2-(7-(4-(but-3-en-1-yl)-4-methylpiperidin-1-yl)-2-(5-(4-fluoro-2-hydroxybenzyl)thiazol-2-yl)-5-methylpyrazolo[1,5-a]pyrimidin-6-yl)-2-(tert-butoxy)acetate (22 mg, 0.034 mmol), (R)-pent-4-en-2-ol (14.58 mg, 0.169 mmol), Ph$_3$P (44.4 mg, 0.169 mmol) in THF (1 mL) was added DIAD (0.033 mL, 0.169 mmol) and the mixture was stirred at rt for 16 h. Water was then added and the mixture was extracted with ether (2×25 mL), dried (Na$_2$SO$_4$), filtered and concentrated. The residue was then purified by Biotage (0-40% EtOAc/hexane) to afford (S)-ethyl 2-(7-(4-(but-3-en-1-yl)-4-methylpiperidin-1-yl)-2-(5-(4-fluoro-2-((R)-pent-4-en-2-yloxy)benzyl)thiazol-2-yl)-5-methylpyrazolo[1,5-a]pyrimidin-6-yl)-2-(tert-butoxy)acetate (15 mg, 0.021 mmol, 61.7% yield) as thick paste. $^1$H NMR (400 MHz, CDCl$_3$) δ 7.65-7.61 (m, 1H), 7.16 (dd, J=8.3, 6.8 Hz, 1H), 7.04 (s, 1H), 6.65-6.60 (m, 2H), 6.05-5.99 (m, 1H), 5.96-5.78 (m, 2H), 5.19-5.00 (m, 5H), 4.29-4.10 (m, 4H), 2.64 (s, 3H), 2.61-2.51 (m, 1H), 2.46-2.34 (m, 1H), 2.18-2.07 (m, 2H), 1.78-1.68 (m, 1H), 1.65-1.59 (m, 2H), 1.58 (s, 3H), 1.57-1.45 (m, 3H), 1.26 (s, 9H), 1.23 (t, J=7.1 Hz, 3H), 1.15 (br. s., 3H). LCMS (M+H)=718.4.

Examples 19 and 20

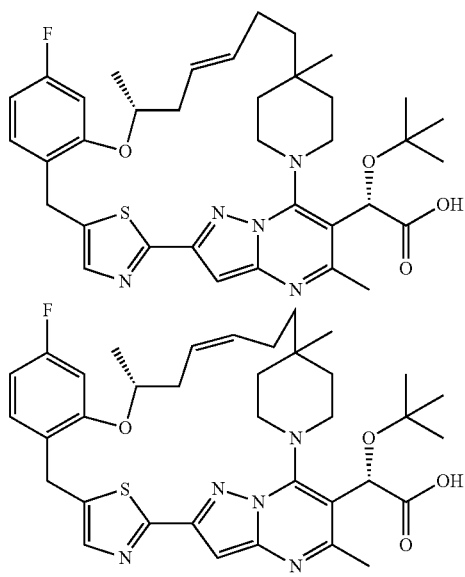

(2S)-2-(tert-Butoxy)-2-[(22R,24E)-18-fluoro-4,22,28-trimethyl-21-oxa-33-thia-1,5,7,8,11-pentaazahexacyclo[26.2.2.1$^{6,9}$.1$^{10,13}$.0$^{2,7}$.0$^{15,20}$]tetratriaconta-2,4,6(34),8,10,12,15(20),16,18,24-decaen-3-yl]acetic acid and (2S)-2-(tert-Butoxy)-2-[(22R,24Z)-18-fluoro-4,22,28-trimethyl-21-oxa-33-thia-1,5,7,8,11-pentaazahexacyclo[26.2.2.1$^{6,9}$.1$^{10,13}$.0$^{2,7}$.0$^{15,20}$]tetratriaconta-2,4,6(34),8,10,12,15(20),16,18,24-decaen-3-yl]acetic acid To a solution of (S)-ethyl 2-(7-(4-(but-3-en-1-yl)-4-methylpiperidin-1-yl)-2-(5-(4-fluoro-2-((R)-pent-4-en-2-yloxy)benzyl)thiazol-2-yl)-5-methylpyrazolo[1,5-a]pyrimidin-6-yl)-2-(tert-butoxy)acetate (15 mg, 0.021 mmol) and CuI (3.98 mg, 0.021 mmol) in DCE (15 mL) at 70° C. was added GrubbsII (1.774 mg, 2.089 μmol) and the mixture was heated at 70° C. for 4 h. Mixture was then cooled, filtered through a pad of selica gel and concentrated. The residue was then treated with 1N NaOH (0.084 mL, 0.084 mmol) in MeOH (3 mL) at 70° C. for 3 h. Mixture was then cooled and purified by prep HPLC to afford two products.

Example 19

(2S)-2-(tert-Butoxy)-2-[(22R,24E)-18-fluoro-4,22,28-trimethyl-21-oxa-33-thia-1,5,7,8,11-pentaazahexacyclo[26.2.2.1$^{6,9}$.1$^{10,13}$.0$^{2,7}$.0$^{15,20}$]tetratriaconta-2,4,6(34),8,10,12,15(20),16,18,24-decaen-3-yl]acetic acid (3.3 mg, 4.99 μmol, 23.87% yield). $^1$H NMR (500 MHz, DMSO-d$_6$) δ 7.90 (s, 1H), 7.37 (t, J=7.5 Hz, 1H), 7.02 (d, J=10.4 Hz, 1H), 6.92 (s, 1H), 6.71 (t, J=7.6 Hz, 1H), 5.92-5.82 (m, 2H), 5.82-5.73 (m, 1H), 4.69 (br. s., 1H), 4.39-4.29 (m, 1H), 4.21 (d, J=14.0 Hz, 1H), 4.08 (d, J=14.0 Hz, 1H), 3.64 (br. s., 1H), 2.62 (d, J=15.9 Hz, 1H), 2.53 (s, 3H), 2.01 (br. s., 2H), 1.72 (d, J=11.9 Hz, 1H), 1.60 (br. s., 1H), 1.58-1.48 (m, 2H), 1.44 (d, J=11.3 Hz, 1H), 1.22-1.13 (m, 12H), 0.99 (s, 3H). LCMS (M+H)=662.7.

Example 20

(2S)-2-(tert-Butoxy)-2-[(22R,24Z)-18-fluoro-4,22,28-trimethyl-21-oxa-33-thia-1,5,7,8,11-pentaazahexacyclo[26.2.2.1$^{6,9}$.1$^{10,13}$.0$^{2,7}$.0$^{15,20}$]tetratriaconta-2,4,6(34),8,10,12,15(20),16,18,24-decaen-3-yl]acetic acid (1.3 mg, 1.964 μmol, 9.40% yield). $^1$H NMR (400 MHz, METHANOL-d$_4$) δ 7.70 (s, 1H), 7.31 (dd, J=8.5, 6.8 Hz, 1H), 6.90 (s, 1H), 6.75 (dd, J=11.4, 2.4 Hz, 1H), 6.60 (td, J=8.3, 2.4 Hz, 1H), 5.81-5.67 (m, 1H), 5.61 (s, 1H), 5.57-5.41 (m, 1H), 4.66-4.52 (m, 1H), 4.25-4.15 (m, 1H), 4.12 (d, J=4.0 Hz, 2H), 3.85 (t, J=8.5 Hz, 1H), 3.74-3.61 (m, 1H), 3.17-3.05 (m, 1H), 2.90-2.79 (m, 1H), 2.70 (dt, J=13.8, 9.2 Hz, 1H), 2.59 (s, 3H), 2.48-2.30 (m, 1H), 2.13 (br. s., 1H), 2.04-1.91 (m, 1H), 1.86-1.74 (m, 1H), 1.72-1.60 (m, 1H), 1.60-1.49 (m, 2H), 1.36 (d, J=6.0 Hz, 3H), 1.22 (s, 9H), 1.11 (s, 3H). LCMS (M+H)=662.7.

Intermediate 75

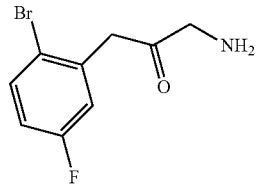

1-Amino-3-(2-bromo-5-fluorophenyl)propan-2-one.HCl

To a −78° C. solution of 1M LiHMDS/THF (35.6 mL, 35.6 mmol) in THF (100 mL) was added dropwise THF (10 mL) solution of methyl 2-isocyanoacetate (3.19 g, 32.2 mmol) over 5 min. After 30 min, a THF (20 mL) solution of 2-(2-bromo-5-fluorophenyl)acetyl chloride (5.4 g, 21.47 mmol) was added over 5 min. After 1 h, the cold bath was removed and the mixture was stirred at rom temp for 16 h. Water (25 mL) was then added and the mixture was extracted with ethyl acetate (100 mL), washed with brine (50 mL), dried (Na$_2$SO$_4$), filtered and concentrated. The residue was then refluxed with conc. HCl (40 mL) for 3 h. Mixture was then cooled to room temperature and concentraetd. The residue was then triturated with ethyl acetate and dried under high vac to afford 1-amino-3-(2-bromo-5-fluorophenyl)propan-2-one.HCl (3.5 g, 12.39 mmol, 57.7% yield) as tan solid. $^1$H NMR (500 MHz, DMSO-d$_6$) δ 7.68 (dd, J=8.8, 5.4 Hz, 1H), 7.34-7.28 (m, 1H), 7.16 (td, J=8.6, 3.2 Hz, 1H), 4.13-4.06 (m, 4H). LCMS (M+2H)=248.0.

Intermediate 76

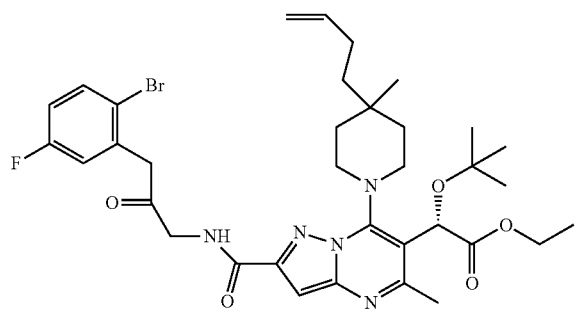

(S)-Ethyl 2-(24(3-(2-bromo-5-fluorophenyl)-2-oxopropyl)carbamoyl)-7-(4-(but-3-en-1-yl)-4-methylpiperidin-1-yl)-5-methylpyrazolo[1,5-a]pyrimidin-6-yl)-2-(tert-butoxy)acetate To a solution of (S)-7-(4-(but-3-en-1-yl)-4-methylpiperidin-1-yl)-6-(1-(tert-butoxy)-2-ethoxy-2-oxo ethyl)-5-methylpyrazolo[1,5-a]pyrimidine-2-carboxylic acid (700 mg, 1.439 mmol) in CH$_2$Cl$_2$ (8 mL) was added oxalyl chloride (0.791 mL, 1.582 mmol) 1 drop of DMF was then added and the mixture was stirred at room temp for 1 h. The crude acid chloride was then added to a pre-stirred solution of 1-amino-3-(2-bromo-5-fluorophenyl)propan-2-one.HCl (610 mg, 2.158 mmol) and DIEA (1.507 mL, 8.63 mmol) in CH$_2$Cl$_2$ (8.00 mL) and the resulting solution was stirred at room temperature for 4 h. Water was then added and the mixture was extracted with dichloromethane, dried (Na$_2$SO$_4$), filtered and concentrated. The crude was then purified by flash column chromatograpgy on silica gel column using (5-70% EtOAc/Hexane as eluant) to afford (S)-ethyl 2-(2-((3-(2-bromo-5-fluorophenyl)-2-oxopropyl)carb amoyl)-7-(4-(but-3-en-1-yl)-4-methylpiperidin-1-yl)-5-methylpyrazolo[1,5-a]pyrimidin-6-yl)-2-(tert-butoxy)acetate (720 mg, 1.007 mmol, 70.0% yield) as light yellow solid. $^1$H NMR (500 MHz, CDCl$_3$) δ 7.83 (t, J=4.7 Hz, 1H), 7.58 (dd, J=8.8, 5.2 Hz, 1H), 7.09-7.05 (m, 1H), 7.00-6.93 (m, 2H), 5.99 (br. s., 1H), 5.89 (ddt, J=17.0, 10.3, 6.5 Hz, 1H), 5.06 (d, J=17.0 Hz, 1H), 4.95 (br. s., 1H), 4.50 (br. s., 1H), 4.29-4.15 (m, 2H), 4.00 (s, 2H), 2.65 (s, 3H), 2.16-2.09 (m, 2H), 1.76 (br. s., 1H), 1.67-1.53 (m, 6H), 1.28-1.21 (m, 12H), 1.17 (s, 3H). 4 missing piperidine protons. LCMS (M+2H)=716.3.

Intermediate 77

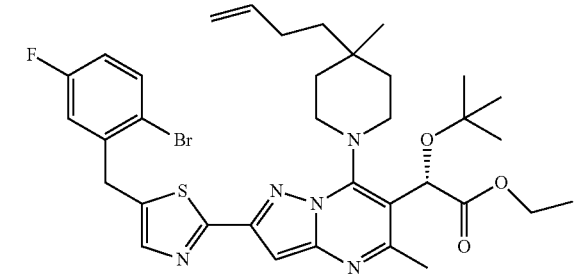

(S)-Ethyl 2-(2-(5-(2-bromo-5-fluorobenzyl)thiazol-2-yl)-7-(4-(but-3-en-1-yl)-4-methylpiperidin-1-yl)-5-methylpyrazolo[1,5-a]pyrimidin-6-yl)-2-(tert-butoxy)acetate To a solution of (S)-ethyl 2-(2-((3-(2-bromo-5-fluorophenyl)-2-oxopropyl)carbamoyl)-7-(4-(but-3-en-1-yl)-4-methylpiperidin-1-yl)-5-methylpyrazolo[1,5-a]pyrimidin-6-yl)-2-(tert-butoxy)acetate (750 mg, 1.049 mmol) in toluene was added Lawesson's Reagent (467 mg, 1.154 mmol) and stirr for 15 min at rt, and 70° C. for 3 h. At this point LCMS indicates completion of reaction. Mixture was then cooled, concentrated and the residue was purified by Biotage (0-30% EtOAc/hexane; 40 g column) to afford (S)-ethyl 2-(2-(5-(2-bromo-5-fluorobenzyl)thiazol-2-yl)-7-(4-(but-3-en-1-yl)-4-methylpiperidin-1-yl)-5-methylpyrazolo[1,5-a]pyrimidin-6-yl)-2-(tert-butoxy)acetate (500 mg, 0.702 mmol, 66.8% yield) as light yellow solid. $^1$H NMR (500 MHz, CDCl$_3$) δ 7.73 (s, 1H), 7.57 (dd, J=8.8, 5.4 Hz, 1H), 7.13 (s, 1H), 7.03 (dd, J=9.1, 3.0 Hz, 1H), 6.91 (td, J=8.3, 3.0 Hz, 1H), 5.97 (s, 1H), 5.94-5.86 (m, 2H), 5.09 (dd, J=17.2, 1.9 Hz, 1H), 4.99 (d, J=10.1 Hz, 1H), 4.33 (s, 2H), 4.29-4.15 (m, 2H), 2.68 (s, 3H), 2.18-2.12 (m, 2H), 1.77 (br. s., 1H), 1.67-1.62 (m, 2H), 1.55 (dd, J=9.1, 3.5 Hz, 3H), 1.29-1.22 (m, 12H), 1.16 (s, 3H). LCMS (M+2H)=714.3.

Intermediate 78

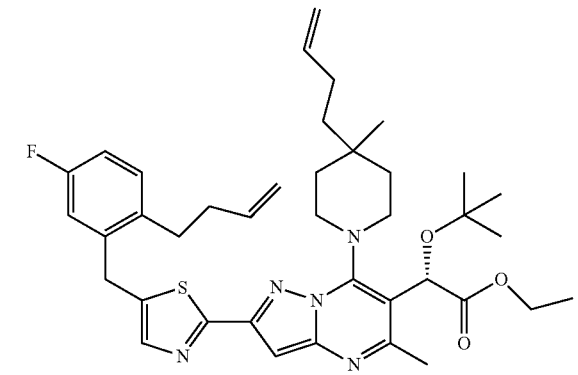

(S)-Ethyl 2-(7-(4-(but-3-en-1-yl)-4-methylpiperidin-1-yl)-2-(5-(2-(but-3-en-1-yl)-5-fluorobenzyl)thiazol-2-yl)-5-methylpyrazolo[1,5-a]pyrimidin-6-yl)-2-(tert-butoxy)acetate A mixture of (S)-ethyl 2-(2-(5-(2-bromo-5-fluorobenzyl)thiazol-2-yl)-7-(4-(but-3-en-1-yl)-4-methylpiperidin-1-yl)-

5-methylpyrazolo[1,5-a]pyrimidin-6-yl)-2-(tert-butoxy)acetate (150 mg, 0.210 mmol), but-3-enyltrifluoroborate (102 mg, 0.631 mmol), Cs$_2$CO$_3$ (206 mg, 0.631 mmol) in toluene (4 mL) and water (0.4 mL) was degassed for 5 min. Pd(OAc)$_2$ (9.45 mg, 0.042 mmol) followed by dicyclohexyl (2',6'-diisopropoxy-[1,1'-biphenyl]-2-yl)phosphine (39.3 mg, 0.084 mmol) was then added and the mixture was heated at 80° C. for 16 h. The reaction mixture was then cooled, diluted with ethyl acetate, washed with water, brine, dried (Na$_2$SO$_4$), filtered and concentrated. The residue was then purified by Biotage (0-30% EtOAc/hexane; 40 g column) to afford (S)-ethyl 2-(7-(4-(but-3-en-1-yl)-4-methylpiperidin-1-yl)-2-(5-(2-(but-3-en-1-yl)-5-fluorobenzyl)thiazol-2-yl)-5-methylpyrazolo[1,5-a]pyrimidin-6-yl)-2-(tert-butoxy)acetate (110 mg, 0.160 mmol, 76% yield) as thick paste. $^1$H NMR (400 MHz, CDCl$_3$) δ 7.58 (t, J=1.0 Hz, 1H), 7.27-7.14 (m, 1H), 7.05 (s, 1H), 7.01-6.87 (m, 2H), 6.02 (s, 1H), 5.99-5.78 (m, 2H), 5.14-4.94 (m, 4H), 4.26-4.05 (m, 5H), 2.79-2.72 (m, 1H), 2.65 (s, 3H), 2.34 (td, J=7.9, 6.5 Hz, 1H), 2.19-2.09 (m, 2H), 1.80-1.70 (m, 1H), 1.66-1.47 (m, 6H), 1.31-1.20 (m, 12H), 1.15 (br. s., 3H). LCMS (M+H)=689.1.

Examples 21, 22 and 23

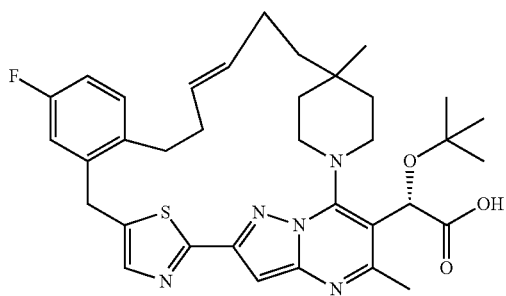

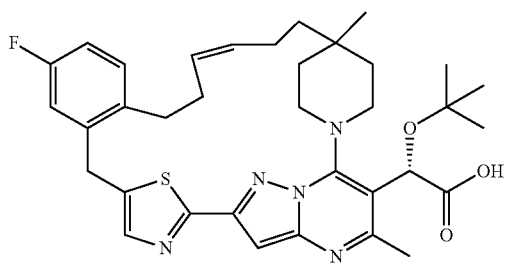

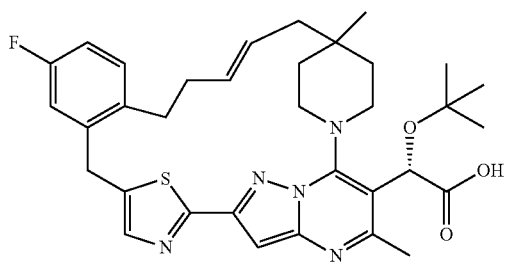

(2S)-2-(tert-Butoxy)-2-[(23E)-17-fluoro-4,27-dimethyl-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,23-decaen-3-yl]acetic acid, (2S)-2-(tert-Butoxy)-2-[(23Z)-17-fluoro-4,27-dimethyl-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,23-decaen-3-yl]acetic acid and (2S)-2-(tert-Butoxy)-2-[(23E)-17-fluoro-4,26-dimethyl-31-thia-1,5,7,8,11-pentaazahexacyclo[24.2.2.1$^{6,9}$.1$^{10,13}$.0$^{2,7}$.0$^{15,20}$]dotriaconta-2,4,6(32),8,10,12,15(20),16,18,23-decaen-3-yl]acetic acid To a solution of (S)-ethyl 2-(7-(4-(but-3-en-1-yl)-4-methylpiperidin-1-yl)-2-(5-(2-(but-3-en-1-yl)-5-fluorobenzyl)thiazol-2-yl)-5-methylpyrazolo[1,5-a]pyrimidin-6-yl)-2-(tert-butoxy)acetate (110 mg, 0.160 mmol) and CuI (30.5 mg, 0.160 mmol) in DCE (100 mL) at 70° C. was added Grubbs II (13.58 mg, 0.016 mmol) and the mixture was heated at 70° C. for 4 h. Mixture was then cooled, filtered through a pad of selica gel and concentrated. The residue was then treated with 1N NaOH (0.640 mL, 0.640 mmol) in MeOH (3 mL) at 70° C. for 3 h. Mixture was then cooled and purified by prep HPLC to afford three products.

Example 21

Third eluting on HPLC (major), (2S)-2-(tert-butoxy)-2-[(23E)-17-fluoro-4,27-dimethyl-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,23-decaen-3-yl]acetic acid (43 mg, 0.068 mmol, 42.6% yield). $^1$H NMR (500 MHz, DMSO-d$_6$) δ 7.90 (s, 1H), 7.33-7.25 (m, 1H), 7.17-6.99 (m, 2H), 6.93 (s, 1H), 5.91 (s, 1H), 5.67-5.58 (m, 1H), 5.58-5.47 (m, 1H), 4.41-4.17 (m, 3H), 3.74 (t, J=11.1 Hz, 1H), 2.95 (d, J=7.0 Hz, 2H), 2.52 (br. s., 3H), 1.92 (br. s., 1H), 1.77 (br. s., 1H), 1.66-1.34 (m, 5H), 1.19 (s, 9H), 0.95 (s, 3H). 4 misssing piperidine hydrogens. LCMS (M+H)=632.4.

Example 22 first eluting, (2S)-2-(tert-butoxy)-2-[(23Z)-17-fluoro-4,27-dimethyl-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,23-decaen-3-yl]acetic acid (5.2 mg, 8.23 μmol, 5.15% yield). $^1$H NMR (500 MHz, DMSO-d$_6$) δ 7.90 (s, 1H), 7.38 (t, J=6.7 Hz, 1H), 7.16-7.00 (m, 2H), 6.86 (s, 1H), 5.95-5.80 (m, 1H), 5.77 (br. s., 1H), 5.71 (d, J=15.9 Hz, 1H), 4.36 (d, J=15.0 Hz, 2H), 4.23 (d, J=15.0 Hz, 1H), 3.96 (br. s., 1H), 3.81 (br. s., 1H), 2.96 (br. s., 1H), 2.53 (s, 3H), 1.99-1.88 (m, 2H), 1.52 (d, J=11.3 Hz, 1H), 1.49-1.37 (m, 2H), 1.33 (d, J=5.8 Hz, 3H), 1.18 (s, 9H), 0.96 (br. s., 3H). LCMS (M+H)=632.4.

Example 23

Second eluting, (2S)-2-(tert-Butoxy)-2-[(23E)-17-fluoro-4,26-dimethyl-31-thia-1,5,7,8,11-pentaazahexacyclo[24.2.2.1$^{6,9}$.1$^{10,13}$.0$^{2,7}$.0$^{15,20}$]dotriaconta-2,4,6(32),8,10,12,15(20),16,18,23-decaen-3-yl]acetic acid (1.9 mg, 3.08 μmol, 1.923% yield). $^1$H NMR (400 MHz, METHANOL-d$_4$) δ 7.81 (s, 1H), 7.26 (dd, J=8.5, 5.8 Hz, 1H), 7.03-6.97 (m, 1H), 6.95-6.90 (m, 1H), 6.89 (s, 1H), 6.00 (s, 1H), 5.83-5.64 (m, 2H), 4.52 (t, J=10.8 Hz, 1H), 4.30-4.14 (m, 1H), 4.05-3.90 (m, 1H), 3.61-3.50 (m, 2H), 3.13 (d, J=10.0 Hz, 1H), 2.65 (s, 3H), 2.63-2.54 (m, 1H), 2.09 (d, J=6.3 Hz, 1H), 1.76-1.61

(m, 2H), 1.58-1.50 (m, 1H), 1.25 (s, 9H), 1.01 (s, 3H). 4 misssing piperidine hydrogens. LCMS (M+H)=618.3.

Intermediate 79

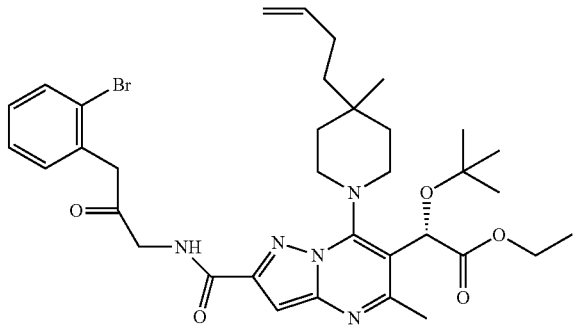

(S)-Ethyl 2-(24(3-(2-bromophenyl)-2-oxopropyl) carbamoyl)-7-(4-(but-3-en-1-yl)-4-methylpiperidin-1-yl)-5-methylpyrazolo[1,5-a]pyrimidin-6-yl)-2-(tert-butoxy)acetate To a solution of (S)-7-(4-(but-3-en-1-yl)-4-methylpiperidin-1-yl)-6-(1-(tert-butoxy)-2-ethoxy-2-oxoethyl)-5-methylpyrazolo[1,5-a]pyrimidine-2-carboxylic acid (500 mg, 1.028 mmol) in $CH_2Cl_2$ (7 mL, contains cat. DMF) was added oxalyl chloride (0.565 mL, 1.130 mmol) and the mixture was stirred at room temp for 1 h. The crude acid chloride was then added to a pre-stirred solution of 1-amino-3-(2-bromophenyl)propan-2-oneFIC1 (408 mg, 1.541 mmol) and DIEA (1.077 mL, 6.17 mmol) in $CH_2Cl_2$ (7.0 mL) and the resulting solution was stirred at room temperature for 4 h. Water was then added and the mixture was extracted with dichloromethane, dried ($Na_2SO_4$), filtered and concentrated. The crude was then purified by flash column chromatograpgy on silica gel column using (5-70% EtOAc/Hexane as eluant) to afford (S)-ethyl 2-(2-((3-(2-bromophenyl)-2-oxopropyl)carbamoyl)-7-(4-(but-3-en-1-yl)-4-methylpiperidin-1-yl)-5-methylpyrazolo[1,5-a]pyrimidin-6-yl)-2-(tert-butoxy)acetate (578 mg, 0.830 mmol, 81% yield) as light yellow solid. $^1$H NMR (500 MHz, $CDCl_3$) 7.84 (t, J=4.6 Hz, 1H), 7.63 (dd, J=8.0, 1.0 Hz, 1H), 7.38-7.30 (m, 2H), 7.25-7.19 (m, 1H), 7.07 (s, 1H), 5.99 (br. s., 1H), 5.89 (ddt, J=17.0, 10.3, 6.5 Hz, 1H), 5.06 (d, J=17.0 Hz, 1H), 4.95 (br. s., 1H), 4.47 (dd, J=4.7, 2.1 Hz, 2H), 4.29-4.12 (m, 3H), 4.01 (s, 2H), 2.65 (s, 3H), 2.18-2.09 (m, 2H), 1.75 (br. s., 1H), 1.63 (t, J=5.5 Hz, 2H), 1.57-1.48 (m, 2H), 1.26 (s, 9H), 1.26-1.22 (m, 3H), 1.17 (br. s., 3H). 4 missing piperidine hydrogens. LCMS (M+2H)=698.5.

Intermediate 80

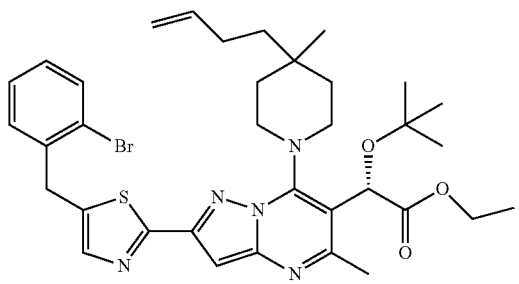

(S)-Ethyl 2-(2-(5-(2-bromobenzyl)thiazol-2-yl)-7-(4-(but-3-en-1-yl)-4-methylpiperidin-1-yl)-5-methylpyrazolo[1,5-a]pyrimidin-6-yl)-2-(tert-butoxy)acetate To a solution of (S)-ethyl 2-(2-((3-(2-bromophenyl)-2-oxopropyl)carbamoyl)-7-(4-(but-3-en-1-yl)-4-methylpiperidin-1-yl)-5-methylpyrazolo[1,5-a]pyrimidin-6-yl)-2-(tert-butoxy)acetate (570 mg, 0.818 mmol) in toluene was added Lawesson's Reagent (364 mg, 0.900 mmol) and stirr for 15 min at rt, and 60° C. for 5 h. At this point LCMS indicates completion of reaction. Mixture was then cooled, concentrated and the residue was purified by Biotage (0-30% EtOAc/hexane; 40 g column) to afford (S)-ethyl 2-(2-(5-(2-bromobenzyl)thiazol-2-yl)-7-(4-(but-3-en-1-yl)-4-methylpiperidin-1-yl)-5-methylpyrazolo[1,5-a]pyrimidin-6-yl)-2-(tert-butoxy)acetate (350 mg, 0.504 mmol, 61.6% yield) as light yellow solid. $^1$H NMR (400 MHz, $CDCl_3$) δ 7.67 (s, 1H), 7.62 (d, J=7.8 Hz, 1H), 7.34-7.30 (m, 2H), 7.17 (d, J=3.0 Hz, 1H), 7.05 (s, 1H), 6.03 (s, 1H), 5.09 (dd, J=17.2, 1.9 Hz, 1H), 5.00 (s, 1H), 4.36 (s, 2H), 4.29-4.11 (m, 3H), 2.65 (s, 3H), 2.12 (br. s., 2H), 1.76-1.72 (m, 1H), 1.65-1.60 (m, 3H), 1.54 (br. s., 2H), 1.27 (s, 9H), 1.24 (t, J=7.2 Hz, 3H), 1.15 (br. s., 3H). 4 missing piperidine hydrogens. LCMS (M+2H)=696.4.

Intermediate 81

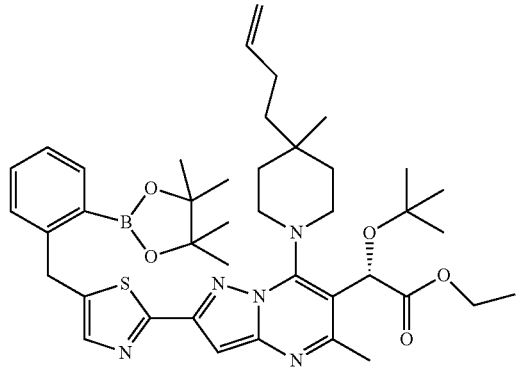

(S)-Ethyl 2-(7-(4-(but-3-en-1-yl)-4-methylpiperidin-1-yl)-5-methyl-2-(5-(2-(4,4,5,5-tetramethyl-1,3,2-dioxaborolan-2-yl)benzyl)thiazol-2-yppyrazolo[1,5-a]pyrimidin-6-yl)-2-(tert-butoxy)acetate: To a solution of (S)-ethyl 2-(2-(5-(2-bromobenzyl)thiazol-2-yl)-7-(4-(but-3-en-1-yl)-4-methylpiperidin-1-yl)-5-methylpyrazolo[1,5-a]pyrimidin-6-yl)-2-(tert-butoxy)acetate (340 mg, 0.489 mmol) in anhydrous DMF (5 mL) was added bis(pinacolato)diborane (137 mg, 0.538 mmol) and potassium acetate (144 mg, 1.468 mmol), and the mixture was degassed for 15 min. To the degassed solution was added $PdCl_2(dppf).CH_2Cl_2$ adduct (40.0 mg, 0.049 mmol) and degassing continued for a further 5 min, after which the reaction was heated at 90° C. for 16 h. At this point LCMS indicates completion of reaction and appearance of desired product. After cooling to room temp, water (5 mL) was added and the mixture was extracted with ethyl ether (25 mL), washed with brine (10 mL), dried ($Na_2SO_4$), filtered and concentrated. Crude was then purified by Biotage using 0-30% EtOAc/hexane to afford (S)-ethyl 2-(7-(4-(but-3-en-1-yl)-4-methylpiperidin-1-yl)-5-methyl-2-(5-(2-(4,4,5,5-tetramethyl-1,3,2-dioxaborolan-2-yl)benzyl)thiazol-2-yl)pyrazolo[1,5-a]pyrimidin-6-yl)-2-(tert-butoxy)acetate as thick paste. $^1$H NMR (400 MHz, $CDCl_3$) δ

7.88 (dd, J=7.4, 1.1 Hz, 1H), 7.64 (s, 1H), 7.47-7.41 (m, 1H), 7.37-7.24 (m, 2H), 7.03 (s, 1H), 6.01 (s, 1H), 5.91 (dtd, J=16.9, 10.4, 6.4 Hz, 1H), 5.14-5.07 (m, 1H), 5.00 (dd, J=10.2, 1.9 Hz, 1H), 4.55 (s, 2H), 4.30-4.09 (m, 3H), 2.63 (s, 3H), 2.18-2.08 (m, 2H), 1.79-1.53 (m, 5H), 1.37 (s, 12H), 1.26 (s, 9H), 1.25-1.21 (m, 3H), 1.14 (br. s., 3H). 4 missing piperidine hydrogens. LCMS (M+H)=742.6.

Intermediate 82

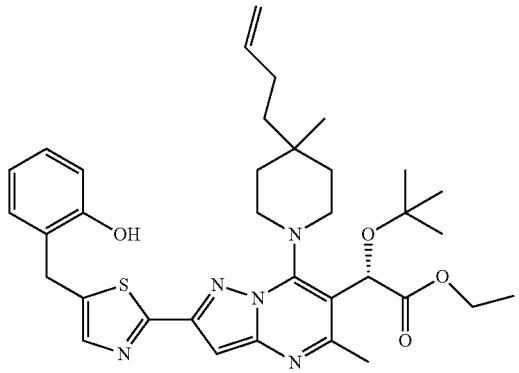

(S)-Ethyl 2-(7-(4-(but-3-en-1-yl)-4-methylpiperidin-1-yl)-2-(5-(2-hydroxybenzyl)thiazol-2-yl)-5-methylpyrazolo[1,5-c]pyrimidin-6-yl)-2-(tert-butoxy)acetate To a solution of (S)-ethyl 2-(7-(4-(but-3-en-1-yl)-4-methylpiperidin-1-yl)-5-methyl-2-(5-(2-(4,4,5,5-tetramethyl-1,3,2-dioxaborolan-2-yl)benzyl)thiazol-2-yl)pyrazolo[1,5-a]pyrimidin-6-yl)-2-(tert-butoxy)acetate (65 mg, 0.088 mmol) in acetone (2 mL) was added solution of oxone (53.9 mg, 0.088 mmol) inWater (2 mL) and the resulting mixture was stirred at room temp for 1 h. Sat. sodium thiosulfate was then added and the mixture was extracted with ethyl acetate, dried (Na$_2$SO$_4$), filtered and concentrated to aford (S)-ethyl 2-(7-(4-(but-3-en-1-yl)-4-methylpiperidin-1-yl)-2-(5-(2-hydroxybenzyl)thiazol-2-yl)-5-methylpyrazolo[1,5-a]pyrimidin-6-yl)-2-(tert-butoxy)acetate (50 mg, 0.079 mmol, 90% yield) as viscous oil. The crude was used in the next step without further purification. $^1$H NMR (400 MHz, CDCl$_3$) δ 7.68 (s, 1H), 7.22 (dd, J=7.5, 1.5 Hz, 1H), 7.18-7.11 (m, 1H), 7.05 (s, 1H), 6.96-6.90 (m, 1H), 6.82 (d, J=7.8 Hz, 1H), 6.02 (s, 1H), 5.98-5.84 (m, 1H), 5.57 (br. s., 1H), 5.15-5.07 (m, 1H), 5.01 (d, J=10.3 Hz, 1H), 4.28-4.10 (m, 6H), 2.64 (s, 3H), 2.22-2.09 (m, 2H), 1.73 (br. s., 1H), 1.55-1.46 (m, 3H), 1.27 (s, 9H), 1.25-1.21 (m, 3H), 1.14 (br. s., 3H). 4 missing piperidine hydrogens. LCMS (M+H)=632.6.

Intermediate 83

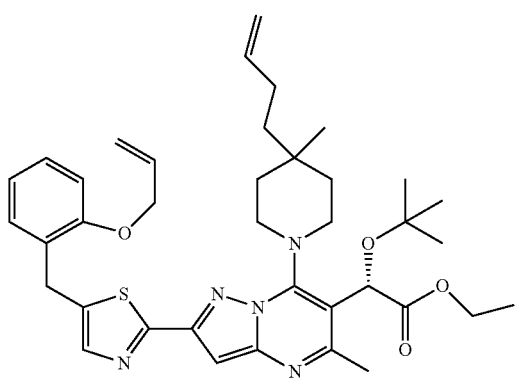

(S)-Ethyl 2-(2-(5-(2-(allyloxy)benzyl)thiazol-2-yl)-7-(4-(but-3-en-1-yl)-4-methylpiperidin-1-yl)-5-methylpyrazolo[1,5-a]pyrimidin-6-yl)-2-(tert-butoxy)acetate A solution of (S)-ethyl 2-(7-(4-(but-3-en-1-yl)-4-methylpiperidin-1-yl)-2-(5-(2-hydroxybenzyl)thiazol-2-yl)-5-methylpyrazolo[1,5-a]pyrimidin-6-yl)-2-(tert-butoxy)acetate (50 mg, 0.079 mmol), allyl alchohol (13.79 mg, 0.237 mmol) and triphenylphosphine (62.3 mg, 0.237 mmol) in dry THF (2 mL) was treated with DEAD (0.038 mL, 0.237 mmol), and the reaction was and the reaction was stirred for 3 hr. Water was then added and the mixture was extracted with ether (25 mL), dried (Na$_2$SO$_4$), filtered and concentrated. The residue was purified by Biotage (0-30% EtOAc/hexane) to afford (S)-ethyl 2-(2-(5-(2-(allyloxy)benzyl)thiazol-2-yl)-7-(4-(but-3-en-1-yl)-4-methylpiperidin-1-yl)-5-methylpyrazolo[1,5-a]pyrimidin-6-yl)-2-(tert-butoxy) acetate (35 mg, 0.052 mmol, 65.8% yield) as thick paste. $^1$H NMR (400 MHz, CDCl$_3$) δ 7.68-7.66 (m, 1H), 7.39-7.30 (m, 1H), 7.27-7.21 (m, 1H), 7.03 (s, 1H), 6.97-6.86 (m, 1H), 6.53 (br. s., 1H), 6.11 (ddt, J=17.3, 10.5, 5.2 Hz, 1H), 6.02 (s, 1H), 5.98-5.75 (m, 3H), 5.45 (dd, J=17.3, 1.5 Hz, 1H), 5.29 (q, J=1.4 Hz, 1H), 5.24 (dd, J=6.9, 1.4 Hz, 2H), 5.20 (s, 2H), 5.13-5.06 (m, 1H), 5.00 (d, J=10.3 Hz, 1H), 4.62 (dt, J=5.2, 1.4 Hz, 2H), 4.26-4.19 (m, 2H), 2.64 (s, 3H), 2.24-2.07 (m, 2H), 1.54-1.47 (m, 2H), 1.26 (s, 9H), 1.23 (t, J=7.2 Hz, 3H), 1.16 (br. s., 3H). 4 missing piperidine hydrogens. LCMS (M+H)=672.6.

Example 24

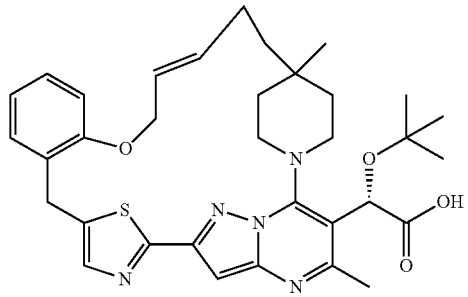 [SMILES: Cc1nc2cc3nn2c(c1[C@H](OC(C)(C)C)C(=O)O)N1CCC(C)(CC/C=C/COc2ccccc2Cc2cnc-3s2)CC1]

(2S)-2-(tert-Butoxy)-2-[(23E)-4,27-dimethyl-21-oxa-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,23-decaen-3-yl]acetic Acid To a solution of (S)-ethyl 2-(2-(5-(2-(allyloxy)benzyl)thiazol-2-yl)-7-(4-(but-3-en-1-yl)-4-methylpiperidin-1-yl)-5-methylpyrazolo[1,5-a]pyrimidin-6-yl)-2-(tert-butoxy)acetate (35 mg, 0.052 mmol) and CuI (9.92 mg, 0.052 mmol) in DCE (35 mL) at 70° C. was added Grubbs II (4.42 mg, 5.21 μmol) and the mixture was heated at 70° C. for 4 h. Mixture was cooled and the solvent was removed by rotary evaporator and the residue was purified by biotage (0-30% EtOAc/hexane). Product fractions were pooled and concentrated under reduced pressure, affording desired ester, which was treated with 1N NaOH (0.208 mL, 0.208 mmol) in MeOH (3 mL) at 70° C. for 3 h. Mixture was then cooled and purified by prep HPLC to afford desired product (10.9 mg, 0.017 mmol, 32.3% yield). $^1$H NMR (500 MHz, DMSO-d$_6$)

δ 7.84 (s, 1H), 7.40-7.28 (m, 1H), 7.20 (t, J=7.8 Hz, 1H), 7.04 (d, J=8.2 Hz, 1H), 6.90 (s, 1H), 6.86 (t, J=7.2 Hz, 1H), 6.11-6.02 (m, 1H), 5.92 (s, 1H), 5.90-5.83 (m, 1H), 4.81-4.72 (m, 2H), 4.36 (t, J=12.5 Hz, 1H), 4.17 (d, J=6.1 Hz, 2H), 3.76 (t, J=10.7 Hz, 1H), 2.99 (d, J=10.7 Hz, 1H), 2.54 (s, 3H), 2.06 (d, J=5.5 Hz, 3H), 1.96-1.80 (m, 2H), 1.71-1.56 (m, 1H), 1.56-1.40 (m, 2H), 1.19 (s, 9H), 0.98 (s, 3H). LCMS (M+H)=616.4.

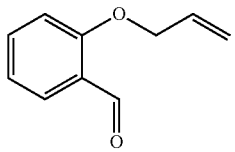

Intermediate 84

2-(Allyloxy)benzaldehyde

To a solution of 2-hydroxybenzaldehyde (15 g, 123 mmol, 1 equiv) and allylbromide (11.7 mL, 135 mmol, 1.1 equiv) in MeCN (250 mL) was added K₂CO₃ (23.8 g, 172 mmol, 1.4 equiv). The yellow slurry was then heated to reflux. After 2 h, TLC indicated complete conversion. The now pale cream colored mixture was removed from heat and filtered. The filtrate was concentrated in vacuo to provide 2-(allyloxy)benzaldehyde (19.15 g, 96%) as a yellow oil. 1H NMR (400 MHz, CDCl3) δ 10.64-10.49 (m, 1H), 7.86 (dd, J=7.7, 1.9 Hz, 1H), 7.61-7.49 (m, 1H), 7.11-6.90 (m, 2H), 6.10 (ddt, J=17.3, 10.5, 5.2 Hz, 1H), 5.47 (dq, J=17.3, 1.5 Hz, 1H), 5.36 (dq, J=10.5, 1.4 Hz, 1H), 4.68 (dt, J=5.1, 1.6 Hz, 2H).

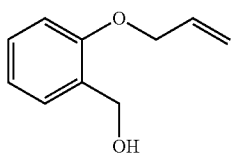

Intermediate 85

(2-(Allyloxy)phenyl)methanol

To a solution of 2-(allyloxy)benzaldehyde (19.15 g, 118 mmol, 1 equiv) in MeOH (240 mL) was added NaBH₄ (5.58 g, 148 mmol, 1.25 equiv) portionwise. Gas evolution and mild warming observed. After 30 min, TLC indicated complete conversion. The reaction was concentrated in vacuo. The residue was then treated with 1 N HCl and extracted with DCM (×2). Combined DCM extracts dried (Na₂SO₄) and concentrated in vacuo to provide (2-(allyloxy)phenyl) methanol (19.60 g, 100%) as a yellow oil. ¹H NMR (400 MHz, CDCl3) δ 7.33-7.25 (m, 2H), 6.97 (td, J=7.4, 1.0 Hz, 1H), 6.90 (d, J=8.3 Hz, 1H), 6.08 (ddt, J=17.3, 10.5, 5.2 Hz, 1H), 5.44 (dq, J=17.3, 1.6 Hz, 1H), 5.37-5.25 (m, 1H), 4.74 (d, J=5.0 Hz, 2H), 4.62 (dt, J=5.1, 1.6 Hz, 2H), 2.35 (t, J=5.9 Hz, 1H).

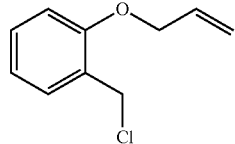

Intermediate 86

1-(Allyloxy)-2-(chloromethyl)benzene

To a solution of (2-(allyloxy)phenyl)methanol (19.60 g, 119 mmol, 1 equiv) in DCM (410 mL) was added dichlorotriphenylphosphorane (45.1 g, 135 mmol, 1.1 equiv). After 18 h, the reaction was concentrated in vacuo. The residue was triturated with pentane and filtered. The filtrate was concentrated in vacuo to provide the crude product. The crude product was purified by silica gel flash chromatography (0-100% DCM/hexane) to provide 1-(allyloxy)-2-(chloromethyl)benzene (11.75 g, 54%) as a pale yellow oil. ¹H NMR (400 MHz, CDCl3) δ 7.38 (dd, J=7.5, 1.8 Hz, 1H), 7.33-7.27 (m, 1H), 6.96 (td, J=7.5, 1.0 Hz, 1H), 6.90 (d, J=8.3 Hz, 1H), 6.16-6.02 (m, 1H), 5.47 (dq, J=17.2, 1.7 Hz, 1H), 5.34-5.29 (m, 1H), 4.71 (s, 2H), 4.63 (dt, J=5.0, 1.6 Hz, 2H).

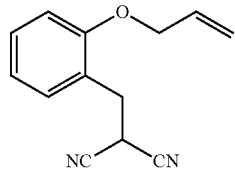

Intermediate 87

2-(2-(Allyloxy)benzyl)malononitrile

Pyrazole synthesis based on Echevarria, A.; Elguero, J. Syn. Comm. 1993, 23, 925-930. To a solution of 1-(allyloxy)-2-(chloromethyl)benzene (0.89 g, 4.87 mmol, 1 equiv) and malononitrile (0.92 g, 14.6 mmol, 3 equiv) in DMF (24 mL) was added NaH (0.55 g of a 60% emulsion in mineral oil, 13.6 mmol, 2.8 equiv). Gas evolution. After 1 h, reaction was cautiously added to 1 N HCl and extracted with ether (×2). Combined ether extracts dried (MgSO₄) and concentrated in vacuo. The crude product was purified by silica gel flash chromatography (0-100% EtOAc/hexane) to provide 2-(2-(allyloxy)benzyl)malononitrile (1.0 g, 97%) as a pale yellow oil. This product was contaminated with ~20% of an unidentified impurity. ¹H NMR (400 MHz, CDCl₃) δ 7.44-7.25 (m, 2H), 7.06-6.87 (m, 2H), 6.15-5.98 (m, 1H), 5.46-5.24 (m, 2H), 4.65-4.59 (m, 2H), 4.22 (t, J=7.7 Hz, 1H), 3.36 (d, J=7.8 Hz, 2H).

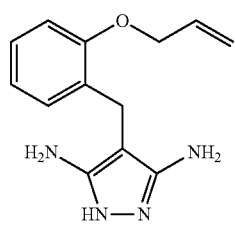

Intermediate 88

4-(2-(Allyloxy)benzyl)-1H-pyrazole-3,5-diamine

To a solution of 2-(2-(allyloxy)benzyl)malononitrile (1.0 g, 4.71 g, 1 equiv) in EtOH (9 mL) was added hydrazine (0.79 mL of a 30% aqueous solution, 7.54 mmol, 1.6 equiv). The yellow solution was heated to reflux for 4 h. The reaction was then removed from heat and concentrated. The crude product was purified by silica gel flash chromatography (0-10% MeOH/CHCl$_3$ with 1% NH$_4$OH) to provide 4-(2-(allyloxy)benzyl)-1H-pyrazole-3,5-diamine (0.35 g, 30%) as a tan foam. $^1$H NMR (400 MHz, CDCl3) δ 7.23-7.14 (m, 2H), 6.96-6.81 (m, 2H), 6.11 (ddt, J=17.3, 10.6, 5.3 Hz, 1H), 5.44 (dq, J=17.3, 1.5 Hz, 1H), 5.33 (dq, J=10.5, 1.3 Hz, 1H), 4.58 (dt, J=5.4, 1.3 Hz, 2H), 4.01-3.65 (m, 4H), 3.58 (s, 2H); LCMS (ESI, M+1): 245.2.

Intermediate 89

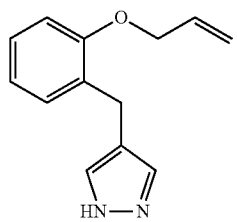

4-(2-(Allyloxy)benzyl)-1H-pyrazole

A solution of 4-(2-(allyloxy)benzyl)-1H-pyrazole-3,5-diamine (0.35 g, 1.43 mmol, 1 equiv) in water (2.9 mL) and hypophosphorous acid (4.45 g, 34.4 mmol, 24 equiv) was cooled to 0° C. (ice/water). To the cooled orange homogenous reaction was added a solution of NaNO$_2$ (0.22 g, 3.15 g, 2.2 equiv) in water (2 mL) dropwise. Reaction significantly darkened to a dark brown with some foaming and some gummy precipitate. After addition is completed, reaction was removed from cooling bath and stirred 2 h. The reaction was then added to 1 N NaOH and extracted with DCM (×4). Combined DCM extractions dried (Na2SO4) and concentrated in vacuo. The crude product was purified by silica gel flash chromatography (0-10 MeOH/CHCl$_3$ with 1% NH$_4$OH) to provide 4-(2-(allyloxy)benzyl)-1H-pyrazole (72 mg, 23%) as a brown oil. $^1$H NMR (500 MHz, CDCl3) δ 7.45 (s, 2H), 7.20 (td, J=7.8, 1.7 Hz, 1H), 7.15 (dd, J=7.5, 1.5 Hz, 1H), 6.93-6.86 (m, 2H), 6.15-6.03 (m, 1H), 5.47-5.39 (m, 1H), 5.30 (dq, J=10.6, 1.5 Hz, 1H), 4.58 (dt, J=5.0, 1.6 Hz, 2H), 3.89 (s, 2H), 2.03 (s, 2H); LCMS (ESI, M+1): 215.23.

Intermediate 90

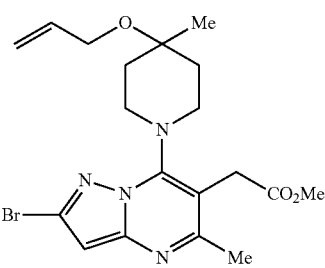

Methyl 2-(7-(4-(allyloxy)-4-methylpiperidin-1-yl)-2-bromo-5-methylpyrazolo[1,5-a]pyrimidin-6-yl)acetate A solution of methyl 2-(2-bromo-7-chloro-5-methylpyrazolo[1,5-a]pyrimidin-6-yl)acetate (13.4 g, 41.9 mmol, 1 equiv, for preparation see WO2012033735), 4-(allyloxy)-4-methylpiperidine (7.16 g, 46.1 mmol, 1.1 equiv), and DIPEA (17.6 mL, 101 mmol, 2.4 equiv) in DMF (84 mL) was heated at 60° C. for 2 h. The reaction was then added to water and extracted with ether (×2). Combined ether extracts dried (MgSO$_4$) and concentrated in vacuo. The crude product was purified via silica gel flash chromatography (0-50% EtOAc/hex) to provide methyl 2-(7-(4-(allyloxy)-4-methylpiperidin-1-yl)-2-bromo-5-methylpyrazolo[1,5-a]pyrimidin-6-yl)acetate (17.7 g, 97%). $^1$H NMR (500 MHz, CDCl3) δ 6.52 (s, 1H), 6.02 (ddt, J=17.2, 10.4, 5.2 Hz, 1H), 5.43 (dd, J=17.2, 1.6 Hz, 1H), 5.22 (dq, J=10.4, 1.5 Hz, 1H), 3.99 (dt, J=5.2, 1.6 Hz, 2H), 3.77 (s, 3H), 3.79-3.76 (m, 2H), 3.70-3.56 (m, J=7.4 Hz, 2H), 3.33 (br. s., 2H), 2.50 (s, 3H), 1.97-1.89 (m, 2H), 1.87-1.78 (m, J=9.3 Hz, 2H), 1.32 (s, 3H); LCMS (ESI, M+1): 437.20.

Intermediate 91

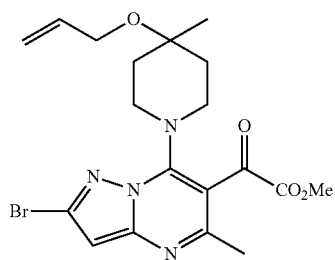

Methyl 2-(7-(4-(allyloxy)-4-methylpiperidin-1-yl)-2-bromo-5-methylpyrazolo[1,5-a]pyrimidin-6-yl)-2-oxoacetate A solution of methyl 2-(7-(4-(allyloxy)-4-methylpiperidin-1-yl)-2-bromo-5-methylpyrazolo[1,5-a]pyrimidin-6-yl)acetate (17.7 g, 40.5 mmol, 1 equiv) in THF (200 mL) was cooled to −78° C. (IPA/CO$_2$). KHMDS (72 mL of a 0.91 M solution in THF, 64.9 mmol, 1.6 equiv) was added dropwise over ~2 min. Reaction turned a deep orange color. After 30 min, 3-phenyl-2-(phenylsulfonyl)-1,2-oxaziridine (15.9 g, 60.8 mmol, 1.2 equiv) was added in a single portion. The reaction significantly darkened. After 30 min, the reaction was added to saturated aqueous sodium bicarbonate and extracted with ether (×2). The combined ether extracts were dried (MgSO$_4$) and concentrated in vacuo to provide the crude product as a brown oil. This was taken up in DCM (200 mL) and Dess-Martin periodinane (20.6 g, 48.6 mmol, 1.2 equiv). After 30 min, the reaction was added to saturated aqueous sodium bicarbonate and extracted with DCM (×3). Combined DCM extracts were dried (Na$_2$SO$_4$) and concentrated in vacuo to provide the crude product. The crude product was purified via silica gel flash chromatography (0-50% EtOAc/hex) to provide methyl 2-(7-(4-(allyloxy)-4-methylpiperidin-1-yl)-2-bromo-5-methylpyrazolo[1,5-a]pyrimidin-6-yl)-2-oxoacetate (9.2 g, 50%). $^1$H NMR (500 MHz, CDCl3) δ 6.55 (s, 1H), 6.07-5.87 (m, 1H), 5.38 (dq, J=17.2, 1.7 Hz, 1H), 5.20 (dq, J=10.4, 1.6 Hz, 1H), 3.95-

3.92 (m, 5H), 3.69 (d, J=12.6 Hz, 2H), 3.59-3.50 (m, 2H), 2.56 (s, 3H), 1.96-1.82 (m, 4H), 1.28 (s, 3H); LCMS (ESI, M+1): 450.95.

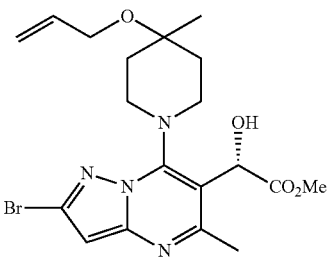

Intermediate 92

(S)-Methyl 2-(7-(4-(allyloxy)-4-methylpiperidin-1-yl)-2-bromo-5-methylpyrazolo[1,5-a]pyrimidin-6-yl)-2-(tert-butoxy)acetate A solution of methyl 2-(7-(4-(allyloxy)-4-methylpiperidin-1-yl)-2-bromo-5-methylpyrazolo[1,5-a]pyrimidin-6-yl)-2-oxoacetate (9.20 g, 20.3 mmol, 1 equiv) and (R)-1-methyl-3,3-diphenylhexahydropyrrolo[1,2-c][1,3,2]oxazaborole (12.2 mL of a 1 M solution in toluene, 12.2 mmol, 0.6 equiv) in toluene (200 mL) was cooled to −25° C. (MeCN/CO$_2$). Catecholborane (6.8 mL of a 50% solution in toluene, 28.4 mmol, 1.4 equiv) was then added and temperature was held between −15° C. and −25° C. for 18 h. At this point, more and (R)-1-methyl-3,3-diphenylhexahydropyrrolo[1,2-c][1,3,2]oxazaborole (4 mL of a 1 M solution in toluene, 4 mmol, 0.2 equiv) and catecholborane (3 mL of a 50% solution in toluene, 12.5 mmol, 0.6 equiv) were added. The reaction was then stirred a further 4 h. The reaction was then quenched with 10% aqueous K$_2$CO$_3$ (100 mL) and EtOAc (100 mL) and removed from cooling bath. After stirring 45 min, the mixture was added to water and extracted with ether (×4). The combined ether extracts were dried (MgSO$_4$) and concentrated in vacuo to provide the crude product as a yellow foam which was carried on un purified to the next step. (S)-methyl 2-(7-(4-(allyloxy)-4-methylpiperidin-1-yl)-2-bromo-5-methylpyrazolo[1,5-a]pyrimidin-6-yl)-2-hydroxyacetate. $^1$H NMR (500 MHz, CDCl3) δ 6.57 (s, 1H), 6.12-5.97 (m, 1H), 5.56-5.47 (m, 2H), 5.28-5.22 (m, 1H), 4.50-3.00 (very broad m, 4H), 4.00 (dt, J=5.0, 1.6 Hz, 2H), 3.82 (s, 3H), 2.59 (s, 3H), 2.01-1.91 (m, 2H), 1.80 (d, J=11.7 Hz, 2H), 1.33 (s, 3H); LCMS (ESI, M+1): 453.00.

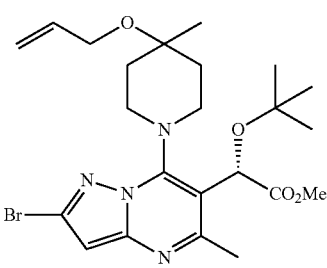

Intermediate 93

(S)-Methyl 2-(7-(4-(allyloxy)-4-methylpiperidin-1-yl)-2-bromo-5-methylpyrazolo[1,5-a]pyrimidin-6-yl)-2-(tert-butoxy)acetate The crude alcohol from the previous step was taken up in DCM (50 mL) and tBuOAc (150 mL). To this solution was added perchloric acid (3.7 mL of a 70% aqueous solution, 60.9 mmol, 3 equiv) to give a cloudy orange solution. After stirring 3 h, the reaction was added cautiously to saturated aqueous sodium bicarbonate and extracted with DCM (×3). The combined DCM extracts were dried (Na$_2$SO$_4$) and concentrated in vacuo to provide the crude product. The crude product was purified via silica gel flash chromatography (0-100% EtOAc/hex) to provide (S)-methyl 2-(7-(4-(allyloxy)-4-methylpiperidin-1-yl)-2-bromo-5-methylpyrazolo[1,5-a]pyrimidin-6-yl)-2-(tert-butoxy)acetate (3.56 g, 34%) and (S)-methyl 2-(7-(4-(allyloxy)-4-methylpiperidin-1-yl)-2-bromo-5-methylpyrazolo[1,5-a]pyrimidin-6-yl)-2-hydroxyacetate (4.53 g, 49%). (S)-methyl 2-(7-(4-(allyloxy)-4-methylpiperidin-1-yl)-2-bromo-5-methylpyrazolo[1,5-a]pyrimidin-6-yl)-2-(tert-butoxy)acetate (3.56 g, 34%) and (S)-methyl 2-(7-(4-(allyloxy)-4-methylpiperidin-1-yl)-2-bromo-5-methylpyrazolo[1,5-a]pyrimidin-6-yl)-2-hydroxyacetate. $^1$H NMR (500 MHz, CDCl$_3$) δ 6.54 (s, 1H), 6.09-5.97 (m, 1H), 5.83 (br. s., 1H), 5.48 (d, J=17.8 Hz, 1H), 5.24 (d, J=9.8 Hz, 1H), 4.50-3.00 (very broad m, 4H), 4.05-3.98 (m, 2H), 3.76 (s, 3H), 2.59 (s, 3H), 2.04-1.90 (m, 2H), 1.36 (s, 3H), 1.24 (s, 9H); LCMS (ESI, M+1): 509.09.

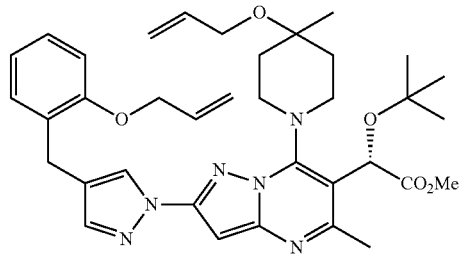

Intermediate 94

(S)-Methyl 2-(7-(4-(allyloxy)-4-methylpiperidin-1-yl)-2-(4-(2-(allyloxy)benzyl)-1H-pyrazol-1-yl)-5-methylpyrazolo[1,5-a]pyrimidin-6-yl)-2-(tert-butoxy)acetate Copper coupling based on Antilla, J. C.; Baskin, J. M.; Barder, T. E.; Buchwald, S. L. J. Org. Chem. 2004, 69, 5578-5587. A solution of (S)-methyl 2-(7-(4-(allyloxy)-4-methylpiperidin-1-yl)-2-bromo-5-methylpyrazolo[1,5-a]pyrimidin-6-yl)-2-(tert-butoxy)acetate (0.17 g, 0.334 mmol, 1 equiv),4-(2-(allyloxy)benzyl)-1H-pyrazole (72 mg, 0.334 mmol, 1 equiv), CuI (6.4 mg, 0.033 mmol, 0.1 mmol), (1R,2R)—N1,N2-dimethylcyclohexane-1,2-diamine, racemic (0.021 mL, 0.133 mmol, 0.4 equiv), and K$_2$CO$_3$ (101 mg, 0.734 mmol, 2.2 equiv) in toluene (1.7 mL) was heated at 110° C. for 18 h. More CuI (14 mg, 0.074 mmol, 0.22 equiv) and (1R,2R)—N1,N2-dimethylcyclohexane-1,2-diamine, racemic (0.021 mL, 0.133 mmol, 0.4 equiv) were added and heating continued for another 40 h. The reaction was then allowed to cool to ambient temperature and purified directly via silica gel flash chromatography (0-100% EtOAc/hex) to provide (S)-methyl 2-(7-(4-(allyloxy)-4-methylpiperidin-1-yl)-2-(4-(2-(allyloxy)benzyl)-1H-pyrazol-1-yl)-5-methylpyrazolo[1,5-a]pyrimidin-6-yl)-2-(tert-butoxy)acetate (127 mg, 59%) as a viscous yellow oil. $^1$H NMR (500 MHz, CDCl3) δ 8.17-8.06 (m, 1H), 7.65 (s, 1H), 7.20 (d, J=7.6 Hz, 2H), 6.96-6.86 (m, 2H), 6.75 (s, 1H), 6.15-5.99 (m, 2H), 5.97-5.86 (m, 1H), 5.45 (dd, J=17.2, 1.6 Hz, 2H), 5.34-5.27 (m, 1H), 5.24-5.18 (m, 1H), 4.61 (dt, J=5.0, 1.6 Hz, 2H), 4.02 (d, J=5.0 Hz, 2H), 3.94 (s, 2H), 3.76 (s, 3H), 2.61 (s, 3H), 2.04-1.67 (m, 4H), 1.36 (s, 3H), 1.26 (s, 9H) [note: 4H of piperidine not observed, expected to be extremely broad]; LCMS (ESI, M+1): 643.5.

Intermediate 95

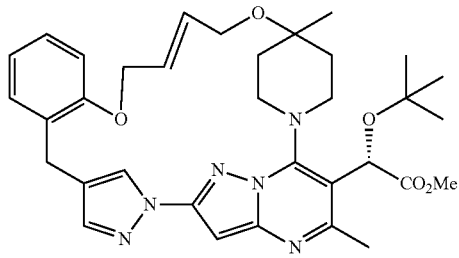

Methyl (2S)-2-(tert-butoxy)-2-[(23E)-4,27-dimethyl-21,26-dioxa-1,5,7,8,10,11-hexaazahexacyclo[25.2.2.1$^{6,9}$.1$^{10,13}$.0$^{2,7}$.0$^{15,20}$]tritriaconta-2,4,6(33),8,11,13(32),15(20),16,18,23-decaen-3-yl]acetate Nitrogen was bubbled through a solution of (S)-methyl 2-(7-(4-(allyloxy)-4-methylpiperidin-1-yl)-2-(4-(2-(allyloxy)benzyl)-1H-pyrazol-1-yl)-5-methylpyrazolo[1,5-a]pyrimidin-6-yl)-2-(tert-butoxy)acetate (116 mg, 0.180 mmol, 1 equiv) in DCE (150 mL) for 15 min. The solution was then heated to 70° C. and Hoveyda-Grubbs catalyst 2nd generation (11 mg, 0.018 mmol, 0.1 equiv) was added. Heating of the slightly pale blue solution was continued for 3 h. The reaction was then allowed to cool to ambient temperature and concentrated in vacuo. The crude product was purified via silica gel flash chromatography (0-100% EtOAc/hex) to provide desired product (82 mg, 74%) as a viscous yellow oil. $^1$H NMR (400 MHz, CDCl3) δ 8.38 (s, 1H), 7.64 (s, 1H), 7.33-7.29 (m, 1H), 7.20 (td, J=7.8, 1.8 Hz, 1H), 6.97-6.85 (m, 2H), 6.75 (s, 1H), 6.32-6.32 (m, 1H), 6.41-6.31 (m, 1H), 6.22-6.13 (m, 1H), 6.21-6.12 (m, 1H), 6.08 (s, 1H), 4.70-4.57 (m, 3H), 4.12-3.91 (m, 4H), 3.77-3.69 (m, 5H), 3.01 (d, J=11.3 Hz, 1H), 2.71-2.60 (m, 4H), 2.07-1.94 (m, 2H), 1.85-1.75 (m, 1H), 1.73-1.62 (m, 1H), 1.28 (s, 9H); LCMS (ESI, M+1): 615.5.

Example 25

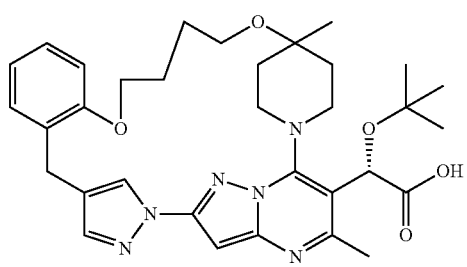 [SMILES: Cc1nc2cc3nn2c(c1[C@H](OC(C)(C)C)C(=O)O)N1CCC(C)(CC1)OCCCCOc1ccccc1Cc1cnn-3c1]

(2S)-2-(tert-Butoxy)-2-{4,27-dimethyl-21,26-dioxa-1,5,7,8,10,11-hexaazahexacyclo[25.2.2.1$^{6,9}$.1$^{10,13}$.0$^{2,7}$.0$^{15,20}$]tritriaconta-2,4,6(33),8,11,13(32),15(20),16,18-nonaen-3-yl}acetic acid A solution of methyl (2S)-2-(tert-butoxy)-2-[(23E)-4,27-dimethyl-21,26-dioxa-1,5,7,8,10,11-hexaazahexacyclo[25.2.2.1^{6,9}.1^{10,13}.0^{2,7}.0^{15,20}]tritriaconta-2,4,6(33),8,11,13(32),15(20),16,18,23-decaen-3-yl]acetate (20 mg, 0.033 mmol, 1 equiv) and 10% Pd/C (16 mg) in EtOH (1 mL) was exposed to a balloon of hydrogen. After 1 h, the reaction was filtered through a plug of Celite eluting with a minimal amount of MeOH. To this filtered solution was added lithium hydroxide monohydrate (27 mg, 0.651 mmol, 20 equiv) and water (2 drops). The reaction was then heated at 60° C. for 18 h. More lithium hydroxide monohydrate (27 mg, 0.651 mmol, 20 equiv) was added and the temperature was raised to 70° C. Upon stirring for 1 h, the reaction was removed from heat and filtered. The filtrate was purified via preparative HPLC to provide desired product (9.1 mg, 46%). 1H NMR (500 MHz, DMSO-d$_6$) δ 8.30 (s, 1H), 7.73 (s, 1H), 7.32 (d, J=7.0 Hz, 1H), 7.20-7.12 (m, 1H), 6.95 (d, J=7.9 Hz, 1H), 6.85 (t, J=7.3 Hz, 1H), 6.57 (s, 1H), 5.76 (br. s., 1H), 4.37 (t, J=11.7 Hz, 1H), 4.15-3.97 (m, 2H), 3.83 (d, J=13.1 Hz, 1H), 3.69 (d, J=13.4 Hz, 2H), 2.53 (br. s., 3H), 2.21-1.98 (m, 3H), 1.76 (d, J=7.9 Hz, 4H), 1.60-1.49 (m, 1H), 1.24 (br. s., 3H), 1.17 (s, 9H) [note: 4H of piperidine not observed, likely under water peak]; LCMS (ESI, M+1): 603.5.

Example 26

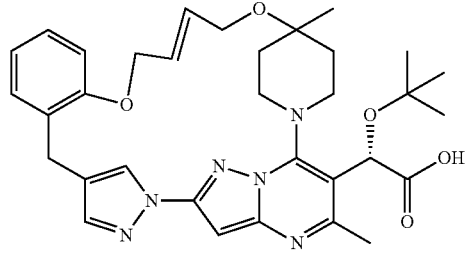 [SMILES: Cc1nc2cc3nn2c(c1[C@H](OC(C)(C)C)C(=O)O)N1CCC(C)(CC1)OC/C=C/COc1ccccc1Cc1cnn-3c1]

(2S)-2-(tert-Butoxy)-2-[(23E)-4,27-dimethyl-21,26-dioxa-1,5,7,8,10,11-hexaazahexacyclo[25.2.2.1$^{6,9}$.1$^{10,13}$.0$^{2,7}$.0$^{15,20}$]tritriaconta-2,4,6(33),8,11,13(32),15(20),16,18,23-decaen-3-yl]acetic acid Prepared via direct saponification of intermediate 95 in 59% yield. $^1$H NMR (500 MHz, DMSO-d$_6$) δ 8.23 (br. s., 1H), 7.73 (s, 1H), 7.34 (d, J=6.7 Hz, 1H), 7.17 (d, J=7.0 Hz, 1H), 6.98 (d, J=7.9 Hz, 1H), 6.88 (t, J=7.6 Hz, 1H), 6.57 (s, 1H), 6.31-6.21 (m, 1H), 6.17-6.09 (m, 1H), 5.78 (br. s., 1H), 4.65 (br. s., 1H), 4.62-4.55 (m, 1H), 4.46 (d, J=11.0 Hz, 1H), 4.09-3.97 (m, 2H), 3.88 (d, J=13.4 Hz, 1H), 3.76-3.59 (m, 4H), 2.53 (br. s., 3H), 2.01 (d, J=11.6 Hz, 1H), 1.87-1.81 (m, 1H), 1.74 (d, J=15.6 Hz, 1H), 1.64-1.53 (m, 1H), 1.27 (br. s., 3H), 1.18 (br. s., 9H); LCMS (ESI, M+1): 601.5.

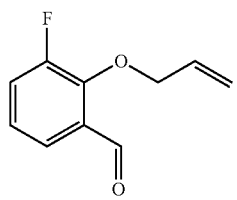

Intermediate 96

2-(Allyloxy)-3-fluorobenzaldehyde

Prepared from 3-fluoro-2-hydroxybenzaldehyde using the same procedure as intermediate 84 in quantitative yield. $^1$H NMR (400 MHz, CDCl3) δ 10.44 (d, J=0.8 Hz, 1H), 7.63 (dq, J=7.8, 0.9 Hz, 1H), 7.35 (ddd, J=11.5, 8.2, 1.6 Hz, 1H), 7.12 (tdd, J=7.9, 4.5, 0.8 Hz, 1H), 6.08 (ddtd, J=16.9, 10.5, 6.1, 1.0 Hz, 1H), 5.41 (dq, J=17.2, 1.4 Hz, 1H), 5.32 (dq, J=10.3, 1.1 Hz, 1H), 4.77 (dq, J=6.1, 1.2 Hz, 2H).

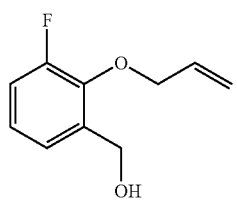

Intermediate 97

(2-(Allyloxy)-3-fluorophenyl)methanol

Prepared from intermediate 96 using the same procedure as intermediate 85 in 90% yield. (2-(allyloxy)-3-fluorophenyl)methanol. $^1$H NMR (500 MHz, CDCl3) δ 7.17-7.11 (m, 1H), 7.09-7.00 (m, 2H), 6.15-6.03 (m, 1H), 5.42 (dq, J=17.1, 1.5 Hz, 1H), 5.34-5.27 (m, 1H), 4.73 (d, J=5.4 Hz, 2H), 4.69 (dq, J=6.0, 1.3 Hz, 2H), 2.16 (t, J=5.8 Hz, 1H).

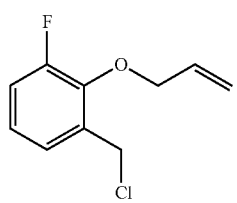

Intermediate 98

2-(Allyloxy)-1-(chloromethyl)-3-fluorobenzene

Prepared from intermediate 97 using the same procedure as intermediate 86 in 67% yield. $^1$H NMR (400 MHz, CDCl$_3$) δ 7.20-7.14 (m, 1H), 7.13-6.98 (m, 2H), 6.20-6.02 (m, 1H), 5.50-5.40 (m, 1H), 5.31-5.27 (m, 1H), 4.75-4.64 (m, 4H).

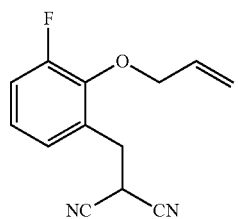

Intermediate 99

2-(2-(Allyloxy)-3-fluorobenzyl)malononitrile

Prepared from intermediate 98 using the same procedure as intermediate 87. Material carried on unpurifed to next step.

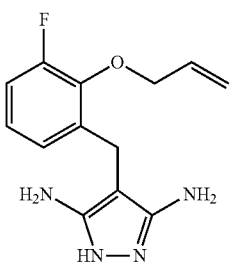

Intermediate 100

4-(2-(Allyloxy)-3-fluorobenzyl)-1H-pyrazole-3,5-diamine

Prepared from intermediate 99 using the same procedure as intermediate 88 in 20% yield (2 steps). $^1$H NMR (400 MHz, CDCl$_3$) δ 7.03-6.91 (m, 3H), 6.14-6.02 (m, 1H), 5.42 (dd, J=17.3, 1.5 Hz, 1H), 5.29 (dd, J=10.3, 1.3 Hz, 1H), 4.61 (dd, J=6.0, 1.0 Hz, 2H), 3.59 (s, 2H).

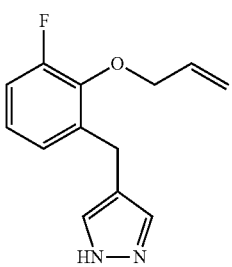

Intermediate 101

4-(2-(Allyloxy)-3-fluorobenzyl)-1H-pyrazole

Prepared from intermediate 100 using the same procedure as intermediate 89 in 19% yield. $^1$H NMR (500 MHz, CDCl3) δ 7.43 (s, 2H), 7.01-6.90 (m, 3H), 6.08-5.99 (m, J=5.8 Hz, 1H), 5.39 (dd, J=17.2, 1.6 Hz, 1H), 5.28-5.23 (m, 1H), 4.56 (dq, J=5.8, 1.2 Hz, 2H), 3.90 (s, 2H).

Intermediate 102

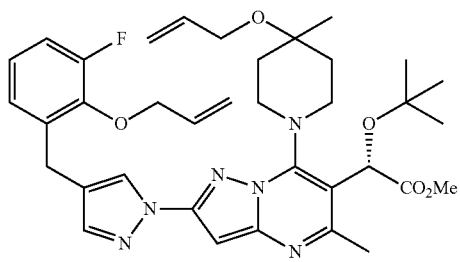

(S)-Methyl 2-(2-(4-(2-(allyloxy)-3-fluorobenzyl)-1H-pyrazol-1-yl)-7-(4-(allyloxy)-4-methylpiperidin-1-yl)-5-methylpyrazolo[1,5-cdpyrimidin-6-yl)-2-(tert-butoxy)acetate Prepared from intermediate 93 and 101 using the same procedure as intermediate 94 in 54% yield. LCMS (ESI, M+1): 661.5.

Intermediate 103

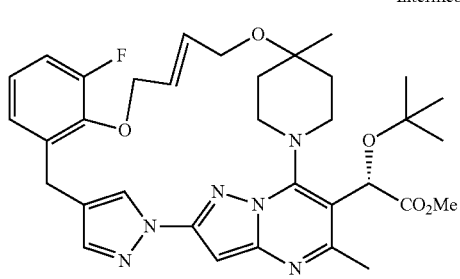

Methyl (2S)-2-(tert-butoxy)-21(23E)-19-fluoro-4,27-dimethyl-21,26-dioxa-1,5,7,8,10,11-hexaaza-hexacyclo[25.2.2.1$^{6,9}$.1$^{10,13}$.0$^{2,7}$.0$^{15,20}$]tritriaconta-2,4,6(33),8,11,13(32),15(20),16,18,23-decaen-3-yl]acetate Prepared from intermediate 102 using the same procedure as intermediate 95 in 48% yield. $^1$H NMR (500 MHz, CDCl3) δ 8.53-8.43 (m, 1H), 7.61-7.57 (m, 1H), 7.16-7.11 (m, 1H), 7.03-6.94 (m, 2H), 6.77-6.72 (m, 1H), 6.30-6.24 (m, 2H), 6.17-6.11 (m, 1H), 4.76-4.52 (m, 3H), 4.12-3.88 (m, 4H), 3.72 (s, 4H), 3.04-2.88 (m, 1H), 2.65 (s, 4H), 2.06-1.97 (m, 2H), 1.83-1.65 (m, 2H), 1.36 (s, 3H), 1.29 (s, 9H); LCMS (ESI, M+1): 633.45.

Example 27

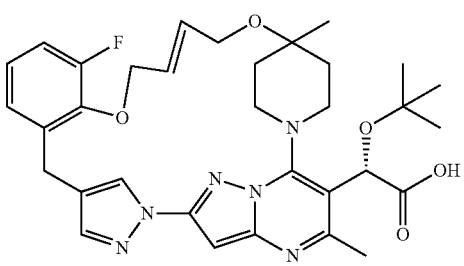 [SMILES: Cc1nc2cc3nn2c(c1[C@H](OC(C)(C)C)C(=O)O)N1CCC(C)(CC1)OC/C=C/COc1c(F)cccc1Cc1cnn-3c1]

(2S)-2-(tert-Butoxy)-2-[(23E)-19-fluoro-4,27-dimethyl-21,26-dioxa-1,5,7,8,10,11-hexaazahexacyclo[25.2.2.1$^{6,9}$.1$^{10,13}$.0$^{2,7}$.0$^{15,20}$]tritriaconta-2,4,6(33),8,11,13(32),15(20),16,18,23-decaen-3-yl]acetic acid Prepared via direct saponification of intermediate 103 in 53% yield, see preparation of example 25. $^1$H NMR (500 MHz, DMSO-d$_6$) δ 8.44-8.33 (m, 1H), 7.76-7.66 (m, 1H), 7.32-7.24 (m, 1H), 7.16-7.00 (m, 2H), 6.66-6.55 (m, 1H), 6.24-6.12 (m, 2H), 6.01-5.87 (m, 1H), 4.59-4.47 (m, 3H), 4.04-3.78 (m, 7H), 2.54 (br. s., 3H), 2.03-1.97 (m, 1H), 1.92-1.86 (m, 1H), 1.79-1.71 (m, 1H), 1.65-1.57 (m, 1H), 1.26 (br. s., 3H), 1.20 (s, 9H); LCMS (ESI, M+1): 619.30.

Example 28

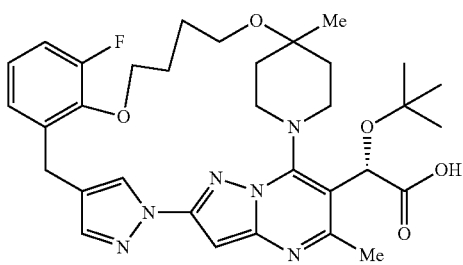 [SMILES: Cc1nc2cc3nn2c(c1[C@H](OC(C)(C)C)C(=O)O)N1CCC(C)(CC1)OCCCCOc1c(F)cccc1Cc1cnn-3c1]

(2S)-2-(tert-Butoxy)-2-{19-fluoro-4,27-dimethyl-21,26-dioxa-1,5,7,8,10,11-hexaazahexacyclo[25.2.2.1$^{6,9}$.1$^{10,13}$.0$^{2,7}$.0$^{15,20}$]tritriaconta-2,4,6(33),8,11,13(32),15(20),16,18-nonaen-3-yl}acetic acid Prepared from intermediate 103 in 60% yield, see preparation of example 25. $^1$H NMR (500 MHz, DMSO-d$_6$) δ 8.45 (s, 1H), 7.68 (s, 1H), 7.25 (d, J=7.3 Hz, 1H), 7.14-7.06 (m, 1H), 7.06-7.00 (m, 1H), 6.61 (s, 1H), 5.93 (s, 1H), 4.46 (br. s., 1H), 4.16-4.04 (m, 2H), 3.95-3.72 (m, 3H), 3.46 (d, J=6.4 Hz, 2H), 3.00 (br. s., 1H), 2.62 (d, J=10.1 Hz, 1H), 2.54 (s, 3H), 2.04-1.83 (m, 6H), 1.75 (d, J=13.4 Hz, 1H), 1.58 (br. s., 1H), 1.24 (s, 3H), 1.20 (s, 9H); LCMS (ESI, M+1): 621.31.

Intermediate 104

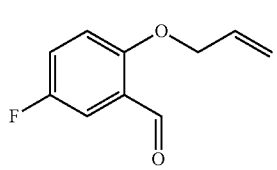

2-(Allyloxy)-5-fluorobenzaldehyde

Prepared from 2-hydroxy-5-fluorobenzaldehyde using the same procedure as intermediate 84 in 96% yield. LCMS (ESI, M+1): 181.15.

Intermediate 105

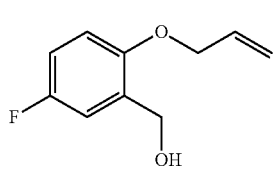

(2-(Allyloxy)-5-fluorophenyl)methanol

Prepared from intermediate 104 using the same procedure as intermediate 85 in 88% yield. $^1$H NMR (400 MHz, CHLOROFORM-d) δ 7.07 (dd, J=8.8, 3.0 Hz, 1H), 6.93 (td, J=8.5, 3.1 Hz, 1H), 6.80 (dd, J=9.0, 4.3 Hz, 1H), 6.05 (ddt, J=17.3, 10.5, 5.2 Hz, 1H), 5.41 (dq, J=17.2, 1.6 Hz, 1H), 5.31 (dq, J=10.5, 1.3 Hz, 1H), 4.70 (s, 2H), 4.56 (dt, J=5.0, 1.5 Hz, 2H). LCMS (ESI, M+1): 183.2.

Intermediate 106

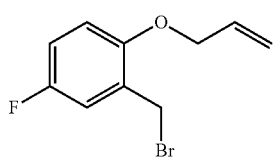

1-(Allyloxy)-2-(bromomethyl)-4-fluorobenzene 2-(Allyloxy)-5-fluorophenyl)methanol (1.06 g, 5.82 mmol, 1 equiv) was dissolved in DCM (11.6 ml). The solution was cooled to 0° C. and to this solution was added PBr$_3$ (0.274 ml, 2.91 mmol, 0.5 equiv) dropwise. The resulted solution was stirred at 0° C. for 1 h. The solvent was concentrated in vacuo and purified by silica gel flash chromatography column (5% EtOAc/hexane) to provide the product (0.60 g, 42%). $^1$H NMR (400 MHz, CDCl$_3$) δ 7.08 (dd, J=8.5, 3.0 Hz, 1H), 6.96 (ddd, J=9.0, 8.0, 3.0 Hz, 1H), 6.81 (dd, J=8.9, 4.4 Hz, 1H), 6.07 (ddt, J=17.3, 10.4, 5.1 Hz, 1H), 5.47 (dd, J=17.3, 1.5 Hz, 1H), 5.31 (dd, J=10.7, 1.4 Hz, 1H), 4.60 (dt, J=5.0, 1.6 Hz, 2H), 4.54 (s, 2H). LCMS (ESI, M+1): 245.00.

Intermediate 107

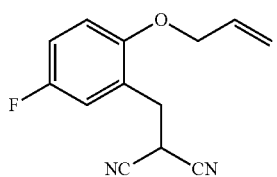

2-(2-(Allyloxy)-5-fluorobenzyl)malononitrile

Prepared from intermediate 106 using the same procedure as intermediate 87 in 75% yield. $^1$H NMR (400 MHz, CDCl$_3$) δ 7.14 (dd, J=8.5, 3.3 Hz, 1H), 7.08-6.99 (m, 3H), 6.87 (dd, J=8.8, 4.5 Hz, 2H), 6.04 (dtt, J=17.2, 10.5, 5.4 Hz, 2H), 5.44-5.33 (m, 3H), 5.32-5.26 (m, 1H), 4.58 (dt, J=5.3, 1.5 Hz, 2H), 4.53 (dt, J=5.0, 1.5 Hz, 2H), 4.22 (t, J=7.7 Hz, 1H), 4.13 (q, J=7.0 Hz, 1H), 3.37 (s, 2H), 3.32 (d, J=7.8 Hz, 2H). LCMS (ESI, M+1): 231.09.

Intermediate 108

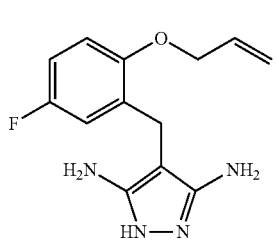

4-(2-(Allyloxy)-5-fluorobenzyl)-1H-pyrazole-3,5-diamine

Prepared from intermediate 107 using the same procedure as intermediate 88 in 55% yield. $^1$H NMR (400 MHz, CDCl$_3$) δ 7.04-6.57 (m, 3H), 6.10-5.90 (m, 1H), 5.44-5.17 (m, 2H), 4.52-4.34 (m, 2H), 3.50-3.38 (m, 1H), 3.05 (m, 1H). LCMS (ESI, M+1): 263.2.

Intermediate 109

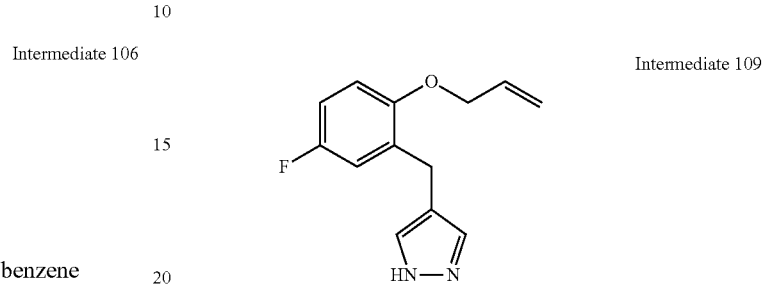

4-(2-(Allyloxy)-5-fluorobenzyl)-1H-pyrazole

Prepared from intermediate 108 using the same procedure as intermediate 89 in 28% yield. LCMS (ESI, M+1): 233.2.

Intermediate 110

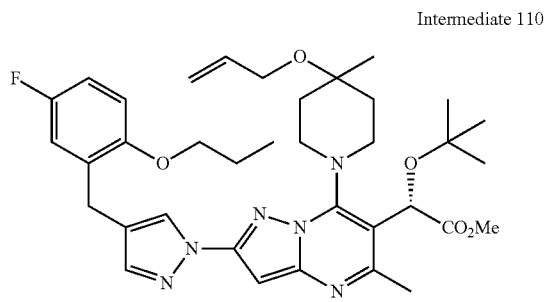 [SMILES: C=CCOC1(C)CCN(c2c([C@H](OC(C)(C)C)C(=O)OC)c(C)nc3cc(-n4cc(Cc5cc(F)ccc5OCCC)cn4)nn23)CC1]

(S)-Methyl 2-(7-(4-(allyloxy)-4-methylpiperidin-1-yl)-2-(4-(2-(allyloxy)-5-fluorobenzyl)-1H-pyrazol-1-yl)-5-methylpyrazolo[1,5-a]pyrimidin-6-yl)-2-(tert-butoxy)acetate Prepared from intermediate 93 and 109 using the same procedure as intermediate 94 in 54% yield. LCMS (ESI, M+1): 661.4.

Intermediate 111

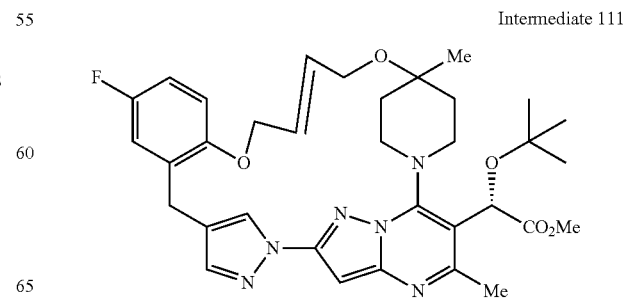

Methyl (2S)-2-(tert-butoxy)-2-[(23E)-17-fluoro-4, 27-dimethyl-21,26-dioxa-1,5,7,8,10,11-hexaaza-hexacyclo[25.2.2.1$^{6,9}$.1$^{10,13}$.0$^{2,7}$.0$^{15,20}$]tritriaconta-2, 4,6(33),8,11,13(32),15(20),16,18,23-decaen-3-yl] acetate Prepared from intermediate 110 using the same procedure as intermediate 95 in 46% yield. LCMS (ESI, M+1): 633.4

Example 29

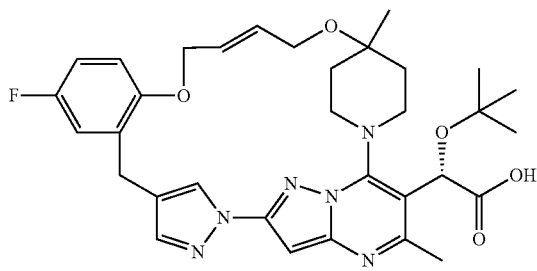 [SMILES: Cc1nc2cc3nn2c(c1[C@H](OC(C)(C)C)C(=O)O)N1CCC(C)(CC1)OC/C=C/COc1ccc(F)cc1Cc1cnn-3c1]

(2S)-2-(tert-Butoxy)-2-[(23E)-17-fluoro-4,27-dim-ethyl-21,26-dioxa-1,5,7,8,10,11-hexaazahexacyclo [25.2.2.1$^{6,9}$.1$^{10,13}$.0$^{2,7}$.0$^{15,20}$]tritriaconta-2,4,6(33),8, 11,13(32),15(20),16,18,23-decaen-3-yl]acetic acid Prepared via direct saponification of intermediate 111 in 46% yield, see preparation of example 25. $^1$H NMR (500 MHz, DMSO-d$_6$) δ 8.25 (s, 1H), 7.75 (s, 1H), 7.25 (d, J=8.5 Hz, 1H), 6.97 (d, J=4.9 Hz, 2H), 6.56 (s, 1H), 6.29-6.20 (m, 1H), 6.17-6.07 (m, 1H), 5.73 (s, 1H), 4.67-4.42 (m, 3H), 4.09-3.95 (m, 2H), 3.91-3.84 (m, 1H), 3.73-3.63 (m, 2H), 3.24 (br. s., 1H), 2.61 (d, J=11.3 Hz, 1H), 2.52 (s, 3H), 2.00 (d, J=12.5 Hz, 1H), 1.82 (d, J=12.8 Hz, 1H), 1.77-1.66 (m, 1H), 1.62-1.51 (m, 1H), 1.26 (s, 3H), 1.16 (s, 9H). LCMS (ESI, M+1): 619.3.

Example 30

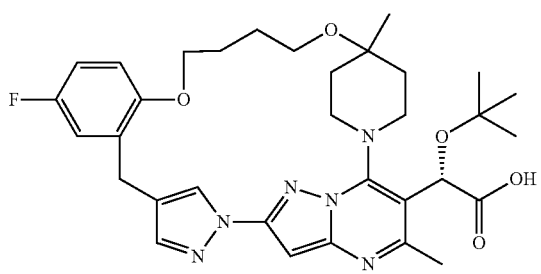 [SMILES: Cc1nc2cc3nn2c(c1[C@H](OC(C)(C)C)C(=O)O)N1CCC(C)(CC1)OCCCCOc1ccc(F)cc1Cc1cnn-3c1]

(2S)-2-(tert-Butoxy)-2-{17-fluoro-4,27-dimethyl-21, 26-dioxa-1,5,7,8,10,11-hexaazahexacyclo [25.2.2.1$^{6,9}$.1$^{10,13}$.0$^{2,7}$.0$^{15,20}$]tritriaconta-2,4,6(33),8, 11,13(32),15(20),16,18-nonaen-3-yl}acetic acid Prepared from intermediate 111 in 38% yield, see preparation of example 25. $^1$H NMR (500 MHz, DMSO-d$_6$) δ 8.30 (s, 1H), 7.76 (s, 1H), 7.23 (d, J=7.0 Hz, 1H), 7.00-6.90 (m, 2H), 6.59 (s, 1H), 5.81 (s, 1H), 4.36 (t, J=11.9 Hz, 1H), 4.10-4.01 (m, 2H), 3.97 (d, J=5.8 Hz, 2H), 3.82 (d, J=14.0 Hz, 2H), 3.68 (d, J=12.8 Hz, 4H), 2.66 (d, J=10.4 Hz, 1H), 2.52 (s, 3H), 2.12 (br. s., 1H), 2.08-1.95 (m, 2H), 1.76 (d, J=14.3 Hz, 4H), 1.59-1.50 (m, 1H), 1.23 (s, 3H), 1.17 (s, 9H). LCMS (ESI, M+1): 621.3.

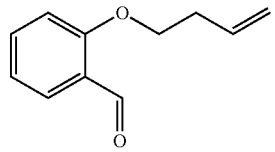

Intermediate 112

2-(But-3-en-1-yloxy)benzaldehyde

To a solution of 2-hydroxybenzaldehyde (10 g, 82 mmol, 1 equiv) in DMF (205 mL) was added NaH (3.6 g of a 60% suspension in mineral oil, 90 mmol, 1.1 equiv). Gas evolution. 4-bromobut-1-ene (10 mL, 98 mmol, 1.2 equiv) was added and the mixture was heated to 90° C. for 4 h. After cooling to ambient temperature, the reaction was partitioned between 1 N NaOH and ether. The ether layer was dried (MgSO$_4$) and concentrated in vacuo to provide intermediate 31a as a yellow oil (6.9 g, 48%). Carried one without purification (contaminated with residual mineral oil). $^1$H NMR (400 MHz, CDCl3) δ 10.51 (d, J=0.8 Hz, 1H), 7.84 (dd, J=7.7, 1.9 Hz, 1H), 7.54 (ddd, J=8.3, 7.3, 1.9 Hz, 1H), 7.10-6.92 (m, 2H), 6.03-5.83 (m, 1H), 5.27-5.09 (m, 2H), 4.15 (t, J=6.5 Hz, 2H), 2.62 (qt, J=6.6, 1.3 Hz, 2H).

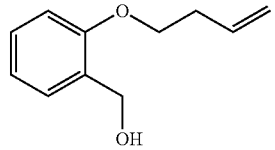

Intermediate 113

(2-(But-3-en-1-yloxy)phenyl)methanol

Prepared from intermediate 112 using the same procedure as intermediate 85 in 59% yield. $^1$H NMR (500 MHz, CDCl3) δ 7.32-7.25 (m, 2H), 6.96 (td, J=7.4, 0.9 Hz, 1H), 6.90 (d, J=7.7 Hz, 1H), 5.93 (ddt, J=17.0, 10.2, 6.8 Hz, 1H), 5.24 (dq, J=17.1, 1.6 Hz, 1H), 5.17 (dq, J=10.2, 1.4 Hz, 1H), 4.70 (d, J=6.8 Hz, 2H), 4.12 (t, J=6.3 Hz, 2H), 2.61 (qt, J=6.4, 1.4 Hz, 2H), 2.53-2.47 (m, 1H).

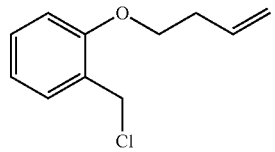

Intermediate 114

1-(But-3-en-1-yloxy)-2-(chloromethyl)benzene

Prepared from intermediate 113 using the same procedure as intermediate 86 in 48% yield. $^1$H NMR (400 MHz, CDCl3) δ 7.37 (dd, J=7.5, 1.5 Hz, 1H), 7.33-7.27 (m, 1H), 6.99-6.92 (m, 1H), 6.89 (d, J=8.0 Hz, 1H), 5.95 (d, J=6.8 Hz, 1H), 5.20 (dd, J=17.1, 1.8 Hz, 1H), 5.15-5.10 (m, 1H), 4.68 (s, 2H), 4.11-4.06 (m, 2H), 2.60 (dt, J=6.6, 1.3 Hz, 2H).

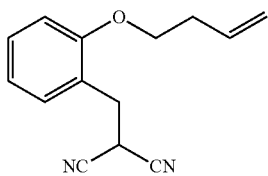

Intermediate 115

2-(2-(But-3-en-1-yloxy)benzyl)malononitrile

Prepared from intermediate 114 using the same procedure as intermediate 87 in 61% yield. LCMS (ESI, M+1): 227.1.

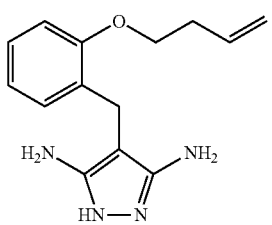

Intermediate 116

4-(2-(But-3-en-1-yloxy)benzyl)-1H-pyrazole-3,5-diamine

Prepared from intermediate 115 using the same procedure as intermediate 88 in 55% yield. LCMS (ESI, M+1): 259.2.

Intermediate 117

4-(2-(But-3-en-1-yloxy)benzyl)-1H-pyrazole

Prepared from intermediate 116 using the same procedure as intermediate 89 in 33% yield. LCMS (ESI, M+1): 229.3.

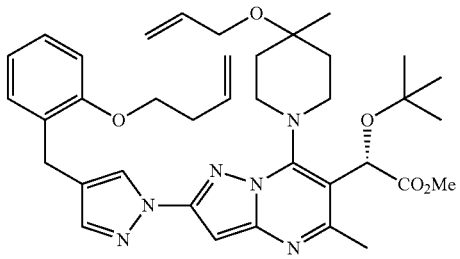

Intermediate 118

(S)-Methyl 2-(7-(4-(allyloxy)-4-methylpiperidin-1-yl)-2-(4-(2-(but-3-en-1-yloxy)benzyl)-1H-pyrazol-1-yl)-5-methylpyrazolo[1,5-a]pyrimidin-6-yl)-2-(tert-butoxy)acetate Prepared from intermediate 93 and 117 using the same procedure as intermediate 94 in 38% yield. LCMS (ESI, M+1): 657.5.

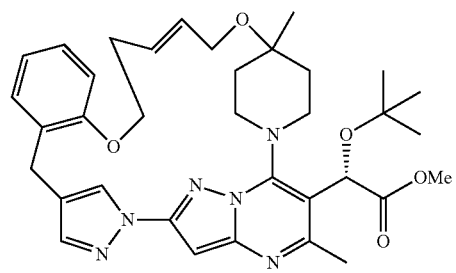

Intermediate 119

Methyl (2S)-2-(tert-butoxy)-2-[(24E)-4,28-dimethyl-21,27-dioxa-1,5,7,8,10,11-hexaazahexacyclo[26.2.2.1$^{6,9}$.1$^{10,13}$.0$^{2,7}$.0$^{15,20}$]tetratriaconta-2,4,6(34),8,11,13(33),15(20),16,18,24-decaen-3-yl]acetate Prepared from intermediate 118 using the same procedure as intermediate 94 in 29% yield. LCMS (ESI, M+1): 629.45.

Example 31

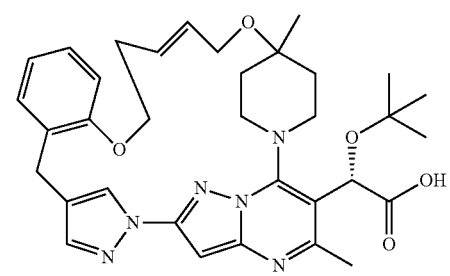 [SMILES: Cc1nc2cc3nn2c(c1[C@H](OC(C)(C)C)C(=O)O)N1CCC(C)(CC1)OC/C=C/CCOc1ccccc1Cc1cnn-3c1]

(2S)-2-(tert-Butoxy)-2-[(24E)-4,28-dimethyl-21,27-dioxa-1,5,7,8,10,11-hexaazahexacyclo[26.2.2.1$^{6,9}$.1$^{10,13}$.0$^{2,7}$.0$^{15,20}$]tetratriaconta-2,4,6(34),8,11,13(33),15(20),16,18,24-decaen-3-yl]acetic acid Prepared via direct saponification of intermediate 119 in 6% yield, see preparation of example 25. $^1$H NMR (400

MHz, METHANOL-d₄) δ 8.35 (s, 1H), 7.66 (s, 1H), 7.38 (dd, J=7.3, 1.5 Hz, 1H), 7.22 (td, J=7.9, 1.8 Hz, 1H), 6.98-6.90 (m, 2H), 6.66 (s, 1H), 6.03-5.83 (m, 3H), 4.59-4.48 (m, 1H), 4.26 (dd, J=10.8, 7.5 Hz, 1H), 4.21-4.02 (m, 3H), 3.98-3.81 (m, 3H), 3.50 (d, J=11.5 Hz, 1H), 2.98-2.89 (m, 3H), 2.68 (s, 3H), 2.21 (d, J=12.0 Hz, 1H), 1.99-1.87 (m, 2H), 1.85-1.74 (m, 1H), 1.39 (s, 3H), 1.31 (s, 9H). LCMS (ESI, M+1): 615.3.

Example 32

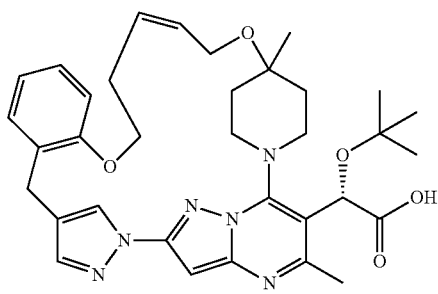 [SMILES: Cc1nc2cc3nn2c(c1[C@H](OC(C)(C)C)C(=O)O)N1CCC(C)(CC1)OC/C=C\CCOc1ccccc1Cc1cnn-3c1]

(2S)-2-(tert-butoxy)-2-[(24Z)-4,28-dimethyl-21,27-dioxa-1,5,7,8,10,11-hexaazahexacyclo[26.2.2.1⁶,⁹.1¹⁰,¹³.0²,⁷.0¹⁵,²⁰]tetratriaconta-2,4,6(34),8,11,13(33),15(20),16,18,24-decaen-3-yl]acetic acid Prepared via direct saponification of intermediate 119 in 11% yield, see preparation of example 25. ¹H NMR (400 MHz, METHANOL-d₄) δ 8.17 (s, 1H), 7.80 (s, 1H), 7.36 (dd, J=7.4, 1.6 Hz, 1H), 7.18 (td, J=7.8, 1.8 Hz, 1H), 7.03-6.89 (m, 2H), 6.68 (s, 1H), 6.29-6.18 (m, 1H), 6.04 (s, 1H), 5.93 (dt, J=15.4, 5.6 Hz, 1H), 4.64-4.53 (m, 1H), 4.24-4.18 (m, 1H), 4.17-4.11 (m, 1H), 4.08 (d, J=5.0 Hz, 2H), 4.03 (d, J=14.1 Hz, 1H), 3.99-3.90 (m, 1H), 3.84 (d, J=14.1 Hz, 1H), 3.30 (d, J=11.3 Hz, 1H), 2.76 (d, J=11.8 Hz, 1H), 2.68 (s, 5H), 2.08 (dd, J=13.9, 2.1 Hz, 1H), 2.01-1.94 (m, 1H), 1.92-1.83 (m, 1H), 1.76 (td, J=13.3, 4.3 Hz, 1H), 1.34 (s, 3H), 1.31 (s, 9H). LCMS (ESI, M+1): 615.3.

Example 33

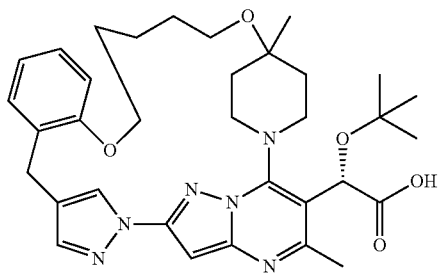 [SMILES: Cc1nc2cc3nn2c(c1[C@H](OC(C)(C)C)C(=O)O)N1CCC(C)(CC1)OCCCCCOc1ccccc1Cc1cnn-3c1]

(2S)-2-(tert-Butoxy)-2-{4,28-dimethyl-21,27-dioxa-1,5,7,8,10,11-hexaazahexacyclo[26.2.2.1⁶,⁹.1¹⁰,¹³.0²,⁷.1¹⁵,²⁰]tetratriaconta-2,4,6(34),8,11,13 (33), 15 (20), 16,18-nonaen-3-yl}acetic acid Prepared from intermediate 119 in 45% yield, see preparation of example 25. ¹H NMR (500 MHz, DMSO-d₆) δ 8.15 (s, 1H), 7.78 (s, 1H), 7.35 (d, J=7.0 Hz, 1H), 7.16-7.09 (m, 1H), 6.92 (d, J=8.2 Hz, 1H), 6.85 (t, J=7.2 Hz, 1H), 6.55 (s, 1H), 5.68 (br. s., 1H), 4.22 (t, J=12.4 Hz, 1H), 4.06 (br. s., 1H), 4.00-3.86 (m, 2H), 3.67 (d, J=13.4 Hz, 2H), 3.47 (br. s., 3H), 2.70 (d, J=11.0 Hz, 1H), 2.51 (br. s., 3H), 1.97 (br. s., 1H), 1.87 (d, J=13.1 Hz, 2H), 1.75 (br. s., 4H), 1.67 (br. s., 2H), 1.60-1.50 (m, 1H), 1.20 (s, 3H), 1.16 (s, 9H). LCMS (ESI, M+1): 617.3.

Intermediate 120

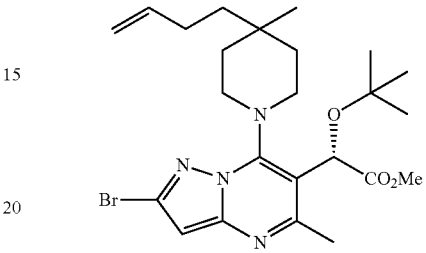

(S)-Methyl 2-(2-bromo-7-(4-(but-3-en-1-yl)-4-methylpiperidin-1-yl)-5-methylpyrazolo[1,5-a]pyrimidin-6-yl)-2-(tert-butoxy)acetate A solution of (S)-methyl 2-(2-bromo-7-chloro-5-methylpyrazolo[1,5-a]pyrimidin-6-yl)-2-(tert-butoxy)acetate( ), 4-(but-3-en-1-yl)-4-methylpiperidine hydrochloride (153 mg, 0.806 mmol, 1.05 equiv), and DIPEA (0.40 mL, 2.304 mmol, 3 equiv) in DMF (3.8 mL) was heated at 65° C. for 20 min. After cooling to ambient temperature, the reaction was diluted with EtOAc. This was washed with saturated aqueous bicarbonate solution, brine, dried (Na₂SO₄) and concentrated in vacuo. The crude product was purified by flash silica gel chromatography (20% EtOAc/hexane) to provide the product (0.35 g, 90%). LCMS (ESI, M+1): 509.4.

Intermediate 121

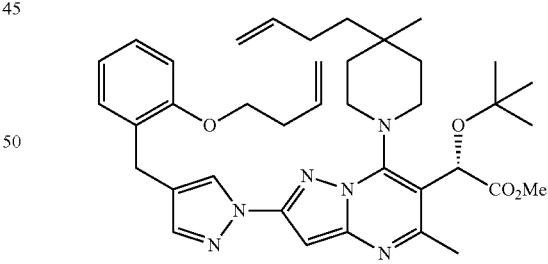

(S)-Methyl 2-(7-(4-(but-3-en-1-yl)-4-methylpiperidin-1-yl)-2-(4-(2-(but-3-en-1-yloxy)benzyl)-1H-pyrazol-1-yl)-5-methylpyrazolo[1,5-a]pyrimidin-6-yl)-2-(tert-butoxy)acetate Prepared from intermediate 89 and 120 using the same procedure as intermediate 94 in 82% yield. LCMS (ESI, M+1): 655.5.

Intermediate 122

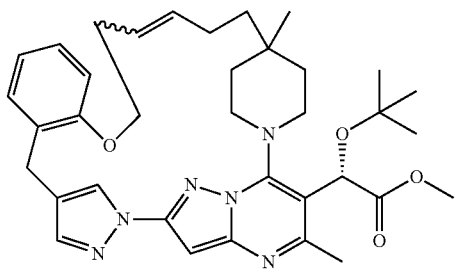

Methyl (2S)-2-(tert-butoxy)-2-[(24E)-4,28-dimethyl-21-oxa-1,5,7,8,10,11-hexaazahexacyclo[26.2.2.1$^{6,9}$.1$^{10,13}$.0$^{2,7}$.0$^{15,20}$]tetratriaconta-2,4,6(34),8,11,13(33),15(20),16,18,24-decaen-3-yl]acetate Prepared from intermediate 121 using the same procedure as intermediate 95 in 82% yield. LCMS (ESI, M+1): 627.5.

Example 34

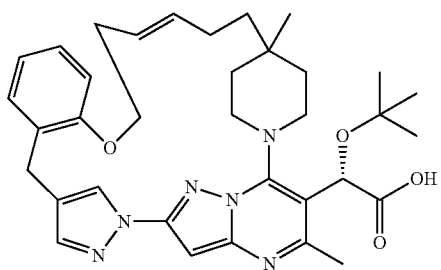 [SMILES: Cc1nc2cc3nn2c(c1[C@H](OC(C)(C)C)C(=O)O)N1CCC(C)(CC/C=C/CCOc2ccccc2Cc2cnn-3c2)CC1]

(2S)-2-(tert-Butoxy)-2-[(24E)-4,28-dimethyl-21-oxa-1,5,7,8,10,11-hexaazahexacyclo[26.2.2.1$^{6,9}$.1$^{10,13}$.0$^{2,7}$.0$^{15,20}$]tetratriaconta-2,4,6(34),8,11,13(33),15(20),16,18,24-decaen-3-yl]acetic acid Prepared via direct saponification of intermediate 122 in 17% yield, see preparation of example 25. $^1$H NMR (500 MHz, DMSO-d$_6$) δ 8.12 (s, 1H), 7.69 (s, 1H), 7.37 (d, J=6.7 Hz, 1H), 7.20-7.12 (m, 1H), 6.96-6.84 (m, 2H), 6.50 (s, 1H), 5.69 (br. s., 1H), 5.56 (d, J=5.8 Hz, 1H), 5.44 (br. s., 1H), 4.24-4.03 (m, 2H), 3.95 (d, J=7.6 Hz, 1H), 3.81-3.71 (m, 2H), 3.63 (br. s., 3H), 2.89 (s, 3H), 2.69 (d, J=6.1 Hz, 2H), 2.20 (br. s., 1H), 1.96 (br. s., 1H), 1.84 (br. s., 1H), 1.76 (br. s., 1H), 1.59 (br. s., 1H), 1.46 (br. s., 2H), 1.40-1.30 (m, 1H), 1.14 (s, 9H), 1.02 (s, 3H). LCMS (ESI, M+1): 613.3.

Example 35

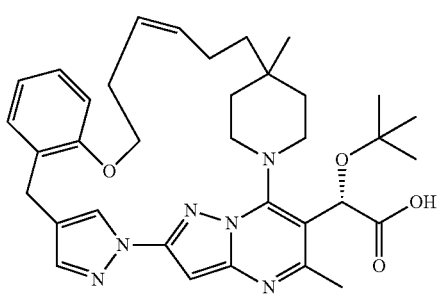 [SMILES: Cc1nc2cc3nn2c(c1[C@H](OC(C)(C)C)C(=O)O)N1CCC(C)(CC/C=C\CCOc2ccccc2Cc2cnn-3c2)CC1]

(2S)-2-(tert-Butoxy)-2-[(24Z)-4,28-dimethyl-21-oxa-1,5,7,8,10,11-hexaazahexacyclo[26.2.2.1$^{6,9}$.1$^{10,13}$.0$^{2,7}$.0$^{15,20}$]tetratriaconta-2,4,6(34),8,11,13(33),15(20),16,18,24-decaen-3-yl]acetic acid Prepared via direct saponification of intermediate 122 in 25% yield, see preparation of example 25. $^1$H NMR (500 MHz, DMSO-d$_6$) 7.97-7.89 (m, 2H), 7.40 (d, J=6.7 Hz, 1H), 7.12 (d, J=7.6 Hz, 1H), 6.96-6.84 (m, 2H), 6.58 (s, 1H), 5.78 (d, J=19.8 Hz, 3H), 4.31-4.21 (m, 1H), 4.11-3.92 (m, 3H), 3.75-3.60 (m, 3H), 3.17 (br. s., 2H), 2.61 (d, J=11.9 Hz, 1H), 2.51 (br. s., 3H), 2.02 (br. s., 2H), 1.85-1.73 (m, 1H), 1.66 (d, J=12.2 Hz, 1H), 1.61-1.36 (m, 4H), 1.16 (s, 9H), 0.97 (s, 3H). LCMS (ESI, M+1): 613.3.

Example 36

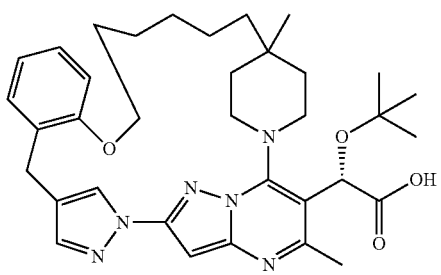 [SMILES: Cc1nc2cc3nn2c(c1[C@H](OC(C)(C)C)C(=O)O)N1CCC(C)(CCCCCCOc2ccccc2Cc2cnn-3c2)CC1]

(2S)-2-(tert-Butoxy)-2-{4,28-dimethyl-21-oxa-1,5,7,8,10,11-hexaazahexacyclo[26.2.2.1$^{6,9}$.1$^{10,13}$.0$^{2,7}$.0$^{15,20}$]tetratriaconta-2,4,6(34),8,11,13(33),15(20),16,18-nonaen-3-yl}acetic acid Prepared from intermediate 122 in 40% yield, see preparation of example 25. $^1$H NMR (500 MHz, DMSO-d$_6$) 8.08 (s, 1H), 7.80 (s, 1H), 7.40 (d, J=7.3 Hz, 1H), 7.18-7.09 (m, 1H), 6.93-6.83 (m, 2H), 6.56 (s, 1H), 5.66 (s, 1H), 4.14 (t, J=11.4 Hz, 1H), 4.05-3.89 (m, 3H), 3.64 (d, J=13.4 Hz, 2H), 3.31 (d, J=11.9 Hz, 2H), 2.77 (d, J=12.8 Hz, 1H), 1.94-1.84 (m, 1H), 1.83-1.70 (m, 3H), 1.68 (br. s., 1H), 1.63-1.53 (m, 3H), 1.52-1.34 (m, 5H), 1.32-1.20 (m, 1H), 1.16 (s, 9H), 0.98 (s, 3H). LCMS (ESI, M+1): 615.3.

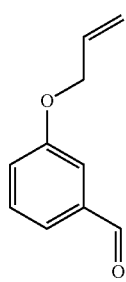

Intermediate 123

3-(Allyloxy)benzaldehyde

Prepared from 3-hydroxybenzaldehyde using the same procedure as intermediate 84. Material carried on crude. $^1$H NMR (400 MHz, CDCl3) δ (s, 1H), 7.57-7.37 (m, 3H), 7.25-7.15 (m, 1H), 6.08 (ddt, J=17.3, 10.5, 5.3 Hz, 1H), 5.45 (dq, J=17.1, 1.7 Hz, 1H), 5.33 (dq, J=10.5, 1.3 Hz, 1H), 4.62 (dt, J=5.3, 1.5 Hz, 2H).

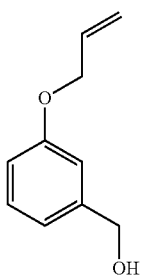

Intermediate 124

(3-(Allyloxy)phenyl)methanol

Prepared from intermediate 123 using the same procedure as intermediate 85 in 92% yield for two steps. $^1$H NMR (400 MHz, CDCl3) δ 7.32-7.23 (m, 1H), 7.01-6.93 (m, 2H), 6.92-6.82 (m, 1H), 6.08 (ddt, J=17.1, 10.5, 5.3 Hz, 1H), 5.43 (dq, J=17.2, 1.6 Hz, 1H), 5.30 (dq, J=10.4, 1.5 Hz, 1H), 4.68 (d, J=5.3 Hz, 2H), 4.57 (dt, J=5.3, 1.5 Hz, 2H), 1.73-1.62 (m, 1H).

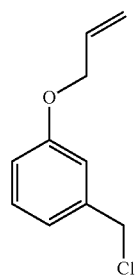

Intermediate 125

1-(Allyloxy)-3-(chloromethyl)benzene

Prepared from intermediate 124 using the same procedure as intermediate 86 in 81% yield. $^1$H NMR (400 MHz, CDCl$_3$) δ 7.31-7.27 (m, 1H), 7.02-6.97 (m, 2H), 6.90 (ddd, J=8.3, 2.5, 0.7 Hz, 1H), 6.08 (ddt, J=17.3, 10.5, 5.3 Hz, 1H), 5.45 (dq, J=17.2, 1.6 Hz, 1H), 5.32 (dq, J=10.5, 1.4 Hz, 1H), 4.62-4.53 (m, 4H).

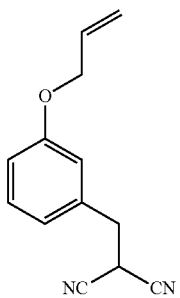

Intermediate 126

2-(3-(But-3-en-1-yloxy)benzyl)malononitrile

Prepared from intermediate 125 using the same procedure as intermediate 87 in 80% yield. $^1$H NMR (400 MHz, CDCl$_3$) δ 7.32 (t, J=8.0 Hz, 1H), 7.02-6.84 (m, 3H), 6.15-6.00 (m, 1H), 5.43 (dd, J=17.2, 1.4 Hz, 1H), 5.34-5.25 (m, 1H), 4.57 (dt, J=5.2, 1.4 Hz, 2H), 3.91 (t, J=6.9 Hz, 2H), 3.27 (d, J=7.0 Hz, 1H).

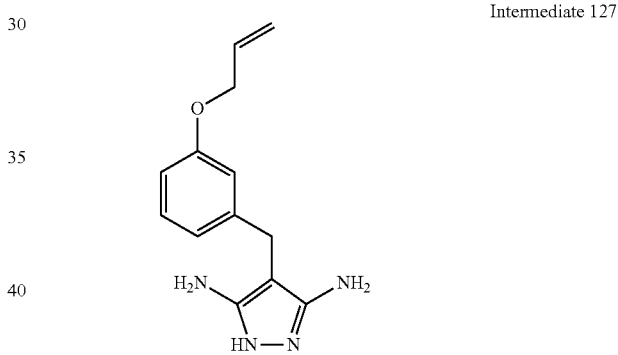

Intermediate 127

4-(3-(Allyloxy)benzyl)-1H-pyrazole-3,5-diamine

Prepared from intermediate 126 using the same procedure as intermediate 88 in 60% yield. $^1$H NMR (400 MHz, CDCl$_3$) δ 7.21 (s, 1H), 6.81 (d, J=10.3 Hz, 3H), 6.12-5.99 (m, 1H), 5.46-5.37 (m, 1H), 5.30 (s, 1H), 4.52 (dt, J=5.3, 1.5 Hz, 2H), 3.60 (s, 2H); LCMS (ESI, M+1): 245.25.

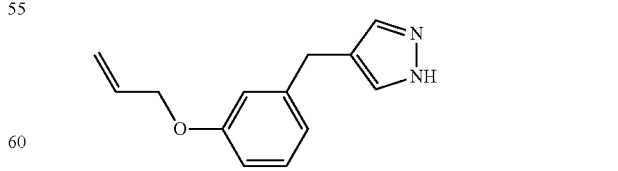

Intermediate 128

4-(3-(Allyloxy)benzyl)-1H-pyrazole

Prepared from intermediate 127 using the same procedure as intermediate 89 in 23% yield. $^1$H NMR (400 MHz, CDCl₃) δ 7.41 (s, 2H), 7.21 (dd, J=8.9, 7.7 Hz, 1H), 6.89-6.70 (m, 3H), 6.14-5.92 (m, 1H), 5.49-5.36 (m, 1H), 5.28 (dd, J=10.4, 1.4 Hz, 1H), 4.52 (dt, J=5.3, 1.4 Hz, 2H), 3.85 (s, 2H); LCMS (ESI, M+1): 216.1.

Intermediate 129

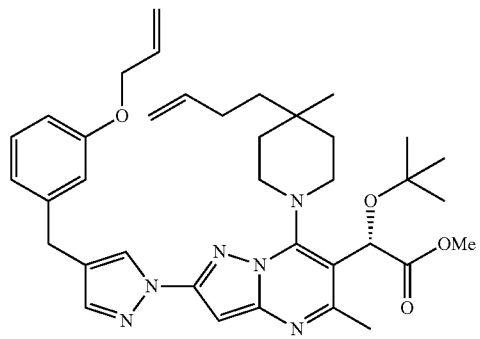

(S)-Methyl 2-(2-(4-(3-(allyloxy)benzyl)-1H-pyrazol-1-yl)-7-(4-(but-3-en-1-yl)-4-methylpiperidin-1-yl)-5-methylpyrazolo[1,5-c]pyrimidin-6-yl)-2-(tert-butoxy)acetate Prepared from intermediate 120 and 128 using the same procedure as intermediate 94 in 87% yield. LCMS (ESI, M+1): 641.5.

Intermediate 130

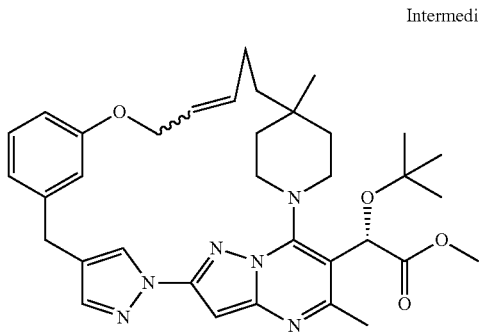

Methyl (2S)-2-(tert-butoxy)-21(22E)-4,26-dimethyl-20-oxa-1,5,7,8,10,11-hexaazahexacyclo[24.2.2.1⁶,⁹.1¹⁰,¹³.1¹⁵,¹⁹.0²,⁷]tritriaconta-2,4,6(33),8,11,13(32),15(31),16,18,22-decaen-3-yl]acetate Prepared from intermediate 371 using the same procedure as intermediate 251 in 92% yield. LCMS (ESI, M+1): 613.5.

Example 37

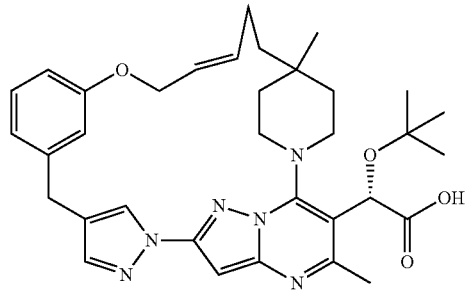 [SMILES: Cc1nc2cc3nn2c(c1[C@H](OC(C)(C)C)C(=O)O)N1CCC(C)(CC/C=C/COc2cccc(c2)Cc2cnn-3c2)CC1]

(2S)-2-(tert-butoxy)-21(22E)-4,26-dimethyl-20-oxa-1,5,7,8,10,11-hexaazahexacyclo[24.2.2.1⁶,⁹.1¹⁰,¹³.1¹⁵,²⁰]tritriaconta-2,4,6(33),8,11,13(32),15(31),16,18,22-decaen-3-yl]acetic acid Prepared via direct saponification of intermediate 130 in 40% yield, see preparation of example 25. ¹H NMR (500 MHz, DMSO-d₆) δ 7.81 (s, 1H), 7.59 (s, 1H), 7.19 (t, J=7.8 Hz, 1H), 7.02 (br. s., 1H), 6.81 (d, J=6.7 Hz, 2H), 6.61 (s, 1H), 5.86-5.74 (m, 2H), 5.66 (d, J=15.9 Hz, 1H), 4.71 (br. s., 2H), 4.08 (t, J=12.2 Hz, 1H), 3.79 (s, 2H), 3.09 (br. s., 2H), 2.60 (d, J=11.6 Hz, 1H), 2.52 (br. s., 3H), 1.99 (d, J=7.0 Hz, 2H), 1.64-1.39 (m, 6H), 1.16 (s, 9H), 0.95 (s, 3H). LCMS (ESI, M+1): 599.3.

Example 38

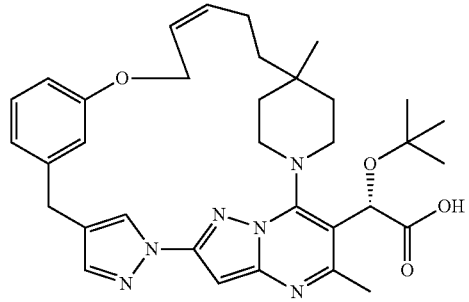 [SMILES: Cc1nc2cc3nn2c(c1[C@H](OC(C)(C)C)C(=O)O)N1CCC(C)(CC/C=C\COc2cccc(c2)Cc2cnn-3c2)CC1]

(2S)-2-(tert-Butoxy)-21(22E)-4,26-dimethyl-20-oxa-1,5,7,8,10,11-hexaazahexacyclo[24.2.2.1⁶,⁹.1¹⁰,¹³.1¹⁵,²⁰]tritriaconta-2,4,6(33),8,11,13(32),15(31),16,18,22-decaen-3-yl]acetic acid Prepared via direct saponification of intermediate 130 in 6% yield, see preparation of example 25. ¹H NMR (500 MHz, DMSO-d₆) δ 8.20 (s, 1H), 7.73 (s, 1H), 7.27 (br. s., 1H), 7.17 (t, J=7.9 Hz, 1H), 6.87 (d, J=7.6 Hz, 1H), 6.76 (d, J=8.9 Hz, 1H), 6.51 (s, 1H), 5.73 (d, J=4.9 Hz, 2H), 5.30 (br. s., 1H), 4.71-4.52 (m, 2H), 3.95-3.77 (m, 4H), 3.73-3.64 (m, 2H), 2.46 (s, 3H), 2.29 (br. s., 1H), 1.90 (s, 3H), 1.63-1.38 (m, 4H), 1.13 (s, 9H), 1.05 (s, 3H). LCMS (ESI, M+1): 599.3.

Example 39

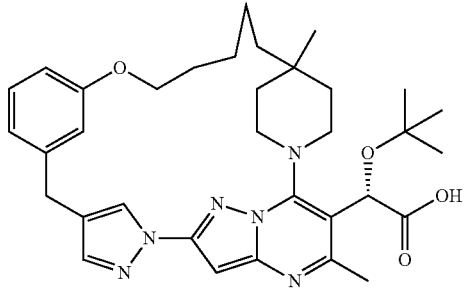 [SMILES: Cc1nc2cc3nn2c(c1[C@H](OC(C)(C)C)C(=O)O)N1CCC(C)(CCCCCOc2cccc(c2)Cc2cnn-3c2)CC1]

(2S)-2-(tert-Butoxy)-2-{4,26-dimethyl-20-oxa-1,5,7,8,10,11-hexaazahexacyclo[24.2.2.1$^{6,9}$.1$^{10,13}$.1$^{15,19}$.0$^{2,7}$]tritriaconta-2,4,6(33),8,11,13(32),15(31),16,18-nonaen-3-yl}acetic acid Prepared from intermediate 130 in 23% yield, see preparation of example 25. $^1$H NMR (500 MHz, DMSO-d$_6$) δ 7.77 (d, J=4.0 Hz, 2H), 7.22-7.17 (m, 1H), 7.11 (s, 1H), 6.81 (d, J=6.4 Hz, 2H), 6.55 (s, 1H), 5.48 (br. s., 1H), 4.20-4.05 (m, 2H), 3.95-3.87 (m, 1H), 3.81 (s, 2H), 3.55 (d, J=9.5 Hz, 2H), 3.43 (br. s., 1H), 2.84 (d, J=11.9 Hz, 1H), 2.48 (s, 3H), 1.84-1.64 (m, 3H), 1.62-1.40 (m, 5H), 1.39-1.15 (m, 4H), 1.13 (s, 9H), 0.96 (s, 3H). LCMS (ESI, M+1): 601.3.

Intermediate 131

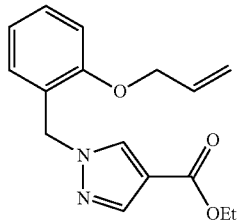

Ethyl 1-(2-(allyloxy)benzyl)-1H-pyrazole-4-carboxylate

To a solution of ethyl 1H-pyrazole-4-carboxylate (0.94 g, 6.71 mmol, 1 equiv) and 1-(allyloxy)-2-(chloromethyl)benzene (1.35 g, 7.38 mmol, 1.1 equiv) in MeCN (34 mL) was added K$_2$CO$_3$ (2.04 g, 14.76 mmol, 2.2 equiv). The slurry was then heated to reflux for 6 h. After cooling to ambient temperature, the mixture was filtered and the filtrate was concentrated in vacuo to provide ethyl 1-(2-(allyloxy)benzyl)-1H-pyrazole-4-carboxylate (2.04 g, 100%) as a pale orange oil. $^1$H NMR (400 MHz, CDCl3) δ 7.91 (s, 1H), 7.91 (s, 1H), 7.31 (td, J=7.9, 1.8 Hz, 1H), 7.17 (dd, J=7.3, 1.5 Hz, 1H), 6.96 (td, J=7.4, 1.0 Hz, 1H), 6.91 (d, J=8.3 Hz, 1H), 6.04 (ddt, J=17.3, 10.5, 5.3 Hz, 1H), 5.43-5.28 (m, 4H), 4.58 (dt, J=5.3, 1.5 Hz, 2H), 4.28 (q, J=7.2 Hz, 2H), 1.34 (t, J=7.2 Hz, 3H); LCMS (ESI, M+1): 287.25.

Intermediate 132

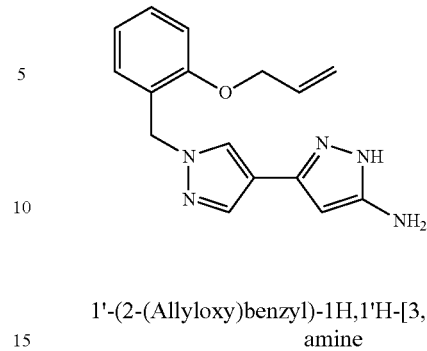

1'-(2-(Allyloxy)benzyl)-1H,1'H-[3,4'-bipyrazol]-5-amine

A solution of MeCN (0.52 mL, 9.97 mmol, 1.4 equiv) in THF (7 mL) was cooled to −78° C. (IPA/CO$_2$). n-BuLi (6.23 mL of a 1.6 M solution in hexanes, 9.97 mmol, 1.4 equiv) was then added and the reaction was stirred 10 min. To this white slurry was added a solution of ethyl 1-(2-(allyloxy)benzyl)-1H-pyrazole-4-carboxylate (2.04 g, 7.12 mmol, 1 equiv) in THF (7 mL). Reaction became a tan colored slurry, then an orange homogenous solution, and finally faded to a pale yellow color. After 10 min, the cooling bath was removed and the reaction was allowed to warm to ambient temperature. Upon stirring for 1 h, the reaction was added to a saturated aqueous solution of NH$_4$Cl and extracted with DCM (×2). The combined DCM extracts were dried (Na$_2$SO$_4$) and concentrated in vacuo to provide the crude 3-(1-(2-(allyloxy)benzyl)-1H-pyrazol-4-yl)-3-oxopropanenitrile. This crude product was taken up in EtOH (36 mL) and hydrazine (0.36 mL, 11.39 mmol, 1.6 equiv) was added. The reaction was then heated at reflux for 2 h and in vacuo to provide the crude product. The crude product was purified by silica gel flash chromatography (0-10% MeOH/CHCl$_3$ with 1% NH$_4$OH) to provide 1'-(2-(allyloxy)benzyl)-1H,1'H-[3,4'-bipyrazol]-5-amine (1.51 g, 72% for 2 steps) as a white solid. $^1$H NMR (500 MHz, CDCl3) δ 7.67 (s, 1H), 7.62 (s, 1H), 7.32 (q, J=0.9 Hz, 1H), 7.18 (dd, J=7.5, 1.7 Hz, 1H), 6.99-6.95 (m, J=0.9 Hz, 1H), 6.92 (d, J=8.2 Hz, 1H), 6.12-6.02 (m, 1H), 5.71 (s, 1H), 5.42 (dd, J=17.3, 1.5 Hz, 1H), 5.39 (s, 2H), 5.33 (dd, J=10.6, 1.4 Hz, 1H), 4.61 (dt, J=5.2, 1.5 Hz, 2H), 3.77-3.61 (m, 2H); LCMS (ESI, M+1): 296.25.

Intermediate 133

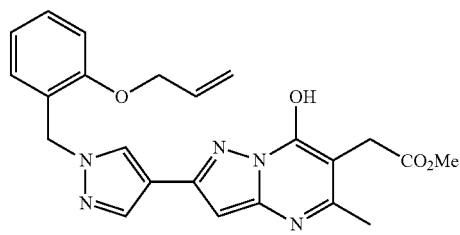

Methyl 2-(2-(1-(2-(allyloxy)benzyl)-1H-pyrazol-4-yl)-7-hydroxy-5-methylpyrazolo[1,5-a]pyrimidin-6-yl)acetate To a slurry of 1'-(2-(allyloxy)benzyl)-1H,1'H-[3,4'-bipyrazol]-5-amine (1.51 g, 5.11 mmol, 1 equiv) in xylene (26 mL) was added dimethyl 2-acetylsuccinate (1.0 mL, 6.14 mmol, 1.2 equiv) and TsOH (2 mg, 0.010 mmol, 0.002 equiv). The reaction was heated to reflux for 4 h and then removed from heating. Upon cooling to ambient temperature. The reaction was diluted with hexane and the pale yellow solid was filtered to provide methyl 2-(2-(1-(2-(allyloxy)benzyl)-1H-pyrazol-4-yl)-7-hydroxy-5-methylpyrazolo[1,5-a]pyrimidin-6-yl)acetate (2.03 g, 92%). $^1$H NMR (400 MHz, CDCl3) δ 7.96-7.87 (m, 1H), 7.86-7.81 (m, 1H), 7.27-7.23 (m, 1H), 7.15-7.07 (m, 1H), 6.95-6.84 (m, 2H), 6.04 (s, 1H), 6.02-5.94 (m, 1H), 5.36 (s, 3H), 5.28-5.21 (m, 1H), 4.57-4.52 (m, 2H), 3.70 (s, 3H), 3.64 (s, 2H), 2.34 (s, 3H); LCMS (ESI, M+1): 434.3.

Intermediate 134

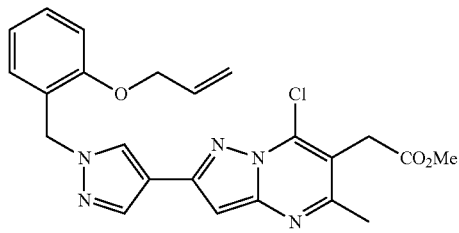

Methyl 2-(2-(1-(2-(allyloxy)benzyl)-1H-pyrazol-4-yl)-7-chloro-5-methylpyrazolo[1,5-a]pyrimidin-6-yl)acetate A solution of methyl 2-(2-(1-(2-(allyloxy)benzyl)-1H-pyrazol-4-yl)-7-hydroxy-5-methylpyrazolo[1,5-a]pyrimidin-6-yl)acetate (1.44 g, 3.32 mmol, 1 equiv) and N,N-dimethylaniline (0.93 mL, 7.31 mmol, 2.2 equiv) in POCl$_3$ (17 mL) was heated to 90° C. for 1 h. The reaction was then allowed to cool to ambient temperature and concentrated in vacuo. The residue was added to saturated aqueous sodium bicarbonate and extracted with CHCl$_3$ (×3). The combined CHCl$_3$ extracts were dried (Na$_2$SO$_4$) and concentrated in vacuo to provide the crude product. The crude product was purified via silica gel flash chromatography (0-100% EtOAc/hex) to provide methyl 2-(2-(1-(2-(allyloxy)benzyl)-1H-pyrazol-4-yl)-7-chloro-5-methylpyrazolo[1,5-a]pyrimidin-6-yl)acetate (0.95 g, 63%). $^1$H NMR (400 MHz, CDCl3) δ 7.99 (d, J=6.8 Hz, 2H) [note: this is probably two very close together singlets], 7.32-7.29 (m, 1H), 7.20-7.13 (m, 1H), 6.99-6.88 (m, 2H), 6.68 (s, 1H), 6.16-6.00 (m, 1H), 5.46-5.39 (m, 3H), 5.35-5.28 (m, 1H), 4.65-4.56 (m, 2H), 3.90 (s, 2H), 3.76 (s, 3H), 2.60 (s, 3H); LCMS (ESI, M+1): 452.3.

Intermediate 135

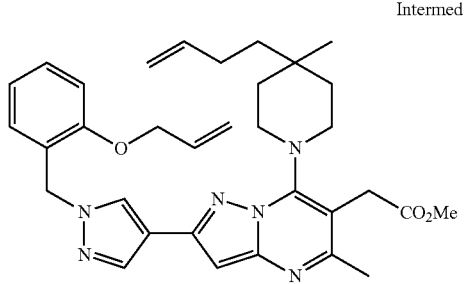

Methyl 2-(2-(1-(2-(allyloxy)benzyl)-1H-pyrazol-4-yl)-7-(4-(but-3-en-1-yl)-4-methylpiperidin-1-yl)-5-methylpyrazolo[1,5-a]pyrimidin-6-yl)acetate A solution of methyl 2 methyl 2-(2-(1-(2-(allyloxy)benzyl)-1H-pyrazol-4-yl)-7-chloro-5-methylpyrazolo[1,5-a]pyrimidin-6-yl)acetate (0.24 g, 0.531 mmol, 1 equiv), 4-(but-3-en-1-yl)-4-methylpiperidine, HCl (111 mg, 0.584 mmol, 1.1 equiv), and DIPEA (2.2 mL, 1.275 mmol, 2.4 equiv) in DMF (2.7 mL) was heated at 60° C. for 6 h. The reaction was then added to saturated aqueous sodium bicarbonate and extracted with EtOAc (×2). Combined EtOAc extracts dried (Na$_2$SO$_4$) and concentrated in vacuo. The crude product was purified via silica gel flash chromatography (10-100% EtOAc/hex) to provide methyl 2-(2-(1-(2-(allyloxy)benzyl)-1H-pyrazol-4-yl)-7-(4-(but-3-en-1-yl)-4-methylpiperidin-1-yl)-5-methylpyrazolo[1,5-a]pyrimidin-6-yl)acetate (0.265 g, 88%). $^1$H NMR (500 MHz, CDCl$_3$) δ 7.99 (d, J=0.6 Hz, 1H), 7.92 (s, 1H), 7.30 (br. s., 1H), 7.18-7.13 (m, 1H), 6.99-6.89 (m, 2H), 6.52 (s, 1H), 6.14-6.05 (m, 1H), 5.95-5.85 (m, 1H), 5.49-5.41 (m, 3H), 5.33 (s, 1H), 5.13-5.05 (m, 1H), 5.02-4.96 (m, 1H), 4.62 (dt, J=5.2, 1.5 Hz, 2H), 3.83 (s, 2H), 3.77 (s, 3H), 2.52 (s, 3H), 2.16-2.08 (m, 2H), 1.70-1.60 (m, 2H), 1.56-1.47 (m, J=8.0, 4.3 Hz, 4H), 1.10 (s, 3H); LCMS (ESI, M+1): 569.45.

Intermediate 136

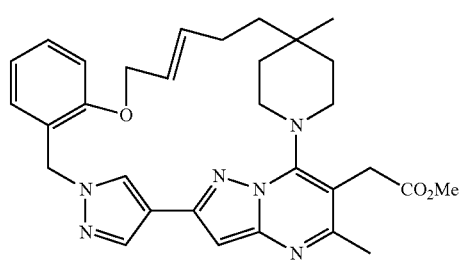

Methyl 2-[(23E)-4,27-dimethyl-21-oxa-1,5,7,8,12,13-hexaazahexacyclo[25.2.2.1$^{6,9}$.1$^{10,13}$.0$^{2,7}$.0$^{15,20}$]tritriaconta-2,4,6(33),8,10(32),11,15(20),16,18,23-decaen-3-yl]acetate Nitrogen was bubbled through a solution of (methyl 2-(2-(1-(2-(allyloxy)benzyl)-1H-pyrazol-4-yl)-7-(4-(but-3-en-1-yl)-4-methylpiperidin-1-yl)-5-methylpyrazolo[1,5-a]pyrimidin-6-yl)acetate (0.26 mg, 0.457 mmol, 1 equiv) in DCE (91 mL) for 5 min. The solution was then heated to 70° C. and Hoveyda-Grubbs catalyst 2nd generation (29 mg, 0.046 mmol, 0.1 equiv) was added. Heating of the slightly pale blue solution was continued for 1 h. The reaction was then allowed to cool to ambient temperature and concentrated in vacuo. The crude product was purified via silica gel flash chromatography (0-100% EtOAc/hex) to provide desired product (0.156 g, 63%) as a tan foam. $^1$H NMR (400 MHz, CDCl$_3$) δ 8.03 (s, 1H), 7.82 (s, 1H), 7.56-7.51 (m, 1H), 7.34-7.29 (m, 1H), 7.00-6.90 (m, 2H), 6.58 (s, 1H), 6.14-6.04 (m, 1H), 5.95-5.82 (m, 1H), 5.37 (s, 2H), 4.64-4.59 (m, 2H), 4.24-4.15 (m, 2H), 3.86 (s, 2H), 3.74 (s, 3H), 2.70-2.61 (m, 2H), 2.53 (s, 3H), 2.15-2.06 (m, 2H), 1.89-1.80 (m, 2H), 1.64-1.56 (m, 4H), 1.01 (s, 3H) LCMS (ESI, M+1): 541.4.

Intermediate 137

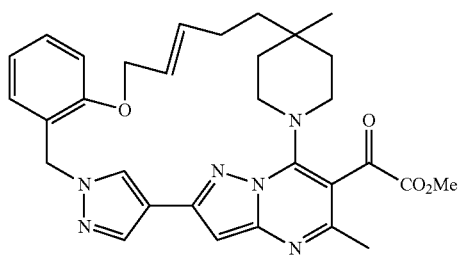

Methyl 2-[(23E)-4,27-dimethyl-21-oxa-1,5,7,8,12,13-hexaazahexacyclo[25.2.2.1⁶,⁹.1¹⁰,¹³.0²,⁷.0¹⁵,²⁰]tritriaconta-2,4,6(33),8,10(32),11,15(20),16,18,23-decaen-3-yl]-2-oxoacetate A solution of methyl 2-[(23E)-4,27-dimethyl-21-oxa-1,5,7,8,12,13-hexaazahexacyclo[25.2.2.1⁶,⁹.1¹⁰,¹³.0²,⁷.0¹⁵,²⁰]tritriaconta-2,4,6(33),8,10(32),11,15(20),16,18,23-decaen-3-yl]acetate (0.156, 0.289 mmol, 1 equiv) in THF (6 mL) was cooled to −78° C. (IPA/CO₂). KHMDS (0.44 mL of a 0.91 M solution in THF, 0.404 mmol, 1.4 equiv) was added. Reaction turned a deep orange yellow color. After 15 min, 3-phenyl-2-(phenylsulfonyl)-1,2-oxaziridine (113 mg, 0.433 mmol, 1.5 equiv) was added in a single portion. After 30 min, the cold reaction was added to saturated aqueous sodium bicarbonate and extracted with EtOAc (×2). The combined EtOAc extracts were dried (Na₂SO₄) and concentrated in vacuo to provide the crude product. This was taken up in DCM (5.8 mL) and Dess-Martin periodinane (172 mg, 0.405 mmol, 1.4 equiv). After 16 h, the reaction was added to saturated aqueous sodium bicarbonate and extracted with DCM (×3). Combined DCM extracts were dried (Na₂SO₄) and concentrated in vacuo to provide the crude product. The crude product was purified via silica gel flash chromatography (10-100% EtOAc/hex) to provide desired product (0.15 g, 94%). ¹H NMR (400 MHz, CDCl3) δ 8.09 (s, 1H), 7.83 (s, 1H), 7.66-7.58 (m, 1H), 7.35-7.29 (m, 1H), 7.04-6.89 (m, 2H), 6.65 (s, 1H), 6.14-6.00 (m, 1H), 5.94-5.83 (m, 1H), 5.37 (s, 2H), 4.82-4.70 (m, 2H), 4.60 (d, J=5.8 Hz, 2H), 4.22-4.10 (m, 2H), 3.97 (s, 3H), 2.91-2.76 (m, 2H), 2.63 (s, 3H), 2.19-2.08 (m, 2H), 1.83-1.74 (m, 2H), 1.71-1.63 (m, 2H), 1.03 (s, 3H); LCMS (ESI, M+1): 555.3.

Intermediate 138

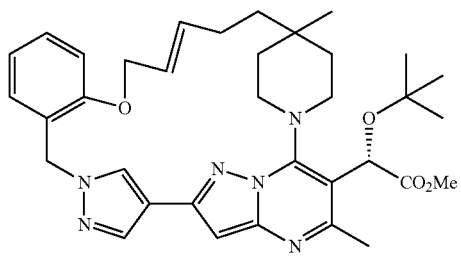

Methyl (2S)-2-(tert-butoxy)-2-[(23E)-4,27-dimethyl-21-oxa-1,5,7,8,12,13-hexaazahexacyclo[25.2.2.1⁶,⁹.1¹⁰,¹³.0²,⁷.0¹⁵,²⁰]tritriaconta-2,4,6(33),8,10(32),11,15(20),16,18,23-decaen-3-yl 1 acetate A solution methyl 2-[(23E)-4,27-dimethyl-21-oxa-1,5,7,8,12,13-hexaazahexacyclo[25.2.2.1⁶,⁹.1¹⁰,¹³.0²,⁷.0¹⁵,²⁰]tri- triaconta-2,4,6(33),8,10(32),11,15(20),16,18,23-decaen-3-yl]-2-oxoacetate (0.15 g, 0.270 mmol, 1 equiv) and (R)-1-methyl-3,3-diphenylhexahydropyrrolo[1,2-c][1,3,2]oxazaborole (120 mg, 0.433 mmol, 1.6 equiv) in toluene (5.4 mL) was cooled to −25° C. (MeCN/CO₂). Catecholborane (0.92 mL of a 50% solution in toluene, 0.433 mmol, 1.6 equiv) was then added and temperature was held between −15° C. and −25° C. for 3 h. The cold reaction was then added to 10% aqueous extracted with EtOAc (×3). The combined EtOAc extracts were dried (Na₂SO₄) and concentrated in vacuo to provide the crude product as a pale yellow foam (290 mg). This was taken up in t-BuOAc (5.4 mL). To this solution was added perchloric acid (0.070 mL of a 70% aqueous solution, 0.810 mmol, 3 equiv) to give a cloudy white solution. To try and improve solubility, DCM (5 mL) and more perchloric acid (0.2 mL of a 70% aqueous solution, 5.7 equiv) were added. After stirring 1 h, the reaction was added cautiously to saturated aqueous sodium bicarbonate and extracted with DCM (×3). The combined DCM extracts were dried (Na₂SO₄) and concentrated in vacuo to provide the crude product. The crude product was purified via silica gel flash chromatography (10-100% EtOAc/hex) to provide desired product (43 mg, 26% 2 steps). ¹H NMR (400 MHz, CDCl3) δ 8.03 (s, 1H), 7.82 (d, J=0.5 Hz, 1H), 7.57-7.51 (m, 1H), 7.35-7.29 (m, 1H), 7.04-6.90 (m, 2H), 6.57 (s, 1H), 6.17 (s, 1H), 6.13-6.04 (m, 1H), 5.93-5.85 (m, J=15.6 Hz, 1H), 5.46-5.38 (m, 1H), 5.36-5.28 (m, 1H), 4.70-4.54 (m, 3H), 4.02-3.91 (m, 1H), 3.69 (s, 3H), 2.92 (d, J=10.5 Hz, 1H), 2.61 (s, 3H), 2.66-2.58 (m, J=18.8 Hz, 1H), 2.16-2.08 (m, 2H), 1.98-1.77 (m, 2H), 1.72-1.60 (m, 4H), 1.27 (s, 9H), 1.04 (s, 3H); LCMS (ESI, M+1): 613.4.

Example 40

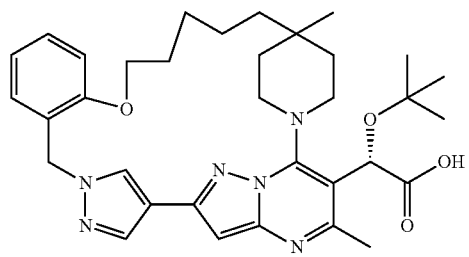 [SMILES: Cc1nc2cc3nn2c(c1[C@H](OC(C)(C)C)C(=O)O)N1CCC(C)(CCCCCOc2ccccc2Cn2cc-3cn2)CC1]

(2S)-2-(tert-Butoxy)-2-{4,27-dimethyl-21-oxa-1,5,7,8,12,13-hexaazahexacyclo[25.2.2.1⁶,⁹.1¹⁰,¹³.0²,⁷.0¹⁵,²⁰]tritriaconta-2,4,6(33),8,10(32),11,15(20),16,18-nonaen-3-yl}acetic acid A solution of methyl (2S)-2-(tert-butoxy)-2-[(23E)-4,27-dimethyl-21-oxa-1,5,7,8,12,13-hexaazahexacyclo[25.2.2.1⁶,⁹.1¹⁰,¹³.0²,⁷.0¹⁵,²⁰]tritriaconta-2,4,6(33),8,10(32),11,15(20),16,18,23-decaen-3-yl]acetate (34 mg, 0.055 mmol, 1 equiv) and 10% Pd/C (12 mg, 0.011 mmol, 0.2 equiv) in MeOH (1.1 mL) was exposed to a balloon of hydrogen. After 6 h, the reaction was filtered through a plug of Celite eluting with a minimal amount of MeOH. To this filtered solution was added lithium hydroxide monohydrate (70 mg, 1.6 mmol, 30 equiv). The reaction was then heated at 60° C. for 18 h. The reaction was removed from heat and filtered. The filtrate was purified via preparative LC/MS with the following conditions: Column: Waters XBridge C18, 19×200 mm, 5-μm particles; Mobile Phase A: water with 20-mM ammonium acetate; Mobile Phase B: 95:5 acetonitrile:water with 20-mM ammonium acetate; gradient: 40-80% B over 20 minutes, then a 5-minute hold at 100% B; Flow: 20 mL/min., to provide desired product (5.9 mg, 16%). $^1$H NMR (500 MHz, DMSO-$d_6$) δ 8.12 (s, 1H), 7.92 (s, 1H), 7.46 (d, J=7.3 Hz, 1H), 7.35-7.29 (m, 1H), 7.05 (d, J=8.2 Hz, 1H), 6.94 (t, J=7.5 Hz, 1H), 6.71 (s, 1H), 5.87 (s, 1H), 5.31 (d, J=9.5 Hz, 2H), 4.48 (br. s., 1H), 4.16-4.00 (m, 2H), 3.75 (br. s., 1H), 3.10 (d, J=9.8 Hz, 1H), 2.61 (d, J=11.6 Hz, 1H), 2.54-2.49 (m, 3H), 1.96 (br. s., 2H), 1.75-1.37 (m, 10H), 1.20 (s, 9H), 0.99 (s, 3H); LCMS (ESI, M+1): 601.5.

Example 41

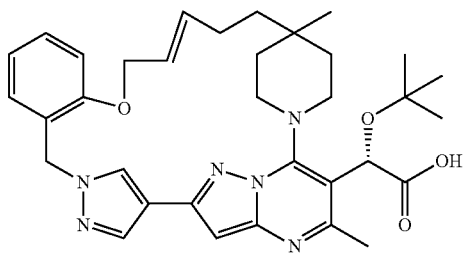 [SMILES: Cc1nc2cc3nn2c(c1[C@H](OC(C)(C)C)C(=O)O)N1CCC(C)(CC/C=C/COc2ccccc2Cn2cc-3cn2)CC1]

(2S)-2-(tert-Butoxy)-21(23E)-4,27-dimethyl-21-oxa-1,5,7,8,12,13-hexaazahexacyclo
[25.2.2.1$^{6,9}$.1$^{10,13}$.0$^{2,7}$.0$^{15,20}$]tritriaconta-2,4,6(33),8,10(32),11,15(20),16,18,23-decaen-3-yl]acetic acid Prepared via direct saponification of intermediate 138 in 82% yield, see procedure for example 40. $^1$H NMR (500 MHz, DMSO-$d_6$) δ 8.02 (s, 1H), 7.94 (s, 1H), 7.48 (d, J=6.1 Hz, 1H), 7.34 (t, J=7.9 Hz, 1H), 7.11 (d, J=7.9 Hz, 1H), 6.97 (t, J=7.3 Hz, 1H), 6.71 (s, 1H), 6.11 (s, 1H), 5.96-5.85 (m, 2H), 5.39 (d, J=14.0 Hz, 1H), 5.24 (d, J=14.0 Hz, 1H), 4.71-4.65 (m, J=6.1 Hz, 1H), 4.62-4.56 (m, J=5.8 Hz, 1H), 4.52 (br. s., 1H), 3.75 (br. s., 1H), 3.07 (d, J=9.5 Hz, 1H), 2.58 (d, J=11.3 Hz, 1H), 2.52 (s, 3H), 2.09 (d, J=7.6 Hz, 2H), 1.90-1.46 (m, 6H), 1.20 (s, 9H), 1.00 (s, 3H). LCMS (ESI, M+1): 599.33.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of Formula I

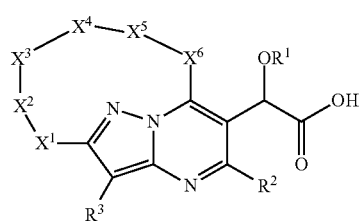

where:
$R^1$ is hydrogen or alkyl;
$R^2$ is hydrogen or alkyl;
$R^3$ is hydrogen, alkyl or halo;
$X^1$ is pyrrolyl, furanyl, thienyl, pyrazolyl, isoxazolyl, isothiazolyl, imidazolyl, oxazolyl, thiazolyl, triazolyl, oxadiazolyl, or thiadiazolyl;
$X^2$ is benzyl wherein the benzyl can be substituted with 0-3 substituents selected from halo, alkyl, haloalkyl, alkoxy, and haloalkoxy;
$X^3$ is O or absent;
$X^4$ is alkylene or alkenylene;
$X^5$ is O or absent; and
$X^6$ is azetidinyl, pyrrolidinyl, piperidinyl, piperazinyl, morpholinyl, homopiperidinyl, homopiperazinyl, or homomorpholinyl, and is substituted with 0-3 halo or alkyl substituents;
or a pharmaceutically acceptable salt thereof.

2. A compound of claim 1 where $R^1$ is alkyl; $R^2$ is alkyl; $R^3$ is hydrogen; $X^1$ is pyrazolyl, oxazolyl, or thiazolyl; $X^2$ is absent or benzyl wherein the benzyl can be substituted with 0-3 substituents selected from halo, alkyl, haloalkyl, alkoxy, and haloalkoxy; $X^3$ is O or absent; $X^4$ is alkylene or alkenylene; $X^5$ is O or absent; and $X^6$ is azetidinyl, pyrrolidinyl, piperidinyl, piperazinyl, morpholinyl, homopiperidinyl, homopiperazinyl, or homomorpholinyl, and is substituted with 0-3 halo or alkyl substituents; or a pharmaceutically acceptable salt thereof.

3. A compound of claim 1 where $R^1$ is alkyl, $R^2$ is alkyl, and $R^3$ is hydrogen.

4. A compound of claim 1 where $X^1$ is pyrazolyl.

5. A compound of claim 1 where $X^1$ is oxazolyl.

6. A compound of claim 1 where $X^1$ is thiazolyl.

7. A compound of claim 1 where $X^4$ is propylene, propenylene, butylene, butenylene, pentylene, pentenylene, hexylene, or hexenylene.

8. A compound of claim 1 where $X^6$ is piperidinyl substituted with 0-1 alkyl substituents.

9. A compound of claim 1 selected from the group consisting of
(2 S)-2-(tert-Butoxy)-2-[(22E)-4,26-dimethyl-25-oxa-31-thia-1,5,7,8,11-pentaazahexacyclo
[24.2.2.1$^{6,9}$.1$^{10,13}$.0$^{2,7}$.0$^{15,20}$]dotriaconta-2,4,6(32),8,10,12,15(20),16,18,22-decaen-3-yl]acetic acid;
(2S)-2-(tert-Butoxy)-2-[(23Z)-4,27-dimethyl-26-oxa-32-thia-1,5,7,8,11-pentaazahexacyclo
[25.2.2.1$^{6,9}$.1$^{10,13}$.0$^{2,7}$.0$^{15,20}$]tritriaconta-2,4,6(33),8,10,12,15 (20),16,18,23-decaen-3-yl]acetic acid;
(2S)-2-(tert-Butoxy)-2-[(22E)-4,26-dimethyl-25-oxa-32-thia-1,5,7,8,11-pentaazahexacyclo
[24.2.2.1$^{6,9}$.1$^{10,13}$1$^{15,19}$.0$^{2,7}$]tritriaconta-2,4,6(33),8,10,12,15(31),16,18,22-decaen-3-yl]acetic acid;
(2S)-2-(tert-Butoxy)-2-{4,26-dimethyl-25-oxa-32-thia-1,5,7,8,11-pentaazahexacyclo
[24.2.2.1$^{6,9}$.1$^{10,13}$1$^{15,19}$.0$^{2,7}$]tritriaconta-2,4,6(33),8,10,12,15(31),16,18-nonaen-3-yl}acetic acid;
(2S)-2-(tert-Butoxy)-2-{4,27-dimethyl-21,26-dioxa-32-thia-1,5,7,8,11-pentaazahexacyclo
[25.2.2.1$^{6,9}$.1$^{10,13}$.0$^{2,7}$.0$^{15,20}$]tritriaconta-2,4,6(33),8,10,12,15(20),16,18-nonaen-3-yl}acetic acid;
(2S)-2-(tert-Butoxy)-2-{4,27-dimethyl-21,26,32-trioxa-1,5,7,8,11-pentaazahexacyclo
[25.2.2.1$^{6,9}$.1$^{10,13}$.0$^{2,7}$.0$^{15,20}$]tritriaconta-2,4,6(33),8,10,12,15(20),16,18-nonaen-3-yl}acetic acid;
(2S)-2-(tert-Butoxy)-2-[(23Z)-4,27-dimethyl-21,26-dioxa-32-thia-1,5,7,8,11-pentaazahexacyclo

[25.2.2.1$^{6,9}$.1$^{10,13}$.0$^{2,7}$.0$^{15,20}$]tritriaconta-2,4,6(33),8,10,12,15(20),16,18,23-decaen-3-yl]acetic acid;

(2S)-2-(tert-Butoxy)-2-[(24E)-4,28-dimethyl-21,27-dioxa-33-thia-1,5,7,8,11-pentaazahexacyclo[26.2.2.1$^{6,9}$.1$^{10,13}$.0$^{2,7}$.0$^{15,20}$]tetratriaconta-2,4,6(34),8,10,12,15(20),16,18,24-decaen-3-yl]acetic acid;

(2S)-2-(tert-Butoxy)-2-{4,28-dimethyl-21,27-dioxa-33-thia-1,5,7,8,11-pentaazahexacyclo[26.2.2.1$^{6,9}$.1$^{10,13}$.0$^{2,7}$.0$^{15,20}$]tetratriaconta-2,4,6(34),8,10,12,15(20),16,18-nonaen-3-yl}acetic acid;

(2S)-2-(tert-Butoxy)-2-[(23E)-4,27-dimethyl-21,26,32-trioxa-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,23-decaen-3-yl]acetic acid;

(2S)-2-(tert-Butoxy)-2-[(22R)-4,22,28-trimethyl-21,27-dioxa-33-thia-1,5,7,8,11-pentaazahexacyclo[26.2.2.1$^{6,9}$.1$^{10,13}$.0$^{2,7}$.0$^{15,20}$]tetratriaconta-2,4,6(34),8,10,12,15(20),16,18-nonaen-3-yl]acetic acid;

(2S)-2-(tert-Butoxy)-2-[(23E,25E)-4,27-dimethyl-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,23,25-undecaen-3-yl]acetic acid;

(2S)-2-(tert-Butoxy)-2-[(25E)-4,27-dimethyl-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,25-decaen-3-yl]acetic acid;

(2S)-2-(tert-Butoxy)-2-{4,27-dimethyl-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18-nonaen-3-yl}acetic acid;

(2S)-2-(tert-Butoxy)-2-[(25E)-18-fluoro-4,27-dimethyl-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,25-decaen-3-yl]acetic acid;

(2S)-2-(tert-Butoxy)-2-[(24E)-18-fluoro-4,26-dimethyl-31-thia-1,5,7,8,11-pentaazahexacyclo[24.2.2.1$^{6,9}$.1$^{10,13}$.0$^{2,7}$.0$^{15,20}$]dotriaconta-2,4,6(32),8,10,12,15(20),16,18,24-decaen-3-yl]acetic acid;

(2S)-2-(tert-Butoxy)-2-[(23E)-18-fluoro-4,27-dimethyl-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,23-decaen-3-yl]acetic acid;

(2S)-2-(tert-Butoxy)-2-[(23E)-18-fluoro-4,26-dimethyl-31-thia-1,5,7,8,11-pentaazahexacyclo[24.2.2.1$^{6,9}$.1$^{10,13}$.0$^{2,7}$.0$^{15,20}$]dotriaconta-2,4,6(32),8,10,12,15(20),16,18,23-decaen-3-yl]acetic acid;

(2S)-2-(tert-Butoxy)-2-[(22R,24E)-18-fluoro-4,22,28-trimethyl-21-oxa-33-thia-1,5,7,8,11-pentaazahexacyclo[26.2.2.1$^{6,9}$.1$^{10,13}$.0$^{2,7}$.0$^{15,20}$]tetratriaconta-2,4,6(34),8,10,12,15(20),16,18,24-decaen-3-yl]acetic acid;

(2S)-2-(tert-Butoxy)-2-[(22R,24Z)-18-fluoro-4,22,28-trimethyl-21-oxa-33-thia-1,5,7,8,11-pentaazahexacyclo[26.2.2.1$^{6,9}$.1$^{10,13}$.0$^{2,7}$.0$^{15,20}$]tetratriaconta-2,4,6(34),8,10,12,15(20),16,18,24-decaen-3-yl]acetic acid;

(2S)-2-(tert-Butoxy)-2-[(23E)-17-fluoro-4,27-dimethyl-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,23-decaen-3-yl]acetic acid;

(2S)-2-(tert-Butoxy)-2-[(23Z)-17-fluoro-4,27-dimethyl-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,23-decaen-3-yl]acetic acid;

(2S)-2-(tert-Butoxy)-2-[(23E)-17-fluoro-4,26-dimethyl-31-thia-1,5,7,8,11-pentaazahexacyclo[24.2.2.1$^{6,9}$.1$^{10,13}$.0$^{2,7}$.0$^{15,20}$]dotriaconta-2,4,6(32),8,10,12,15(20),16,18,23-decaen-3-yl]acetic acid;

(2S)-2-(tert-Butoxy)-2-[(23E)-4,27-dimethyl-21-oxa-32-thia-1,5,7,8,11-pentaazahexacyclo[25.2.2.1$^{6,9}$.1$^{10,13}$.0$^{2,7}$.0$^{15,20}$]tritriaconta-2,4,6(33),8,10,12,15(20),16,18,23-decaen-3-yl]acetic acid;

(2S)-2-(tert-Butoxy)-2-{4,27-dimethyl-21,26-dioxa-1,5,7,8,10,11-hexaazahexacyclo[25.2.2.1$^{6,9}$.1$^{10,13}$.0$^{2,7}$.0$^{15,20}$]tritriaconta-2,4,6(33),8,11,13(32),15(20),16,18-nonaen-3-yl}acetic acid;

(2S)-2-(tert-Butoxy)-2-[(23E)-4,27-dimethyl-21,26-dioxa-1,5,7,8,10,11-hexaazahexacyclo[25.2.2.1$^{6,9}$.1$^{10,13}$.0$^{2,7}$.0$^{15,20}$]tritriaconta-2,4,6(33),8,11,13(32),15(20),16,18,23-decaen-3-yl]acetic acid;

(2S)-2-(tert-Butoxy)-2-[(23E)-19-fluoro-4,27-dimethyl-21,26-dioxa-1,5,7,8,10,11-hexaazahexacyclo[25.2.2.1$^{6,9}$.1$^{10,13}$.0$^{2,7}$.0$^{15,20}$]tritriaconta-2,4,6(33),8,11,13(32),15(20),16,18,23-decaen-3-yl]acetic acid;

(2S)-2-(tert-Butoxy)-2-{19-fluoro-4,27-dimethyl-21,26-dioxa-1,5,7,8,10,11-hexaazahexacyclo[25.2.2.1$^{6,9}$.1$^{10,13}$.0$^{2,7}$.0$^{15,20}$]tritriaconta-2,4,6(33),8,11,13(32),15(20),16,18-nonaen-3-yl}acetic acid;

(2S)-2-(tert-Butoxy)-2-[(23E)-17-fluoro-4,27-dimethyl-21,26-dioxa-1,5,7,8,10,11-hexaazahexacyclo[25.2.2.1$^{6,9}$.1$^{10,13}$.0$^{2,7}$.0$^{15,20}$]tritriaconta-2,4,6(33),8,11,13(32),15(20),16,18,23-decaen-3-yl]acetic acid;

(2S)-2-(tert-Butoxy)-2-{17-fluoro-4,27-dimethyl-21,26-dioxa-1,5,7,8,10,11-hexaazahexacyclo[25.2.2.1$^{6,9}$.1$^{10,13}$.0$^{2,7}$.0$^{15,20}$]tritriaconta-2,4,6(33),8,11,13(32),15(20),16,18-nonaen-3-yl}acetic acid;

(2S)-2-(tert-Butoxy)-2-[(24E)-4,28-dimethyl-21,27-dioxa-1,5,7,8,10,11-hexaazahexacyclo[26.2.2.1$^{6,9}$.1$^{10,13}$.0$^{2,7}$.0$^{15,20}$]tetratriaconta-2,4,6(34),8,11,13(33),15(20),16,18,24-decaen-3-yl]acetic acid;

(2S)-2-(tert-butoxy)-2-[(24Z)-4,28-dimethyl-21,27-dioxa-1,5,7,8,10,11-hexaazahexacyclo[26.2.2.1$^{6,9}$.1$^{10,13}$.0$^{2,7}$.0$^{15,20}$]tetratriaconta-2,4,6(34),8,11,13(33),15(20),16,18,24-decaen-3-yl]acetic acid;

(2S)-2-(tert-Butoxy)-2-{4,28-dimethyl-21,27-dioxa-1,5,7,8,10,11-hexaazahexacyclo[26.2.2.1$^{6,9}$.1$^{10,13}$.0$^{2,7}$.0$^{15,20}$]tetratriaconta-2,4,6(34),8,11,13(33),15(20),16,18-nonaen-3-yl}acetic acid;

(2S)-2-(tert-Butoxy)-2-[(24E)-4,28-dimethyl-21-oxa-1,5,7,8,10,11-hexaazahexacyclo[26.2.2.1$^{6,9}$.1$^{10,13}$.0$^{2,7}$.0$^{15,20}$]tetratriaconta-2,4,6(34),8,11,13(33),15(20),16,18,24-decaen-3-yl]acetic acid;

(2S)-2-(tert-Butoxy)-2-[(24Z)-4,28-dimethyl-21-oxa-1,5,7,8,10,11-hexaazahexacyclo[26.2.2.1$^{6,9}$.1$^{10,13}$.0$^{2,7}$.0$^{15,20}$]tetratriaconta-2,4,6(34),8,11,13(33),15(20),16,18,24-decaen-3-yl]acetic acid;

(2S)-2-(tert-Butoxy)-2-{4,28-dimethyl-21-oxa-1,5,7,8,10,11-hexaazahexacyclo[26.2.2.1$^{6,9}$.1$^{10,13}$.0$^{2,7}$.0$^{15,20}$]tetratriaconta-2,4,6(34),8,11,13(33),15(20),16,18-nonaen-3-yl}acetic acid;

(2S)-2-(tert-butoxy)-2-[(22E)-4,26-dimethyl-20-oxa-1,5,7,8,10,11-hexaazahexacyclo[24.2.2.1$^{6,9}$.1$^{10,13}$.1$^{15,19}$.0$^{2,7}$]tritriaconta-2,4,6(33),8,11,13(32),15(31),16,18,22-decaen-3-yl]acetic acid;

(2S)-2-(tert-Butoxy)-2-[(22Z)-4,26-dimethyl-20-oxa-1,5,7,8,10,11-hexaazahexacyclo[24.2.2.1$^{6,9}$.1$^{10,13}$.1$^{15,19}$.0$^{2,7}$]tritriaconta-2,4,6(33),8,11,13(32),15(31),16,18,22-decaen-3-yl]acetic acid;

(2S)-2-(tert-Butoxy)-2-{4,26-dimethyl-20-oxa-1,5,7,8,10,11-hexaazahexacyclo[24.2.2.1$^{6,9}$.1$^{10,13}$.1$^{15,19}$.0$^{2,7}$]tritriaconta-2,4,6(33),8,11,13(32),15(31),16,18-nonaen-3-yl}acetic acid;

(2S)-2-(tert-Butoxy)-2-{4,27-dimethyl-21-oxa-1,5,7,8,12,13-hexaazahexacyclo[25.2.2.1$^{6,9}$.1$^{10,13}$.0$^{2,7}$.0$^{15,20}$]

tritriaconta-2,4,6(33),8,10(32),11,15(20),16,18-nonaen-3-yl}acetic acid; and pharmaceutically acceptable salts thereof.

10. A composition useful for treating HIV infection comprising a therapeutic amount of a compound of claim 1 and a pharmaceutically acceptable carrier.

11. The composition of claim 10 further comprising a therapeutically effective amount at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

12. A method for treating HIV infection comprising administering a therapeutically effective amount of a compound of claim 1, or a pharmaceutically acceptable salt thereof, to a patient in need thereof.

13. The method of claim 12 further comprising administering a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

* * * * *